US008859569B2

(12) United States Patent
Follmann et al.

(10) Patent No.: US 8,859,569 B2
(45) Date of Patent: Oct. 14, 2014

(54) SUBSTITUTED ANNELLATED PYRIMIDINES AND USE THEREOF

(75) Inventors: Markus Follmann, Wülfrath (DE); Johannes-Peter Stasch, Solingen (DE); Gorden Redlich, Bochum (DE); Nils Griebenow, Dormagen (DE); Dieter Lang, Velbert (DE); Frank Wunder, Wuppertal (DE); Walter Hübsch, Wuppertal (DE); Niels Lindner, Wuppertal (DE); Alexandros Vakalopoulos, Hilden (DE); Adrian Tersteegen, Wuppertal (DE)

(73) Assignees: Bayer Pharma Aktiengesellschaft, Berlin (DE); Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 13/599,975

(22) Filed: Aug. 30, 2012

(65) Prior Publication Data

US 2013/0338137 A1 Dec. 19, 2013

(30) Foreign Application Priority Data

Sep. 2, 2011 (DE) .......................... 10 2011 082 041
Jan. 11, 2012 (DE) .......................... 10 2012 200 351

(51) Int. Cl.
| | | |
|---|---|---|
| A01N 43/90 | (2006.01) | |
| A61K 31/519 | (2006.01) | |
| C07D 487/00 | (2006.01) | |
| A61K 31/541 | (2006.01) | |
| A61K 31/5383 | (2006.01) | |
| A61K 31/5377 | (2006.01) | |
| C07D 498/08 | (2006.01) | |
| C07D 519/00 | (2006.01) | |
| C07D 471/04 | (2006.01) | |
| A61K 45/06 | (2006.01) | |
| C07D 487/04 | (2006.01) | |
| C07D 491/20 | (2006.01) | |

(52) U.S. Cl.
CPC ............ *C07D 487/04* (2013.01); *A61K 31/541* (2013.01); *A61K 31/5383* (2013.01); *A61K 31/5377* (2013.01); *C07D 498/08* (2013.01); *C07D 519/00* (2013.01); *C07D 471/04* (2013.01); *A61K 45/06* (2013.01); *A61K 31/519* (2013.01); *C07D 491/20* (2013.01)
USPC ...................... 514/265.1; 544/280

(58) Field of Classification Search
None
See application file for complete search history.

(56) References Cited

U.S. PATENT DOCUMENTS

| | | |
|---|---|---|
| 5,976,523 A | 11/1999 | Awaya et al. |
| 6,180,656 B1 | 1/2001 | Fürstner et al. |
| 6,451,805 B1 | 9/2002 | Straub et al. |
| 6,743,798 B1 | 6/2004 | Straub et al. |
| 6,833,364 B1 | 12/2004 | Straub et al. |
| 6,903,089 B1 | 6/2005 | Stasch et al. |
| 7,173,037 B2 | 2/2007 | Alonso-Alija et al. |
| 7,410,973 B2 | 8/2008 | Fuerer et al. |
| 7,414,136 B2 | 8/2008 | Matsumura et al. |
| 8,242,272 B2 | 8/2012 | Jimenez et al. |
| 8,293,900 B2 | 10/2012 | Jian et al. |
| 8,309,551 B2 | 11/2012 | Schirok et al. |
| 2004/0235863 A1 | 11/2004 | Feurer et al. |
| 2011/0218202 A1 | 9/2011 | Brockunier et al. |
| 2011/0224197 A1 | 9/2011 | Henkel et al. |
| 2013/0072492 A1 | 3/2013 | Raghavan et al. |
| 2013/0172372 A1 | 7/2013 | Follmann et al. |
| 2013/0178475 A1 | 7/2013 | Moore et al. |

FOREIGN PATENT DOCUMENTS

| | | |
|---|---|---|
| CA | 2804470 | 1/2012 |
| CA | 2809911 | 3/2012 |
| CA | 2833698 | 10/2012 |
| CA | 2834901 | 11/2012 |
| CN | 1613849 | 5/2005 |
| EP | 0634413 | 1/1995 |
| WO | 0183490 | 11/2001 |

OTHER PUBLICATIONS

Becker et al.,"NO-Independent Regulatory Site of Direct sGC Stimulators like YC-1 and BAY 41-2272," BMC Pharmacology, 2001, 1: 13.
Cheng et al.,"Potential Purine Antagonists VII. Synthesis of 6-Alkylpyrazolo-[3,4-d]pyrimidines," J. Org. Chem., 1958, 23:191-200.
Evgenov et al.,"NO-independent stimulators and activators of soluble guanylate cyclase: discovery and therapeutic potential," Nat. Rev. Drug. Disc, Sep. 2006, 5:543-547.
Glass et al., "Stimulation of Human Platelet Guanylate Cyclase by Fatty Acids," J. Biol. Chem., 1977, 252, 1279-1285.
Hassan et al.,"Aryl-Aryl Bond Formation One Century after the Discovery of the Ullmann Reaction," Chem. Rev. 2002, 102: 1359-1469.
Hughes,"Progress in the Mitsunobu Reaction. A Review," Org. Prep. Procedures Int., 1996, 28(2):127-164.
Ko et al., "YC-1, a Novel Activator of Platelet Guanylate Cyclase," Blood, Dec. 1994, 84(12): 4226-4233.
Maarten van den Buuse,"Circadian Rythyms of Blood Pressure, Heart Rate, and Locomotor Activity in Spontaneously Hypertensive Rats as Measured with Radio-Telemetry," Physiology & Behavior, 1994, 55(4):783-787.

(Continued)

*Primary Examiner* — Jeffrey H Murray
(74) *Attorney, Agent, or Firm* — Karen B. King

(57) ABSTRACT

The present application relates to novel substituted annellated pyrimidines, methods for production thereof, use thereof alone or in combinations for treating and/or preventing diseases and use thereof for the production of medicinal products for treating and/or preventing diseases, in particular for treating and/or preventing cardiovascular diseases.

8 Claims, No Drawings

(56) References Cited

OTHER PUBLICATIONS

Mittendorf et al., "Discovery of Riociguat (BAY 63-2521): A Potent, Oral Stimulator of Soluble Guanylate Cyclase for the Treatment of Pulmonary Hypertension," Chem. Med. Chem., 2009, 4: 853-865.

Mülsch et al., "Effect of YC-1, an NO-independent, superoxide-sensitive stimulator of soluble guanylyl cyclase, on smooth muscle responsiveness to nitrovasodilators," Brit. J. Pharm., 1997, 120: 681-689.

Pettibone et al., "A Structurally Novel Stimulator of Guanylate Cyclase with Long-Lasting Hypotensive Activity in the Dog," Euro. J. of Pharmacology, 1985, 116: 307-312.

Sharkovska et al.,"Nitric oxide-independent stimulation of soluble guanylate cyclase reduces organ damage in experimental low-renin and high-renin models," J. Hypertension, 2010, 28(8):1666-1675.

Stasch et al., "Soluble Guanylate Cyclase as an Emerging Therapeutic Target in Cardiopulmonary Disease," Circulation, May 2011, 123: 2263-2273.

Wilson et al.,"Development of a Scaleable Synthesis of a Partial Nicotinic Acid Receptor Agonist," Organic Process Research & Development, 2009, 13: 543-547.

Winn et al., "2-(Alkylamino)nicotinic Acid and Analogs. Potent Angiotensin II Antagonists," J. Med. Chem 1993, 36: 2676-2688.

Witte et al.,"Experimental heart failure in rats: effects on cardiovascular circadian rhythms and on myocardial β-adrenergic signaling," Cardiovascular Research, 2000, 47: 350-358.

Wu et al., "YC-1 inhibited human platelet aggregation through NO-independent activation of soluble guanylate cyclase," Br J. Pharmacol. Oct. 1995, 116(3):1973-1978.

Wunder et al., "A cell-based cGMP assay useful for ultra-high-throughput screening and identification of modulators of the nitric oxide/cGMP pathway," Anal. Biochem., 2005, 339:104-112.

Yu et al., "Vasorelaxant Effect of Isoliquiritigenin, A novel soluble guanylate cyclase activator, in rat aorta," Brit. J. of Pharmacology, 1995, 114: 1587-1594.

U.S. Appl. No. 13/806,425.
U.S. Appl. No. 13/736,692.
U.S. Appl. No. 14/115,870.

SUBSTITUTED ANNELLATED PYRIMIDINES AND USE THEREOF

The present application relates to novel substituted annellated pyrimidines, methods of production thereof, use thereof alone or in combinations for treating and/or preventing diseases and use thereof for the production of medicinal products for treating and/or preventing diseases, in particular for treating and/or preventing cardiovascular diseases.

One of the most important cellular transmission systems in mammalian cells is cyclic guanosine monophosphate (cGMP). Together with nitric oxide (NO), which is released from the endothelium and transmits hormonal and mechanical signals, it forms the NO/cGMP system. The guanylate cyclases catalyse the biosynthesis of cGMP from guanosine triphosphate (GTP). The currently known representatives of this family can be divided, both on the basis of structural features and according to the type of ligands, into two groups: the particulate guanylate cyclases that can be stimulated by natriuretic peptides, and the soluble guanylate cyclases that can be stimulated by NO. The soluble guanylate cyclases consist of two subunits and most probably contain one haem per heterodimer, which is a part of the regulatory centre. This is of central importance for the activation mechanism NO can bind to the iron atom of haem and thus greatly increase the activity of the enzyme. In contrast, haem-free preparations cannot be stimulated by NO. Carbon monoxide (CO) is also capable of binding to the central iron atom of haem, but stimulation by CO is far less than by NO.

Through the formation of cGMP and the resultant regulation of phosphodiesterases, ion channels and protein kinases, guanylate cyclase plays a decisive role in various physiological processes, in particular in the relaxation and proliferation of smooth muscle cells, in platelet aggregation and adhesion, in neuronal signal transmission and in diseases that result from disturbance of the aforementioned processes. In pathophysiological conditions, the NO/cGMP system can be suppressed, which can lead for example to high blood pressure, platelet activation, increased cellular proliferation, endothelial dysfunction, arteriosclerosis, angina pectoris, heart failure, myocardial infarction, thromboses, stroke and sexual dysfunction.

A possible NO-independent treatment for such diseases that aims to influence the cGMP signalling pathway in organisms is a promising approach in view of the expected high efficiency with few side-effects.

Up till now, compounds such as organic nitrates, whose action is based on NO, have been used exclusively for therapeutic stimulation of the soluble guanylate cyclase. The NO is formed by bioconversion and activates the soluble guanylate cyclase by acting on the central iron atom of the haem. In addition to the side-effects, the decisive disadvantages of this method of treatment include development of tolerance.

Some years ago, some substances were described that stimulate soluble guanylate cyclase directly, i.e. without prior release of NO, such as for example 3-(5'-hydroxymethyl-2'-furyl)-1-benzylindazole [YC-1; Wu et al., *Blood* 84 (1994), 4226; Mülsch et al., *Brit. J. Pharmacol.* 120 (1997), 681]. The newer stimulators of soluble guanylate cyclase include inter alia BAY 41-2272, BAY 41-8543 and riociguat (BAY 63-2521) (see e.g. Stasch J.-P. et al., *Nat. Rev. Drug Disc.* 2006; 5: 755-768; Stasch J.-P. et al., *ChemMedChem* 2009; 4: 853-865. Stasch J.-P. et al., *Circulation* 2011; 123: 2263-2273). Interestingly, some of these sGC stimulators, for example YC-1 or BAY 41-2272, display PDE5-inhibitory action in addition to direct guanylate cyclase stimulation. To maximize the cGMP-pathway, it is pharmacologically desirable to stimulate the synthesis of cGMP and simultaneously inhibit the degradation via PDE-5. This dual principle is especially advantageous pharmacologically (cf. Oudout et al., *Eur. Urol.* 2011, 60, 1020-1026).

The dual principle is fulfilled, in the sense of the present invention, if the compounds according to the invention display an action on recombinant guanylate cyclase reporter cell lines according to the test under B-2 as minimal effective concentration (MEC) of ≤3 μm and inhibition of human phosphodiesterase 5 (PDE5) according to the test under B-6 as IC50<100 nm.

Phosphodiesterase-5 (PDE5) is the name for one of the enzymes that cleave the phosphoric acid ester bond in cGMP, with formation of 5'-guanosine monophosphate (5'-GMP). In humans, phosphodiesterase-5 occurs mainly in the smooth muscles of the cavernous body of the penis (corpus cavernosum penis) and the pulmonary arteries. Blocking of cGMP degradation through inhibition of PDE5 (with for example sildenafil, vardenafil or tadalafil) leads to increased signals of the relaxation signalling pathways and especially to increased blood supply to the cavernous body of the penis and lowering of pressure in the blood vessels of the lung. They are used for treating erectile dysfunction and pulmonary arterial hypertension. In addition to PDE5, there are other phosphodiesterases exclusively cleaving cGMP (Stasch J.-P. et al. *Circulation* 2011).

As stimulators of soluble guanylate cyclase, annellated pyrazole derivatives are disclosed in WO 00/06568 and WO 00/06569 and carbamate-substituted 3-pyrimidinyl-pyrazolopyridines in WO 03/095451. 3-Pyrimidinyl-pyrazolopyridines with phenylamide substituents are described in E. M. Becker et al., *BMC Pharmacology* 1 (13), 2001. WO 2004/009590 describes pyrazolopyridines with substituted 4-aminopyrimidines for treating CNS disorders. WO 2010/065275 and WO 2011/149921 disclose substituted pyrrolo- and dihydropyridopyrimidines as sGC activators. As sGC stimulators, annellated aminopyrimidines are described in WO 2012/004259 and annellated pyrimidines and triazines in WO 2012/004258. WO 2012/28647 discloses pyrazolopyridines with various azaheterocycles for treating cardiovascular diseases.

The problem to be solved by the present invention was to provide novel substances that act as stimulators of soluble guanylate cyclase and as stimulators of soluble guanylate cyclase and inhibitors of phosphodiesterase-5 (dual principle) and have an equal or improved therapeutic profile versus the compounds known from the prior art, for example with respect to their in-vivo properties, for example their pharmacokinetic and pharmacodynamic behaviour and/or their metabolic profile and/or their dose-effect relation.

The present invention relates to compounds of general formula (I)

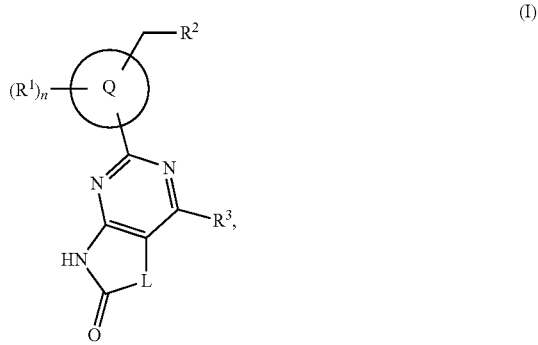

in which
L stands for a group $\#^1\text{—}CR^{7A}R^{7B}\text{—}(CR^{8A}R^{8B})_m\text{—}\#^2$, wherein
$^1$ stands for the point of attachment to the carbonyl group,
$^2$ stands for the point of attachment to the pyrimidine ring,
m stands for a number 0, 1 or 2,
$R^{7A}$ stands for hydrogen, fluorine, $(C_1-C_4)$-alkyl, hydroxyl or amino,
  in which $(C_1-C_4)$-alkyl can be substituted with 1 to 3 substituents selected independently of one another from the group fluorine, trifluoromethyl, hydroxy, hydroxycarbonyl, $(C_1-C_4)$-alkoxycarbonyl and amino,
$R^{7B}$ stands for hydrogen, fluorine, difluoromethyl, trifluoromethyl, $(C_1-C_6)$-alkyl, $(C_1-C_4)$-alkoxycarbonylamino, cyano, $(C_3-C_7)$-cycloalkyl, difluoromethoxy, trifluoromethoxy, phenyl or a group of formula -M-$R^{13}$,
  in which $(C_1-C_6)$-alkyl can be substituted with 1 to 3 substituents selected independently of one another from the group fluorine, cyano, trifluoromethyl, $(C_3-C_7)$-cycloalkyl, hydroxy, difluoromethoxy, trifluoromethoxy, $(C_1-C_4)$-alkoxy, hydroxycarbonyl, $(C_1-C_4)$-alkoxycarbonyl and amino,
  and in which
  M stands for a bond or $(C_1-C_4)$-alkanediyl,
  $R^{13}$ stands for —(C=O)$_r$—OR$^{14}$, —(C=O)$_r$—NR$^{14}$R$^{15}$, —C(=S)—NR$^{14}$R$^{15}$, —NR$^{14}$—(C=O)—R$^{17}$, —NR$^{14}$—(C=O)—NR$^{15}$R$^{16}$, —NR$^{14}$—SO$_2$—NR$^{15}$R$^{16}$, —NR$^{14}$—SO$_2$—R$^{17}$, —S(O)$_s$—R$^{17}$, —SO$_2$—NR$^{14}$R$^{15}$, 4- to 7-membered heterocyclyl, phenyl or 5- or 6-membered heteroaryl,
    in which
    r denotes the number 0 or 1,
    denotes the number 0, 1 or 2,
    $R^{14}$, $R^{15}$ and $R^{16}$ each stand, independently of one another, for hydrogen, $(C_1-C_6)$-alkyl, $(C_3-C_8)$-cycloalkyl, 4- to 7-membered heterocyclyl, phenyl or 5- or 6-membered heteroaryl,
    or
    $R^{14}$ and $R^{15}$ form, together with the respective atom(s) to which they are bound, a 4- to 7-membered heterocycle,
      in which for its part the 4- to 7-membered heterocycle can be substituted with 1 or 2 substituents selected independently of one another from the group cyano, trifluoromethyl, $(C_1-C_6)$-alkyl, hydroxy, oxo, $(C_1-C_6)$-alkoxy, trifluoromethoxy, $(C_1-C_6)$-alkoxycarbonyl, amino, mono-$(C_1-C_6)$-alkylamino and di$(C_1-C_6)$-alkylamino,
    or
    $R^{15}$ and $R^{16}$ form, together with the respective atom(s) to which they are bound, a 4- to 7-membered heterocycle,
    in which for its part the 4- to 7-membered heterocycle can be substituted with 1 or 2 substituents selected independently of one another from the group cyano, trifluoromethyl, $(C_1-C_6)$-alkyl, hydroxy, oxo, $(C_1-C_6)$-alkoxy, trifluoromethoxy, $(C_1-C_6)$-alkoxycarbonyl, amino, mono-$(C_1-C_6)$-alkylamino and di$(C_1-C_6)$-alkylamino,
    $R^{17}$ stands for $(C_1-C_6)$-alkyl or $(C_3-C_7)$-cycloalkyl,
    or
    $R^{14}$ and $R^{17}$ form, together with the respective atom(s) to which they are bound, a 4- to 7-membered heterocycle,
      in which for its part the 4- to 7-membered heterocycle can be substituted with 1 or 2 substituents selected independently of one another from the group cyano, trifluoromethyl, $(C_1-C_6)$-alkyl, hydroxy, oxo, $(C_1-C_6)$-alkoxy, trifluoromethoxy, $(C_1-C_6)$-alkoxycarbonyl, amino, mono-$(C_1-C_6)$-alkylamino and di$(C_1-C_6)$-alkylamino,
    and
    in which for their part the 4- to 7-membered heterocyclyl, phenyl and 5- or 6-membered heteroaryl can be substituted with 1 to 3 substituents selected independently of one another from the group halogen, cyano, difluoromethyl, trifluoromethyl, $(C_1-C_6)$-alkyl, $(C_3-C_7)$-cycloalkyl, hydroxy, oxo, thiooxo and $(C_1-C_4)$-alkoxy,
    and
    in which the aforementioned $(C_1-C_4)$-alkyl, $(C_1-C_6)$-alkyl, $(C_3-C_8)$-cycloalkyl, $(C_3-C_7)$-cycloalkyl and 4- to 7-membered heterocyclyl groups, unless stated otherwise, can in each case be further substituted independently of one another with 1 to 3 substituents selected independently of one another from the group fluorine, difluoromethyl, trifluoromethyl, $(C_1-C_4)$-alkyl, $(C_3-C_7)$-cycloalkyl, hydroxy, difluoromethoxy, trifluoromethoxy, $(C_1-C_4)$-alkoxy, hydroxycarbonyl, $(C_1-C_4)$-alkoxycarbonyl, amino, phenyl, 4- to 7-membered heterocyclyl and 5- or 6-membered heteroaryl,
or
$R^{7A}$ and $R^{7B}$ together with the carbon atom to which they are bound, form a $(C_2-C_4)$-alkenyl group, an oxo group, a 3- to 6-membered carbocycle or a 4- to 7-membered heterocycle,
  in which the 3- to 6-membered carbocycle and the 4- to 7-membered heterocycle can be substituted with 1 or 2 substituents selected independently of one another from the group fluorine and $(C_1-C_4)$-alkyl,
$R^{8A}$ stands for hydrogen, fluorine, $(C_1-C_4)$-alkyl or hydroxy,
$R^{8B}$ stands for hydrogen, fluorine, $(C_1-C_4)$-alkyl or trifluoromethyl,
the ring Q stands for 8- or 9-membered heteroaryl,
$R^3$ stands for —OR$^4$ or —NR$^5$R$^6$,
  wherein
    $R^4$ stands for hydrogen, $(C_1-C_6)$-alkyl, $(C_3-C_7)$-cycloalkyl, 4- to 7-membered heterocyclyl, phenyl or 5- or 6-membered heteroaryl,
    in which $(C_1-C_6)$-alkyl, $(C_3-C_7)$-cycloalkyl, 4- to 7-membered heterocyclyl, phenyl and 5- or 6-membered heteroaryl can be substituted with 1 to 3 substituents selected independently of one another from the group fluorine, difluoromethyl, trifluoromethyl, $(C_1-C_6)$-alkyl, $(C_3-C_6)$-cycloalkyl, difluoromethoxy, trifluoromethoxy, oxo, —(C=O)$_p$—OR$^9$, —C(=O)$_p$—NR$^9$R$^{10}$, —NR$^9$—(C=O)—R$^{10}$, —NR$^9$—(C=O)—OR$^{10}$, —NR$^9$—(C=O)—NR$^{10}$R$^{11}$, —NR$^9$—SO$_2$—R$^{10}$, —S(O)$_q$—R$^{12}$ and —SO$_2$—NR$^9$R$^{10}$,
    in which
    p denotes the number 0 or 1,
    q denotes the number 0, 1 or 2,
    $R^9$, $R^{10}$ and $R^{11}$ each stand, independently of one another, for hydrogen, $(C_1-C_6)$-alkyl or $(C_3-C_8)$-cycloalkyl,
    in which $(C_1-C_6)$-alkyl for its part can be substituted with 1 or 2 substituents selected independently of one another from the group fluorine, difluoromethyl, trifluoromethyl, hydroxy, $(C_1-C_6)$-alkoxy, difluoromethoxy, trifluoromethoxy, $(C_1-C_6)$-alkoxycarbonyl, amino, mono-$(C_1-C_6)$-alkylamino, di$(C_1-C_6)$-alkylamino and 4- to 7-membered heterocyclyl, or $R^9$ and $R^{10}$ form, together with the respective atom(s) to which they are bound, a 4- to 7-membered heterocycle, in which for its part the 4- to 7-membered heterocycle can be substituted with 1 or 2 substituents selected independently of one another from the group fluorine, trifluoromethyl, $(C_1-C_6)$-alkyl, hydroxy, oxo, $(C_1-C_6)$-alkoxy, trifluoromethoxy, $(C_1-C_6)$-alkoxycarbonyl, amino, mono-$(C_1-C_6)$-alkylamino and di$(C_1-C_6)$-alkylamino, or $R^{10}$ and $R^{11}$ form, together with the respective atom(s) to which they are bound, a 4- to 7-membered heterocycle, in which for its part the 4- to 7-membered heterocycle can be substituted with 1 or 2 substituents selected independently of one another from the group fluorine, trifluoromethyl, $(C_1-C_6)$-alkyl, hydroxy, oxo, $(C_1-C_6)$-alkoxy, trifluoromethoxy, $(C_1-C_6)$-alkoxycarbonyl, amino, mono-$(C_1-C_6)$-alkylamino and di$(C_1-C_6)$-alkylamino, and in which $R^{12}$ stands for $(C_1-C_6)$-alkyl or $(C_3-C_7)$-cycloalkyl, and in which the aforementioned $(C_1-C_4)$-alkyl, $(C_3-C_8)$-cycloalkyl, $(C_3-C_7)$-cycloalkyl and 4- to 7-membered heterocyclyl groups, unless stated otherwise, can in each case be further substituted independently of one another with 1 to 3 substituents selected independently of one another from the group fluorine, difluoromethyl, trifluoromethyl, $(C_1-C_4)$-alkyl, $(C_3-C_7)$-cycloalkyl, hydroxy, difluoromethoxy, trifluoromethoxy, $(C_1-C_4)$-alkoxy, hydroxycarbonyl, $(C_1-C_4)$-alkoxycarbonyl, amino, phenyl, 4- to 7-membered heterocyclyl and 5- or 6-membered heteroaryl, $R^5$ stands for hydrogen or $(C_1-C_4)$-alkyl, $R^6$ stands for $(C_1-C_6)$-alkyl, $(C_3-C_7)$-cycloalkyl, 4- to 7-membered heterocyclyl, phenyl or 5- or 6-membered heteroaryl, in which $(C_1-C_6)$-alkyl, $(C_3-C_7)$-cycloalkyl, 4- to 7-membered heterocyclyl, phenyl and 5- or 6-membered heteroaryl can be substituted with 1 to 3 substituents selected independently of one another from the group fluorine, difluoromethyl, trifluoromethyl, $(C_1-C_6)$-alkyl, $(C_3-C_7)$-cycloalkyl, difluoromethoxy, trifluoromethoxy, oxo, —(C=O)$_p$—OR$^9$, —(C=O)$_p$—NR$^9$R$^{10}$, —NR$^9$—(C=O)—R$^{10}$, —NR$^9$—(C=O)—OR$^{10}$, —NR$^9$—(C=O)—NR$^{10}$R$^{11}$, —NR$^9$—SO$_2$—R$^{10}$, —S(O)$_q$—R$^{12}$, —SO$_2$—NR$^9$R$^{10}$, phenyl, 4- to 7-membered heterocyclyl and 5- or 6-membered heteroaryl, in which p denotes the number 0 or 1, q denotes the number 0, 1 or 2, $R^9$, $R^{10}$ and $R^{11}$ each stand, independently of one another, for hydrogen, $(C_1-C_6)$-alkyl or $(C_3-C_8)$-cycloalkyl, in which $(C_1-C_6)$-alkyl for its part can be substituted with 1 to 3 substituents selected independently of one another from the group fluorine, difluoromethyl, trifluoromethyl, $(C_3-C_7)$-cycloalkyl, difluoromethoxy, trifluoromethoxy and $(C_1-C_4)$-alkoxy, or $R^9$ and $R^{10}$ form, together with the respective atom(s) to which they are bound, a 4- to 7-membered heterocycle, in which for its part the 4- to 7-membered heterocycle can be substituted with 1 or 2 substituents selected independently of one another from the group fluorine, cyano, trifluoromethyl, $(C_1-C_6)$-alkyl, hydroxy, oxo, $(C_1-C_6)$-alkoxy, trifluoromethoxy, $(C_1-C_6)$-alkoxycarbonyl, amino, mono-$(C_1-C_6)$-alkylamino and di$(C_1-C_6)$-alkylamino, or $R^{10}$ and $R^{11}$ form, together with the respective atom(s) to which they are bound, a 4- to 7-membered heterocycle, in which for its part the 4- to 7-membered heterocycle can be substituted with 1 or 2 substituents selected independently of one another from the group cyano, trifluoromethyl, $(C_1-C_6)$-alkyl, hydroxy, oxo, $(C_1-C_6)$-alkoxy, trifluoromethoxy, $(C_1-C_6)$-alkoxycarbonyl, amino, mono-$(C_1-C_6)$-alkylamino and di$(C_1-C_6)$-alkylamino, in which $R^{12}$ stands for $(C_1-C_6)$-alkyl or $(C_3-C_7)$-cycloalkyl, and in which phenyl, 4- to 7-membered heterocyclyl and 5- or 6-membered heteroaryl for their part can be substituted with 1 to substituents selected independently of one another from the group halogen, cyano, difluoromethyl, trifluoromethyl, $(C_1-C_4)$-alkyl, $(C_3-C_7)$-cycloalkyl, hydroxy, oxo, difluoromethoxy, trifluoromethoxy and $(C_1-C_4)$-alkoxy, or $R^5$ and $R^6$ form, together with the nitrogen atom to which they are bound, a 4- to 7-membered heterocycle or a 5- or 6-membered heteroaryl, in which the 4- to 7-membered heterocycle and the 5- or 6-membered heteroaryl can be substituted with 1 to 3 substituents selected independently of one another from the group fluorine, cyano, difluoromethyl, trifluoromethyl, $(C_1-C_6)$-alkyl, $(C_3-C_7)$-cycloalkyl, hydroxy, oxo, $(C_1-C_6)$-alkoxy, difluoromethoxy, trifluoromethoxy, $(C_1-C_6)$-alkoxycarbonyl, $(C_1-C_6)$-alkylcarbonylamino, amino, mono-$(C_1-C_6)$-alkylamino, di$(C_1-C_6$-alkylamino and 4- to 7-membered heterocyclyl, and in which the aforementioned $(C_1-C_4)$-alkyl, $(C_1-C_6)$-alkyl, $(C_3-C_8)$-cycloalkyl, $(C_3-C_7)$-cycloalkyl and 4- to 7-membered heterocyclyl groups, unless stated otherwise, can in each case be further substituted independently of one another with 1 to 3 substituents selected independently of one another from the group fluorine, difluoromethyl, trifluoromethyl, $(C_1-C_4)$-alkyl, $(C_3-C_7)$-cycloalkyl, hydroxy, difluoromethoxy, trifluoromethoxy, alkoxy, hydroxycarbonyl, $(C_1-C_4)$-alkoxycarbonyl, amino, phenyl, 4- to 7-membered heterocyclyl and 5- or 6-membered heteroaryl, $R^1$ stands for fluorine, chlorine, cyano, difluoromethyl, trifluoromethyl, $(C_1-C_4)$-alkyl, $(C_3-C_7)$-cycloalkyl or $(C_1-C_4)$-alkoxy, n stands for a number 0, 1 or 2, $R^2$ stands for trifluoromethyl, $(C_1-C_6)$-alkyl, $(C_3-C_8)$-cycloalkyl, phenyl or 5- or 6-membered heteroaryl, wherein (C$_1$-C$_6$)-alkyl is substituted with a substituent selected from the group difluoromethyl and trifluoromethyl, wherein (C$_1$-C$_6$)-alkyl can be substituted with 1 to 3 fluorine substituents, wherein (C$_3$-C$_8$)-cycloalkyl can be substituted with 1 or 2 substituents selected independently of one another from the group fluorine, methyl and methoxy, wherein phenyl is substituted with 1 to 3 fluorine substituents, wherein phenyl can be substituted with 1 or 2 substituents selected independently of one another from the group methyl and methoxy, and wherein 5- and 6-membered heteroaryl can be substituted with 1 or 2 substituents selected independently of one another from the group fluorine, trifluoromethyl and methyl.

and their N-oxides, salts, solvates, salts of the N-oxides and solvates of the N-oxides and salts.

Compounds according to the invention are the compounds of formula (I) and their N-oxides, salts, solvates and solvates of the N-oxides and salts, the compounds covered by formula (I) with the formulae stated hereunder and their N-oxides, salts, solvates and solvates of the N-oxides and salts and the compounds covered by formula (I) stated hereunder as practical examples and their N-oxides, salts, solvates and solvates of the N-oxides and salts, provided the compounds stated hereunder that are covered by formula (I) are not already N-oxides, salts, solvates and solvates of the N-oxides and salts.

Physiologically harmless salts of the compounds according to the invention are preferred as salts in the context of the present invention. Salts that are not suitable themselves for pharmaceutical applications, but can be used for example for isolating or purifying the compounds according to the invention, are also covered.

Physiologically harmless salts of the compounds according to the invention comprise acid addition salts of mineral acids, carboxylic acids and sulphonic acids, e.g. salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, formic acid, acetic acid, trifluoroacetic acid, propionic acid, lactic acid, tartaric acid, malic acid, citric acid, fumaric acid, maleic acid and benzoic acid.

Physiologically harmless salts of the compounds according to the invention also comprise salts of usual bases, for example and preferably alkali metal salts (e.g. sodium and potassium salts), alkaline-earth salts (e.g. calcium and magnesium salts) and ammonium salts, derived from ammonia or organic amines with 1 to 16 carbon atoms, for example and preferably ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

The term "solvates" denotes, in the context of the invention, those forms of the compounds according to the invention that form a complex in the solid or liquid state by coordination with solvent molecules. Hydrates are a special form of the solvates, in which coordination takes place with water. Hydrates are preferred as solvates in the context of the present invention.

Depending on their structure, the compounds according to the invention can exist in various stereoisomeric forms, i.e. in the form of configurational isomers or optionally also as conformational isomers (enantiomers and/or diastereomers, including those that are atropisomers). The present invention therefore comprises the enantiomers and diastereomers and their respective mixtures. The stereoisomerically uniform constituents can be isolated in a known way from said mixtures of enantiomers and/or diastereomers; chromatographic methods are preferably used for this, in particular achiral or chiral phase HPLC chromatography.

If the compounds according to the invention can exist in tautomeric forms, the present invention comprises all tautomeric forms.

The present invention also comprises all suitable isotopic variants of the compounds according to the invention. "Isotopic variant of a compound according to the invention" means a compound in which at least one atom within the compound according to the invention is exchanged for another atom of the same atomic number, but with an atomic mass different from the atomic mass usually or mainly occurring naturally. Examples of isotopes that can be incorporated in a compound according to the invention are those of hydrogen, carbon, nitrogen, oxygen, phosphorus, sulphur, fluorine, chlorine, bromine and iodine, such as $^2$H (deuterium), $^3$H (tritium), $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I. Certain isotopic variants of a compound according to the invention, such as in particular those in which one or more radioactive isotopes are incorporated, can be useful for example for investigating the mechanism of action or the distribution of active substances in the body; owing to the comparative ease of production and detection, compounds labelled with $^3$H- or $^{14}$C-isotopes are particularly suitable for this. Furthermore, the incorporation of isotopes, for example deuterium, can lead to certain therapeutic advantages as a result of increased metabolic stability of the compound, for example a longer half-life in the body or a decrease in the effective dose required; such modifications of the compounds according to the invention can therefore optionally also represent a preferred embodiment of the present invention. Isotopic variants of the compounds according to the invention can be produced by methods that are known by a person skilled in the art, for example the methods described hereunder and the specifications presented in the practical examples, in which corresponding isotopic modifications of the respective reagents and/or starting compounds are used.

Moreover, the present invention also comprises prodrugs of the compounds according to the invention. The term "prodrugs" denotes compounds that can themselves be biologically active or inactive, but during their residence time in the body they are converted to compounds according to the invention (for example metabolically or by hydrolysis).

In the context of the present invention, the substituents have the following meanings, unless stated otherwise:

In the context of the invention, alkyl stands for a linear or branched alkyl residue with the number of carbon atoms stated in each case. For example and preferably, we may mention: methyl, ethyl, n-propyl, isopropyl, n-butyl, isobutyl, 1-methylpropyl, tert.-butyl, n-pentyl, iso-pentyl, 1-ethylpropyl, 1-methylbutyl, 2-methylbutyl, 3-methylbutyl, n-hexyl, 1-methylpentyl, 2-methylpentyl, 3-methylpentyl, 4-methylpentyl, 3,3-dimethylbutyl, 1-ethylbutyl and 2-ethylbutyl.

In the context of the invention, cycloalkyl or carbocycle stands for a monocyclic, saturated alkyl residue with the number of carbon atoms stated in each case. For example and preferably, we may mention: cyclopropyl, cyclobutyl, cyclopentyl, cyclohexyl and cycloheptyl.

In the context of the invention, 5- to 7-membered saturated or partially unsaturated carbocycle stands for a saturated or partially unsaturated cyclic alkyl residue with the number of carbon atoms stated in each case. For example and preferably, we may mention: cyclopentyl, cyclohexyl, cycloheptyl, cyclopentenyl, cyclohexenyl and cycloheptenyl.

In the context of the invention, alkanediyl stands for a linear or branched divalent alkyl residue with 1 to 4 carbon atoms. For example and preferably, we may mention: methylene, ethane-1,2-diyl, ethane-1,1-diyl, propane-1,3-diyl, propane-1,1-diyl, propane-1,2-diyl, propane-2,2-diyl, butane-1,4-diyl, butane-1,2-diyl, butane-1,3-diyl and butane-2,3-diyl.

In the context of the invention, alkenyl stands for a linear or branched alkenyl residue with 2 to 4 carbon atoms and a double bond. For example and preferably, we may mention: vinyl, allyl, isopropenyl and n-but-2-en-1-yl.

In the context of the invention, alkoxy stands for a linear or branched alkoxy residue with 1 to 6 or 1 to 4 carbon atoms. We may mention, for example: methoxy, ethoxy, n-propoxy, isopropoxy, 1-methylpropoxy, n-butoxy, iso-butoxy, tert.-butoxy, n-pentoxy, iso-pentoxy, 1-ethylpropoxy, 1-methylbutoxy, 2-methylbutoxy, 3-methylbutoxy and n-hexoxy. A linear or branched alkoxy residue with 1 to 4 carbon atoms is preferred. For example and preferably, we may mention: methoxy, ethoxy, n-propoxy, isopropoxy, 1-methylpropoxy, n-butoxy, iso-butoxy, tert.-butoxy.

In the context of the invention, alkoxycarbonyl stands for a linear or branched alkoxy residue with 1 to 4 carbon atoms and a carbonyl group attached to the oxygen. For example and preferably, we may mention: methoxycarbonyl, ethoxycarbonyl, n-propoxycarbonyl, isopropoxycarbonyl and tert.-butoxycarbonyl.

In the context of the invention, alkoxycarbonylamino stands for an amino group with a linear or branched alkoxycarbonyl substituent, which has 1 to 4 carbon atoms in the alkyl chain and is joined to the N-atom via the carbonyl group. For example and preferably, we may mention: methoxycarbonylamino, ethoxycarbonylamino, propoxycarbonylamino, n-butoxycarbonylamino, iso-butoxycarbonylamino and tert.-butoxycarbonylamino.

In the context of the invention, mono-alkylamino stands for an amino group with a linear or branched alkyl substituent having 1 to 6 carbon atoms. For example and preferably, we may mention: methylamino, ethylamino, n-propylamino, isopropylamino and tert.-butylamino.

In the context of the invention, di-alkylamino stands for an amino group with two identical or different linear or branched alkyl substituents, with in each case 1 to 6 carbon atoms. For example and preferably, we may mention: N,N-dimethylamino, N,N-diethylamino, N-ethyl-N-methylamino, N-methyl-N-n-propylamino, N-isopropyl-N-n-propylamino, N-tert.-butyl-N-methylamino, N-ethyl-N-n-pentylamino and N-n-hexyl-N-methylamino.

In the context of the invention, 5- to 7-membered saturated or partially unsaturated heterocycle stands for a saturated or partially unsaturated heterocycle with a total of 5 to 7 ring atoms, which contains a ring-heteroatom from the group N, O, S, SO and/or $SO_2$. We may mention, for example: pyrrolidinyl, tetrahydrofuranyl, piperidinyl, tetrahydropyranyl, dihydropyrrolyl, dihydropyridyl.

In the context of the invention, heterocyclyl or heterocycle stands for a saturated heterocycle with a total of 4 to 7 ring atoms, which contains one or two ring-heteroatoms from the group N, O, S, SO and/or $SO_2$. We may mention, for example: azetidinyl, oxetanyl, pyrrolidinyl, pyrazolidinyl, imidazolinyl, tetrahydrofuranyl, piperidinyl, piperazinyl, tetrahydropyranyl, morpholinyl, thiomorpholinyl and dioxidothiomorpholinyl. Azetidinyl, oxetanyl, pyrrolidinyl, tetrahydrofuranyl, piperidinyl, tetrahydropyranyl and morpholinyl are preferred.

In the context of the invention, 5- or 6-membered heteroaryl stands for a monocyclic aromatic heterocycle (heteroaromatic) with a total of 5 or 6 ring atoms, which contains up to three identical or different ring-heteroatoms from the group N, O and/or S and is joined via a ring carbon atom or optionally via a ring nitrogen atom. For example and preferably, we may mention: furyl, pyrrolyl, thienyl, pyrazolyl, imidazolyl, thiazolyl, oxazolyl, isoxazolyl, isothiazolyl, triazolyl, oxadiazolyl, thiadiazolyl, pyridyl, pyrimidinyl, pyridazinyl, pyrazinyl and triazinyl. The following are preferred: pyrazolyl, oxazolyl, thiazolyl, triazolyl, oxadiazolyl, thiadiazolyl, pyridyl and pyrimidinyl.

In the context of the invention, 8- or 9-membered heteroaryl stands for a bicyclic aromatic or partially unsaturated heterocycle with a total of 8 or 9 ring atoms, which contains at least two nitrogen atoms and up to two further, identical or different ring-heteroatoms from the group N, O and/or S. We may mention, for example: dihydrothienopyrazolyl, thienopyrazolyl, pyrazolopyrazolyl, imidazothiazolyl, tetrahydrocyclopentapyrazolyl, dihydrocyclopentapyrazolyl, tetrahydroindazolyl, dihydroindazolyl, indazolyl, pyrazolopyridyl, tetrahydropyrazolopyridyl, pyrazolopyrimidinyl, imidazopyridyl and imidazopyridazinyl. The following are preferred: indazolyl, pyrazolo[3,4-b]pyridyl, pyrazolo[3,4-b]pyrimidinyl and imidazo[1,5-a]pyridyl.

In the context of the invention, halogen stands for fluorine, chlorine, bromine and iodine. Bromine and iodine are preferred.

In the context of the invention, an oxo group stands for an oxygen atom, which is bound to a carbon atom via a double bond.

In the context of the invention, a thiooxo group stands for a sulphur atom, which is bound to a carbon atom via a double bond.

In the formula of the group for which L or Q can stand, the end point of the line at which there is the symbol $\#^1$, $\#^2$, * and ** does not stand for a carbon atom or a $CH_2$ group, but is a component of the bond to the atom that is designated in each case, to which L or Q is bound.

If residues in the compounds according to the invention are substituted, the residues can, unless stated otherwise, be substituted one or more times. In the context of the present invention, for all residues that occur more than once, their meaning is independent of one another. Substitution with one, two or three identical or different substituents is preferred.

In the sense of the present invention, the term "treatment" or "treat" comprises inhibiting, delaying, maintaining, alleviating, mitigating, restricting, decreasing, suppressing, repressing or healing a disease, a condition, an ailment, an injury or a disorder, the development, the course or the progression of said states and/or the symptoms of said states. The term "therapy" is to be understood as a synonym of the term "treatment".

In the context of the present invention, the terms "prevention" and "prophylaxis" are used synonymously and denote avoiding or reducing the risk of acquiring, experiencing, suffering or having a disease, a condition, an ailment, an injury or a disorder, development or progression of said states and/or the symptoms of said states.

The treatment or the prevention of a disease, a condition, an ailment, an injury or a disorder can be partial or complete.

Compounds of formula (I) that are preferred in the context of the present invention are those in which L stands for a group $\#^1\!-\!CR^{7A}R^{7B}\!-\!(CR^{8A}R^{8B})_m\!-\!\#^2$, wherein
- $\#^1$ stands for the point of attachment to the carbonyl group,
- $\#^2$ stands for the point of attachment to the pyrimidine ring,
- m stands for a number 0, 1 or 2,
- $R^{7A}$ stands for hydrogen, fluorine, $(C_1\text{-}C_4)$-alkyl, hydroxyl or amino,
  - in which $(C_1\text{-}C_4)$-alkyl can be substituted with 1 to 3 substituents selected independently of one another from the group fluorine, trifluoromethyl, hydroxy, hydroxycarbonyl, $(C_1\text{-}C_4)$-alkoxycarbonyl and amino,
- $R^{7B}$ stands for hydrogen, fluorine, difluoromethyl, trifluoromethyl, $(C_1\text{-}C_6)$-alkyl, $(C_1\text{-}C_4)$-alkoxycarbonylamino, cyano, $(C_3\text{-}C_7)$-cycloalkyl, difluoromethoxy, trifluoromethoxy, phenyl or a group of formula -M-$R^{13}$,
  - in which $(C_1\text{-}C_6)$-alkyl can be substituted with 1 to 3 substituents selected independently of one another from the group fluorine, cyano, trifluoromethyl, $(C_3\text{-}C_7)$-cycloalkyl, hydroxy, difluoromethoxy, trifluoromethoxy, $(C_1\text{-}C_4)$-alkoxy, hydroxycarbonyl, $(C_1\text{-}C_4)$-alkoxycarbonyl and amino,
  - and in which
    - M stands for a bond or $(C_1\text{-}C_4)$-alkanediyl,
    - $R^{13}$ stands for —$(C{=}O)_r$—$OR^{14}$, —$(C{=}O)_r$—$NR^{14}R^{15}$, —$C({=}S)$—$NR^{14}R^{15}$, —$NR^{14}$—$(C{=}O)$—$R^{17}$, —$NR^{14}$—$(C{=}O)$—$NR^{15}R^{16}$, —$NR^{14}$—$SO_2$—$NR^{15}R^{16}$, —$NR^{14}$—$SO_2$—$R^{17}$, —$S(O)_s$—$R^{17}$, —$SO_2$—$NR^{14}R^{15}$, 4- to 7-membered heterocyclyl, phenyl or 5- or 6-membered heteroaryl,
    - in which
      - r denotes the number 0 or 1,
      - s denotes the number 0, 1 or 2,
      - $R^{14}$, $R^{15}$ and $R^{16}$ each stand, independently of one another, for hydrogen, $(C_1\text{-}C_6)$-alkyl, $(C_3\text{-}C_8)$-cycloalkyl, 4- to 7-membered heterocyclyl, phenyl or 5- or 6-membered heteroaryl,
      - or
      - $R^{14}$ and $R^{15}$ form, together with the respective atom(s) to which they are bound, a 4- to 7-membered heterocycle,
        - in which for its part the 4- to 7-membered heterocycle can be substituted with 1 or 2 substituents selected independently of one another from the group cyano, trifluoromethyl, $(C_1\text{-}C_6)$-alkyl, hydroxy, oxo, $(C_1\text{-}C_6)$-alkoxy, trifluoromethoxy, $(C_1\text{-}C_6)$-alkoxycarbonyl, amino, mono-$(C_1\text{-}C_6)$-alkylamino and di$(C_1\text{-}C_6)$-alkylamino,
      - or
      - $R^{15}$ and $R^{16}$ form, together with the respective atom(s) to which they are bound, a 4- to 7-membered heterocycle,
        - in which for its part the 4- to 7-membered heterocycle can be substituted with 1 or 2 substituents selected independently of one another from the group cyano, trifluoromethyl, $(C_1\text{-}C_6)$-alkyl, hydroxy, oxo, $(C_1\text{-}C_6)$-alkoxy, trifluoromethoxy, $(C_1\text{-}C_6)$-alkoxycarbonyl, amino, mono-$(C_1\text{-}C_6)$-alkylamino and di$(C_1\text{-}C_6)$-alkylamino,
      - $R^{17}$ stands for $(C_1\text{-}C_6)$-alkyl or $(C_3\text{-}C_7)$-cycloalkyl,
      - or
      - $R^{14}$ and $R^{17}$ form, together with the respective atom(s) to which they are bound, a 4- to 7-membered heterocycle,
        - in which for its part the 4- to 7-membered heterocycle can be substituted with 1 or 2 substituents selected independently of one another from the group cyano, trifluoromethyl, $(C_1\text{-}C_6)$-alkyl, hydroxy, oxo, $(C_1\text{-}C_6)$-alkoxy, trifluoromethoxy, $(C_1\text{-}C_6)$-alkoxycarbonyl, amino, mono-$(C_1\text{-}C_6)$-alkylamino and di$(C_1\text{-}C_6)$-alkylamino,
    - and
    - in which for their part the 4- to 7-membered heterocyclyl, phenyl and 5- or 6-membered heteroaryl can be substituted with 1 to 3 substituents selected independently of one another from the group halogen, cyano, difluoromethyl, trifluoromethyl, $(C_1\text{-}C_6)$-alkyl, $(C_3\text{-}C_7)$-cycloalkyl, hydroxy, oxo, thiooxo and $(C_1\text{-}C_4)$-alkoxy,
    - and
    - in which the aforementioned $(C_1\text{-}C_4)$-alkyl-, $(C_1\text{-}C_6)$-alkyl-, $(C_3\text{-}C_8)$-cycloalkyl- and 4- to 7-membered heterocyclyl groups, unless stated otherwise, can in each case be further substituted independently of one another with 1 to 3 substituents selected independently of one another from the group fluorine, difluoromethyl, trifluoromethyl, $(C_1\text{-}C_6)$-alkyl, $(C_3\text{-}C_7)$-cycloalkyl, hydroxy, difluoromethoxy, trifluoromethoxy, $(C_1\text{-}C_4)$-alkoxy, hydroxycarbonyl, $(C_1\text{-}C_4)$-alkoxycarbonyl, amino, phenyl, 4- to 7-membered heterocyclyl and 5- or 6-membered heteroaryl,
- or
- $R^{7A}$ and $R^{7B}$ together with the carbon atom to which they are bound, form a $(C_2\text{-}C_4)$-alkenyl group, an oxo group, a 3- to 6-membered carbocycle or a 4- to 7-membered heterocycle,
  - in which the 3- to 6-membered carbocycle and the 4- to 7-membered heterocycle can be substituted with 1 or 2 substituents selected independently of one another from the group fluorine and $(C_1\text{-}C_4)$-alkyl,
- $R^{8A}$ stands for hydrogen, fluorine, $(C_1\text{-}C_4)$-alkyl or hydroxy,
- $R^{8B}$ stands for hydrogen, fluorine, $(C_1\text{-}C_4)$-alkyl or trifluoromethyl, the ring Q stands for 8- or 9-membered heteroaryl, $R^3$ stands for —$OR^4$ or —$NR^5R^6$, wherein
- $R^4$ stands for hydrogen, $(C_1\text{-}C_6)$-alkyl, $(C_3\text{-}C_7)$-cycloalkyl, 4- to 7-membered heterocyclyl, phenyl or 5- or 6-membered heteroaryl,
  - in which $(C_1\text{-}C_6)$-alkyl, $(C_3\text{-}C_7)$-cycloalkyl, 4- to 7-membered heterocyclyl, phenyl and 5- or 6-membered heteroaryl can be substituted with 1 to 3 substituents selected independently of one another from the group fluorine, difluoromethyl, trifluoromethyl, $(C_1\text{-}C_6)$-alkyl, $(C_3\text{-}C_6)$-cycloalkyl, difluoromethoxy, trifluoromethoxy, oxo, —$(C{=}O)_p$—$OR^9$, —$C({=}O)_p$—$NR^9R^{10}$, —$NR^9$—$(C{=}O)$—$R^{10}$, —$NR^9$—$(C{=}O)$—$OR^{10}$, —$NR^9$—$(C{=}O)$—$NR^{10}R^{11}$, —$NR^9$—$SO_2$—$R^{10}$, —$S(O)_q$—$R^{12}$ and —$SO_2$—$NR^9R^{10}$,
  - in which
    - p denotes the number 0 or 1,
    - q denotes the number 0, 1 or 2, $R^9$, $R^{10}$ and $R^{11}$ each stand, independently of one another, for hydrogen, $(C_1-C_6)$-alkyl or $(C_3-C_8)$-cycloalkyl,
  in which $(C_1-C_6)$-alkyl for its part can be substituted with 1 or 2 substituents selected independently of one another from the group fluorine, difluoromethyl, trifluoromethyl, hydroxy, $(C_1-C_6)$-alkoxy, difluoromethoxy, trifluoromethoxy, $(C_1-C_6)$-alkoxycarbonyl, amino, mono-$(C_1-C_6)$-alkylamino, di$(C_1-C_6)$-alkylamino and 4- to 7-membered heterocyclyl,
or
$R^9$ and $R^{10}$ form, together with the respective atom(s) to which they are bound, a 4- to 7-membered heterocycle,
  in which for its part the 4- to 7-membered heterocycle can be substituted with 1 or 2 substituents selected independently of one another from the group fluorine, trifluoromethyl, $(C_1-C_6)$-alkyl, hydroxy, oxo, $(C_1-C_6)$-alkoxy, trifluoromethoxy, $(C_1-C_6)$-alkoxycarbonyl, amino, mono-$(C_1-C_6)$-alkylamino and di$(C_1-C_6)$-alkylamino,
or
$R^{10}$ and $R^{11}$ form, together with the respective atom(s) to which they are bound, a 4- to 7-membered heterocycle,
  in which for its part the 4- to 7-membered heterocycle can be substituted with 1 or 2 substituents selected independently of one another from the group fluorine, trifluoromethyl, $(C_1-C_6)$-alkyl, hydroxy, oxo, $(C_1-C_6)$-alkoxy, trifluoromethoxy, $(C_1-C_6)$-alkoxycarbonyl, amino, mono-$(C_1-C_6)$-alkylamino and di$(C_1-C_6)$-alkylamino,
  and in which
    $R^{12}$ stands for $(C_1-C_6)$-alkyl or $(C_3-C_7)$-cycloalkyl,
and
in which the aforementioned $(C_1-C_4)$-alkyl, $(C_1-C_6)$-alkyl, $(C_3-C_8)$-cycloalkyl and 4- to 7-membered heterocyclyl groups, unless stated otherwise, can in each case be further substituted independently of one another with 1 to 3 substituents selected independently of one another from the group fluorine, difluoromethyl, trifluoromethyl, $(C_3-C_7)$-cycloalkyl, hydroxy, difluoromethoxy, trifluoromethoxy, $(C_1-C_4)$-alkoxy, hydroxycarbonyl, $(C_1-C_4)$-alkoxycarbonyl, amino, phenyl, 4- to 7-membered heterocyclyl and 5- or 6-membered heteroaryl,
$R^5$ stands for hydrogen or $(C_1-C_4)$-alkyl,
$R^6$ stands for $(C_1-C_6)$-alkyl, $(C_3-C_7)$-cycloalkyl, 4- to 7-membered heterocyclyl, phenyl or 5- or 6-membered heteroaryl,
  in which $(C_1-C_6)$-alkyl, $(C_3-C_7)$-cycloalkyl, 4- to 7-membered heterocyclyl, phenyl and 5- or 6-membered heteroaryl can be substituted with 1 to 3 substituents selected independently of one another from the group fluorine, difluoromethyl, trifluoromethyl, $(C_1-C_6)$-alkyl, $(C_3-C_7)$-cycloalkyl, difluoromethoxy, trifluoromethoxy, oxo, $-(C=O)_p-OR^9$, $-(C=O)_p-NR^9R^{10}$, $-NR^9-(C=O)-R^{10}$, $-NR^9-(C=O)-OR^{10}$, $-NR^9-(C=O)-NR^{10}R^{11}$, $-NR^9-SO_2-R^{10}$, $-S(O)_q-R^{12}$, $-SO_2-NR^9R^{10}$, phenyl, 4- to 7-membered heterocyclyl and 5- or 6-membered heteroaryl,
  in which
    p denotes the number 0 or 1,
    q denotes the number 0, 1 or 2, $R^9$, $R^{10}$ and $R^{11}$ each stand, independently of one another, for hydrogen, $(C_1-C_6)$-alkyl or $(C_3-C_8)$-cycloalkyl,
  in which $(C_1-C_6)$-alkyl for its part can be substituted with 1 to 3 substituents selected independently of one another from the group fluorine, difluoromethyl, trifluoromethyl, $(C_3-C_7)$-cycloalkyl, difluoromethoxy, trifluoromethoxy and $(C_1-C_4)$-alkoxy,
or
$R^9$ and $R^{10}$ form, together with the respective atom(s) to which they are bound, a 4- to 7-membered heterocycle,
  in which for its part the 4- to 7-membered heterocycle can be substituted with 1 or 2 substituents selected independently of one another from the group fluorine, cyano, trifluoromethyl, $(C_1-C_6)$-alkyl, hydroxy, oxo, $(C_1-C_6)$-alkoxy, trifluoromethoxy, $(C_1-C_6)$-alkoxycarbonyl, amino, mono-$(C_1-C_6)$-alkylamino and di$(C_1-C_6)$-alkylamino,
or
$R^{10}$ and $R^{11}$ form, together with the respective atom(s) to which they are bound, a 4- to 7-membered heterocycle,
  in which for its part the 4- to 7-membered heterocycle can be substituted with 1 or 2 substituents selected independently of one another from the group cyano, trifluoromethyl, $(C_1-C_6)$-alkyl, hydroxy, oxo, $(C_1-C_6)$-alkoxy, trifluoromethoxy, $(C_1-C_6)$-alkoxycarbonyl, amino, mono-$(C_1-C_6)$-alkylamino and di$(C_1-C_6)$-alkylamino,
  in which
    $R^{12}$ stands for $(C_1-C_6)$-alkyl or $(C_3-C_7)$-cycloalkyl,
  and
  in which phenyl, 4- to 7-membered heterocyclyl and 5- or 6-membered heteroaryl for their part can be substituted with 1 to substituents selected independently of one another from the group halogen, cyano, difluoromethyl, trifluoromethyl, $(C_1-C_4)$-alkyl, $(C_3-C_7)$-cycloalkyl, hydroxy, oxo, difluoromethoxy, trifluoromethoxy and $(C_1-C_4)$-alkoxy,
or
$R^5$ and $R^6$ form, together with the nitrogen atom to which they are bound, a 4- to 7-membered heterocycle or a 5- or 6-membered heteroaryl,
  in which the 4- to 7-membered heterocycle and the 5- or 6-membered heteroaryl can be substituted with 1 to 3 substituents selected independently of one another from the group fluorine, cyano, difluoromethyl, trifluoromethyl, $(C_1-C_6)$-alkyl, $(C_3-C_7)$-cycloalkyl, hydroxy, oxo, $(C_1-C_6)$-alkoxy, difluoromethoxy, trifluoromethoxy, $(C_1-C_6)$-alkoxycarbonyl, amino, mono-$(C_1C_6)$-alkylamino and di $(C_1-C_6)$-alkylamino,
and
in which the aforementioned $(C_1-C_4)$-alkyl-, $(C_1-C_6)$-alkyl-, $(C_3-C_8)$-cycloalkyl- and 4- to 7-membered heterocyclyl groups, unless stated otherwise, can in each case be further substituted independently of one another with 1 to 3 substituents selected independently of one another from the group fluorine, difluoromethyl, trifluoromethyl, $(C_3-C_7)$-cycloalkyl, hydroxy, difluoromethoxy, trifluoromethoxy, $(C_1-C_4)$-alkoxy, hydroxycarbonyl, $(C_3-C_4)$-alkoxycarbonyl, amino, phenyl, 4- to 7-membered heterocyclyl and 5- or 6-membered heteroaryl, $R^1$ stands for fluorine, chlorine, cyano, difluoromethyl, trifluoromethyl, $(C_1-C_4)$-alkyl, $(C_3-C_7)$-cycloalkyl or $(C_1-C_4)$-alkoxy, n stands for a number 0, 1 or 2, $R^2$ stands for trifluoromethyl, $(C_1-C_6)$-alkyl, $(C_3-C_8)$-cycloalkyl, phenyl or 5- or 6-membered heteroaryl,
  wherein $(C_1-C_6)$-alkyl is substituted with a substituent selected from the group difluoromethyl and trifluoromethyl,
  wherein $(C_1-C_6)$-alkyl can be substituted with 1 to 3 fluorine substituents,
  wherein $(C_3-C_8)$-cycloalkyl can be substituted with 1 or 2 substituents selected independently of one another from the group fluorine, methyl and methoxy,
  wherein phenyl is substituted with 1 to 3 fluorine substituents,
  wherein phenyl can be substituted with 1 or 2 substituents selected independently of one another from the group methyl and methoxy,
  and
  wherein 5- and 6-membered heteroaryl can be substituted with 1 or 2 substituents selected independently of one another from the group fluorine, trifluoromethyl and methyl, and their N-oxides, salts, solvates, salts of the N-oxides and solvates of the N-oxides and salts.

In the context of the present invention, compounds of formula (I) are preferred in which L stands for a group $\#^1$—$CR^{7A}R^{7B}$—$(CR^{8A}R^{8B})_m$—$\#^2$,
  wherein
  $\#^1$ stands for the point of attachment to the carbonyl group,
  $\#^2$ stands for the point of attachment to the pyrimidine ring,
  m stands for a number 0 or 1,
  $R^{7A}$ stands for hydrogen, fluorine, methyl, ethyl, hydroxy or amino,
  $R^{7B}$ stands for hydrogen, fluorine, difluoromethyl, trifluoromethyl, $(C_1-C_4)$-alkyl, methoxycarbonylamino, cyano, cyclopropyl, cyclobutyl, cyclopentyl, phenyl or a group of formula -M-$R^{13}$,
    in which $(C_1-C_4)$-alkyl can be substituted with 1 to 3 substituents selected independently of one another from the group fluorine, cyano, trifluoromethyl, cyclopropyl, cyclobutyl, cyclopentyl, hydroxy, difluoromethoxy, trifluoromethoxy, methoxy, ethoxy, hydroxycarbonyl, methoxycarbonyl, ethoxycarbonyl and amino,
    and in which
    M stands for a bond or methylene,
    $R^{13}$ stands for —$(C=O)_r$—$NR^{14}R^{15}$, —$C(=S)$—$NR^{14}R^{15}$, oxadiazolonyl, oxadiazolethionyl, phenyl, oxazolyl, thiazolyl, pyrazolyl, triazolyl, oxadiazolyl, thiadiazolyl, pyridyl, pyrimidinyl or pyrazinyl,
      in which
      r denotes the number 0 or 1,
      $R^{14}$ and $R^{15}$ each stand, independently of one another, for hydrogen, methyl, ethyl, isopropyl, cyclopropyl, cyclobutyl, cyclopentyl, oxetanyl, azetidinyl, tetrahydrofuranyl, pyrrolidinyl, tetrahydropyranyl, piperidinyl, piperazinyl, morpholinyl, phenyl, pyrazolyl or pyridyl,
        in which methyl, ethyl and iso-propyl can be further substituted with 1 or 2 substituents selected independently of one another from the group fluorine, difluoromethyl, trifluoromethyl, cyclopropyl, cyclobutyl, cyclopentyl, hydroxy, difluoromethoxy, trifluoromethoxy, methoxy, ethoxy, hydroxycarbonyl, methoxycarbonyl, ethoxycarbonyl and amino,
    and
    in which oxadiazolonyl, oxadiazolethionyl, phenyl, oxazolyl, thiazolyl, pyrazolyl, triazolyl, oxadiazolyl, thiadiazolyl, pyridyl, pyrimidinyl and pyrazinyl for their part can be substituted with 1 or 2 substituents selected independently of one another from the group fluorine, chlorine, cyano, difluoromethyl, trifluoromethyl, methyl, ethyl, isopropyl, 2,2,2-trifluoroethyl, 1,1,2,2,2-pentafluoroethyl, cyclopropyl, cyclobutyl, cyclopropylmethyl, cyclobutylmethyl, hydroxy, methoxy and ethoxy, or $R^{7A}$ and $R^{7B}$ together with the carbon atom to which they are bound, form a cyclopropyl, cyclobutyl, cyclopentyl, azetidinyl, tetrahydrofuranyl, pyrrolidinyl or tetrahydropyranyl ring,
  in which the cyclopropyl, cyclobutyl, cyclopentyl, azetidinyl, tetrahydrofuranyl, pyrrolidinyl and tetrahydropyranyl ring can be substituted with 1 or 2 substituents selected independently of one another from the group fluorine and methyl, $R^{8A}$ stands for hydrogen, fluorine, methyl, ethyl or hydroxy, $R^{8B}$ stands for hydrogen, fluorine, methyl, ethyl or trifluoromethyl, the ring Q stands for a group of formula

(a-1)

(b-1)

(c-1)

(d-1)

(e-1) 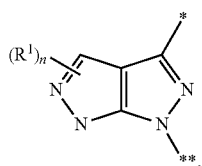

(f-1) 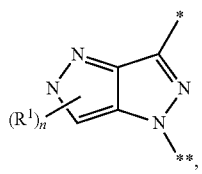

(g-1) 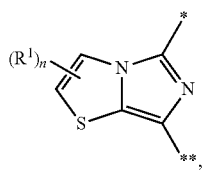

(h-1) 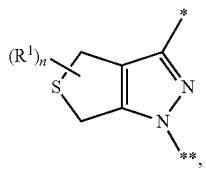

(i-1) 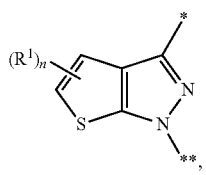

(j-1) 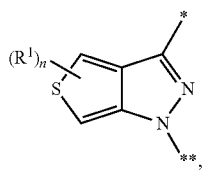

(k-1) 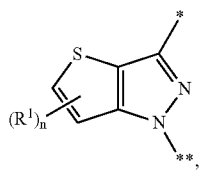

(l-1) 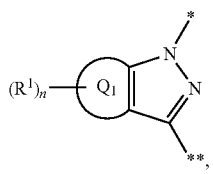

(m-1) 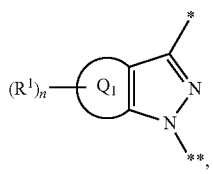

(n-1) 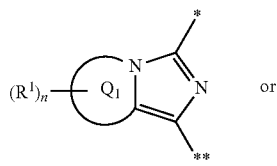

or (o-1) 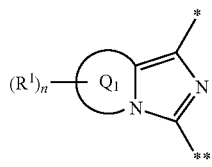

wherein

* stands for the point of attachment to —CH$_2$—R$^2$,
** stands for the point of attachment to the pyrimidine,
the ring Q$_1$ together with the atoms to which it is bound, forms a 5- to 7-membered saturated or partially unsaturated carbocycle or a 5- to 7-membered saturated or partially unsaturated heterocycle,
R$^1$ stands for fluorine, chlorine or methyl,
n stands for a number 0, 1 or 2,
A$^1$, A$^2$, A$^3$ and A$^4$ independently of one another stand in each case for N, CH or CR$^1$,
with the proviso that at most two of the groups A$^1$, A$^2$, A$^3$ and A$^4$ stand for N,
R$^3$ stands for —OR$^4$ or —NR$^5$R$^6$,
wherein
R$^4$ stands for (C$_1$-C$_6$)-alkyl, cyclopropyl, cyclobutyl, cyclopentyl, oxetanyl, azetidinyl, tetrahydrofuranyl, pyrrolidinyl, tetrahydropyranyl, piperidinyl, piperazinyl, morpholinyl, phenyl, pyrazolyl, oxazolyl, thiazolyl, triazolyl, oxadiazolyl, thiadiazolyl, pyridyl or pyrimidinyl,
in which (C$_1$-C$_6$)-alkyl can be substituted with 1 to 3 substituents selected independently of one another from the group fluorine, difluoromethyl, trifluoromethyl, cyclopropyl, cyclobutyl, cyclopentyl, difluoromethoxy, trifluoromethoxy, —(C=O)$_p$—OR$^9$, —(C=O)$_p$—NR$^9$R$^{10}$, and —NR$^9$—(C=O)—R$^{10}$, and
in which cyclopropyl, cyclobutyl, cyclopentyl, oxetanyl, azetidinyl, tetrahydrofuranyl, pyrrolidinyl, tetrahydropyranyl, piperidinyl, piperazinyl, morpholinyl, phenyl, pyrazolyl, oxazolyl, thiazolyl, triazolyl, oxadiazolyl, thiadiazolyl, pyridyl or pyrimidinyl can be substituted with 1 to 3 substituents selected independently of one another from the group fluorine, difluoromethyl, trifluoromethyl, 2,2,2-trifluoroethyl, 1,1,2,2,2-pentafluoroethyl, methyl, ethyl, isopropyl, cyclopropyl, cyclobutyl, cyclopentyl, difluoromethoxy, trifluoromethoxy, oxo, —(C=O)$_p$—OR$^9$ and —(C=O)$_p$—NR$^9$R$^{10}$,
in which
p denotes the number 0 or 1,
R$^9$ and R$^{10}$ each stand, independently of one another, for hydrogen, methyl, ethyl, isopropyl, trifluoromethyl, 2,2,2-trifluoroethyl, 1,1,2,2,2-pentafluoroethyl, cyclopropyl, cyclobutyl or cyclopentyl,
or
R$^9$ and R$^{10}$ form, together with the respective atom(s) to which they are bound, an azetidinyl, pyrrolidinyl, piperidinyl, piperazinyl or morpholinyl ring, in which the azetidinyl, pyrrolidinyl, piperidinyl, piperazinyl and morpholinyl ring for its part can be substituted with 1 or 2 substituents selected independently of one another from the group fluorine, trifluoromethyl, methyl, ethyl, hydroxy, oxo, methoxy, ethoxy, amino, methylamino, ethylamino, dimethylamino and diethylamino, $R^5$ stands for hydrogen, methyl or ethyl, $R^6$ stands for $(C_1-C_6)$-alkyl, cyclopropyl, $(C_3-C_6)$-cycloalkyl, oxetanyl, azetidinyl, tetrahydrofuranyl, pyrrolidinyl, tetrahydropyranyl, piperidinyl, piperazinyl, morpholinyl, phenyl, pyrazolyl, oxazolyl, thiazolyl, triazolyl, oxadiazolyl, thiadiazolyl, pyridyl or pyrimidinyl, in which $(C_1-C_6)$-alkyl and $(C_3-C_6)$-cycloalkyl are substituted with 1 to 3 substituents selected independently of one another from the group fluorine, difluoromethyl, trifluoromethyl, methyl, ethyl, cyclopropyl, cyclobutyl, cyclopentyl, difluoromethoxy, trifluoromethoxy, —(C=O)$_p$—OR$^9$, —(C=O)$_p$—NR$^9$R$^{10}$, —NR$^9$—(C=O)—R$^{10}$, oxetanyl, azetidinyl, tetrahydrofuranyl, pyrrolidinyl, tetrahydropyranyl, piperidinyl, piperazinyl, morpholinyl, phenyl, furanyl, pyrazolyl, imidazolyl, oxazolyl, thiazolyl, triazolyl, oxadiazolyl, thiadiazolyl, pyridyl and pyrimidinyl, in which cyclopropyl, cyclobutyl, cyclopentyl, oxetanyl, azetidinyl, tetrahydrofuranyl, pyrrolidinyl, tetrahydropyranyl, piperidinyl, piperazinyl, morpholinyl, phenyl, furanyl, pyrazolyl, imidazolyl, oxazolyl, thiazolyl, triazolyl, oxadiazolyl, thiadiazolyl, pyridyl and pyrimidinyl for their part can be substituted with 1 or 2 substituents selected independently of one another from the group fluorine, chlorine, cyano, difluoromethyl, trifluoromethyl, methyl, ethyl, cyclopropyl, cyclobutyl, cyclopentyl, hydroxy, oxo, difluoromethoxy, trifluoromethoxy, methoxy and ethoxy, in which oxetanyl, azetidinyl, tetrahydrofuranyl, pyrrolidinyl, tetrahydropyranyl, piperidinyl, piperazinyl, morpholinyl, phenyl, pyrazolyl, oxazolyl, thiazolyl, triazolyl, oxadiazolyl, thiadiazolyl, pyridyl and pyrimidinyl can be substituted with 1 to 3 substituents selected independently of one another from the group fluorine, difluoromethyl, trifluoromethyl, methyl, ethyl, cyclopropyl, cyclobutyl, cyclopentyl, difluoromethoxy, trifluoromethoxy, oxo, —(C=O)$_p$—OR$^9$ and —(C=O)$_p$—NR$^9$R$^{10}$, in which p denotes the number 0 or 1, $R^9$ and $R^{10}$ each stand, independently of one another, for hydrogen, methyl, ethyl, isopropyl, trifluoromethyl, 2,2,2-trifluoroethyl, 1,1,2,2,2-pentafluoroethyl, cyclopropyl, cyclobutyl or cyclopentyl, or $R^9$ and $R^{10}$ form, together with the respective atom(s) to which they are bound, an azetidinyl, pyrrolidinyl, piperidinyl, piperazinyl or morpholinyl ring, in which the azetidinyl, pyrrolidinyl, piperidinyl, piperazinyl and morpholinyl ring for its part can be substituted with 1 or 2 substituents selected independently of one another from the group fluorine, trifluoromethyl, methyl, ethyl, hydroxy, oxo, methoxy, ethoxy, amino, methylamino, ethylamino, dimethylamino and diethylamino, or $R^5$ and $R^6$ form, together with the nitrogen atom to which they are bound, an azetidinyl, pyrrolidinyl, imidazolidinyl, piperidinyl, dihydropiperidinyl, piperazinyl, morpholinyl, pyrazolyl, imidazolyl or triazolyl ring, in which the azetidinyl, pyrrolidinyl, imidazolidinyl, piperidinyl, dihydropiperidinyl, piperazinyl, morpholinyl, pyrazolyl, imidazolyl and triazolyl ring can be substituted with 1 or 2 substituents selected independently of one another from the group fluorine, cyano, difluoromethyl, trifluoromethyl, 2,2,2-trifluoroethyl, 1,1,2,2,2-pentafluoroethyl, methyl, ethyl, 1-hydroxyethyl, cyclopropyl, cyclobutyl, cyclopentyl, hydroxy, oxo, methoxy, ethoxy, difluoromethoxy, trifluoromethoxy, oxetanyl, azetidinyl, tetrahydrofuranyl, pyrrolidinyl, tetrahydropyranyl, piperidinyl, piperazinyl and morpholinyl, $R^2$ stands for trifluoromethyl, 2,2,2-trifluoroethyl, 3,3,3-trifluoroprop-1-yl, 2,2,3,3,3-pentafluoroprop-1-yl, cyclopropyl, cyclobutyl, cyclopentyl, cyclohexyl, phenyl, pyridyl, pyrimidinyl, pyrazinyl or pyridazinyl, wherein phenyl is substituted with 1 to 3 fluorine substituents, and wherein cyclopropyl, cyclobutyl, cyclopentyl, cyclohexyl, pyridyl, pyrimidinyl, pyrazinyl and pyridazinyl can be substituted with 1 or 2 fluorine substituents, and their salts, solvates and solvates of the salts.

In the context of the present invention, compounds of formula (I) are preferred in which L stands for a group $\#^1$—CR$^{7A}$R$^{7B}$—(CR$^{8A}$R$^{8B}$)$_m$—$\#^2$, wherein $\#^1$ stands for the point of attachment to the carbonyl group, $\#^2$ stands for the point of attachment to the pyrimidine ring, m stands for a number 0 or 1, $R^{7A}$ stands for hydrogen, fluorine, methyl, ethyl, hydroxy or amino, $R^{7B}$ stands for hydrogen, fluorine, difluoromethyl, trifluoromethyl, $(C_1-C_4)$-alkyl, methoxycarbonylamino, cyano, cyclopropyl, cyclobutyl, cyclopentyl, phenyl or a group of formula -M-R$^{13}$, in which $(C_1-C_4)$-alkyl can be substituted with 1 to 3 substituents selected independently of one another from the group fluorine, cyano, trifluoromethyl, cyclopropyl, cyclobutyl, cyclopentyl, hydroxy, difluoromethoxy, trifluoromethoxy, methoxy, ethoxy, hydroxycarbonyl, methoxycarbonyl, ethoxycarbonyl and amino, and in which M stands for a bond or methylene, $R^{13}$ stands for —(C=O)$_r$—NR$^{14}$R$^{15}$, —C(=S)—NR$^{14}$R$^{15}$, oxadiazolonyl, oxadiazolethionyl, phenyl, oxazolyl, thiazolyl, pyrazolyl, triazolyl, oxadiazolyl, thiadiazolyl, pyridyl, pyrimidinyl or pyrazinyl, in which r denotes the number 0 or 1, $R^{14}$ and $R^{15}$ each stand, independently of one another, for hydrogen, methyl, ethyl, isopropyl, cyclopropyl, cyclobutyl, cyclopentyl, oxetanyl, azetidinyl, tetrahydrofuranyl, pyrrolidinyl, tetrahydropyranyl, piperidinyl, piperazinyl, morpholinyl, phenyl, pyrazolyl or pyridyl, in which methyl, ethyl and iso-propyl can be further substituted with 1 or 2 substituents selected independently of one another from the group fluorine, difluoromethyl, trifluoromethyl, cyclopropyl, cyclobutyl, cyclopentyl, hydroxy, difluoromethoxy, trifluoromethoxy, methoxy, ethoxy, hydroxycarbonyl, methoxycarbonyl, ethoxycarbonyl and amino, and in which oxadiazolonyl, oxadiazolethionyl, phenyl, oxazolyl, thiazolyl, pyrazolyl, triazolyl, oxadiazolyl, thiadiazolyl, pyridyl, pyrimidinyl and pyrazinyl for their part can be substituted with 1 or 2 substituents selected independently of one another from the group fluorine, chlorine, cyano, difluoromethyl, trifluoromethyl, methyl, ethyl, isopropyl, 2,2,2-trifluoroethyl, 1,1,2,2,2-pentafluoroethyl, cyclopropyl, cyclobutyl, cyclopropylmethyl, cyclobutylmethyl, hydroxy, methoxy and ethoxy, or $R^{7A}$ and $R^{7B}$ together with the carbon atom to which they are bound, form a cyclopropyl, cyclobutyl, cyclopentyl, azetidinyl, tetrahydrofuranyl, pyrrolidinyl or tetrahydropyranyl ring, in which the cyclopropyl, cyclobutyl, cyclopentyl, azetidinyl, tetrahydrofuranyl, pyrrolidinyl and tetrahydropyranyl ring can be substituted with 1 or 2 substituents selected independently of one another from the group fluorine and methyl, $R^{8A}$ stands for hydrogen, fluorine, methyl, ethyl or hydroxy, $R^{8B}$ stands for hydrogen, fluorine, methyl, ethyl or trifluoromethyl, the ring Q stands for a group of formula (a-1)

(b-1)

(c-1)

(d-1)

(e-1)

(f-1)

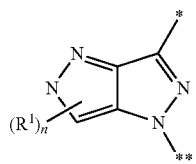

(g-1)

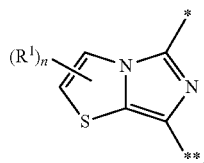

(h-1)

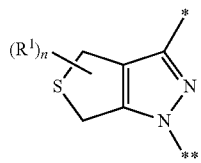

(i-1)

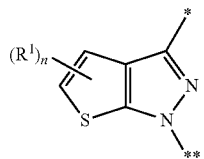

(j-1)

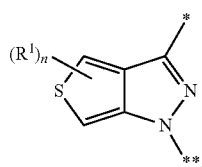

(k-1)

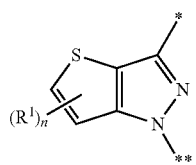

(l-1)

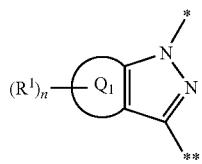

(m-1)

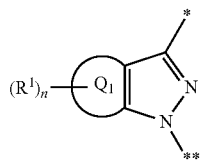

(n-1)

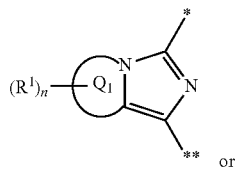

or

-continued (o-1)

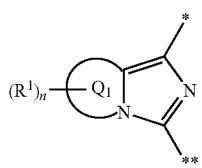

wherein
* stands for the point of attachment to —CH$_2$—R$^2$,
** stands for the point of attachment to the pyrimidine,
the ring Q$_1$ together with the atoms to which it is bound, forms a 5- to 7-membered saturated or partially unsaturated carbocycle or a 5- to 7-membered saturated or partially unsaturated heterocycle,
R$^1$ stands for fluorine, chlorine or methyl,
n stands for a number 0, 1 or 2,
A$^1$, A$^2$, A$^3$ and A$^4$ independently of one another stand in each case for N, CH or CR$^1$, with the proviso that at most two of the groups A$^1$, A$^2$, A$^3$ and A$^4$ stand for N,
R$^3$ stands for —OR$^4$ or —NR$^5$R$^6$,
  wherein
    R$^4$ stands for (C$_1$-C$_6$)-alkyl, cyclopropyl, cyclobutyl, cyclopentyl, oxetanyl, azetidinyl, tetrahydrofuranyl, pyrrolidinyl, tetrahydropyranyl, piperidinyl, piperazinyl, morpholinyl, phenyl, pyrazolyl, oxazolyl, thiazolyl, triazolyl, oxadiazolyl, thiadiazolyl, pyridyl or pyrimidinyl,
      in which (C$_1$-C$_6$)-alkyl can be substituted with 1 to 3 substituents selected independently of one another from the group fluorine, difluoromethyl, trifluoromethyl, cyclopropyl, cyclobutyl, cyclopentyl, difluoromethoxy, trifluoromethoxy, —(C=O)$_p$—OR$^9$, —(C=O)$_p$—NR$^9$R$^{10}$, and —NR$^9$—(C=O)—R$^{10}$,
      and
      in which cyclopropyl, cyclobutyl, cyclopentyl, oxetanyl, azetidinyl, tetrahydrofuranyl, pyrrolidinyl, tetrahydropyranyl, piperidinyl, piperazinyl, morpholinyl, phenyl, pyrazolyl, oxazolyl, thiazolyl, triazolyl, oxadiazolyl, thiadiazolyl, pyridyl or pyrimidinyl can be substituted with 1 to 3 substituents selected independently of one another from the group fluorine, difluoromethyl, trifluoromethyl, 2,2,2-trifluoroethyl, 1,1,2,2,2-pentafluoroethyl, methyl, ethyl, isopropyl, cyclopropyl, cyclobutyl, cyclopentyl, difluoromethoxy, trifluoromethoxy, oxo, —(C=O)$_p$—OR$^9$ and —(C=O)$_p$—NR$^9$R$^{10}$,
      in which
      p denotes the number 0 or 1,
      R$^9$ and R$^{10}$ each stand, independently of one another, for hydrogen, methyl, ethyl, isopropyl, trifluoromethyl, 2,2,2-trifluoroethyl, 1,1,2,2,2-pentafluoroethyl, cyclopropyl, cyclobutyl or cyclopentyl,
      or
      R$^9$ and R$^{10}$ form, together with the respective atom(s) to which they are bound, an azetidinyl, pyrrolidinyl, piperidinyl, piperazinyl or morpholinyl ring,
        in which the azetidinyl, pyrrolidinyl, piperidinyl, piperazinyl and morpholinyl ring for its part can be substituted with 1 or 2 substituents selected independently of one another from the group fluorine, trifluoromethyl, methyl, ethyl, hydroxy, oxo, methoxy, ethoxy, amino, methylamino, ethylamino, dimethylamino and diethylamino, R$^5$ stands for hydrogen, methyl or ethyl,
R$^6$ stands for (C$_1$-C$_6$)-alkyl, cyclopropyl, cyclobutyl, cyclopentyl, oxetanyl, azetidinyl, tetrahydrofuranyl, pyrrolidinyl, tetrahydropyranyl, piperidinyl, piperazinyl, morpholinyl, phenyl, pyrazolyl, oxazolyl, thiazolyl, triazolyl, oxadiazolyl, thiadiazolyl, pyridyl or pyrimidinyl,
  in which (C$_1$-C$_6$)-alkyl, cyclopropyl, cyclobutyl and cyclopentyl are substituted with 1 to 3 substituents selected independently of one another from the group fluorine, difluoromethyl, trifluoromethyl, methyl, ethyl, cyclopropyl, cyclobutyl, cyclopentyl, difluoromethoxy, trifluoromethoxy, —(C=O)$_p$—OR$^9$, —(C=O)$_p$—NR$^9$R$^{10}$, —NR$^9$—(C=O)—R$^{10}$, oxetanyl, azetidinyl, tetrahydrofuranyl, pyrrolidinyl, tetrahydropyranyl, piperidinyl, piperazinyl, morpholinyl, phenyl, furanyl, pyrazolyl, imidazolyl, oxazolyl, thiazolyl, triazolyl, oxadiazolyl, thiadiazolyl, pyridyl and pyrimidinyl,
    in which oxetanyl, azetidinyl, tetrahydrofuranyl, pyrrolidinyl, tetrahydropyranyl, piperidinyl, piperazinyl, morpholinyl, phenyl, furanyl, pyrazolyl, imidazolyl, oxazolyl, thiazolyl, triazolyl, oxadiazolyl, thiadiazolyl, pyridyl and pyrimidinyl for their part can be substituted with 1 or 2 substituents selected independently of one another from the group fluorine, chlorine, cyano, difluoromethyl, trifluoromethyl, methyl, ethyl, cyclopropyl, cyclobutyl, cyclopentyl, hydroxy, oxo, difluoromethoxy, trifluoromethoxy, methoxy and ethoxy,
  in which oxetanyl, azetidinyl, tetrahydrofuranyl, pyrrolidinyl, tetrahydropyranyl, piperidinyl, piperazinyl, morpholinyl, phenyl, pyrazolyl, oxazolyl, thiazolyl, triazolyl, oxadiazolyl, thiadiazolyl, pyridyl and pyrimidinyl can be substituted with 1 to 3 substituents selected independently of one another from the group fluorine, difluoromethyl, trifluoromethyl, methyl, ethyl, cyclopropyl, cyclobutyl, cyclopentyl, difluoromethoxy, trifluoromethoxy, oxo, —(C=O)$_p$—OR$^9$ and —(C=O)$_p$—NR$^9$R$^{10}$,
    in which
    p denotes the number 0 or 1,
    R$^9$ and R$^{10}$ each stand, independently of one another, for hydrogen, methyl, ethyl, isopropyl, trifluoromethyl, 2,2,2-trifluoroethyl, 1,1,2,2,2-pentafluoroethyl, cyclopropyl, cyclobutyl or cyclopentyl,
    or
    R$^9$ and R$^{10}$ form, together with the respective atom(s) to which they are bound, an azetidinyl, pyrrolidinyl, piperidinyl, piperazinyl or morpholinyl ring,
      in which the azetidinyl, pyrrolidinyl, piperidinyl, piperazinyl and morpholinyl ring for its part can be substituted with 1 or 2 substituents selected independently of one another from the group fluorine, trifluoromethyl, methyl, ethyl, hydroxy, oxo, methoxy, ethoxy, amino, methylamino, ethylamino, dimethylamino and diethylamino,
or
R$^5$ and R$^6$ form, together with the nitrogen atom to which they are bound, an azetidinyl, pyrrolidinyl, imidazolidinyl, piperidinyl, dihydropiperidinyl, piperazinyl, morpholinyl, pyrazolyl, imidazolyl or triazolyl ring,
  in which the azetidinyl, pyrrolidinyl, imidazolidinyl, piperidinyl, dihydropiperidinyl, piperazinyl, morpholinyl, pyrazolyl, imidazolyl and triazolyl ring can be substituted with 1 or 2 substituents selected independently of one another from the group fluorine, cyano, difluoromethyl, trifluoromethyl, 2,2,2-trifluoroethyl, 1,1,2,2,2-pentafluoroethyl, methyl, ethyl, 1-hydroxyethyl, cyclopropyl, cyclobutyl, cyclopentyl, hydroxy, oxo, methoxy, ethoxy, difluoromethoxy and trifluoromethoxy, $R^2$ stands for trifluoromethyl, 2,2,2-trifluoroethyl, 3,3,3-trifluoroprop-1-yl, 2,2,3,3,3-pentafluoroprop-1-yl, cyclopropyl, cyclobutyl, cyclopentyl, cyclohexyl, phenyl, pyridyl, pyrimidinyl, pyrazinyl or pyridazinyl, wherein phenyl is substituted with 1 to 3 fluorine substituents, and wherein cyclopropyl, cyclobutyl, cyclopentyl, cyclohexyl, pyridyl, pyrimidinyl, pyrazinyl and pyridazinyl can be substituted with 1 or 2 fluorine substituents, and their salts, solvates and solvates of the salts.

In the context of the present invention, compounds of formula (I) are also preferred in which L stands for a group $\#^1$—$CR^{7A}R^{7B}$—$(CR^{8A}R^{8B})_m$—$\#^2$,
wherein
$\#^1$ stands for the point of attachment to the carbonyl group,
$\#^2$ stands for the point of attachment to the pyrimidine ring,
m stands for a number 0,
$R^{7A}$ stands for hydrogen, fluorine, methyl, ethyl, hydroxy or amino,
$R^{7B}$ stands for hydrogen, fluorine, difluoromethyl, trifluoromethyl, methyl, ethyl, methoxycarbonylamino, cyclopropyl, cyclobutyl, cyclopentyl, or a group of formula -M-$R^{13}$,
in which methyl and ethyl can be substituted with 1 to 3 substituents selected independently of one another from the group fluorine, cyano, trifluoromethyl, cyclopropyl, cyclobutyl, hydroxy, difluoromethoxy, trifluoromethoxy, methoxy, ethoxy, hydroxycarbonyl, methoxycarbonyl, ethoxycarbonyl and amino,
and in which
M stands for a bond,
$R^{13}$ stands for —(C=O)$_r$—$NR^{14}R^{15}$, phenyl, thiazolyl, triazolyl, oxadiazolyl, thiadiazolyl or pyrimidinyl,
in which
r denotes the number 1,
$R^{14}$ and $R^{15}$ independently of one another stand in each case for hydrogen or cyclopropyl,
and
in which phenyl, thiazolyl, triazolyl, oxadiazolyl, thiadiazolyl and pyrimidinyl for their part can be substituted with 1 or 2 substituents selected independently of one another from the group fluorine, difluoromethyl, trifluoromethyl, methyl, ethyl, isopropyl, 2,2,2-trifluoroethyl, 1,1,2,2,2-pentafluoroethyl, cyclopropyl, cyclobutyl, cyclopropylmethyl and cyclobutylmethyl,
or
$R^{7A}$ and $R^{7B}$ together with the carbon atom to which they are bound, form a cyclopropyl, cyclobutyl, cyclopentyl, azetidinyl, tetrahydrofuranyl, pyrrolidinyl or tetrahydropyranyl ring,
in which the cyclopropyl, cyclobutyl, cyclopentyl, azetidinyl, tetrahydrofuranyl, pyrrolidinyl and tetrahydropyranyl ring can be substituted with 1 or 2 substituents selected independently of one another from the group fluorine and methyl, the ring Q stands for a group of formula

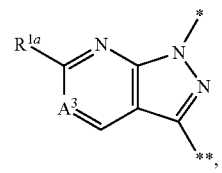
(a-1)

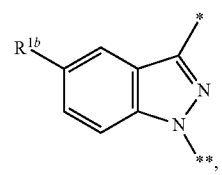
(b-1)

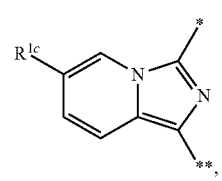
(c-1a)

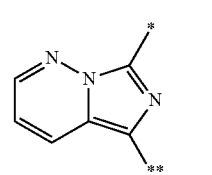
(c-1a)

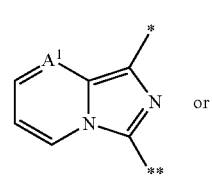
(d-1)

or

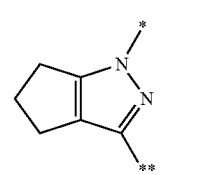
(l-1)

wherein
* stands for the point of attachment to —$CH_2$—$R^2$,
** stands for the point of attachment to the pyrimidine,
$R^{1a}$ stands for hydrogen or methyl,
$R^{1b}$ stands for hydrogen or fluorine,
$R^{1c}$ stands for hydrogen or chlorine,
$A^1$ stands for N or CH,
$A^3$ stands for N, CH or C—F,
$R^3$ stands for —$OR^4$ or —$NR^5R^6$,
wherein
$R^4$ stands for $(C_1$-$C_6)$-alkyl or pyrazolyl,
in which $(C_1$-$C_6)$-alkyl can be substituted with 1 to 3 substituents selected independently of one another from the group fluorine, trifluoromethyl, —(C=O)$_p$—$OR^9$ and —(C=O)$_p$—$NR^9R^{10}$,
in which
p denotes the number 0 or 1,
$R^9$ and $R^{10}$ each stand, independently of one another, for hydrogen, or methyl, and
in which pyrazolyl can be substituted with 1 or 2 substituents selected independently of one another from the group fluorine, difluoromethyl, trifluoromethyl, 2,2,2-trifluoroethyl, 1,1,2,2,2-pentafluoroethyl, methyl, cyclopropyl, cyclobutyl, cyclopentyl.

$R^5$ stands for hydrogen, methyl or ethyl, $R^6$ stands for $(C_1-C_6)$-alkyl, oxetanyl, azetidinyl, tetrahydrofuranyl, pyrrolidinyl, tetrahydropyranyl, piperidinyl, piperazinyl, morpholinyl, phenyl, pyrazolyl, oxazolyl, thiazolyl, triazolyl, oxadiazolyl, thiadiazolyl, pyridyl or pyrimidinyl, in which $(C_1-C_6)$-alkyl is substituted with 1 or 2 substituents selected independently of one another from the group fluorine, difluoromethyl, trifluoromethyl cyclopropyl, cyclobutyl, cyclopentyl, trifluoromethoxy, —(C=O)$_p$—OR$^9$, —(C=O)$_p$—NR$^9$R$^{10}$, tetrahydrofuranyl, pyrrolidinyl, tetrahydropyranyl, phenyl, furanyl, pyrazolyl, imidazolyl, triazolyl and pyridyl, in which
p denotes the number 0 or 1,
$R^9$ and $R^{10}$ each stand, independently of one another, for hydrogen, methyl, ethyl, trifluoromethyl, 2,2,2-trifluoroethyl, 1,1,2,2,2-pentafluoroethyl, cyclopropyl or cyclobutyl, and
in which tetrahydrofuranyl, pyrrolidinyl, tetrahydropyranyl, phenyl, furanyl, pyrazolyl, imidazolyl, triazolyl and pyridyl for their part can be substituted with 1 or 2 substituents selected independently of one another from the group fluorine, chlorine, cyano, difluoromethyl, trifluoromethyl, methyl, ethyl and oxo, in which oxetanyl, azetidinyl, tetrahydrofuranyl, pyrrolidinyl, tetrahydropyranyl, piperidinyl, piperazinyl, morpholinyl, phenyl, pyrazolyl, oxazolyl, thiazolyl, triazolyl, oxadiazolyl, thiadiazolyl, pyridyl and pyrimidinyl can be substituted with 1 or 2 substituents selected independently of one another from the group fluorine, difluoromethyl, trifluoromethyl, methyl, ethyl and oxo, or
$R^5$ and $R^6$ form, together with the nitrogen atom to which they are bound, an azetidinyl, pyrrolidinyl, imidazolidinyl, piperidinyl, dihydropiperidinyl, piperazinyl, morpholinyl, pyrazolyl or imidazolyl ring,
in which the azetidinyl, pyrrolidinyl, imidazolidinyl, piperidinyl, dihydropiperidinyl, piperazinyl, morpholinyl, pyrazolyl and imidazolyl ring can be substituted with 1 or 2 substituents selected independently of one another from the group fluorine, cyano, difluoromethyl, trifluoromethyl, 2,2,2-trifluoroethyl, 1,1,2,2,2-pentafluoroethyl, methyl, ethyl, 1-hydroxyethyl, cyclopropyl, cyclobutyl, cyclopentyl, hydroxy, oxo, methoxy, ethoxy, difluoromethoxy and trifluoromethoxy, $R^2$ stands for 3,3,3-trifluoroprop-1-yl, 2,2,3,3-tetrafluoroprop-1-yl, 2,2,3,3,3-pentafluoroprop-1-yl, phenyl or pyridyl,
wherein phenyl is substituted with 1 to 3 fluorine substituents,
and
wherein pyridyl can be substituted with 1 fluorine substituent,
and their salts, solvates and solvates of the salts.

In the context of the present invention, compounds of formula (I) are especially preferred in which
L stands for a group $\#^1$—CR$^{7A}$R$^{7B}$—(CR$^{8A}$R$^{8B}$)$_m$—$\#^2$,
wherein
$\#^1$ stands for the point of attachment to the carbonyl group,
$\#^2$ stands for the point of attachment to the pyrimidine ring,
m stands for a number 0,
R$^{7A}$ stands for hydrogen, fluorine, methyl or hydroxy,
R$^{7B}$ stands for hydrogen, fluorine, trifluoromethyl, 2,2,2-trifluoroethyl or methyl,
the ring Q stands for a group of formula

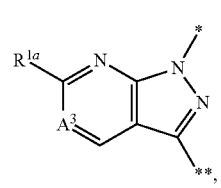

(a-1)

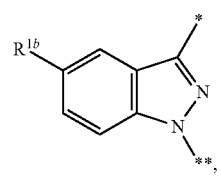

(b-1)

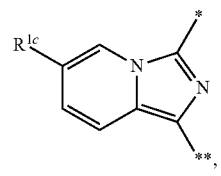

(c-1a)

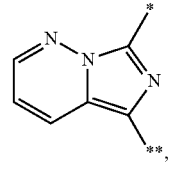

(c-1a)

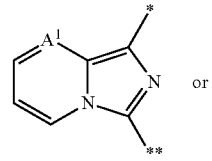

(d-1)

or

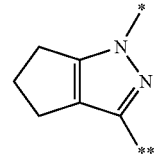

(l-1)

wherein
* stands for the point of attachment to —CH$_2$—R$^2$,
** stands for the point of attachment to the pyrimidine,
R$^{1a}$ stands for hydrogen or methyl,
R$^{1b}$ stands for hydrogen or fluorine,
R$^{1c}$ stands for hydrogen or chlorine,
$A^1$ stands for N or CH,
$A^3$ stands for N, CH or C—F,
$R^3$ stands for —OR$^4$ or —NR$^5$R$^6$, wherein R⁴ stands for $(C_1-C_6)$-alkyl or pyrazolyl, in which $(C_1-C_6)$-alkyl can be substituted with 1 to 3 substituents selected independently of one another from the group fluorine, trifluoromethyl, —(C=O)$_p$—OR⁹ and —(C=O)$_p$—NR⁹R¹⁰, in which p denotes the number 0 or 1, R⁹ and R¹⁰ independently of one another stand in each case for hydrogen or methyl, and in which pyrazolyl can be substituted with 1 or 2 substituents selected independently of one another from the group fluorine, difluoromethyl, trifluoromethyl, 2,2,2-trifluoroethyl, 1,1,2,2,2-pentafluoroethyl, methyl, cyclopropyl, cyclobutyl, cyclopentyl, R⁵ stands for hydrogen, methyl or ethyl, R⁶ stands for $(C_1-C_6)$-alkyl, oxetanyl, azetidinyl, tetrahydrofuranyl, pyrrolidinyl, tetrahydropyranyl, piperidinyl, piperazinyl, morpholinyl, phenyl, pyrazolyl, oxazolyl, thiazolyl, triazolyl, oxadiazolyl, thiadiazolyl, pyridyl or pyrimidinyl, in which $(C_1-C_6)$-alkyl is substituted with 1 or 2 substituents selected independently of one another from the group fluorine, difluoromethyl, trifluoromethyl cyclopropyl, cyclobutyl, cyclopentyl, trifluoromethoxy, —(C=O)$_p$—OR⁹, —(C=O)$_p$—NR⁹R¹⁰, tetrahydrofuranyl, pyrrolidinyl, tetrahydropyranyl, phenyl, furanyl, pyrazolyl, imidazolyl, triazolyl and pyridyl, in which p denotes the number 0 or 1, R⁹ and R¹⁰ each stand, independently of one another, for hydrogen, methyl, ethyl, trifluoromethyl, 2,2,2-trifluoroethyl, 1,1,2,2,2-pentafluoroethyl, cyclopropyl or cyclobutyl, and in which tetrahydrofuranyl, pyrrolidinyl, tetrahydropyranyl, phenyl, furanyl, pyrazolyl, imidazolyl, triazolyl and pyridyl for their part can be substituted with 1 or 2 substituents selected independently of one another from the group fluorine, chlorine, cyano, difluoromethyl, trifluoromethyl, methyl, ethyl and oxo, in which oxetanyl, azetidinyl, tetrahydrofuranyl, pyrrolidinyl, tetrahydropyranyl, piperidinyl, piperazinyl, morpholinyl, phenyl, pyrazolyl, oxazolyl, thiazolyl, triazolyl, oxadiazolyl, thiadiazolyl, pyridyl and pyrimidinyl can be substituted with 1 or 2 substituents selected independently of one another from the group fluorine, difluoromethyl, trifluoromethyl, methyl, ethyl and oxo, or R⁵ and R⁶ form, together with the nitrogen atom to which they are bound, an azetidinyl, pyrrolidinyl, imidazolidinyl, piperidinyl, dihydropiperidinyl, piperazinyl, morpholinyl, pyrazolyl or imidazolyl ring, in which the azetidinyl, pyrrolidinyl, imidazolidinyl, piperidinyl, dihydropiperidinyl, piperazinyl, morpholinyl, pyrazolyl and imidazolyl ring can be substituted with 1 or 2 substituents selected independently of one another from the group fluorine, cyano, difluoromethyl, trifluoromethyl, 2,2,2-trifluoroethyl, 1,1,2,2-pentafluoroethyl, methyl, ethyl, 1-hydroxyethyl, cyclopropyl, cyclobutyl, cyclopentyl, hydroxy, oxo, methoxy, ethoxy, difluoromethoxy and trifluoromethoxy, R² stands for 3,3,3-trifluoroprop-1-yl, 2,2,3,3,3-pentafluoroprop-1-yl, phenyl or pyridyl, wherein phenyl is substituted with 1 to 3 fluorine substituents, and wherein pyridyl can be substituted with 1 fluorine substituent, and their salts, solvates and solvates of the salts.

In the context of the present invention, compounds of formula (I) are also preferred in which L stands for a group #¹—CR⁷ᴬR⁷ᴮ—(CR⁸ᴬR⁸ᴮ)$_m$—#², wherein

¹ stands for the point of attachment to the carbonyl group,

² stands for the point of attachment to the pyrimidine ring, m stands for a number 0, R⁷ᴬ stands for hydrogen, fluorine, methyl or hydroxy, R⁷ᴮ stands for hydrogen, fluorine, trifluoromethyl, methyl or 2,2,2-trifluoroethyl, or R⁷ᴬ and R⁷ᴮ together with the carbon atom to which they are bound, form a tetrahydrofuranyl ring, the ring Q stands for a group of formula

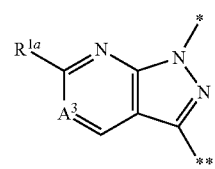

(a-1)

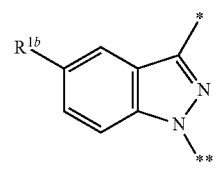

(b-1)

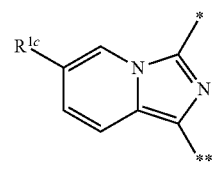

(c-1a)

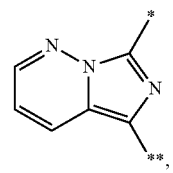

(c-1a)

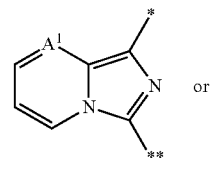

(d-1)

or

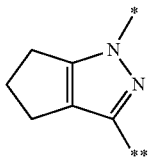
(l-1)

wherein
* stands for the point of attachment to —CH$_2$—R$^2$,
** stands for the point of attachment to the pyrimidine,
R$^{1a}$ stands for hydrogen or methyl,
R$^{1b}$ stands for hydrogen or fluorine,
R$^{1c}$ stands for hydrogen or chlorine,
A$^1$ stands for N or CH,
A$^3$ stands for N, CH or C—F,
R$^3$ stands for —NR$^5$R$^6$,
  wherein
  R$^5$ stands for hydrogen,
  R$^6$ stands for (C$_1$-C$_6$)-alkyl,
    in which (C$_1$-C$_6$)-alkyl is substituted with 1 or 2 substituents selected independently of one another from the group fluorine, difluoromethyl, trifluoromethyl or —(C=O)$_p$—OR$^9$,
    in which
    p denotes the number 0,
    R$^9$ stands for hydrogen,
R$^2$ stands for 2-fluorophenyl, 2,3-difluorophenyl or 3-fluoropyrid-2-yl,
and their salts, solvates and solvates of the salts.

In the context of the present invention, compounds of formula (I) are also especially preferred in which
L stands for a group #$^1$—CR$^{7A}$R$^{7B}$—(CR$^{8A}$R$^{8B}$)$_m$—#$^2$,
  wherein
  #$^1$ stands for the point of attachment to the carbonyl group,
  #$^2$ stands for the point of attachment to the pyrimidine ring,
  m stands for a number 0,
  R$^{7A}$ stands for methyl,
  R$^{7B}$ stands for methyl,
the ring Q stands for a group of formula

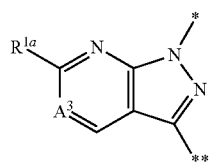
(a-1)

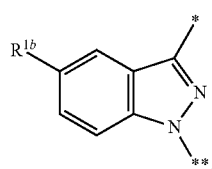
(b-1)

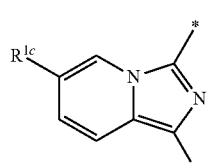
(c-1a)

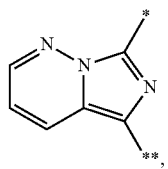
(c-1a)

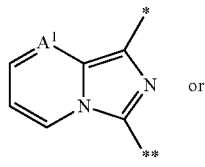
(d-1) or

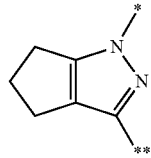
(l-1)

wherein
* stands for the point of attachment to —CH$_2$—R$^2$,
** stands for the point of attachment to the pyrimidine,
R$^{1a}$ stands for hydrogen or methyl,
R$^{1b}$ stands for hydrogen or fluorine,
R$^{1c}$ stands for hydrogen or chlorine,
A$^1$ stands for N or CH,
A$^3$ stands for N, CH or C—F,
R$^3$ stands for —NR$^5$R$^6$,
  wherein
  R$^5$ stands for hydrogen, methyl or ethyl,
  R$^6$ stands for (C$_1$-C$_6$)-alkyl, oxetanyl, azetidinyl, tetrahydrofuranyl, pyrrolidinyl, tetrahydropyranyl, piperidinyl, piperazinyl, morpholinyl, phenyl, pyrazolyl, oxazolyl, thiazolyl, triazolyl, oxadiazolyl, thiadiazolyl, pyridyl or pyrimidinyl,
    in which (C$_1$-C$_6$)-alkyl is substituted with 1 or 2 substituents selected independently of one another from the group fluorine, difluoromethyl, trifluoromethyl cyclopropyl, cyclobutyl, cyclopentyl, trifluoromethoxy, —(C=O)$_p$—OR$^9$, —(C=O)$_p$—NR$^9$R$^{10}$, tetrahydrofuranyl, pyrrolidinyl, tetrahydropyranyl, phenyl, furanyl, pyrazolyl, imidazolyl, triazolyl and pyridyl,
    in which
    p denotes the number 0 or 1,
    R$^9$ and R$^{10}$ each stand, independently of one another, for hydrogen, methyl, ethyl, trifluoromethyl, 2,2,2-trifluoroethyl, 1,1,2,2,2-pentafluoroethyl, cyclopropyl or cyclobutyl,
    and
    in which tetrahydrofuranyl, pyrrolidinyl, tetrahydropyranyl, phenyl, furanyl, pyrazolyl, imidazolyl, triazolyl and pyridyl for their part can be substituted with 1 or 2 substituents selected independently of one another from the group fluorine, chlorine, cyano, difluoromethyl, trifluoromethyl, methyl, ethyl and oxo,
  in which oxetanyl, azetidinyl, tetrahydrofuranyl, pyrrolidinyl, tetrahydropyranyl, piperidinyl, piperazinyl, morpholinyl, phenyl, pyrazolyl, oxazolyl, thiazolyl, triazolyl, oxadiazolyl, thiadiazolyl, pyridyl and pyrimidinyl can be substituted with 1 or 2 substituents selected independently of one another from the group fluorine, difluoromethyl, trifluoromethyl, methyl, ethyl and oxo,
or
$R^5$ and $R^6$ form, together with the nitrogen atom to which they are bound, an azetidinyl, pyrrolidinyl, imidazolidinyl, piperidinyl, dihydropiperidinyl, piperazinyl, morpholinyl, pyrazolyl or imidazolyl ring,
in which the azetidinyl, pyrrolidinyl, imidazolidinyl, piperidinyl, dihydropiperidinyl, piperazinyl, morpholinyl, pyrazolyl and imidazolyl ring can be substituted with 1 or 2 substituents selected independently of one another from the group fluorine, cyano, difluoromethyl, trifluoromethyl, 2,2,2-trifluoroethyl, 1,1,2,2,2-pentafluoroethyl, methyl, ethyl, 1-hydroxyethyl, cyclopropyl, cyclobutyl, cyclopentyl, hydroxy, oxo, methoxy, ethoxy, difluoromethoxy and trifluoromethoxy, $R^2$ stands for 3,3,3-trifluoroprop-1-yl, 2,2,3,3,3-pentafluoroprop-1-yl, phenyl or pyridyl,
wherein phenyl is substituted with 1 to 3 fluorine substituents,
and
wherein pyridyl can be substituted with 1 fluorine substituent,
and their salts, solvates and solvates of the salts.

In the context of the present invention, compounds of formula (I) are also especially preferred in which
L stands for a group $\#^1$—$CR^{7A}R^{7B}$—$(CR^{8A}R^{8B})_m$—$\#^2$,
wherein
$\#^1$ stands for the point of attachment to the carbonyl group,
$\#^2$ stands for the point of attachment to the pyrimidine ring,
m stands for a number 0,
$R^{7A}$ stands for hydrogen, fluorine, methyl, hydroxy,
$R^{7B}$ stands for hydrogen, fluorine, methyl or trifluoromethyl,
or
$R^{7A}$ and $R^{7B}$ together with the carbon atom to which they are bound, form a tetrahydrofuranyl ring,
the ring Q stands for a group of formula

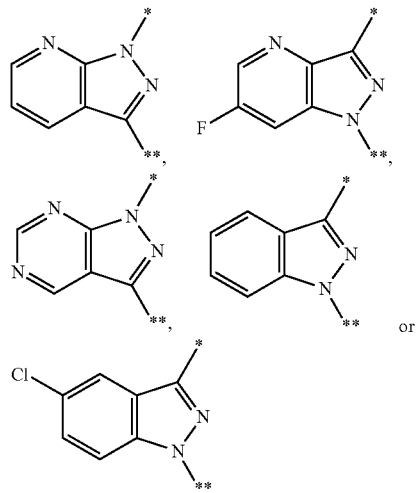

wherein
\* stands for the point of attachment to —$CH_2$—$R^2$,
\*\* stands for the point of attachment to the pyrimidine,
$R^3$ stands for —$OR^4$ or —$NR^5R^6$, wherein
$R^4$ stands for $(C_1\text{-}C_6)$-alkyl or pyrazolyl,
in which $(C_1\text{-}C_6)$-alkyl can be substituted with 1 to 3 substituents selected independently of one another from the group fluorine, trifluoromethyl, —$(C=O)_p$—$OR^9$ and —$(C=O)_p$—$NR^9R^{10}$,
in which
p denotes the number 0 or 1,
$R^9$ and $R^{10}$ independently of one another stand in each case for hydrogen or methyl,
and
in which pyrazolyl can be substituted with 1 or 2 substituents selected independently of one another from the group fluorine, difluoromethyl, trifluoromethyl, 2,2,2-trifluoroethyl, 1,1,2,2,2-pentafluoroethyl, methyl, cyclopropyl, cyclobutyl, cyclopentyl.
$R^5$ stands for hydrogen, methyl or ethyl,
$R^6$ stands for $(C_1\text{-}C_6)$-alkyl, oxetanyl, azetidinyl, tetrahydrofuranyl, pyrrolidinyl, tetrahydropyranyl, piperidinyl, piperazinyl, morpholinyl, phenyl, pyrazolyl, oxazolyl, thiazolyl, triazolyl, oxadiazolyl, thiadiazolyl, pyridyl or pyrimidinyl,
in which $(C_1\text{-}C_6)$-alkyl is substituted with 1 or 2 substituents selected independently of one another from the group fluorine, difluoromethyl, trifluoromethyl cyclopropyl, cyclobutyl, cyclopentyl, trifluoromethoxy, —$(C=O)_p$—$OR^9$, —$(C=O)_p$—$NR^9R^{10}$, tetrahydrofuranyl, pyrrolidinyl, tetrahydropyranyl, phenyl, furanyl, pyrazolyl, imidazolyl, triazolyl and pyridyl,
in which
p denotes the number 0 or 1,
$R^9$ and $R^{10}$ each stand, independently of one another, for hydrogen, methyl, ethyl, trifluoromethyl, 2,2,2-trifluoroethyl, 1,1,2,2,2-pentafluoroethyl, cyclopropyl or cyclobutyl,
and
in which cyclopropyl, cyclobutyl, cyclopentyl, tetrahydrofuranyl, pyrrolidinyl, tetrahydropyranyl, phenyl, furanyl, pyrazolyl, imidazolyl, triazolyl and pyridyl for their part can be substituted with 1 or 2 substituents selected independently of one another from the group fluorine, chlorine, cyano, difluoromethyl, trifluoromethyl, methyl, ethyl, oxo and hydroxy,
in which oxetanyl, azetidinyl, tetrahydrofuranyl, pyrrolidinyl, tetrahydropyranyl, piperidinyl, piperazinyl, morpholinyl, phenyl, pyrazolyl, oxazolyl, thiazolyl, triazolyl, oxadiazolyl, thiadiazolyl, pyridyl and pyrimidinyl can be substituted with 1 or 2 substituents selected independently of one another from the group fluorine, difluoromethyl, trifluoromethyl, methyl, ethyl, oxo, azetidinyl and pyrrolidinyl,
or
$R^5$ and $R^6$ form, together with the nitrogen atom to which they are bound, an azetidinyl, pyrrolidinyl, imidazolidinyl, piperidinyl, dihydropiperidinyl, piperazinyl, morpholinyl, pyrazolyl or imidazolyl ring,
in which the azetidinyl, pyrrolidinyl, imidazolidinyl, piperidinyl, dihydropiperidinyl, piperazinyl, morpholinyl, pyrazolyl and imidazolyl ring can be substituted with 1 or 2 substituents selected independently of one another from the group fluorine, cyano, difluoromethyl, trifluoromethyl, 2,2,2-trifluoroethyl, 1,1,2,2,2-pentafluoroethyl, methyl, ethyl, 1-hydroxyethyl, cyclopropyl, cyclobutyl, cyclopentyl, hydroxy, oxo, methoxy, ethoxy, difluoromethoxy and trifluoromethoxy, $R^2$ stands for 2-fluorophenyl, 2,3-difluorophenyl or 3-fluoropyrid-2-yl, and their salts, solvates and solvates of the salts.

In the context of the present invention, compounds of formula (I) are also preferred in which L stands for a group $\#^1$—$CR^{7A}R^{7B}$—$(CR^{8A}R^{8B})_m$—$\#^2$,
  wherein
  $\#^1$ stands for the point of attachment to the carbonyl group,
  $\#^2$ stands for the point of attachment to the pyrimidine ring,
  m stands for a number 0, 1 or 2,
  $R^{7A}$ stands for hydrogen, fluorine, $(C_1-C_4)$-alkyl, hydroxyl or amino,
    in which $(C_1-C_4)$-alkyl can be substituted with 1 to 3 substituents selected independently of one another from the group fluorine, trifluoromethyl, hydroxy, hydroxycarbonyl, $(C_1-C_4)$-alkoxycarbonyl and amino,
  $R^{7B}$ stands for hydrogen, fluorine, $(C_1-C_4)$-alkyl, trifluoromethyl, $(C_1-C_4)$-alkoxycarbonylamino or phenyl,
    in which $(C_1-C_4)$-alkyl can be substituted with 1 to 3 substituents selected independently of one another from the group fluorine, trifluoromethyl, hydroxy, hydroxycarbonyl, $(C_1-C_4)$-alkoxycarbonyl and amino,
  or
  $R^{7A}$ and $R^{7B}$ together with the carbon atom to which they are bound, form a $(C_2-C_4)$-alkenyl group, an oxo group, a 3- to 6-membered carbocycle or a 4- to 7-membered heterocycle,
    in which the 3- to 6-membered carbocycle and the 4- to 7-membered heterocycle can be substituted with 1 or 2 substituents selected independently of one another from the group fluorine and $(C_1-C_4)$-alkyl,
  $R^{8A}$ stands for hydrogen, fluorine, $(C_1-C_4)$-alkyl or hydroxy,
  $R^{8B}$ stands for hydrogen, fluorine, $(C_1-C_4)$-alkyl or trifluoromethyl, the ring Q stands for 8- or 9-membered heteroaryl, $R^3$ stands for —$OR^4$ or —$NR^5R^6$,
  wherein
  $R^4$ stands for hydrogen, $(C_1-C_6)$-alkyl, $(C_3-C_7)$-cycloalkyl, 4- to 7-membered heterocyclyl or 5- or 6-membered heteroaryl,
    in which $(C_1-C_6)$-alkyl, $(C_3-C_7)$-cycloalkyl, 4- to 7-membered heterocyclyl and 5- or 6-membered heteroaryl can be substituted with 1 to 3 substituents selected independently of one another from the group fluorine, difluoromethyl, trifluoromethyl, $(C_3-C_6)$-cycloalkyl, difluoromethoxy, trifluoromethoxy, —(C=O)$_p$—$OR^9$, —C(=O)$_p$—$NR^9R^{10}$, —$NR^9$—(C=O)—$R^{10}$, —$NR^9$—(C=O)—$OR^{10}$, —$NR^9$—(C=O)—$NR^{10}R^{11}$, —$NR^9$—$SO_2$—$R^{10}$, —$S(O)_q$—$R^{12}$ and —$SO_2$—$NR^9R^{10}$,
    in which
    p denotes the number 0 or 1,
    q denotes the number 0, 1 or 2,
    $R^9$, $R^{10}$ and $R^{11}$ each stand, independently of one another, for hydrogen, $(C_1-C_6)$-alkyl or $(C_3-C_8)$-cycloalkyl,
      in which $(C_1-C_6)$-alkyl for its part can be substituted with 1 or 2 substituents selected independently of one another from the group fluorine, difluoromethyl, trifluoromethyl, hydroxy, $(C_1-C_6)$-alkoxy, difluoromethoxy, trifluoromethoxy, $(C_1-C_6)$-alkoxycarbonyl, amino, mono-$(C_1-C_6)$-alkylamino, di$(C_1-C_6)$-alkylamino and 4- to 7-membered heterocyclyl,
    or
    $R^9$ and $R^{10}$ form, together with the respective atom(s) to which they are bound, a 4- to 7-membered heterocycle,
      in which for its part the 4- to 7-membered heterocycle can be substituted with 1 or 2 substituents selected independently of one another from the group fluorine, trifluoromethyl, $(C_1-C_6)$-alkyl, hydroxy, oxo, $(C_1-C_6)$-alkoxy, trifluoromethoxy, $(C_1-C_6)$-alkoxycarbonyl, amino, mono-$(C_1-C_6)$-alkylamino and di$(C_1-C_6)$-alkylamino,
    or
    $R^{10}$ and $R^{11}$ form, together with the respective atom(s) to which they are bound, a 4- to 7-membered heterocycle,
      in which for its part the 4- to 7-membered heterocycle can be substituted with 1 or 2 substituents selected independently of one another from the group fluorine, trifluoromethyl, $(C_1-C_6)$-alkyl, hydroxy, oxo, $(C_1-C_6)$-alkoxy, trifluoromethoxy, $(C_1-C_6)$-alkoxycarbonyl, amino, mono-$(C_1-C_6)$-alkylamino and di$(C_1-C_6)$-alkylamino,
    and in which
    $R^{12}$ stands for $(C_1-C_6)$-alkyl or $(C_3-C_7)$-cycloalkyl, $R^5$ stands for hydrogen or $(C_1-C_4)$-alkyl, $R^6$ stands for $(C_1-C_6)$-alkyl, $(C_3-C_7)$-cycloalkyl, 4- to 7-membered heterocyclyl or 5- or 6-membered heteroaryl,
  in which $(C_1-C_6)$-alkyl, $(C_3-C_7)$-cycloalkyl, 4- to 7-membered heterocyclyl and 5- or 6-membered heteroaryl can be substituted with 1 to 3 substituents selected independently of one another from the group fluorine, difluoromethyl, trifluoromethyl, difluoromethoxy, trifluoromethoxy, —(C=O)$_p$—$OR^9$, —C(=O)$_p$—$NR^9R^{10}$, —$NR^9$—(C=O)—$R^{10}$, —$NR^9$—(C=O)—$OR^{10}$, —$NR^9$—(C=O)—$NR^{10}R^{11}$, —$NR^9$—$SO_2$—$R^{10}$, —$S(O)_q$—$R^{12}$ and —$SO_2$—$NR^9R^{10}$,
  in which
  p denotes the number 0 or 1,
  q denotes the number 0, 1 or 2,
  $R^9$, $R^{10}$ and $R^{11}$ each stand, independently of one another, for hydrogen, $(C_1-C_6)$-alkyl or $(C_3-C_8)$-cycloalkyl,
  or
  $R^9$ and $R^{10}$ form, together with the respective atom(s) to which they are bound, a 4- to 7-membered heterocycle,
    in which for its part the 4- to 7-membered heterocycle can be substituted with 1 or 2 substituents selected independently of one another from the group cyano, trifluoromethyl, $(C_1-C_6)$-alkyl, hydroxy, oxo, $(C_1-C_6)$-alkoxy, trifluoromethoxy, $(C_1-C_6)$-alkoxycarbonyl, amino, mono-$(C_1-C_6)$-alkylamino and di$(C_1-C_6)$-alkylamino,
  or
  $R^{10}$ and $R^{11}$ form, together with the respective atom(s) to which they are bound, a 4- to 7-membered heterocycle,
    in which for its part the 4- to 7-membered heterocycle can be substituted with 1 or 2 substituents selected independently of one another from the group cyano, trifluoromethyl, $(C_1-C_6)$-alkyl, hydroxy, oxo, $(C_1-C_6)$-alkoxy, trifluoromethoxy, $(C_1-C_6)$-alkoxycarbonyl, amino, mono-$(C_1-C_6)$-alkylamino and di$(C_1-C_6)$-alkylamino, and in which $R^{12}$ stands for $(C_1-C_6)$-alkyl or $(C_3-C_7)$-cycloalkyl, or $R^5$ and $R^6$ form, together with the nitrogen atom to which they are bound, a 4- to 7-membered heterocycle, in which the 4- to 7-membered heterocycle can be substituted with 1 or 2 substituents selected independently of one another from the group fluorine, trifluoromethyl, $(C_1-C_6)$-alkyl, hydroxy, oxo, $(C_1-C_6)$-alkoxy, trifluoromethoxy, $(C_1-C_6)$-alkoxycarbonyl, amino, mono-$(C_1-C_6)$-alkylamino and di$(C_1-C_6)$-alkylamino, $R^1$ stands for fluorine, chlorine or methyl, n stands for a number 0, 1 or 2, $R^2$ stands for $(C_1-C_6)$-alkyl, $(C_3-C_8)$-cycloalkyl, phenyl or 5- or 6-membered heteroaryl, wherein $(C_1-C_6)$-alkyl is substituted with a trifluoromethyl substituent, wherein $(C_1-C_6)$-alkyl can be substituted with 1 to 3 fluorine substituents, wherein phenyl is substituted with 1 to 3 fluorine substituents, and wherein 5- and 6-membered heteroaryl can be substituted with 1 or 2 substituents selected independently of one another from the group fluorine and methyl, and their N-oxides, salts, solvates, salts of the N-oxides and solvates of the N-oxides and salts.

In the context of the present invention, compounds of formula (I) are also preferred in which L stands for a group $\#^1$—$CR^{7A}R^{7B}$—$(CR^{8A}R^{8B})_m$—$\#^2$, wherein $\#^1$ stands for the point of attachment to the carbonyl group, $\#^2$ stands for the point of attachment to the pyrimidine ring, m stands for a number 0 or 1, $R^{7A}$ stands for hydrogen, fluorine, methyl, ethyl or hydroxy, $R^{7B}$ stands for hydrogen, fluorine, methyl, ethyl, trifluoromethyl, methoxycarbonylamino or phenyl, in which methyl and ethyl can be substituted with 1 to 3 substituents selected independently of one another from the group fluorine, trifluoromethyl and hydroxy, or $R^{7A}$ and $R^{7B}$ together with the carbon atom to which they are bound, form a cyclopropyl, cyclobutyl, cyclopentyl, azetidinyl, pyrrolidinyl, tetrahydrofuranyl, piperidinyl or tetrahydropyranyl ring form, in which the cyclopropyl, cyclobutyl, cyclopentyl, azetidinyl, pyrrolidinyl, tetrahydrofuranyl, piperidinyl and tetrahydropyranyl ring can be substituted with 1 or 2 substituents selected independently of one another from the group fluorine and methyl, $R^{7A}$ stands for hydrogen, fluorine, methyl, ethyl or hydroxy, $R^{8B}$ stands for hydrogen, fluorine, methyl, ethyl or trifluoromethyl, the ring Q stands for a group of formula

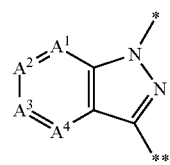

(a-1)

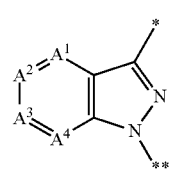

(b-1)

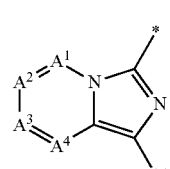

(c-1)

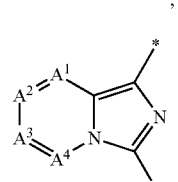

(d-1)

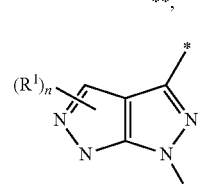

(e-1)

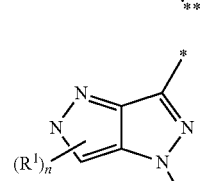

(f-1)

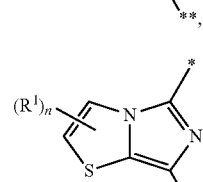

(g-1)

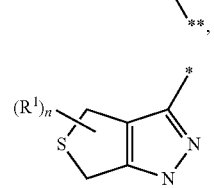

(h-1)

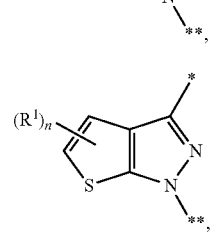

(i-1)

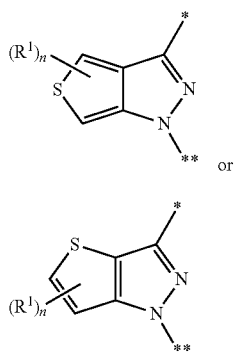

(j-1)

(k-1)

wherein
* stands for the point of attachment to —CH$_2$—R$^2$,
** stands for the point of attachment to the pyrimidine,
R$^1$ stands for fluorine, chlorine or methyl,
n stands for a number 0, 1 or 2,
A$^1$, A$^2$, A$^3$ and A$^4$ independently of one another stand in each case for N, CH or CR$^1$,
with the proviso that at most two of the groups A$^1$, A$^2$, A$^3$ and A$^4$ stand for N,
R$^3$ stands for —OR$^4$ or —NR$^5$R$^6$,
  wherein
  R$^4$ stands for hydrogen, (C$_1$-C$_6$)-alkyl or (C$_3$-C$_7$)-cycloalkyl,
    in which (C$_1$-C$_6$)-alkyl can be substituted with 1 or 2 substituents selected independently of one another from the group fluorine, difluoromethyl, trifluoromethyl, difluoromethoxy, trifluoromethoxy, —(C=O)$_p$—OR$^9$ and —C(=O)$_p$—NR$^9$R$^{10}$,
    in which
    p denotes the number 0,
    R$^9$ and R$^{10}$ each stand, independently of one another, for hydrogen, methyl or ethyl,
    or
    R$^9$ and R$^{10}$ form, together with the nitrogen atom to which they are bound, an azetidinyl, pyrrolidinyl, piperidinyl, piperazinyl or morpholinyl ring,
      in which the azetidinyl, pyrrolidinyl, piperidinyl, piperazinyl and morpholinyl ring for its part can be substituted with 1 or 2 substituents selected independently of one another from the group fluorine, trifluoromethyl, methyl, ethyl, hydroxy, oxo, methoxy, ethoxy, amino, methylamino, ethylamino, dimethylamino and diethylamino,
  R$^5$ stands for hydrogen or methyl,
  R$^6$ stands for (C$_1$-C$_6$)-alkyl or (C$_3$-C$_7$)-cycloalkyl,
    in which (C$_1$-C$_6$)-alkyl can be substituted with 1 or 2 substituents selected independently of one another from the group fluorine, difluoromethyl, trifluoromethyl, difluoromethoxy, trifluoromethoxy, —(C=O)$_p$—OR$^9$ and —C(=O)$_p$—NR$^9$R$^{10}$,
    in which
    p denotes the number 0,
    R$^9$ and R$^{10}$ each stand, independently of one another, for hydrogen, methyl or ethyl,
    or
    R$^9$ and R$^{10}$ form, together with the nitrogen atom to which they are bound, an azetidinyl, pyrrolidinyl, piperidinyl, piperazinyl or morpholinyl ring,
      in which the azetidinyl, pyrrolidinyl, piperidinyl, piperazinyl and morpholinyl ring for its part can be substituted with 1 or 2 substituents selected independently of one another from the group fluorine, trifluoromethyl, methyl, ethyl, hydroxy, oxo, methoxy, ethoxy, amino, methylamino, ethylamino, dimethylamino and diethylamino,
    or
  R$^5$ and R$^6$ form, together with the nitrogen atom to which they are bound, an azetidinyl, pyrrolidinyl, piperidinyl, piperazinyl or morpholinyl ring,
    in which the azetidinyl, pyrrolidinyl, piperidinyl, piperazinyl and morpholinyl ring for its part can be substituted with 1 or 2 substituents selected independently of one another from the group fluorine, trifluoromethyl, methyl, ethyl, hydroxy, oxo, methoxy, ethoxy, amino, methylamino, ethylamino, dimethylamino and diethylamino,
R$^2$ stands for trifluoromethyl, 2,2,2-trifluoroethyl, 3,3,3-trifluoroprop-1-yl, 2,2,3,3,3-pentafluoroprop-1-yl, cyclopropyl, cyclobutyl, cyclopentyl, cyclohexyl, phenyl, pyridyl, pyrimidinyl, pyrazinyl or pyridazinyl,
  wherein phenyl is substituted with 1 to 3 fluorine substituents,
  and
  wherein pyridyl, pyrimidinyl, pyrazinyl and pyridazinyl can be substituted with 1 or 2 fluorine substituents.
and their salts, solvates and solvates of the salts.

In the context of the present invention, compounds of formula (I) are also especially preferred in which
L stands for a group #$^1$—CR$^{7A}$R$^{7B}$—(CR$^{8A}$R$^{8B}$)$_m$—#$^2$,
  wherein
  #$^1$ stands for the point of attachment to the carbonyl group,
  #$^2$ stands for the point of attachment to the pyrimidine ring,
  m stands for a number 0,
  R$^{7A}$ stands for hydrogen, fluorine, methyl or hydroxy,
  R$^{7B}$ stands for hydrogen, fluorine, methyl or trifluoromethyl,
  or
  R$^{7A}$ and R$^{7B}$ together with the carbon atom to which they are bound, form a cyclopropyl or cyclobutyl ring,
    in which the cyclopropyl and the cyclobutyl ring can be substituted with 1 or 2 substituents selected independently of one another from the group fluorine and methyl,
the ring Q stands for a group of formula

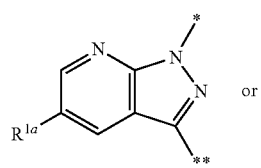

(a-1a)

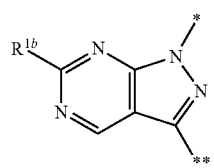

(a-1b)

wherein
* stands for the point of attachment to —CH$_2$—R$^2$,
** stands for the point of attachment to the pyrimidine, $R^{1a}$ stands for hydrogen or fluorine,
$R^{1b}$ stands for hydrogen or methyl,
$R^3$ stands for —$OR^4$ or —$NR^5R^6$,
  wherein
  $R^4$ stands for hydrogen or $(C_1-C_6)$-alkyl,
    in which $(C_1-C_6)$-alkyl can be substituted with 1 or 2 substituents selected independently of one another from the group fluorine, difluoromethyl, trifluoromethyl, difluoromethoxy, trifluoromethoxy, —$(C=O)_p$—$OR^9$ and —$C(=O)_p$—$NR^9R^{10}$,
    in which
    p denotes the number 0,
    $R^9$ and $R^{10}$ independently of one another in each case stand for hydrogen,
  $R^5$ stands for hydrogen,
  $R^6$ stands for $(C_1-C_6)$-alkyl,
    in which $(C_1-C_6)$-alkyl is substituted with 1 or 2 substituents selected independently of one another from the group fluorine, difluoromethyl, trifluoromethyl, difluoromethoxy, trifluoromethoxy, —$(C=O)_p$—$OR^9$ and —$C(=O)_p$—$NR^9R^{10}$,
    in which
    p denotes the number 0,
    $R^9$ and $R^{10}$ independently of one another in each case stand for hydrogen,
$R^2$ stands for 2,2,3,3,3-pentafluoroprop-1-yl, 2-fluorophenyl or 2,3,6-trifluorophenyl,
and their salts, solvates and solvates of the salts.

In the context of the present invention, compounds of formula (I) are also preferred in which
$R^3$ stands for —$OR^4$ or —$NR^5R^6$,
  wherein
  $R^4$ stands for $(C_1-C_6)$-alkyl or $(C_3-C_7)$-cycloalkyl,
    in which $(C_1-C_6)$-alkyl can be substituted with 1 or 2 substituents selected independently of one another from the group fluorine, difluoromethyl, trifluoromethyl, difluoromethoxy, trifluoromethoxy, —$(C=O)_p$—$OR^9$ and —$C(=O)_p$—$NR^9R^{10}$,
    in which
    p denotes the number 0,
    $R^9$ and $R^{10}$ each stand, independently of one another, for hydrogen, methyl or ethyl,
    or
    $R^9$ and $R^{10}$ form, together with the nitrogen atom to which they are bound, an azetidinyl, pyrrolidinyl, piperidinyl, piperazinyl or morpholinyl ring,
      in which the azetidinyl, pyrrolidinyl, piperidinyl, piperazinyl and morpholinyl ring for its part can be substituted with 1 or 2 substituents selected independently of one another from the group fluorine, trifluoromethyl, methyl, ethyl, hydroxy, oxo, methoxy, ethoxy, amino, methylamino, ethylamino, dimethylamino and diethylamino,
  $R^5$ stands for hydrogen or methyl,
  $R^6$ stands for $(C_1-C_6)$-alkyl or $(C_3-C_7)$-cycloalkyl,
    in which $(C_1-C_6)$-alkyl can be substituted with 1 or 2 substituents selected independently of one another from the group fluorine, difluoromethyl, trifluoromethyl, difluoromethoxy, trifluoromethoxy, —$(C=O)_p$—$OR^9$ and —$C(=O)_p$—$NR^9R^{10}$,
    in which
    p denotes the number 0,
    $R^9$ and $R^{10}$ each stand, independently of one another, for hydrogen, methyl or ethyl,
    or
    $R^9$ and $R^{10}$ form, together with the nitrogen atom to which they are bound, an azetidinyl, pyrrolidinyl, piperidinyl, piperazinyl or morpholinyl ring,
      in which the azetidinyl, pyrrolidinyl, piperidinyl, piperazinyl and morpholinyl ring for its part can be substituted with 1 or 2 substituents selected independently of one another from the group fluorine, trifluoromethyl, methyl, ethyl, hydroxy, oxo, methoxy, ethoxy, amino, methylamino, ethylamino, dimethylamino and diethylamino,
  or
  $R^5$ and $R^6$ form, together with the nitrogen atom to which they are bound, an azetidinyl, pyrrolidinyl, piperidinyl, piperazinyl or morpholinyl ring,
    in which the azetidinyl, pyrrolidinyl, piperidinyl, piperazinyl and morpholinyl ring for its part can be substituted with 1 or 2 substituents selected independently of one another from the group fluorine, trifluoromethyl, methyl, ethyl, hydroxy, oxo, methoxy, ethoxy, amino, methylamino, ethylamino, dimethylamino and diethylamino,
n, L, Q, $R^1$ and $R^2$ have the respective meanings given above,
and their salts, solvates and solvates of the salts.

In the context of the present invention, compounds of formula (I) are also preferred in which
$R^3$ stands for —$NR^5R^6$,
  wherein
  $R^5$ stands for hydrogen or methyl,
  $R^6$ stands for $(C_1-C_6)$-alkyl or $(C_3-C_7)$-cycloalkyl,
    in which $(C_1-C_6)$-alkyl can be substituted with 1 or 2 substituents selected independently of one another from the group fluorine, difluoromethyl, trifluoromethyl, difluoromethoxy, trifluoromethoxy, —$(C=O)_p$—$OR^9$ and —$C(=O)_p$—$NR^9R^{10}$,
    in which
    p denotes the number 0,
    $R^9$ and $R^{10}$ each stand, independently of one another, for hydrogen, methyl or ethyl,
    or
    $R^9$ and $R^{10}$ form, together with the nitrogen atom to which they are bound, an azetidinyl, pyrrolidinyl, piperidinyl, piperazinyl or morpholinyl ring,
      in which the azetidinyl, pyrrolidinyl, piperidinyl, piperazinyl and morpholinyl ring for its part can be substituted with 1 or 2 substituents selected independently of one another from the group fluorine, trifluoromethyl, methyl, ethyl, hydroxy, oxo, methoxy, ethoxy, amino, methylamino, ethylamino, dimethylamino and diethylamino,
  or
  $R^5$ and $R^6$ form, together with the nitrogen atom to which they are bound, an azetidinyl, pyrrolidinyl, piperidinyl, piperazinyl or morpholinyl ring,
    in which the azetidinyl, pyrrolidinyl, piperidinyl, piperazinyl and morpholinyl ring for its part can be substituted with 1 or 2 substituents selected independently of one another from the group fluorine, trifluoromethyl, methyl, ethyl, hydroxy, oxo, methoxy, ethoxy, amino, methylamino, ethylamino, dimethylamino and diethylamino,
n, L, Q, $R^1$ and $R^2$ have the respective meanings given above,
and their salts, solvates and solvates of the salts.

In the context of the present invention, compounds of formula (I) are also preferred in which $R^3$ stands for —$NR^5R^6$, wherein $R^5$ stands for hydrogen or methyl, $R^6$ stands for $(C_1-C_6)$-alkyl or $(C_3-C_7)$-cycloalkyl, in which $(C_1-C_6)$-alkyl and $(C_3-C_7)$-cycloalkyl are substituted with 1 or 2 substituents selected independently of one another from the group fluorine, difluoromethyl, trifluoromethyl, difluoromethoxy, trifluoromethoxy, —$(C=O)_p$—$OR^9$ and —$C(=O)_p$—$NR^9R^{10}$, in which p denotes the number 0, $R^9$ and $R^{10}$ each stand, independently of one another, for hydrogen, methyl or ethyl, or $R^9$ and $R^{10}$ form, together with the nitrogen atom to which they are bound, an azetidinyl, pyrrolidinyl, piperidinyl, piperazinyl or morpholinyl ring, in which the azetidinyl, pyrrolidinyl, piperidinyl, piperazinyl and morpholinyl ring for its part can be substituted with 1 or 2 substituents selected independently of one another from the group fluorine, trifluoromethyl, methyl, ethyl, hydroxy, oxo, methoxy, ethoxy, amino, methylamino, ethylamino, dimethylamino and diethylamino, or $R^5$ and $R^6$ form, together with the nitrogen atom to which they are bound, an azetidinyl, pyrrolidinyl, piperidinyl, piperazinyl or morpholinyl ring, in which the azetidinyl, pyrrolidinyl, piperidinyl, piperazinyl and morpholinyl ring for its part can be substituted with 1 or 2 substituents selected independently of one another from the group fluorine, trifluoromethyl, methyl, ethyl, hydroxy, oxo, methoxy, ethoxy, amino, methylamino, ethylamino, dimethylamino and diethylamino, n, L, Q, $R^1$ and $R^2$ have the respective meanings given above, and their salts, solvates and solvates of the salts.

In the context of the present invention, compounds of formula (I) are also preferred in which the ring Q stands for a group of formula

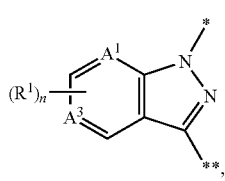

(a-1)

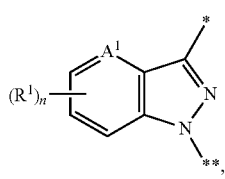

(b-1)

-continued

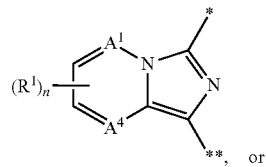

(c-1)

or

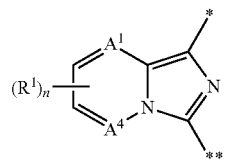

(d-1)

wherein

* stands for the point of attachment to —$CH_2$—$R^2$,

** stands for the point of attachment to the pyrimidine, $A^1$, $A^3$ and $A^4$ independently of one another stand in each case for N, CH or $CR^1$, in which $R^1$ stands for fluorine, chlorine or methyl, n stands for a number 0, 1 or 2, with the proviso that at most two of the groups $A^1$, $A^3$ and $A^4$ stand for N, $R^3$ stands for —$NR^5R^6$, wherein $R^5$ stands for hydrogen or methyl, $R^6$ stands for $(C_1-C_6)$-alkyl, in which $(C_1-C_6)$-alkyl is substituted with 1 or 2 substituents selected independently of one another from the group fluorine, difluoromethyl and trifluoromethyl, L and $R^2$ have the respective meanings given above, and their salts, solvates and solvates of the salts.

In the context of the present invention, compounds of formula (I) are also preferred in which the ring Q stands for a group of formula

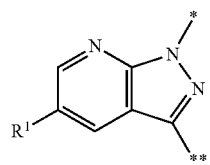

(a-1)

wherein

* stands for the point of attachment to —$CH_2$—$R^2$,

** stands for the point of attachment to the pyrimidine, $R^1$ stands for hydrogen or fluorine, $R^3$ stands for —$NR^5R^6$, wherein $R^5$ stands for hydrogen or methyl, $R^6$ stands for $(C_1-C_6)$-alkyl, in which $(C_1-C_6)$-alkyl is substituted with 1 or 2 substituents selected independently of one another from the group fluorine, difluoromethyl and trifluoromethyl, stands for 2-fluorophenyl or 3-fluoropyrid-2-yl, and L and $R^2$ have the respective meanings given above, and their salts, solvates and solvates of the salts.

In the context of the present invention, compounds of formula (I) are also preferred in which
$R^3$ stands for —$NR^5R^6$,
wherein
$R^5$ stands for hydrogen or methyl,
$R^6$ stands for ($C_1$-$C_6$)-alkyl,
in which ($C_1$-$C_6$)-alkyl is substituted with 1 or 2 substituents selected independently of one another from the group fluorine, difluoromethyl and trifluoromethyl,
n, L, Q, $R^1$ and $R^2$ have the respective meanings given above, and their salts, solvates and solvates of the salts.

In the context of the present invention, compounds of formula (I) are also preferred in which
$R^3$ stands for —$NR^5R^6$,
wherein
$R^5$ stands for hydrogen or methyl,
$R^6$ stands for ($C_1$-$C_6$)-alkyl,
in which ($C_1$-$C_6$)-alkyl is substituted with 1 or 2 substituents selected independently of one another from the group fluorine, difluoromethyl, trifluoromethyl and —(C=O)$_p$—$OR^9$,
in which
p denotes the number 0,
$R^9$ stands for hydrogen,
n, L, Q, $R^1$ and $R^2$ have the respective meanings given above, and their salts, solvates and solvates of the salts.

In the context of the present invention, compounds of formula (I) are also preferred in which
L stands for a group $\#^1$—$CR^{7A}R^{7B}$—$(CR^{8A}R^{8B})_m$—$\#^2$,
wherein
$\#^1$ stands for the point of attachment to the carbonyl group,
$\#^2$ stands for the point of attachment to the pyrimidine ring,
m stands for a number 0,
$R^{7A}$ stands for methyl,
$R^{7B}$ stands for methyl,
$R^3$ stands for —$NR^5R^6$,
wherein
$R^5$ stands for hydrogen or methyl,
$R^6$ stands for ($C_1$-$C_6$)-alkyl,
in which ($C_1$-$C_6$)-alkyl is substituted with 1 or 2 substituents selected independently of one another from the group fluorine, difluoromethyl, trifluoromethyl and —(C=O)$_p$—$OR^9$,
in which
p denotes the number 0,
$R^9$ stands for hydrogen,
n, Q, $R^1$ and $R^2$ have the respective meanings given above, and their salts, solvates and solvates of the salts.

In the context of the present invention, compounds of formula (I) are also preferred in which
L stands for a group $\#^1$—$CR^{7A}R^{7B}$—$(CR^{8A}R^{8B})_m$—$\#^2$,
wherein
$\#^1$ stands for the point of attachment to the carbonyl group,
$\#^2$ stands for the point of attachment to the pyrimidine ring,
m stands for a number 0,
$R^{7A}$ stands for hydrogen, fluorine, methyl or hydroxy,
$R^{7B}$ stands for hydrogen, fluorine, methyl or trifluoromethyl,
$R^3$ stands for —$NR^5R^6$,
wherein
$R^5$ stands for hydrogen or methyl,
$R^6$ stands for ($C_1$-$C_6$)-alkyl,
in which ($C_1$-$C_6$)-alkyl is substituted with 1 or 2 substituents selected independently of one another from the group fluorine, difluoromethyl, trifluoromethyl and —(C=O)$_p$—$OR^9$,
in which
p denotes the number 0,
$R^9$ stands for hydrogen,
n, Q, $R^1$ and $R^2$ have the respective meanings given above, and their salts, solvates and solvates of the salts.

In the context of the present invention, compounds of formula (I) are also preferred in which
$R^3$ stands for —$OR^4$,
wherein
$R^4$ stands for hydrogen, ($C_1$-$C_6$)-alkyl or ($C_3$-$C_7$)-cycloalkyl,
in which ($C_1$-$C_6$)-alkyl can be substituted with 1 or 2 substituents selected independently of one another from the group fluorine, difluoromethyl, trifluoromethyl, difluoromethoxy, trifluoromethoxy, —(C=O)$_p$—$OR^9$ and —C(=O)$_p$—$NR^9R^{10}$,
in which
p denotes the number 0,
$R^9$ and $R^{10}$ each stand, independently of one another, for hydrogen, methyl or ethyl,
or
$R^9$ and $R^{10}$ form, together with the nitrogen atom to which they are bound, an azetidinyl, pyrrolidinyl, piperidinyl, piperazinyl or morpholinyl ring,
in which the azetidinyl, pyrrolidinyl, piperidinyl, piperazinyl and morpholinyl ring for its part can be substituted with 1 or 2 substituents selected independently of one another from the group fluorine, trifluoromethyl, methyl, ethyl, hydroxy, oxo, methoxy, ethoxy, amino, methylamino, ethylamino, dimethylamino and diethylamino,
n, L, Q, $R^1$ and $R^2$ have the respective meanings given above, and their salts, solvates and solvates of the salts.

In the context of the present invention, compounds of formula (I) are also preferred in which
$R^3$ stands for —$OR^4$,
wherein
$R^4$ stands for hydrogen,
n, L, Q, $R^1$ and $R^2$ have the respective meanings given above, and their salts, solvates and solvates of the salts.

In the context of the present invention, compounds of formula (I) are also preferred in which
the ring Q stands for a group of formula

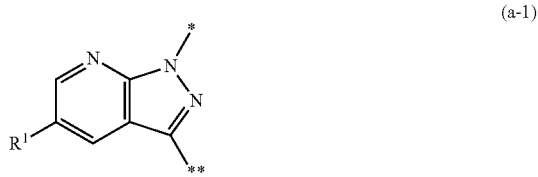

(a-1)

wherein
* stands for the point of attachment to —$CH_2$—$R^2$,
** stands for the point of attachment to the pyrimidine,
$R^1$ stands for hydrogen or fluorine,
$R^3$ stands for —$OR^4$,
wherein
$R^4$ stands for hydrogen,
n, L, Q, $R^1$ and $R^2$ have the respective meanings given above, and their salts, solvates and solvates of the salts.

In the context of the present invention, compounds of formula (I) are also preferred in which $R^1$ stands for H, and their salts, solvates and solvates of the salts.

In the context of the present invention, compounds of formula (I) are also preferred in which $R^1$ stands for fluoro, and their salts, solvates and solvates of the salts.

In the context of the present invention, compounds of formula (I) are also preferred in which $R^1$ stands for methyl, and their salts, solvates and solvates of the salts.

In the context of the present invention, compounds of formula (I) are also especially preferred in which
$R^2$ stands for 2,2,3,3,3-pentafluoroprop-1-yl, 2-fluorophenyl, 2,3-difluorophenyl, 2,3,6-trifluorophenyl, 3-fluoropyrid-2-yl or pyrimidin-2-yl,
and their salts, solvates and solvates of the salts.

In the context of the present invention, compounds of formula (I) are also especially preferred in which
$R^2$ stands for 2-fluorophenyl or 3-fluoropyrid-2-yl,
and their salts, solvates and solvates of the salts.

In the context of the present invention, compounds of formula (I) are also especially preferred in which
$R^2$ stands for 2-fluorophenyl,
and their salts, solvates and solvates of the salts.

In the context of the present invention, compounds of formula (I) are also especially preferred in which
$R^2$ stands for 3-fluoropyrid-2-yl or pyrimidin-2-yl,
and their salts, solvates and solvates of the salts.

In the context of the present invention, compounds of formula (I) are also preferred in which
L stands for a group $\#^1$—$CR^{7A}R^{7B}$—$(CR^{8A}R^{8B})_m$—$\#^2$,
wherein
$\#^1$ stands for the point of attachment to the carbonyl group,
$\#^2$ stands for the point of attachment to the pyrimidine ring,
m stands for a number 0,
$R^{7A}$ stands for hydrogen, fluorine, methyl or hydroxy,
$R^{7B}$ stands for hydrogen, fluorine, methyl or trifluoromethyl,
or
$R^{7A}$ and $R^{7B}$ together with the carbon atom to which they are bound, form a cyclopropyl or cyclobutyl ring,
in which the cyclopropyl and the cyclobutyl ring can be substituted with 1 or 2 substituents selected independently of one another from the group fluorine and methyl,
n, Q, $R^1$, $R^2$ and $R^3$ have the respective meanings given above,
and their salts, solvates and solvates of the salts.

In the context of the present invention, compounds of formula (I) are also preferred in which
L stands for a group $\#^1$—$CR^{7A}R^{7B}$—$(CR^{8A}R^{8B})_m$—$\#^2$,
wherein
$\#^1$ stands for the point of attachment to the carbonyl group,
$\#^2$ stands for the point of attachment to the pyrimidine ring,
m stands for a number 0,
$R^{7A}$ stands for hydrogen, fluorine, methyl or hydroxy,
$R^{7B}$ stands for hydrogen, fluorine, methyl or trifluoromethyl,
n, Q, $R^1$, $R^2$ and $R^3$ have the respective meanings given above,
and their salts, solvates and solvates of the salts.

In the context of the present invention, compounds of formula (I) are also preferred in which
L stands for a group $\#^1$—$CR^{7A}R^{7B}$—$(CR^{8A}R^{8B})_m$—$\#^2$,
wherein
$\#^1$ stands for the point of attachment to the carbonyl group,
$\#^2$ stands for the point of attachment to the pyrimidine ring,
m stands for a number 0,
$R^{7A}$ stands for methyl,
$R^{7B}$ stands for methyl,
n, Q, $R^1$, $R^2$ and $R^3$ have the respective meanings given above,
and their salts, solvates and solvates of the salts.

In the context of the present invention, compounds of formula (I) are also preferred in which
L stands for a group $\#^1$—$CR^{7A}R^{7B}$—$(CR^{8A}R^{8B})_m$—$\#^2$,
wherein
$\#^1$ stands for the point of attachment to the carbonyl group,
$\#^2$ stands for the point of attachment to the pyrimidine ring,
m stands for a number 0,
$R^{7A}$ stands for methyl,
$R^{7B}$ stands for methyl,
or
$R^{7A}$ and $R^{7B}$ together with the carbon atom to which they are bound, form a tetrahydrofuranyl ring,
n, Q, $R^1$, $R^2$ and $R^3$ have the respective meanings given above,
and their salts, solvates and solvates of the salts.

In the context of the present invention, compounds of formula (I) are also preferred in which
L stands for a group $\#^1$—$CR^{7A}R^{7B}$—$(CR^{8A}R^{8B})_m$—$\#^2$,
wherein
$\#^1$ stands for the point of attachment to the carbonyl group,
$\#^2$ stands for the point of attachment to the pyrimidine ring,
m stands for a number 0,
$R^{7A}$ stands for hydrogen, fluorine, methyl, ethyl, hydroxy or amino,
$R^{7B}$ stands for a group of formula -M-$R^{13}$,
in which
M stands for a bond,
$R^{13}$ stands for —$(C=O)_r$—$NR^{14}R^{15}$, phenyl, thiazolyl, triazolyl, oxadiazolyl, thiadiazolyl or pyrimidinyl,
in which
r denotes the number 1,
$R^{14}$ and $R^{15}$ independently of one another stand in each case for hydrogen or cyclopropyl,
and
in which phenyl, thiazolyl, triazolyl, oxadiazolyl, thiadiazolyl and pyrimidinyl for their part can be substituted with 1 or 2 substituents selected independently of one another from the group fluorine, difluoromethyl, trifluoromethyl, methyl, ethyl, isopropyl, 2,2,2-trifluoroethyl, 1,1,2,2,2-pentafluoroethyl, cyclopropyl, cyclobutyl, cyclopropylmethyl and cyclobutylmethyl,
and their salts, solvates and solvates of the salts.

In the context of the present invention, compounds of formula (I) are also preferred in which
$R^3$ stands for —$NR^5R^6$,
wherein
$R^5$ stands for hydrogen or methyl,
$R^6$ stands for $(C_1$-$C_6)$-alkyl or $(C_3$-$C_7)$-cycloalkyl,
in which $(C_1$-$C_6)$-alkyl can be substituted with 1 or 2 substituents selected independently of one another from the group fluorine, difluoromethyl, trifluoromethyl, difluoromethoxy, trifluoromethoxy, —$(C=O)_p$—$OR^9$ and —$C(=O)_p$—$NR^9R^{10}$,
in which
p denotes the number 0,
$R^9$ and $R^{10}$ each stand, independently of one another, for hydrogen, methyl or ethyl,
or
$R^9$ and $R^{10}$ form, together with the nitrogen atom to which they are bound, an azetidinyl, pyrrolidinyl, piperidinyl, piperazinyl or morpholinyl ring,
in which the azetidinyl, pyrrolidinyl, piperidinyl, piperazinyl and morpholinyl ring for its part can be substituted with 1 or 2 substituents selected independently of one another from the group fluorine, trifluoromethyl, methyl, ethyl, hydroxy, oxo, methoxy, ethoxy, amino, methylamino, ethylamino, dimethylamino and diethylamino, or $R^5$ and $R^6$ form, together with the nitrogen atom to which they are bound, an azetidinyl, pyrrolidinyl, piperidinyl, piperazinyl or morpholinyl ring, in which the azetidinyl, pyrrolidinyl, piperidinyl, piperazinyl and morpholinyl ring for its part can be substituted with 1 or 2 substituents selected independently of one another from the group fluorine, trifluoromethyl, methyl, ethyl, hydroxy, oxo, methoxy, ethoxy, amino, methylamino, ethylamino, dimethylamino and diethylamino, the ring Q stands for a group of formula

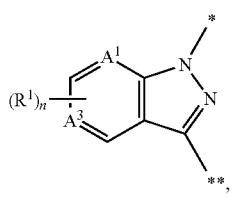
(a-1)

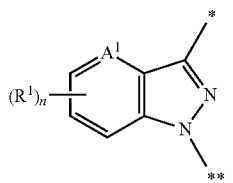
(b-1)

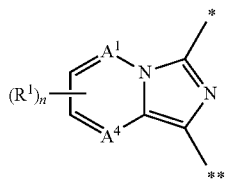
(c-1)

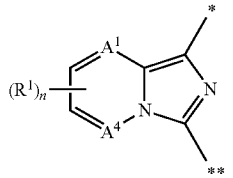
(d-1)

wherein

\* stands for the point of attachment to —$CH_2$—$R^2$,

\*\* stands for the point of attachment to the pyrimidine, $A^1$, $A^3$ and $A^4$ independently of one another stand in each case for N, CH or $CR^1$, in which $R^1$ stands for fluorine, chlorine or methyl, n stands for a number 0, 1 or 2, with the proviso that at most two of the groups $A^1$, $A^3$ and $A^4$ stand for N, and their salts, solvates and solvates of the salts.

In the context of the present invention, compounds of formula (I) are also preferred in which the ring Q stands for a group of formula

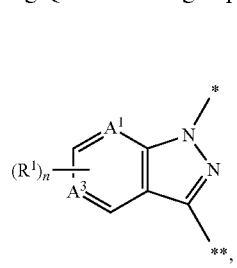
(a-1)

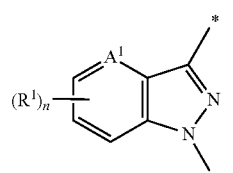
(b-1)

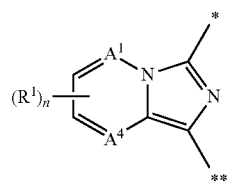
(c-1)

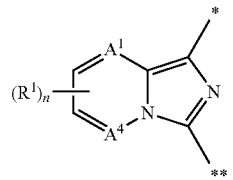
(d-1)

wherein

\* stands for the point of attachment to —$CH_2$—$R^2$,

\*\* stands for the point of attachment to the pyrimidine, $A^1$, $A^3$ and $A^4$ independently of one another stand in each case for N, CH or $CR^1$, in which $R^1$ stands for fluorine, chlorine or methyl, n stands for a number 0, 1 or 2, with the proviso that at most two of the groups $A^1$, $A^3$ and $A^4$ stand for N, $R^3$ stands for —$OR^4$ or —$NR^5R^6$, wherein $R^4$ stands for hydrogen or $(C_1-C_6)$-alkyl, in which $(C_1-C_6)$-alkyl can be substituted with 1 or 2 substituents selected independently of one another from the group fluorine, difluoromethyl, trifluoromethyl, difluoromethoxy, trifluoromethoxy, —$(C=O)_p$—$OR^9$ and —$C(=O)_p$—$NR^9R^{10}$, in which p denotes the number 0, $R^9$ and $R^{10}$ independently of one another in each case stand for hydrogen, $R^5$ stands for hydrogen, $R^6$ stands for $(C_1-C_6)$-alkyl, in which $(C_1-C_6)$-alkyl is substituted with 1 or 2 substituents selected independently of one another from the group fluorine, difluoromethyl, trifluoromethyl, difluoromethoxy, trifluoromethoxy, —$(C=O)_p$—$OR^9$ and —$C(=O)_p$—$NR^9R^{10}$, in which
p denotes the number 0,
R⁹ and R¹⁰ independently of one another in each case stand for hydrogen,
and their salts, solvates and solvates of the salts.

In the context of the present invention, compounds of formula (I) are also preferred in which
the ring Q stands for a group of formula

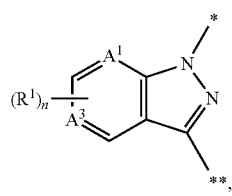
(a-1)

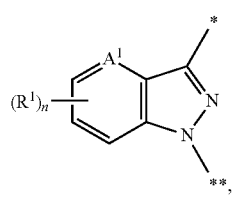
(b-1)

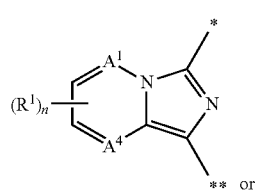
(c-1)

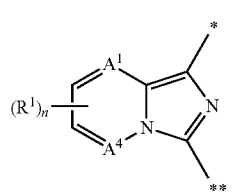
(d-1)

wherein
* stands for the point of attachment to —CH₂—R²,
** stands for the point of attachment to the pyrimidine,
A¹, A³ and A⁴ independently of one another stand in each case for N, CH or CR¹,
  in which
  R¹ stands for fluorine, chlorine or methyl,
  n stands for a number 0, 1 or 2,
with the proviso that at most two of the groups A¹, A³ and A⁴ stand for N,
and their salts, solvates and solvates of the salts.

In the context of the present invention, compounds of formula (I) are also preferred in which
L stands for a group $\#^1$—CR$^{7A}$R$^{7B}$—(CR$^{8A}$R$^{8B}$)$_m$—$\#^2$,
  wherein
  $\#^1$ stands for the point of attachment to the carbonyl group,
  $\#^2$ stands for the point of attachment to the pyrimidine ring,
  m stands for a number 0,
  R$^{7A}$ stands for hydrogen, fluorine, methyl or hydroxy,
  R$^{7B}$ stands for hydrogen, fluorine, trifluoromethyl, 2,2,2-trifluoroethyl or methyl, the ring Q stands for a group of formula

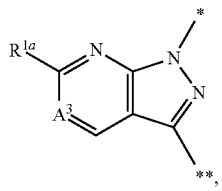
(a-1)

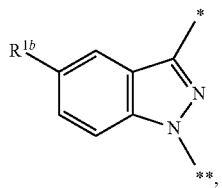
(b-1)

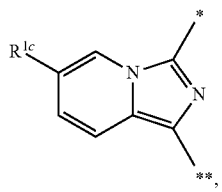
(c-1a)

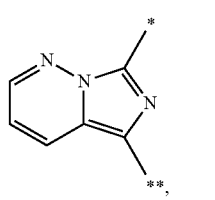
(c-1a)

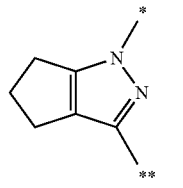
(d-1)

or (1-1)

wherein
* stands for the point of attachment to —CH₂—R²,
** stands for the point of attachment to the pyrimidine,
R$^{1a}$ stands for hydrogen or methyl,
R$^{1b}$ stands for hydrogen or fluorine,
R$^{1c}$ stands for hydrogen or chlorine,
A¹ stands for N or CH,
A³ stands for N, CH or C—F,
R² and R³ have the respective meanings given above,
and their salts, solvates and solvates of the salts.

In the context of the present invention, compounds of formula (I) are also preferred in which
L stands for a group $\#^1$—CR$^{7A}$R$^{7B}$—(CR$^{8A}$R$^{8B}$)$_m$—$\#^2$, wherein
¹ stands for the point of attachment to the carbonyl group,
² stands for the point of attachment to the pyrimidine ring,
m stands for a number 0 or 1,
R⁷ᴬ stands for hydrogen, fluorine, methyl, ethyl, hydroxy or amino,
R⁷ᴮ stands for hydrogen, fluorine, difluoromethyl, trifluoromethyl, methyl, ethyl, methoxycarbonylamino, cyclopropyl, cyclobutyl, cyclopentyl, or a group of formula -M-R¹³,
  in which methyl and ethyl can be substituted with 1 to 3 substituents selected independently of one another from the group fluorine, cyano, trifluoromethyl, cyclopropyl, cyclobutyl, hydroxy, difluoromethoxy, trifluoromethoxy, methoxy, ethoxy, hydroxycarbonyl, methoxycarbonyl, ethoxycarbonyl and amino,
  and in which
  M stands for a bond,
  R¹³ stands for —(C═O)ᵣ—NR¹⁴R¹⁵, phenyl, thiazolyl, triazolyl, oxadiazolyl, thiadiazolyl or pyrimidinyl,
    in which
    r denotes the number 1,
    R¹⁴ and R¹⁵ independently of one another stand in each case for hydrogen or cyclopropyl,
    and
    in which phenyl, thiazolyl, triazolyl, oxadiazolyl, thiadiazolyl and pyrimidinyl for their part can be substituted with 1 or 2 substituents selected independently of one another from the group fluorine, difluoromethyl, trifluoromethyl, methyl, ethyl, isopropyl, 2,2,2-trifluoroethyl, 1,1,2,2,2-pentafluoroethyl, cyclopropyl, cyclobutyl, cyclopropylmethyl and cyclobutylmethyl,
or
R⁷ᴬ and R⁷ᴮ together with the carbon atom to which they are bound, form a cyclopropyl, cyclobutyl, cyclopentyl, azetidinyl, tetrahydrofuranyl, pyrrolidinyl or tetrahydropyranyl ring,
  in which the cyclopropyl, cyclobutyl, cyclopentyl, azetidinyl, tetrahydrofuranyl, pyrrolidinyl and tetrahydropyranyl ring can be substituted with 1 or 2 substituents selected independently of one another from the group fluorine and methyl,
R⁸ᴬ stands for hydrogen, fluorine, methyl or hydroxy,
R⁸ᴮ stands for hydrogen, fluorine, methyl or trifluoromethyl,
the ring Q stands for a group of formula

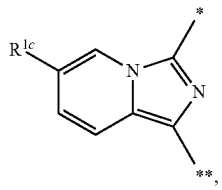

(a-1)

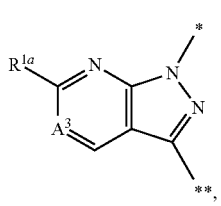

(b-1)

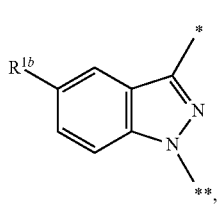

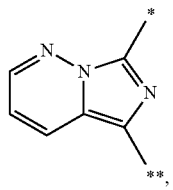

(c-1a)

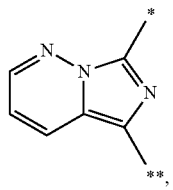

(c-1a)

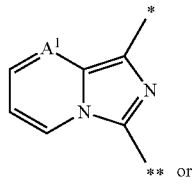

(d-1)

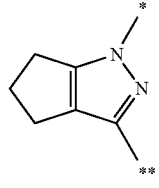

(1-1)

wherein
* stands for the point of attachment to —CH₂—R²,
** stands for the point of attachment to the pyrimidine,
R¹ᵃ stands for hydrogen or methyl,
R¹ᵇ stands for hydrogen or fluorine,
R¹ᶜ stands for hydrogen or chlorine,
A¹ stands for N or CH,
A³ stands for N, CH or C—F,
R² and R³ have the respective meanings given above,
and their salts, solvates and solvates of the salts.

The following compounds of formula (I) are also preferred in the context of the present invention:
2-[1-(2-fluorobenzyl)-1H-pyrazolo[3,4-b]pyridin-3-yl]-4-methoxy-5,5-dimethyl-5,7-dihydro-6H-pyrrolo[2,3-d]pyrimidin-6-one,
2-[5-fluoro-1-(2-fluorobenzyl)-1H-pyrazolo[3,4-b]pyridin-3-yl]-4-[(2-hydroxyethyl)amino]-5,5-dimethyl-5,7-dihydro-6H-pyrrolo[2,3-d]pyrimidin-6-one,
4-[(2-amino-2-methylpropyl)amino]-2-[5-fluoro-1-(2-fluorobenzyl)-1H-pyrazolo[3,4-b]pyridin-3-yl]-5,5-dimethyl-5,7-dihydro-6H-pyrrolo[2,3-d]pyrimidin-6-one,
2-[5-fluoro-1-(2-fluorobenzyl)-1H-pyrazolo[3,4-b]pyridin-3-yl]-4-[(2-hydroxy-2-methylpropyl)amino]-5,5-dimethyl-5,7-dihydro-6H-pyrrolo[2,3-d]pyrimidin-6-one,
2-[5-fluoro-1-(2-fluorobenzyl)-1H-pyrazolo[3,4-b]pyridin-3-yl]-5,5-dimethyl-4-[(3,3,3-trifluoropropyl)amino]-5,7-dihydro-6H-pyrrolo[2,3-d]pyrimidin-6-one,
4-[(2,2-difluoroethyl)amino]-2-[5-fluoro-1-(2-fluorobenzyl)-1H-pyrazolo[3,4-b]pyridin-3-yl]-5,5-dimethyl-5,7-dihydro-6H-pyrrolo[2,3-d]pyrimidin-6-one,
4-(3-fluoroazetidin-1-yl)-2-[5-fluoro-1-(2-fluorobenzyl)-1H-pyrazolo[3,4-b]pyridin-3-yl]-5,5-dimethyl-5,7-dihydro-6H-pyrrolo[2,3-d]pyrimidin-6-one, 4-[(cyclopropylmethyl)amino]-2-[5-fluoro-1-(2-fluorobenzyl)-1H-pyrazolo[3,4-b]pyridin-3-yl]-5,5-dimethyl-5,7-dihydro-6H-pyrrolo[2,3-d]pyrimidin-6-one, 2-[5-fluoro-1-(2-fluorobenzyl)-1H-pyrazolo[3,4-b]pyridin-3-yl]-5,5-dimethyl-4-[(2,2,2-trifluoroethyl)amino]-5,7-dihydro-6H-pyrrolo[2,3-d]pyrimidin-6-one, 2-{5-fluoro-1-[(3-fluoropyridin-2-yl)methyl]-1H-pyrazolo[3,4-b]pyridin-3-yl}-5,5-dimethyl-4-[(3,3,3-trifluoropropyl)amino]-5,7-dihydro-6H-pyrrolo[2,3-d]pyrimidin-6-one, 2-{5-fluoro-1-[(3-fluoropyridin-2-yl)methyl]-1H-pyrazolo[3,4-b]pyridin-3-yl}-5,5-dimethyl-4-[(2,2,2-trifluoroethyl)amino]-5,7-dihydro-6H-pyrrolo[2,3-d]pyrimidin-6-one, 4-[(cyclopropylmethyl)amino]-2-{5-fluoro-1-[(3-fluoropyridin-2-yl)methyl]-1H-pyrazolo[3,4-b]pyridin-3-yl}-5,5-dimethyl-5,7-dihydro-6H-pyrrolo[2,3-d]pyrimidin-6-one, 4-(3-ethyl-2-oxoimidazolidin-1-yl)-2-[1-(2-fluorobenzyl)-1H-pyrazolo[3,4-b]pyridin-3-yl]-5,5-dimethyl-5,7-dihydro-6H-pyrrolo[2,3-d]pyrimidin-6-one, 2-[1-(2-fluorobenzyl)-1H-pyrazolo[3,4-b]pyridin-3-yl]-4-(4-hydroxy-1H-pyrazol-1-yl)-5,5-dimethyl-5,7-dihydro-6H-pyrrolo[2,3-d]pyrimidin-6-one, 2-[1-(2-fluorobenzyl)-1H-pyrazolo[3,4-b]pyridin-3-yl]-5,5-dimethyl-4-(1H-pyrazol-4-yloxy)-5,7-dihydro-6H-pyrrolo[2,3-d]pyrimidin-6-one, 2-[1-(2-fluorobenzyl)-1H-pyrazolo[3,4-b]pyridin-3-yl]-4-[3-(1-hydroxyethyl)-1H-pyrazol-1-yl]-5,5-dimethyl-5,7-dihydro-6H-pyrrolo[2,3-d]pyrimidin-6-one, 2-[5-fluoro-3-(2-fluorobenzyl)-1H-indazol-1-yl]-4-hydroxy-5,5-dimethyl-5,7-dihydro-6H-pyrrolo[2,3-d]pyrimidin-6-one, 4-[(cyclopropylmethyl)amino]-2-[5-fluoro-3-(2-fluorobenzyl)-1H-indazol-1-yl]-5,5-dimethyl-5,7-dihydro-6H-pyrrolo[2,3-d]pyrimidin-6-one, 2-[1-(2-fluorobenzyl)-1H-pyrazolo[3,4-b]pyridin-3-yl]-4-[(2-hydroxypropyl)amino]-5,5-dimethyl-5,7-dihydro-6H-pyrrolo[2,3-d]pyrimidin-6-one, N-(1-{2-[1-(2-fluorobenzyl)-1H-pyrazolo[3,4-b]pyridin-3-yl]-5,5-dimethyl-6-oxo-6,7-dihydro-5H-pyrrolo[2,3-d]pyrimidin-4-yl}pyrrolidin-3-yl)acetamide, 2-[1-(2-fluorobenzyl)-1H-pyrazolo[3,4-b]pyridin-3-yl]-4-[(trans-4-hydroxycyclohexyl)amino]-5,5-dimethyl-5,7-dihydro-6H-pyrrolo[2,3-d]pyrimidin-6-one, 2-[5-fluoro-1-(2-fluorobenzyl)-1H-pyrazolo[3,4-b]pyridin-3-yl]-5,5-dimethyl-4-[(3,3,3-trifluoro-2-hydroxypropyl)amino]-5,7-dihydro-6H-pyrrolo[2,3-d]pyrimidin-6-one (Enantiomer 1), 2-[5-fluoro-1-(2-fluorobenzyl)-1H-pyrazolo[3,4-b]pyridin-3-yl]-5,5-dimethyl-4-[(3,3,3-trifluoro-2-hydroxypropyl)amino]-5,7-dihydro-6H-pyrrolo[2,3-d]pyrimidin-6-one (Enantiomer 2), 4-{[(2,2-difluorocyclopropyl)methyl]amino}-2-[5-fluoro-1-(2-fluorobenzyl)-1H-pyrazolo[3,4-b]pyridin-3-yl]-5,5-dimethyl-5,7-dihydro-6H-pyrrolo[2,3-d]pyrimidin-6-one, 2-[5-fluoro-1-(2-fluorobenzyl)-1H-pyrazolo[3,4-b]pyridin-3-yl]-4-{[(1-hydroxycyclopropyl)methyl]amino}-5,5-dimethyl-5,7-dihydro-6H-pyrrolo[2,3-d]pyrimidin-6-one, ethyl-2-[1-(2-fluorobenzyl)-1H-pyrazolo[3,4-b]pyridin-3-yl]-4-hydroxy-5-methyl-6-oxo-6,7-dihydro-5H-pyrrolo[2,3-d]pyrimidine-5-carboxylate, 2-[5-fluoro-1-(2-fluorobenzyl)-1H-pyrazolo[3,4-b]pyridin-3-yl]-4-hydroxy-5,5-dimethyl-5,7-dihydro-6H-pyrrolo[2,3-d]pyrimidin-6-one, 4-(3-aminopyrrolidin-1-yl)-2-[1-(2-fluorobenzyl)-1H-pyrazolo[3,4-b]pyridin-3-yl]-5,5-dimethyl-5,7-dihydro-6H-pyrrolo[2,3-d]pyrimidin-6-one, 2-[1-(2-fluorobenzyl)-6-methyl-1H-pyrazolo[3,4-d]pyrimidin-3-yl]-5,5-dimethyl-4-[(3,3,3-trifluoropropyl)amino]-5,7-dihydro-6H-pyrrolo[2,3-d]pyrimidin-6-one, 2-[1-(2-fluorobenzyl)-1H-pyrazolo[3,4-b]pyridin-3-yl]-4-hydroxy-5,5-dimethyl-5,7-dihydro-6H-pyrrolo[2,3-d]pyrimidin-6-one, 2-[1-(2,3-difluorobenzyl)-5-fluoro-1H-pyrazolo[3,4-b]pyridin-3-yl]-4-hydroxy-5,5-dimethyl-5,7-dihydro-6H-pyrrolo[2,3-d]pyrimidin-6-one, 2-[1-(2-fluorobenzyl)-1H-pyrazolo[3,4-b]pyridin-3-yl]-4-(2-hydroxyethoxy)-5,5-dimethyl-5,7-dihydro-6H-pyrrolo[2,3-d]pyrimidin-6-one, and their salts, solvates and solvates of the salts.

Compounds of the present invention according to formula (I) are also preferred

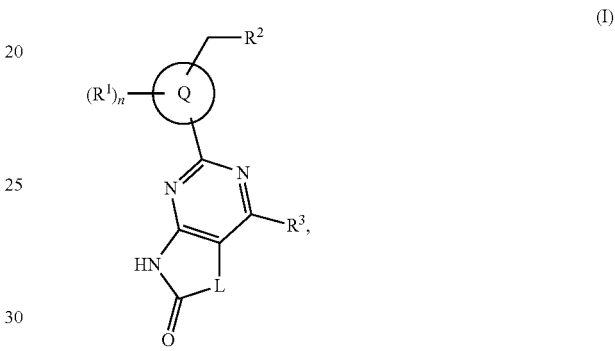

(I)

in which

L stands for a group $\#^1$—$CR^{7A}R^{7B}$—$(CR^{8A}R^{8B})_m$—$\#^2$, wherein $\#^1$ stands for the point of attachment to the carbonyl group, $\#^2$ stands for the point of attachment to the pyrimidine ring, m stands for a number 0, 1 or 2, $R^{7A}$ stands for hydrogen, fluorine, $(C_1-C_4)$-alkyl, hydroxyl or amino, in which $(C_1-C_4)$-alkyl can be substituted with 1 to 3 substituents selected independently of one another from the group fluorine, trifluoromethyl, hydroxy, hydroxycarbonyl, $(C_1-C_4)$-alkoxycarbonyl and amino, $R^{7B}$ stands for hydrogen, fluorine, difluoromethyl, trifluoromethyl, $(C_1-C_6)$-alkyl, $(C_1-C_4)$-alkoxycarbonylamino, cyano, $(C_3-C_7)$-cycloalkyl, difluoromethoxy, trifluoromethoxy, phenyl or a group of formula -M-$R^{13}$, in which $(C_1-C_6)$-alkyl can be substituted with 1 to 3 substituents selected independently of one another from the group fluorine, cyano, trifluoromethyl, $(C_3-C_7)$-cycloalkyl, hydroxy, difluoromethoxy, trifluoromethoxy, $(C_1-C_4)$-alkoxy, hydroxycarbonyl, $(C_1-C_4)$-alkoxycarbonyl and amino, and in which M stands for a bond or $(C_1-C_4)$-alkanediyl, $R^{13}$ stands for —$(C=O)_r$—$OR^{14}$, —$(C=O)_r$—$NR^{14}R^{15}$, —$C(=S)$—$NR^{14}R^{15}$, —$NR^{14}$—$(C=O)$—$R^{17}$, —$NR^{14}$—$(C=O)$—$NR^{15}R^{16}$, —$NR^{14}$—$SO_2$—$NR^{15}R^{16}$, —$NR^{14}$—$SO_2$—$R^{17}$, —$S(O)_s$—$R^{17}$, —$SO_2$—$NR^{14}R^{15}$, 4- to 7-membered heterocyclyl, phenyl or 5- or 6-membered heteroaryl, in which r denotes the number 0 or 1, s denotes the number 0, 1 or 2, $R^{14}$, $R^{15}$ and $R^{16}$ each stand, independently of one another, for hydrogen, $(C_1-C_6)$-alkyl, $(C_3-C_8)$-cycloalkyl, 4- to 7-membered heterocyclyl, phenyl or 5- or 6-membered heteroaryl, or $R^{14}$ and $R^{15}$ form, together with the respective atom(s) to which they are bound, a 4- to 7-membered heterocycle, in which for its part the 4- to 7-membered heterocycle can be substituted with 1 or 2 substituents selected independently of one another from the group cyano, trifluoromethyl, $(C_1-C_6)$-alkyl, hydroxy, oxo, $(C_1-C_6)$-alkoxy, trifluoromethoxy, $(C_1-C_6)$-alkoxycarbonyl, amino, mono-$(C_1-C_6)$-alkylamino and di$(C_1-C_6)$-alkylamino, or $R^{15}$ and $R^{16}$ form, together with the respective atom(s) to which they are bound, a 4- to 7-membered heterocycle, in which for its part the 4- to 7-membered heterocycle can be substituted with 1 or 2 substituents selected independently of one another from the group cyano, trifluoromethyl, $(C_1-C_6)$-alkyl, hydroxy, oxo, $(C_1-C_6)$-alkoxy, trifluoromethoxy, $(C_1-C_6)$-alkoxycarbonyl, amino, mono-$(C_1-C_6)$-alkylamino and di$(C_1-C_6)$-alkylamino, $R^{17}$ stands for $(C_1-C_6)$-alkyl or $(C_3-C_7)$-cycloalkyl, or $R^{14}$ and $R^{17}$ form, together with the respective atom(s) to which they are bound, a 4- to 7-membered heterocycle, in which for its part the 4- to 7-membered heterocycle can be substituted with 1 or 2 substituents selected independently of one another from the group cyano, trifluoromethyl, $(C_1-C_6)$-alkyl, hydroxy, oxo, $(C_1-C_6)$-alkoxy, trifluoromethoxy, $(C_1-C_6)$-alkoxycarbonyl, amino, mono-$(C_1-C_6)$-alkylamino and di$(C_1-C_6)$-alkylamino, and in which for their part the 4- to 7-membered heterocyclyl, phenyl and 5- or 6-membered heteroaryl can be substituted with 1 to 3 substituents selected independently of one another from the group halogen, cyano, difluoromethyl, trifluoromethyl, $(C_1-C_6)$-alkyl, $(C_3-C_7)$-cycloalkyl, hydroxy, oxo, thiooxo and $(C_1-C_4)$-alkoxy, and in which the aforementioned $(C_1-C_4)$-alkyl, $(C_1-C_6)$-alkyl, $(C_3-C_8)$-cycloalkyl, $(C_3-C_7)$-cycloalkyl and 4- to 7-membered heterocyclyl groups, unless stated otherwise, can in each case be further substituted independently of one another with 1 to 3 substituents selected independently of one another from the group fluorine, difluoromethyl, trifluoromethyl, $(C_1-C_4)$-alkyl, $(C_3-C_7)$-cycloalkyl, hydroxy, difluoromethoxy, trifluoromethoxy, $(C_1-C_4)$-alkoxy, hydroxycarbonyl, $(C_1-C_4)$-alkoxycarbonyl, amino, phenyl, 4- to 7-membered heterocyclyl and 5- or 6-membered heteroaryl, or $R^{7A}$ and $R^{7B}$ together with the carbon atom to which they are bound, form a $(C_2-C_4)$-alkenyl group, an oxo group, a 3- to 6-membered carbocycle or a 4- to 7-membered heterocycle, in which the 3- to 6-membered carbocycle and the 4- to 7-membered heterocycle can be substituted with 1 or 2 substituents selected independently of one another from the group fluorine and $(C_1-C_4)$-alkyl, $R^{8A}$ stands for hydrogen, fluorine, $(C_1-C_4)$-alkyl or hydroxy, $R^{8B}$ stands for hydrogen, fluorine, $(C_1-C_4)$-alkyl or trifluoromethyl, the ring Q stands for 8- or 9-membered heteroaryl, $R^3$ stands for —$OR^4$ or —$NR^5R^6$, wherein $R^4$ stands for hydrogen, $(C_1-C_6)$-alkyl, $(C_3-C_7)$-cycloalkyl, 4- to 7-membered heterocyclyl, phenyl or 5- or 6-membered heteroaryl, in which $(C_1-C_6)$-alkyl, $(C_3-C_7)$-cycloalkyl, 4- to 7-membered heterocyclyl, phenyl and 5- or 6-membered heteroaryl can be substituted with 1 to 3 substituents selected independently of one another from the group fluorine, difluoromethyl, trifluoromethyl, $(C_1-C_6)$-alkyl, $(C_3-C_6)$-cycloalkyl, difluoromethoxy, trifluoromethoxy, oxo, —$(C=O)_p$—$OR^9$, —$C(=O)_p$—$NR^9R^{10}$, —$NR^9$—$(C=O)$—$R^{10}$, —$NR^9$—$(C=O)$—$OR^{10}$, —$NR^9$—$(C=O)$—$NR^{10}R^{11}$, —$NR^9$—$SO_2$—$R^{10}$, —$S(O)_q$—$R^{12}$ and —$SO_2$—$NR^9R^{10}$, in which p denotes the number 0 or 1, q denotes the number 0, 1 or 2, $R^9$, $R^{10}$ and $R^{11}$ each stand, independently of one another, for hydrogen, $(C_1-C_6)$-alkyl or $(C_3-C_8)$-cycloalkyl, in which $(C_1-C_6)$-alkyl for its part can be substituted with 1 or 2 substituents selected independently of one another from the group fluorine, difluoromethyl, trifluoromethyl, hydroxy, $(C_1-C_6)$-alkoxy, difluoromethoxy, trifluoromethoxy, $(C_1-C_6)$-alkoxycarbonyl, amino, mono-$(C_1-C_6)$-alkylamino, di$(C_1-C_6)$-alkylamino and 4- to 7-membered heterocyclyl, or $R^9$ and $R^{10}$ form, together with the respective atom(s) to which they are bound, a 4- to 7-membered heterocycle, in which for its part the 4- to 7-membered heterocycle can be substituted with 1 or 2 substituents selected independently of one another from the group fluorine, trifluoromethyl, $(C_1-C_6)$-alkyl, hydroxy, oxo, $(C_1-C_6)$-alkoxy, trifluoromethoxy, $(C_1-C_6)$-alkoxycarbonyl, amino, mono-$(C_1-C_6)$-alkylamino and di$(C_1-C_6)$-alkylamino, or $R^{10}$ and $R^{11}$ form, together with the respective atom(s) to which they are bound, a 4- to 7-membered heterocycle, in which for its part the 4- to 7-membered heterocycle can be substituted with 1 or 2 substituents selected independently of one another from the group fluorine, trifluoromethyl, $(C_1-C_6)$-alkyl, hydroxy, oxo, $(C_1-C_6)$-alkoxy, trifluoromethoxy, $(C_1-C_6)$-alkoxycarbonyl, amino, mono-$(C_1-C_6)$-alkylamino and di$(C_1-C_6)$-alkylamino, and in which $R^{12}$ stands for $(C_1-C_6)$-alkyl or $(C_3-C_7)$-cycloalkyl, and in which the aforementioned $(C_1\text{-}C_4)$-alkyl, $(C_1\text{-}C_6)$-alkyl, $(C_3\text{-}C_8)$-cycloalkyl, $(C_3\text{-}C_7)$-cycloalkyl and 4- to 7-membered heterocyclyl groups, unless stated otherwise, can in each case be further substituted independently of one another with 1 to 3 substituents selected independently of one another from the group fluorine, difluoromethyl, trifluoromethyl, $(C_1\text{-}C_4)$-alkyl, $(C_3\text{-}C_7)$-cycloalkyl, hydroxy, difluoromethoxy, trifluoromethoxy, $(C_1\text{-}C_4)$-alkoxy, hydroxycarbonyl, $(C_1\text{-}C_4)$-alkoxycarbonyl, amino, phenyl, 4- to 7-membered heterocyclyl and 5- or 6-membered heteroaryl, $R^5$ stands for hydrogen or $(C_1\text{-}C_4)$-alkyl, $R^6$ stands for $(C_1\text{-}C_6)$-alkyl, $(C_3\text{-}C_7)$-cycloalkyl, 4- to 7-membered heterocyclyl, phenyl or 5- or 6-membered heteroaryl, in which $(C_1\text{-}C_6)$-alkyl, $(C_3\text{-}C_7)$-cycloalkyl, 4- to 7-membered heterocyclyl, phenyl and 5- or 6-membered heteroaryl can be substituted with 1 to 3 substituents selected independently of one another from the group fluorine, difluoromethyl, trifluoromethyl, $(C_1\text{-}C_6)$-alkyl, $(C_3\text{-}C_7)$-cycloalkyl, difluoromethoxy, trifluoromethoxy, oxo, —(C=O)$_p$—OR$^9$, —(C=O)$_p$—NR$^9$R$^{10}$, —NR$^9$—(C=O)—R$^{10}$, —NR$^9$—(C=O)—OR$^{10}$, —NR$^9$—(C=O)—NR$^{10}$R$^{11}$, —NR$^9$—SO$_2$—R$^{10}$, —S(O)$_q$—R$^{12}$, —SO$_2$—NR$^9$R$^{10}$, phenyl, 4- to 7-membered heterocyclyl and 5- or 6-membered heteroaryl, in which p denotes the number 0 or 1, q denotes the number 0, 1 or 2, $R^9$, $R^{10}$ and $R^{11}$ each stand, independently of one another, for hydrogen, $(C_1\text{-}C_6)$-alkyl or $(C_3\text{-}C_8)$-cycloalkyl, in which $(C_1\text{-}C_6)$-alkyl for its part can be substituted with 1 to 3 substituents selected independently of one another from the group fluorine, difluoromethyl, trifluoromethyl, $(C_3\text{-}C_7)$-cycloalkyl, difluoromethoxy, trifluoromethoxy and $(C_1\text{-}C_4)$-alkoxy, or $R^9$ and $R^{10}$ form, together with the respective atom(s) to which they are bound, a 4- to 7-membered heterocycle, in which for its part the 4- to 7-membered heterocycle can be substituted with 1 or 2 substituents selected independently of one another from the group fluorine, cyano, trifluoromethyl, $(C_1\text{-}C_6)$-alkyl, hydroxy, oxo, $(C_1\text{-}C_6)$-alkoxy, trifluoromethoxy, $(C_1\text{-}C_6)$-alkoxycarbonyl, amino, mono-$(C_1\text{-}C_6)$-alkylamino and di$(C_1\text{-}C_6)$-alkylamino, or $R^{10}$ and $R^{11}$ form, together with the respective atom(s) to which they are bound, a 4- to 7-membered heterocycle, in which for its part the 4- to 7-membered heterocycle can be substituted with 1 or 2 substituents selected independently of one another from the group cyano, trifluoromethyl, $(C_1\text{-}C_6)$-alkyl, hydroxy, oxo, $(C_1\text{-}C_6)$-alkoxy, trifluoromethoxy, $(C_1\text{-}C_6)$-alkoxycarbonyl, amino, mono-$(C_1\text{-}C_6)$-alkylamino and di$(C_1\text{-}C_6)$-alkylamino, in which $R^{12}$ stands for $(C_1\text{-}C_6)$-alkyl or $(C_3\text{-}C_7)$-cycloalkyl, and in which phenyl, 4- to 7-membered heterocyclyl and 5- or 6-membered heteroaryl for their part can be substituted with 1 to substituents selected independently of one another from the group halogen, cyano, difluoromethyl, trifluoromethyl, $(C_1\text{-}C_4)$-alkyl, $(C_3\text{-}C_7)$-cycloalkyl, hydroxy, oxo, difluoromethoxy, trifluoromethoxy and $(C_1\text{-}C_4)$-alkoxy, or $R^5$ and $R^6$ form, together with the nitrogen atom to which they are bound, a 4- to 7-membered heterocycle or a 5- or 6-membered heteroaryl, in which the 4- to 7-membered heterocycle and the 5- or 6-membered heteroaryl can be substituted with 1 to 3 substituents selected independently of one another from the group fluorine, cyano, difluoromethyl, trifluoromethyl, $(C_1\text{-}C_6)$-alkyl, $(C_3\text{-}C_7)$-cycloalkyl, hydroxy, oxo, $(C_1\text{-}C_6)$-alkoxy, difluoromethoxy, trifluoromethoxy, $(C_1\text{-}C_6)$-alkoxycarbonyl, $(C_1\text{-}C_6)$-alkylcarbonylamino, amino, mono-$(C_1\text{-}C_6)$-alkylamino, di$(C_1\text{-}C_6)$-alkylamino and 4- to 7-membered heterocyclyl, and in which the aforementioned $(C_1\text{-}C_4)$-alkyl, $(C_1\text{-}C_6)$-alkyl, $(C_3\text{-}C_8)$-cycloalkyl, $(C_3\text{-}C_7)$-cycloalkyl and 4- to 7-membered heterocyclyl groups, unless stated otherwise, can in each case be further substituted independently of one another with 1 to 3 substituents selected independently of one another from the group fluorine, difluoromethyl, trifluoromethyl, $(C_1\text{-}C_4)$-alkyl, $(C_3\text{-}C_7)$-cycloalkyl, hydroxy, difluoromethoxy, trifluoromethoxy, $(C_1\text{-}C_4)$-alkoxy, hydroxycarbonyl, $(C_1\text{-}C_4)$-alkoxycarbonyl, amino, phenyl, 4- to 7-membered heterocyclyl and 5- or 6-membered heteroaryl, $R^1$ stands for fluorine, chlorine, cyano, difluoromethyl, trifluoromethyl, $(C_1\text{-}C_4)$-alkyl, $(C_3\text{-}C_7)$-cycloalkyl or $(C_1\text{-}C_4)$-alkoxy, n stands for a number 0, 1 or 2, $R^2$ stands for trifluoromethyl, $(C_1\text{-}C_6)$-alkyl, $(C_3\text{-}C_8)$-cycloalkyl, phenyl or 5- or 6-membered heteroaryl, wherein $(C_1\text{-}C_6)$-alkyl is substituted with a substituent selected from the group difluoromethyl and trifluoromethyl, wherein $(C_1\text{-}C_6)$-alkyl can be substituted with 1 to 3 fluorine substituents, wherein $(C_3\text{-}C_8)$-cycloalkyl can be substituted with 1 or 2 substituents selected independently of one another from the group fluorine, methyl and methoxy, wherein phenyl is substituted with 1 to 3 fluorine substituents, wherein phenyl can be substituted with 1 or 2 substituents selected independently of one another from the group methyl and methoxy, and wherein 5- and 6-membered heteroaryl can be substituted with 1 or 2 substituents selected independently of one another from the group fluorine, trifluoromethyl and methyl, and their N-oxides, salts, solvates, salts of the N-oxides and solvates of the N-oxides and salts.

Compounds of the present invention according to formula (I) are also preferred in which L stands for a group #$^1$—CR$^{7A}$R$^{7B}$—(CR$^{8A}$R$^{8B}$)$_m$—#$^2$, wherein

$^1$ stands for the point of attachment to the carbonyl group,

$^2$ stands for the point of attachment to the pyrimidine ring, m stands for a number 0 or 1, $R^{7A}$ stands for hydrogen, fluorine, methyl, ethyl, hydroxy or amino, $R^{7B}$ stands for hydrogen, fluorine, difluoromethyl, trifluoromethyl, $(C_1-C_4)$-alkyl, methoxycarbonylamino, cyano, cyclopropyl, cyclobutyl, cyclopentyl, phenyl or a group of formula -M-$R^{13}$, in which $(C_1-C_4)$-alkyl can be substituted with 1 to 3 substituents selected independently of one another from the group fluorine, cyano, trifluoromethyl, cyclopropyl, cyclobutyl, cyclopentyl, hydroxy, difluoromethoxy, trifluoromethoxy, methoxy, ethoxy, hydroxycarbonyl, methoxycarbonyl, ethoxycarbonyl and amino, and in which M stands for a bond or methylene, $R^{13}$ stands for —(C=O)$_r$—$NR^{14}R^{15}$, —C(=S)—$NR^{14}R^{15}$, oxadiazolonyl, oxadiazolethionyl, phenyl, oxazolyl, thiazolyl, pyrazolyl, triazolyl, oxadiazolyl, thiadiazolyl, pyridyl, pyrimidinyl or pyrazinyl, in which r denotes the number 0 or 1, $R^{14}$ and $R^{15}$ each stand, independently of one another, for hydrogen, methyl, ethyl, isopropyl, cyclopropyl, cyclobutyl, cyclopentyl, oxetanyl, azetidinyl, tetrahydrofuranyl, pyrrolidinyl, tetrahydropyranyl, piperidinyl, piperazinyl, morpholinyl, phenyl, pyrazolyl or pyridyl, in which methyl, ethyl and iso-propyl can be further substituted with 1 or 2 substituents selected independently of one another from the group fluorine, difluoromethyl, trifluoromethyl, cyclopropyl, cyclobutyl, cyclopentyl, hydroxy, difluoromethoxy, trifluoromethoxy, methoxy, ethoxy, hydroxycarbonyl, methoxycarbonyl, ethoxycarbonyl and amino, and in which oxadiazolonyl, oxadiazolethionyl, phenyl, oxazolyl, thiazolyl, pyrazolyl, triazolyl, oxadiazolyl, thiadiazolyl, pyridyl, pyrimidinyl and pyrazinyl for their part can be substituted with 1 or 2 substituents selected independently of one another from the group fluorine, chlorine, cyano, difluoromethyl, trifluoromethyl, methyl, ethyl, isopropyl, 2,2,2-trifluoroethyl, 1,1,2,2,2-pentafluoroethyl, cyclopropyl, cyclobutyl, cyclopropylmethyl, cyclobutylmethyl, hydroxy, methoxy and ethoxy, or $R^{7A}$ and $R^{7B}$ together with the carbon atom to which they are bound, form a cyclopropyl, cyclobutyl, cyclopentyl, azetidinyl, tetrahydrofuranyl, pyrrolidinyl or tetrahydropyranyl ring, in which the cyclopropyl, cyclobutyl, cyclopentyl, azetidinyl, tetrahydrofuranyl, pyrrolidinyl and tetrahydropyranyl ring can be substituted with 1 or 2 substituents selected independently of one another from the group fluorine and methyl, $R^{8A}$ stands for hydrogen, fluorine, methyl, ethyl or hydroxy, $R^{8B}$ stands for hydrogen, fluorine, methyl, ethyl or trifluoromethyl, the ring Q stands for a group of formula

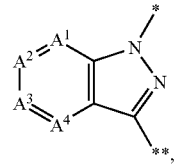
(a-1)

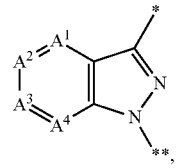
(b-1)

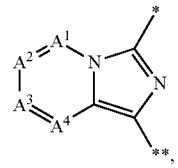
(c-1)

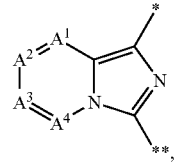
(d-1)

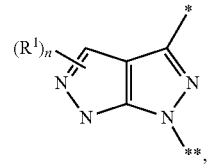
(e-1)

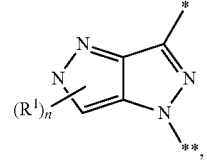
(f-1)

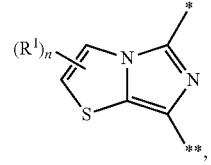
(g-1)

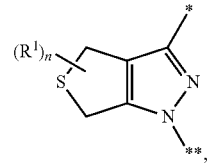
(h-1)

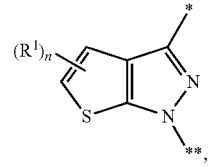
(i-1)

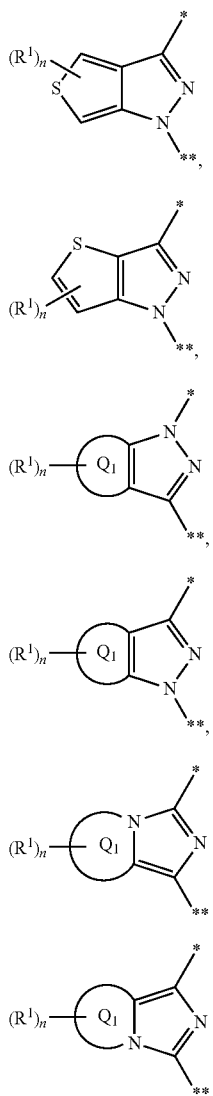

wherein
* stands for the point of attachment to —CH₂—R²,
** stands for the point of attachment to the pyrimidine,
the ring $Q_1$ together with the atoms to which it is bound, forms a 5- to 7-membered saturated or partially unsaturated carbocycle or a 5- to 7-membered saturated or partially unsaturated heterocycle,
$R^1$ stands for fluorine, chlorine or methyl,
n stands for a number 0, 1 or 2,
$A^1, A^2, A^3$ and $A^4$ independently of one another stand in each case for N, CH or $CR^1$,
with the proviso that at most two of the groups $A^1, A^2, A^3$ and $A^4$ stand for N,
$R^3$ stands for —OR⁴ or —NR⁵R⁶,
wherein
$R^4$ stands for $(C_1-C_6)$-alkyl, cyclopropyl, cyclobutyl, cyclopentyl, oxetanyl, azetidinyl, tetrahydrofuranyl, pyrrolidinyl, tetrahydropyranyl, piperidinyl, piperazinyl, morpholinyl, phenyl, pyrazolyl, oxazolyl, thiazolyl, triazolyl, oxadiazolyl, thiadiazolyl, pyridyl or pyrimidinyl,
in which $(C_1-C_6)$-alkyl can be substituted with 1 to 3 substituents selected independently of one another from the group fluorine, difluoromethyl, trifluoromethyl, cyclopropyl, cyclobutyl, cyclopentyl, difluoromethoxy, trifluoromethoxy, —(C=O)$_p$—OR⁹, —(C=O)$_p$—NR⁹R¹⁰, and —NR⁹—(C=O)—R¹⁰, and
in which cyclopropyl, cyclobutyl, cyclopentyl, oxetanyl, azetidinyl, tetrahydrofuranyl, pyrrolidinyl, tetrahydropyranyl, piperidinyl, piperazinyl, morpholinyl, phenyl, pyrazolyl, oxazolyl, thiazolyl, triazolyl, oxadiazolyl, thiadiazolyl, pyridyl or pyrimidinyl can be substituted with 1 to 3 substituents selected independently of one another from the group fluorine, difluoromethyl, trifluoromethyl, 2,2,2-trifluoroethyl, 1,1,2,2,2-pentafluoroethyl, methyl, ethyl, isopropyl, cyclopropyl, cyclobutyl, cyclopentyl, difluoromethoxy, trifluoromethoxy, oxo, —(C=O)$_p$—OR⁹ and —(C=O)$_p$—NR⁹R¹⁰,
in which
p denotes the number 0 or 1,
$R^9$ and $R^{10}$ each stand, independently of one another, for hydrogen, methyl, ethyl, isopropyl, trifluoromethyl, 2,2,2-trifluoroethyl, 1,1,2,2,2-pentafluoroethyl, cyclopropyl, cyclobutyl or cyclopentyl,
or
$R^9$ and $R^{10}$ form, together with the respective atom(s) to which they are bound, an azetidinyl, pyrrolidinyl, piperidinyl, piperazinyl or morpholinyl ring,
in which the azetidinyl, pyrrolidinyl, piperidinyl, piperazinyl and morpholinyl ring for its part can be substituted with 1 or 2 substituents selected independently of one another from the group fluorine, trifluoromethyl, methyl, ethyl, hydroxy, oxo, methoxy, ethoxy, amino, methylamino, ethylamino, dimethylamino and diethylamino,
$R^5$ stands for hydrogen, methyl or ethyl,
$R^6$ stands for $(C_1-C_6)$-alkyl, cyclopropyl, $(C_3-C_6)$-cycloalkyl, oxetanyl, azetidinyl, tetrahydrofuranyl, pyrrolidinyl, tetrahydropyranyl, piperidinyl, piperazinyl, morpholinyl, phenyl, pyrazolyl, oxazolyl, thiazolyl, triazolyl, oxadiazolyl, thiadiazolyl, pyridyl or pyrimidinyl,
in which $(C_1-C_6)$-alkyl and $(C_3-C_6)$-cycloalkyl are substituted with 1 to 3 selected independently of one another from the group fluorine, difluoromethyl, trifluoromethyl methyl, ethyl, cyclopropyl, cyclobutyl, cyclopentyl, difluoromethoxy, trifluoromethoxy, —(C=O)$_p$—OR⁹, —(C=O)$_p$—NR⁹R¹⁰, —NR⁹—(C=O)—R¹⁰, oxetanyl, azetidinyl, tetrahydrofuranyl, pyrrolidinyl, tetrahydropyranyl, piperidinyl, piperazinyl, morpholinyl, phenyl, furanyl, pyrazolyl, imidazolyl, oxazolyl, thiazolyl, triazolyl, oxadiazolyl, thiadiazolyl, pyridyl and pyrimidinyl,
in which cyclopropyl, cyclobutyl, cyclopentyl, oxetanyl, azetidinyl, tetrahydrofuranyl, pyrrolidinyl, tetrahydropyranyl, piperidinyl, piperazinyl, morpholinyl, phenyl, furanyl, pyrazolyl, imidazolyl, oxazolyl, thiazolyl, triazolyl, oxadiazolyl, thiadiazolyl, pyridyl and pyrimidinyl for their part can be substituted with 1 or 2 substituents selected independently of one another from the group fluorine, chlorine, cyano, difluoromethyl, trifluoromethyl, methyl, ethyl, cyclopropyl, cyclobutyl, cyclopentyl, hydroxy, oxo, difluoromethoxy, trifluoromethoxy, methoxy and ethoxy, in which oxetanyl, azetidinyl, tetrahydrofuranyl, pyrrolidinyl, tetrahydropyranyl, piperidinyl, piperazinyl, morpholinyl, phenyl, pyrazolyl, oxazolyl, thiazolyl, triazolyl, oxadiazolyl, thiadiazolyl, pyridyl and pyrimidinyl can be substituted with 1 to 3 substituents selected independently of one another from the group fluorine, difluoromethyl, trifluoromethyl, methyl, ethyl, cyclopropyl, cyclobutyl, cyclopentyl, difluoromethoxy, trifluoromethoxy, oxo, —(C=O)$_p$—OR$^9$ and —(C=O)$_p$—NR$^9$R$^{10}$, in which
p denotes the number 0 or 1,
R$^9$ and R$^{10}$ each stand, independently of one another, for hydrogen, methyl, ethyl, isopropyl, trifluoromethyl, 2,2,2-trifluoroethyl, 1,1,2,2,2-pentafluoroethyl, cyclopropyl, cyclobutyl or cyclopentyl, or R$^9$ and R$^{10}$ form, together with the respective atom(s) to which they are bound, an azetidinyl, pyrrolidinyl, piperidinyl, piperazinyl or morpholinyl ring,
in which the azetidinyl, pyrrolidinyl, piperidinyl, piperazinyl and morpholinyl ring for its part can be substituted with 1 or 2 substituents selected independently of one another from the group fluorine, trifluoromethyl, methyl, ethyl, hydroxy, oxo, methoxy, ethoxy, amino, methylamino, ethylamino, dimethylamino and diethylamino, or
R$^5$ and R$^6$ form, together with the nitrogen atom to which they are bound, an azetidinyl, pyrrolidinyl, imidazolidinyl, piperidinyl, dihydropiperidinyl, piperazinyl, morpholinyl, pyrazolyl, imidazolyl or triazolyl ring,
in which the azetidinyl, pyrrolidinyl, imidazolidinyl, piperidinyl, dihydropiperidinyl, piperazinyl, morpholinyl, pyrazolyl, imidazolyl and triazolyl ring can be substituted with 1 or 2 substituents selected independently of one another from the group fluorine, cyano, difluoromethyl, trifluoromethyl, 2,2,2-trifluoroethyl, 1,1,2,2,2-pentafluoroethyl, methyl, ethyl, 1-hydroxyethyl, cyclopropyl, cyclobutyl, cyclopentyl, hydroxy, oxo, methoxy, ethoxy, difluoromethoxy, trifluoromethoxy, oxetanyl, azetidinyl, tetrahydrofuranyl, pyrrolidinyl, tetrahydropyranyl, piperidinyl, piperazinyl and morpholinyl, R$^2$ stands for trifluoromethyl, 2,2,2-trifluoroethyl, 3,3,3-trifluoroprop-1-yl, 2,2,3,3,3-pentafluoroprop-1-yl, cyclopropyl, cyclobutyl, cyclopentyl, cyclohexyl, phenyl, pyridyl, pyrimidinyl, pyrazinyl or pyridazinyl,
wherein phenyl is substituted with 1 to 3 fluorine substituents,
and
wherein cyclopropyl, cyclobutyl, cyclopentyl, cyclohexyl, pyridyl, pyrimidinyl, pyrazinyl and pyridazinyl can be substituted with 1 or 2 fluorine substituents, and their salts, solvates and solvates of the salts.

Compounds of the present invention according to formula (I) are also preferred in which L stands for a group #$^1$—CR$^{7A}$R$^{7B}$—(CR$^{8A}$R$^{8B}$)$_m$—#$^2$,
wherein
$^1$ stands for the point of attachment to the carbonyl group,
$^2$ stands for the point of attachment to the pyrimidine ring,
m stands for a number 0,
R$^{7A}$ stands for hydrogen, fluorine, methyl or hydroxy,
R$^{7B}$ stands for hydrogen, fluorine, trifluoromethyl, methyl or 2,2,2-trifluoroethyl, or
R$^{7A}$ and R$^{7B}$ together with the carbon atom to which they are bound, form a tetrahydrofuranyl ring, the ring Q stands for a group of formula

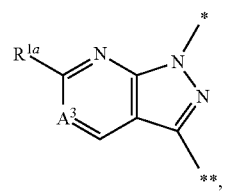

(a-1)

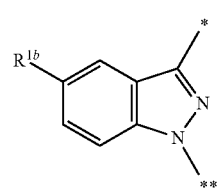

(b-1)

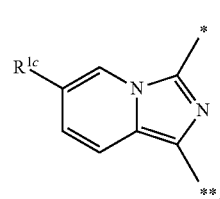

(c-1a)

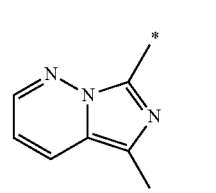

(c-1a)

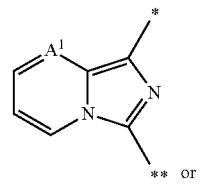

(d-1)

or

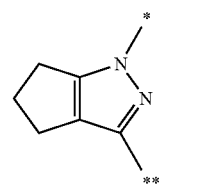

(1-1)

wherein
* stands for the point of attachment to —CH$_2$—R$^2$,
** stands for the point of attachment to the pyrimidine,
R$^{1a}$ stands for hydrogen or methyl,
R$^{1b}$ stands for hydrogen or fluorine,
R$^{1c}$ stands for hydrogen or chlorine,
A$^1$ stands for N or CH,
A$^3$ stands for N, CH or C—F,
R$^3$ stands for —NR$^5$R$^6$,
wherein
R$^5$ stands for hydrogen, $R^6$ stands for $(C_1-C_6)$-alkyl,
in which $(C_1-C_6)$-alkyl is substituted with 1 or 2 substituents selected independently of one another from the group fluorine, difluoromethyl, trifluoromethyl or $-(C=O)_p-OR^9$,
in which
p denotes the number 0,
$R^9$ stands for hydrogen,
$R^2$ stands for 2-fluorophenyl, 2,3-difluorophenyl or 3-fluoropyrid-2-yl,
and their salts, solvates and solvates of the salts.

Compounds of the present invention according to formula (I) are also preferred in which
L stands for a group $\#^1-CR^{7A}R^{7B}-(CR^{8A}R^{8B})_m-\#^2$,
wherein
$\#^1$ stands for the point of attachment to the carbonyl group,
$\#^2$ stands for the point of attachment to the pyrimidine ring,
m stands for a number 0,
$R^{7A}$ stands for methyl,
$R^{7B}$ stands for methyl,
the ring Q stands for a group of formula

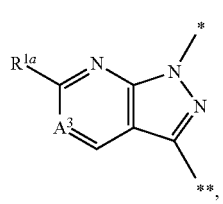
(a-1)

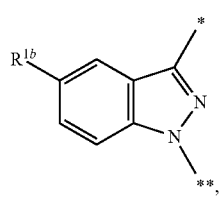
(b-1)

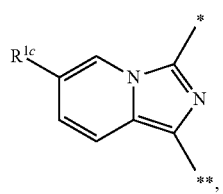
(c-1a)

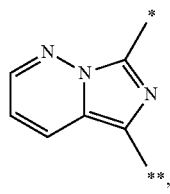
(c-1a)

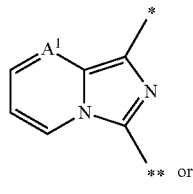
(d-1)

** or

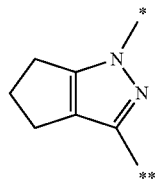
(1-1)

wherein
* stands for the point of attachment to $-CH_2-R^2$,
** stands for the point of attachment to the pyrimidine,
$R^{1a}$ stands for hydrogen or methyl,
$R^{1b}$ stands for hydrogen or fluorine,
$R^{1c}$ stands for hydrogen or chlorine,
$A^1$ stands for N or CH,
$A^3$ stands for N, CH or C—F,
$R^3$ stands for $-NR^5R^6$,
wherein
$R^5$ stands for hydrogen, methyl or ethyl,
$R^6$ stands for $(C_1-C_6)$-alkyl, oxetanyl, azetidinyl, tetrahydrofuranyl, pyrrolidinyl, tetrahydropyranyl, piperidinyl, piperazinyl, morpholinyl, phenyl, pyrazolyl, oxazolyl, thiazolyl, triazolyl, oxadiazolyl, thiadiazolyl, pyridyl or pyrimidinyl,
in which $(C_1-C_6)$-alkyl is substituted with 1 or 2 substituents selected independently of one another from the group fluorine, difluoromethyl, trifluoromethyl cyclopropyl, cyclobutyl, cyclopentyl, trifluoromethoxy, $-(C=O)_p-OR^9$, $-(C=O)_p-NR^9R^{10}$, tetrahydrofuranyl, pyrrolidinyl, tetrahydropyranyl, phenyl, furanyl, pyrazolyl, imidazolyl, triazolyl and pyridyl,
in which
p denotes the number 0 or 1,
$R^9$ and $R^{10}$ each stand, independently of one another, for hydrogen, methyl, ethyl, trifluoromethyl, 2,2,2-trifluoroethyl, 1,1,2,2,2-pentafluoroethyl, cyclopropyl or cyclobutyl,
and
in which tetrahydrofuranyl, pyrrolidinyl, tetrahydropyranyl, phenyl, furanyl, pyrazolyl, imidazolyl, triazolyl and pyridyl for their part can be substituted with 1 or 2 substituents selected independently of one another from the group fluorine, chlorine, cyano, difluoromethyl, trifluoromethyl, methyl, ethyl and oxo,
in which oxetanyl, azetidinyl, tetrahydrofuranyl, pyrrolidinyl, tetrahydropyranyl, piperidinyl, piperazinyl, morpholinyl, phenyl, pyrazolyl, oxazolyl, thiazolyl, triazolyl, oxadiazolyl, thiadiazolyl, pyridyl and pyrimidinyl can be substituted with 1 or 2 substituents selected independently of one another from the group fluorine, difluoromethyl, trifluoromethyl, methyl, ethyl and oxo,
or
$R^5$ and $R^6$ form, together with the nitrogen atom to which they are bound, an azetidinyl, pyrrolidinyl, imidazolidinyl, piperidinyl, dihydropiperidinyl, piperazinyl, morpholinyl, pyrazolyl or imidazolyl ring,
in which the azetidinyl, pyrrolidinyl, imidazolidinyl, piperidinyl, dihydropiperidinyl, piperazinyl, morpholinyl, pyrazolyl and imidazolyl ring can be substituted with 1 or 2 substituents selected independently of one another from the group fluorine, cyano, difluoromethyl, trifluoromethyl, 2,2,2-trifluoroethyl, 1,1,2,2,2-pentafluoroethyl, methyl, ethyl, 1-hydroxyethyl, cyclopropyl, cyclobutyl, cyclopentyl, hydroxy, oxo, methoxy, ethoxy, difluoromethoxy and trifluoromethoxy, $R^2$ stands for 3,3,3-trifluoroeth-1-yl, 2,2,3,3,3-pentafluoroprop-1-yl, phenyl or pyridyl, wherein phenyl is substituted with 1 to 3 fluorine substituents, and wherein pyridyl can be substituted with 1 fluorine substituent, and their salts, solvates and solvates of the salts.

Compounds of the present invention according to formula (I) are also preferred in which L stands for a group $\#^1$—$CR^{7A}R^{7B}$—$(CR^{8A}$—$R^{8B})_m$—$\#^2$, wherein $\#^1$ stands for the point of attachment to the carbonyl group, $\#^2$ stands for the point of attachment to the pyrimidine ring, m stands for a number 0, $R^{7A}$ stands for hydrogen, fluorine, methyl, hydroxy, $R^{7B}$ stands for hydrogen, fluorine, methyl or trifluoromethyl, or $R^{7A}$ and $R^{7B}$ together with the carbon atom to which they are bound, form a tetrahydrofuranyl ring, the ring Q stands for a group of formula

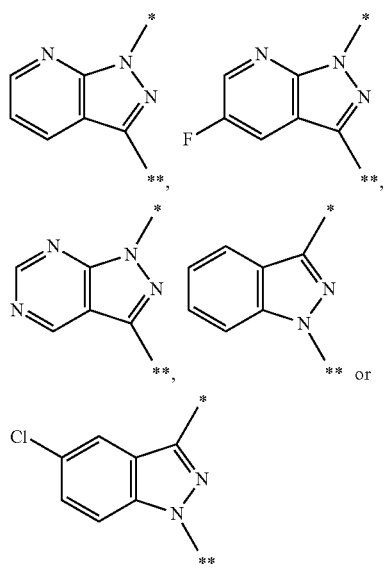

wherein

* stands for the point of attachment to —$CH_2$—$R^2$,

** stands for the point of attachment to the pyrimidine, $R^3$ stands for —$OR^4$ or —$NR^5R^6$, wherein $R^4$ stands for $(C_1$-$C_6)$-alkyl or pyrazolyl, in which $(C_1$-$C_6)$-alkyl can be substituted with 1 to 3 substituents selected independently of one another from the group fluorine, trifluoromethyl, —$(C=O)_p$—$OR^9$ and —$(C=O)_p$—$NR^9R^{10}$, in which p denotes the number 0 or 1, $R^9$ and $R^{10}$ independently of one another stand in each case for hydrogen or methyl, and in which pyrazolyl can be substituted with 1 or 2 substituents selected independently of one another from the group fluorine, difluoromethyl, trifluoromethyl, 2,2,2-trifluoroethyl, 1,1,2,2,2-pentafluoroethyl, methyl, cyclopropyl, cyclobutyl, cyclopentyl.

$R^5$ stands for hydrogen, methyl or ethyl, $R^6$ stands for $(C_1$-$C_6)$-alkyl, oxetanyl, azetidinyl, tetrahydrofuranyl, pyrrolidinyl, tetrahydropyranyl, piperidinyl, piperazinyl, morpholinyl, phenyl, pyrazolyl, oxazolyl, thiazolyl, triazolyl, oxadiazolyl, thiadiazolyl, pyridyl or pyrimidinyl, in which $(C_1$-$C_6)$-alkyl is substituted with 1 or 2 substituents selected independently of one another from the group fluorine, difluoromethyl, trifluoromethyl cyclopropyl, cyclobutyl, cyclopentyl, trifluoromethoxy, —$(C=O)_p$—$OR^9$, —$(C=O)_p$—$NR^9R^{10}$, tetrahydrofuranyl, pyrrolidinyl, tetrahydropyranyl, phenyl, furanyl, pyrazolyl, imidazolyl, triazolyl and pyridyl, in which p denotes the number 0 or 1, $R^9$ and $R^{10}$ each stand, independently of one another, for hydrogen, methyl, ethyl, trifluoromethyl, 2,2,2-trifluoroethyl, 1,1,2,2,2-pentafluoroethyl, cyclopropyl or cyclobutyl, and in which cyclopropyl, cyclobutyl, cyclopentyl, tetrahydrofuranyl, pyrrolidinyl, tetrahydropyranyl, phenyl, furanyl, pyrazolyl, imidazolyl, triazolyl and pyridyl for their part can be substituted with 1 or 2 substituents selected independently of one another from the group fluorine, chlorine, cyano, difluoromethyl, trifluoromethyl, methyl, ethyl, oxo and hydroxy, in which oxetanyl, azetidinyl, tetrahydrofuranyl, pyrrolidinyl, tetrahydropyranyl, piperidinyl, piperazinyl, morpholinyl, phenyl, pyrazolyl, oxazolyl, thiazolyl, triazolyl, oxadiazolyl, thiadiazolyl, pyridyl and pyrimidinyl can be substituted with 1 or 2 substituents selected independently of one another from the group fluorine, difluoromethyl, trifluoromethyl, methyl, ethyl, oxo, azetidinyl and pyrrolidinyl, or $R^5$ and $R^6$ form, together with the nitrogen atom to which they are bound, an azetidinyl, pyrrolidinyl, imidazolidinyl, piperidinyl, dihydropiperidinyl, piperazinyl, morpholinyl, pyrazolyl or imidazolyl ring, in which the azetidinyl, pyrrolidinyl, imidazolidinyl, piperidinyl, dihydropiperidinyl, piperazinyl, morpholinyl, pyrazolyl and imidazolyl ring can be substituted with 1 or 2 substituents selected independently of one another from the group fluorine, cyano, difluoromethyl, trifluoromethyl, 2,2,2-trifluoroethyl, 1,1,2,2,2-pentafluoroethyl, methyl, ethyl, 1-hydroxyethyl, cyclopropyl, cyclobutyl, cyclopentyl, hydroxy, oxo, methoxy, ethoxy, difluoromethoxy and trifluoromethoxy, $R^2$ stands for 2-fluorophenyl, 2,3-difluorophenyl or 3-fluoropyrid-2-yl, and their salts, solvates and solvates of the salts.

Compounds of the present invention according to formula (I) are also preferred in which L stands for a group $\#^1$—$CR^{7A}R^{7B}$—$(CR^{8A}R^{8B})_m$—$\#^2$, wherein $\#^1$ stands for the point of attachment to the carbonyl group, $\#^2$ stands for the point of attachment to the pyrimidine ring, m stands for a number 0,
$R^{7A}$ stands for methyl,
$R^{7B}$ stands for methyl,
or
$R^{7A}$ and $R^{7B}$ together with the carbon atom to which they are bound, form a tetrahydrofuranyl ring,
the ring Q stands for a group of formula

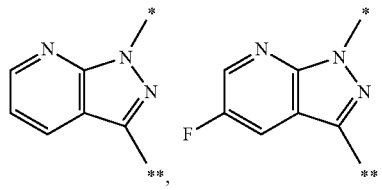

wherein
* stands for the point of attachment to —$CH_2$—$R^2$,
** stands for the point of attachment to the pyrimidine,
$R^3$ stands for —$OR^4$ or —$NR^5R^6$,
  wherein
  $R^4$ stands for ($C_1$-$C_6$)-alkyl or pyrazolyl,
    in which ($C_1$-$C_6$)-alkyl can be substituted with 1 to 3 substituents selected independently of one another from the group fluorine, trifluoromethyl, —(C=O)$_p$—$OR^9$ and —(C=O)$_p$—$NR^9R^{10}$,
      in which
      p denotes the number 0 or 1,
      $R^9$ and $R^{10}$ independently of one another stand in each case for hydrogen or methyl,
    and
    in which pyrazolyl can be substituted with 1 or 2 substituents selected independently of one another from the group fluorine, difluoromethyl, trifluoromethyl, 2,2,2-trifluoroethyl, 1,1,2,2,2-pentafluoroethyl, methyl, cyclopropyl, cyclobutyl, cyclopentyl,
  $R^5$ stands for hydrogen, methyl or ethyl,
  $R^6$ stands for ($C_1$-$C_6$)-alkyl, oxetanyl, azetidinyl, tetrahydrofuranyl, pyrrolidinyl, tetrahydropyranyl, piperidinyl, piperazinyl, morpholinyl, phenyl, pyrazolyl, oxazolyl, thiazolyl, triazolyl, oxadiazolyl, thiadiazolyl, pyridyl or pyrimidinyl,
    in which ($C_1$-$C_6$)-alkyl is substituted with 1 or 2 substituents selected independently of one another from the group fluorine, difluoromethyl, trifluoromethyl, cyclopropyl, cyclobutyl, cyclopentyl, trifluoromethoxy, —(C=O)$_p$—$OR^9$, —(C=O)$_p$—$NR^9R^{10}$, tetrahydrofuranyl, pyrrolidinyl, tetrahydropyranyl, phenyl, furanyl, pyrazolyl, imidazolyl, triazolyl and pyridyl,
      in which
      p denotes the number 0 or 1,
      $R^9$ and $R^{10}$ each stand, independently of one another, for hydrogen, methyl, ethyl, trifluoromethyl, 2,2,2-trifluoroethyl, 1,1,2,2,2-pentafluoroethyl, cyclopropyl or cyclobutyl,
      and
      in which cyclopropyl, cyclobutyl, cyclopentyl, tetrahydrofuranyl, pyrrolidinyl, tetrahydropyranyl, phenyl, furanyl, pyrazolyl, imidazolyl, triazolyl and pyridyl for their part can be substituted with 1 or 2 substituents selected independently of one another from the group fluorine, chlorine, cyano, difluoromethyl, trifluoromethyl, methyl, ethyl, oxo and hydroxy,
    in which oxetanyl, azetidinyl, tetrahydrofuranyl, pyrrolidinyl, tetrahydropyranyl, piperidinyl, piperazinyl, morpholinyl, phenyl, pyrazolyl, oxazolyl, thiazolyl, triazolyl, oxadiazolyl, thiadiazolyl, pyridyl and pyrimidinyl can be substituted with 1 or 2 substituents selected independently of one another from the group fluorine, difluoromethyl, trifluoromethyl, methyl, ethyl, oxo, azetidinyl and pyrrolidinyl,
  or
  $R^5$ and $R^6$ form, together with the nitrogen atom to which they are bound, an azetidinyl, pyrrolidinyl, imidazolidinyl, piperidinyl, dihydropiperidinyl, piperazinyl, morpholinyl, pyrazolyl or imidazolyl ring,
    in which the azetidinyl, pyrrolidinyl, imidazolidinyl, piperidinyl, dihydropiperidinyl, piperazinyl, morpholinyl, pyrazolyl and imidazolyl ring can be substituted with 1 or 2 substituents selected independently of one another from the group fluorine, cyano, difluoromethyl, trifluoromethyl, 2,2,2-trifluoroethyl, 1,1,2,2,2-pentafluoroethyl, methyl, ethyl, 1-hydroxyethyl, cyclopropyl, cyclobutyl, cyclopentyl, hydroxy, oxo, methoxy, ethoxy, difluoromethoxy and trifluoromethoxy,
$R^2$ stands for 2-fluorophenyl, 2,3-difluorophenyl or 3-fluoropyrid-2-yl,
and their salts, solvates and solvates of the salts.

Compounds of the present invention according to formula (I) are also preferred that display an action on recombinant guanylate cyclase reporter cell lines according to the test under B-2 as minimal effective concentration (MEC) of ≤3 μm and display inhibition of human phosphodiesterase 5 (PDE5) according to the test under B-6 as IC50<100 nm,
and their salts, solvates and solvates of the salts.

Compounds of the present invention according to claim 1 and examples 1-117 are especially preferred that display an action on recombinant guanylate cyclase reporter cell lines according to the test under B-2 as minimal effective concentration (MEC) of <3 μm and display inhibition of human phosphodiesterase 5 (PDE5) according to the test under B-6 as IC50<100 nm,
and their salts, solvates and solvates of the salts.

The definitions of residues given in detail in the respective combinations or preferred combinations of residues are also replaced by any definitions of residues of other combinations independently of the respective combinations stated.

Combinations of two or more of the aforementioned preferred ranges are especially preferred.

The compounds according to the invention of formula (I), in which $R^3$ stands for hydroxyl (I-A), can also be in the tautomeric keto form (I'-A) (see Scheme 7 below); both tautomeric forms are expressly covered by the present invention.

Scheme 7

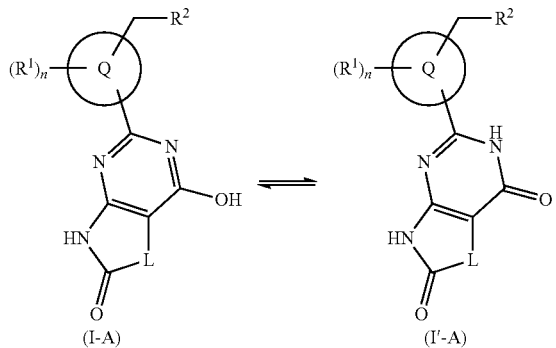

The invention further relates to a method of production of the compounds according to the invention of formula (I), characterized in that a compound of formula (II)

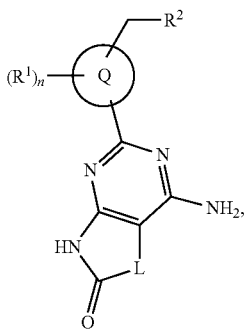

(II)

in which n, L, Q, R$^1$ and R$^2$ have the respective meanings given above,
is converted in an inert solvent with iso-pentyl nitrite and a halogen equivalent to a compound of formula (III)

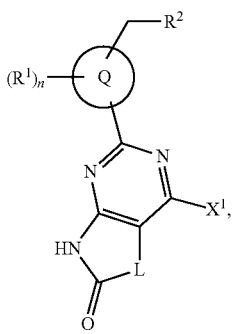

(III)

in which n, L, Q, R$^1$ and R$^2$ have the respective meanings given above and
X$^1$ stands for chlorine, bromine or iodine
and this is then reacted in an inert solvent optionally in the presence of a suitable base with a compound of formula (IV)

R$^3$—H    (IV), in which R$^3$ has the meaning given above,
to a compound of formula (I)

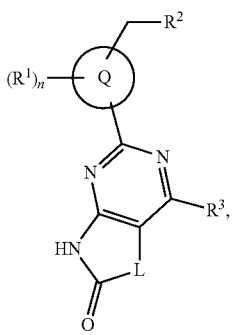

(I)

in which n, L, Q, R$^1$, R$^2$ and R$^3$ have the respective meanings given above,
and optionally the resultant compounds of formula (I) are converted optionally with the corresponding (i) solvents and/or (ii) acids or bases to their solvates, salts and/or solvates of the salts.

The process step (II)→(III) takes place with or without solvent. All organic solvents that are inert under the reaction conditions are suitable as solvent. The preferred solvent is dimethoxyethane.

The reaction (II)→(III) generally takes place in a temperature range from +20° C. to +100° C., preferably in the range from +50° C. to +100° C., optionally in a microwave. The reaction can be carried out at normal, increased or reduced pressure (e.g. in the range from 0.5 to 5 bar). It is generally carried out at normal pressure.

For example diiodomethane, a mixture of caesium iodide, iodine and copper(I) iodide or copper(II) bromide are suitable as halogen source in the reaction (II)→(III).

Inert solvents for the process step (III)+(IV)→(I) are for example ethers such as diethyl ether, dioxane, dimethoxyethane, tetrahydrofuran, glycol dimethyl ether or diethylene glycol dimethyl ether, hydrocarbons such as benzene, xylene, toluene, hexane, cyclohexane or petroleum fractions, or other solvents such as dimethylformamide (DMF), dimethylsulphoxide (DMSO), N,N'-dimethylpropylene urea (DMPU), N-methylpyrrolidone (NMP), pyridine, acetonitrile or sulpholane. It is also possible to use mixtures of the aforementioned solvents. NMP is preferred.

In the case when R$^3$=—OR$^4$, the reaction (III)+(IV)→(I) preferably takes place without solvent.

In the case when R$^3$=—OR$^4$, the reaction (III)+(IV)→(I) takes place in the presence of a suitable copper catalyst, for example copper(I) iodide, with addition of 3,4,7,8-tetramethyl-1,10-phenanthroline, and a suitable base, for example alkaline-earth carbonates such as lithium, sodium, potassium, calcium or caesium carbonate, preferably caesium carbonate.

Alternatively, in the case when R$^3$=—OR$^4$, the compounds of formula (I) can also be prepared under Mitsunobu conditions [see: a) Hughes, D. L. "The Mitsunobu reaction," *Organic Reactions*; John Wiley & Sons, Ltd, 1992, Vol. 42, p. 335. b) Hughes, D. L. *Org. Prep. Proceed. Int.* 1996, 28, 127.] starting from a compound of formula (I-A)

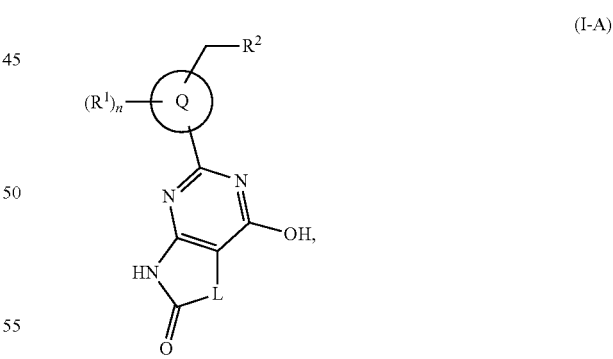

(I-A)

in which n, L, Q, R$^1$ and R$^2$ have the respective meanings given above.

The Mitsunobu reaction takes place herein using triphenyl phosphine, or tri-n-butylphosphine, 1,2-bis(diphenylphosphino)ethane (DPPE), diphenyl(2-pyridyl)phosphine (Ph2P-Py), (p-dimethylaminophenyl)diphenylphosphine (DAP-DP), Tris(4-dimethylaminophenyl)-phosphine (Tris-DAP) and a suitable dialkyl azodicarboxylate, for example diethyl azodicarboxylate (DEAD), diisopropyl azodicarboxylate (DIAD), di-tert-butyl azodicarboxylate, N,N,N',N'-tetramethyl azodicarboxamide (TMAD), 1,1'-(azodicarbonyl)-dipiperidine (ADDP) or 4,7-dimethyl-3,5,7-hexahydro-1,2,4,7-tetrazocin-3,8-dione (DHTD). Preferably triphenyl phosphine and diisopropyl azodicarboxylate (DIAD) are used, or a suitable azodicarbonamide, for example N,N,N',N'-tetramethyldiazene-1,2-dicarboxamide.

Inert solvents for the Mitsunobu reaction (I-A)+(IV)→(I) are for example ethers such as tetrahydrofuran, diethyl ether, hydrocarbons such as benzene, toluene, xylene, halohydrocarbons such as dichloromethane, dichloroethane or other solvents such as acetonitrile, DMF or NMP. It is also possible to use mixtures of the aforementioned solvents. THF is preferably used.

The Mitsunobu reaction (III)+(IV)→(I) generally takes place in a temperature range from −78° C. to +180° C., preferably at 0° C. to +50° C., optionally in a microwave. The reactions can be carried out at normal, increased or reduced pressure (e.g. from 0.5 to 5 bar).

Alternatively, in the case when $R^3$=—$OR^4$, the compounds of formula (I) can also be prepared under alkylation conditions starting from a compound of formula (I-A). For this, an alkyl halide, preferably alkyl iodide, is reacted with (I-A) with addition of a base in an inert solvent.

Suitable bases for the process step (I-A)→(I) are the usual inorganic or organic bases. These preferably include alkali hydroxides, for example lithium, sodium or potassium hydroxide, alkali or alkaline-earth carbonates such as lithium, sodium, potassium, calcium or caesium carbonate, alkali alcoholates such as sodium or potassium methanolate, sodium or potassium ethanolate or sodium or potassium tert.-butylate, alkali hydrides such as sodium or potassium hydride or amides such as sodium amide, lithium or potassium bis(trimethylsilyl)amide or lithium diisopropylamide. Caesium carbonate is preferably used.

Inert solvents are for example ethers such as tetrahydrofuran, diethyl ether, hydrocarbons such as benzene, toluene, xylene, and other solvents such as DMF or NMP. It is also possible to use mixtures of the aforementioned solvents. DMF is preferably used.

The alkylation reaction generally takes place in a temperature range from −78° C. to +180° C., preferably at 0° C. to +130° C., optionally in a microwave. The reactions can be carried out at normal, increased or reduced pressure (e.g. from 0.5 to 5 bar).

In the case when $R^3$=—$NR^5R^6$, if $R^5$ and $R^6$, together with the nitrogen atom to which they are bound, form a 5- or 6-membered heteroaryl, which can be substituted in the range of meanings stated above, the reaction (III)+(IV)→(I) takes place in the presence of a suitable copper catalyst, for example copper(I) oxide, with addition of 2-hydroxybenzaldehyde-oxime, and a suitable base, for example alkaline-earth carbonates such as lithium, sodium, potassium, calcium or caesium carbonate, preferably caesium carbonate.

The reaction (III)+(IV)→(I) is generally carried out in a temperature range from +20° C. to +200° C., preferably at +150° C. to +200° C., preferably in a microwave. The reaction can take place at normal, increased or reduced pressure (e.g. from 0.5 to 5 bar).

The method of production described can be illustrated for example by the following synthesis scheme (Scheme 1):

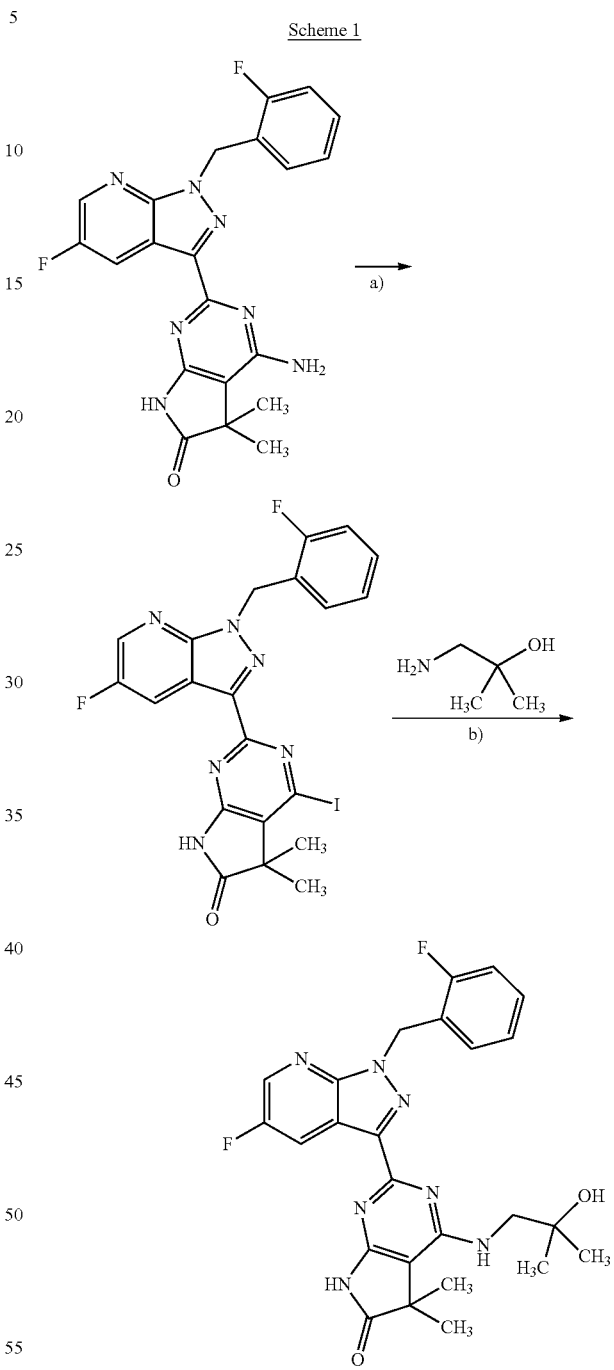

[a]: diiodomethane, isopentyl nitrite; b): NMP, microwave, 150° C.].

Compounds of formula (I-A) are obtained as by-products in the production of the compounds of formula (III).

Compounds of formula (I-A) can alternatively also be obtained starting from compounds of formula (V) by reaction with compounds of formula (VIII)

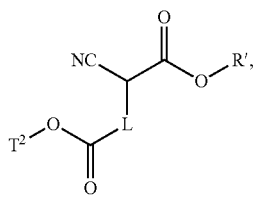

(VIII)

in which L has the meaning given above,
T² stands for (C₁-C₄)-alkyl and
R' stands for (C₁-C₄)-alkyl,
as described e.g. in Foeldi, et al., Chemische Berichte, 1942, vol. 75, p. 760.

Compounds of formula (I-A) can also be prepared in another alternative method starting from compounds of formula (II) by reaction with nitrites in acids, optionally with addition of water. Sodium nitrite in a mixture of trifluoroacetic acid and water is preferred.

The reaction (II))→(I-A) is generally carried out in a temperature range from −15° C. to +70° C., preferably at 0° C. to +40° C., with addition of the nitrite in portions. The reaction can take place at normal, increased or reduced pressure (e.g. from 0.5 to 5 bar).

The method of production described above can be illustrated for example by the following synthesis scheme (Scheme 2):

Scheme 2

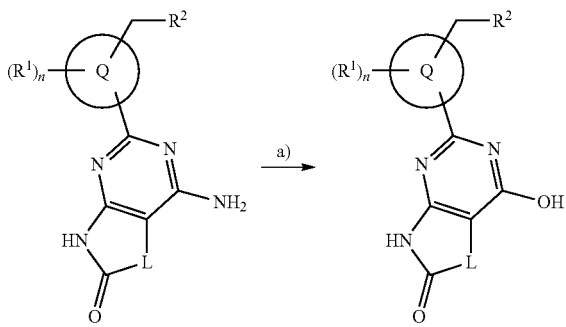

[a]: sodium nitrite, trifluoroacetic acid, water, 0° C.-RT].

The compounds of formula (II) are known from the literature (see e.g. WO 2010/065275, WO 2011/115804 and WO 2011/149921) or can be produced by analogy with methods known from the literature.

The compounds of formula (II) can be produced by reacting a compound of formula (V)

(V)

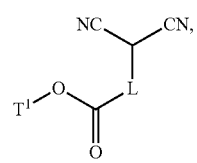

in which n, Q¹, R¹ and R² have the respective meanings given above, in an inert solvent in the presence of a suitable base with a compound of formula (VI)

(VI)

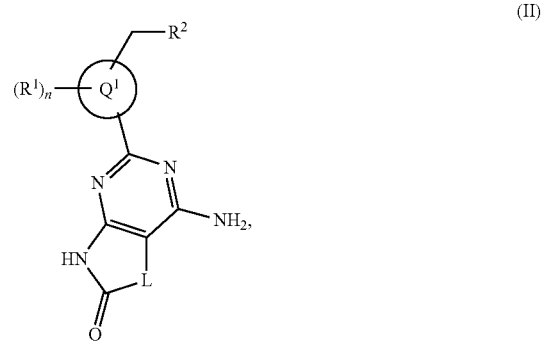

in which L has the meaning given above and
T¹ stands for (C₁-C₄)-alkyl,
to a compound of formula (II)

(II)

in which n, L, Q¹, R¹ and R² have the respective meanings given above.

Inert solvents for the process step (V)+(VI)→(II) are for example alcohols such as methanol, ethanol, n-propanol, isopropanol, n-butanol or tert.-butanol, ethers such as diethyl ether, dioxane, dimethoxyethane, tetrahydrofuran, glycol dimethyl ether or diethylene glycol dimethyl ether, hydrocarbons such as benzene, xylene, toluene, hexane, cyclohexane or petroleum fractions, or other solvents such as dimethylformamide (DMF), dimethylsulphoxide (DMSO), N,N'-dimethylpropylene urea (DMPU), N-methylpyrrolidone (NMP), pyridine, acetonitrile, sulpholane or also water. It is also possible to use mixtures of the aforementioned solvents. tert.-Butanol or methanol is preferred.

Suitable bases for the process step (V)+(VI)→(II) are alkali hydroxides, for example lithium, sodium or potassium hydroxide, alkali carbonates such as lithium, sodium, potassium or caesium carbonate, alkali hydrogen carbonates such as sodium or potassium hydrogen carbonate, alkali alcoholates such as sodium or potassium methanolate, sodium or potassium ethanolate or potassium tert.-butylate, or organic amines such as triethylamine, diisopropyl ethylamine, pyridine, 1,8-diazabicyclo[5.4.0]undec-7-ene (DBU) or 1,5-diazabicyclo[4.3.0]non-5-ene (DBN). Potassium tert.-butylate or sodium methanolate is preferred.

The reaction (V)+(VI)→(II) is generally carried out in a temperature range from +20° C. to +150° C., preferably at +75° C. to +100° C., optionally in a microwave. The reaction can take place at normal, increased or reduced pressure (e.g. from 0.5 to 5 bar). It is generally carried out at normal pressure.

The method of production described above can be illustrated for example by the following synthesis scheme (Scheme 3):

Scheme 3
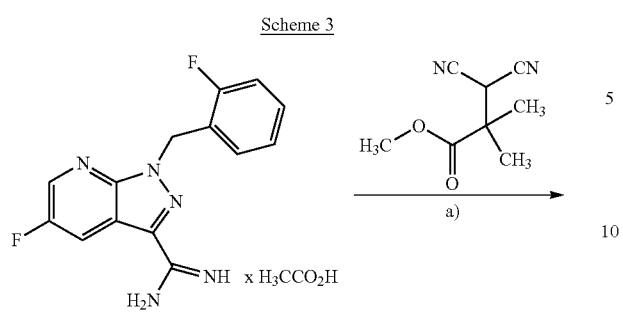
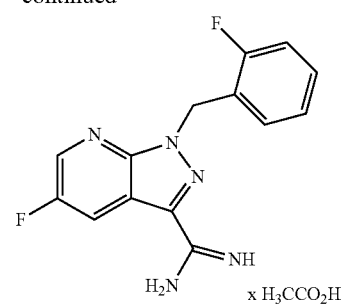
[a]: KOt-Bu, tert.-butanol].
The compounds of formula (V) are known from the literature (see e.g. WO 03/095451, example 6A) or can be prepared as in the following synthesis schemes (Schemes 4 to 6)
Scheme 4
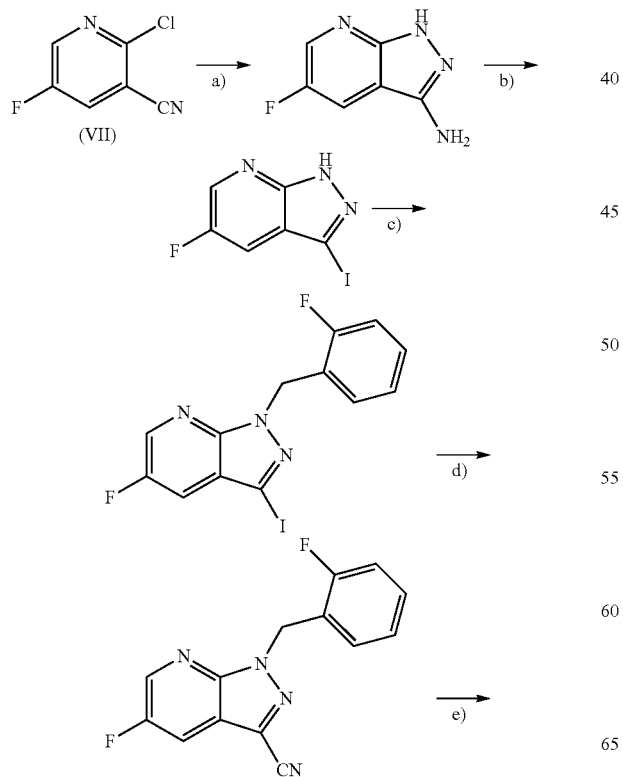
[a]: hydrazine hydrate, 1,2-ethanediol; b): isopentyl nitrite, NaI, THF; b): 2-fluorobenzyl bromide, $Cs_2CO_3$, DMF; d): CuCN, DMSO, e): 1. NaOMe, MeOH, 2. $NH_4Cl$, acetic acid].
Scheme 5
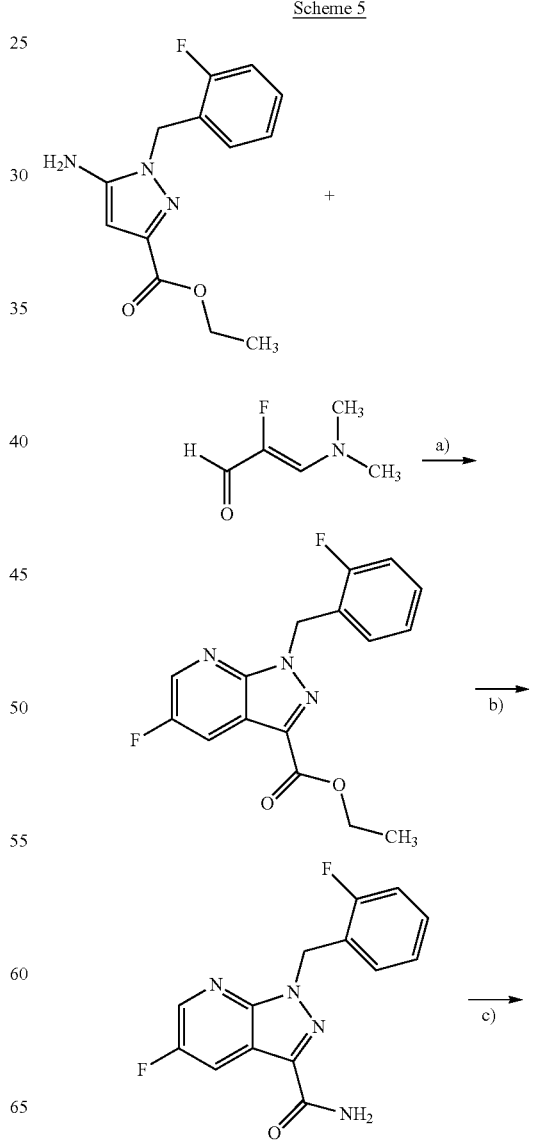

81
-continued

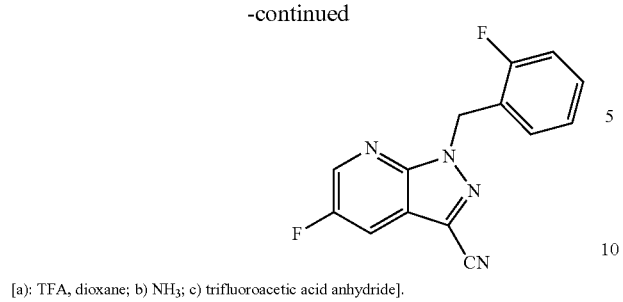

[a): TFA, dioxane; b) NH₃; c) trifluoroacetic acid anhydride].

Scheme 6

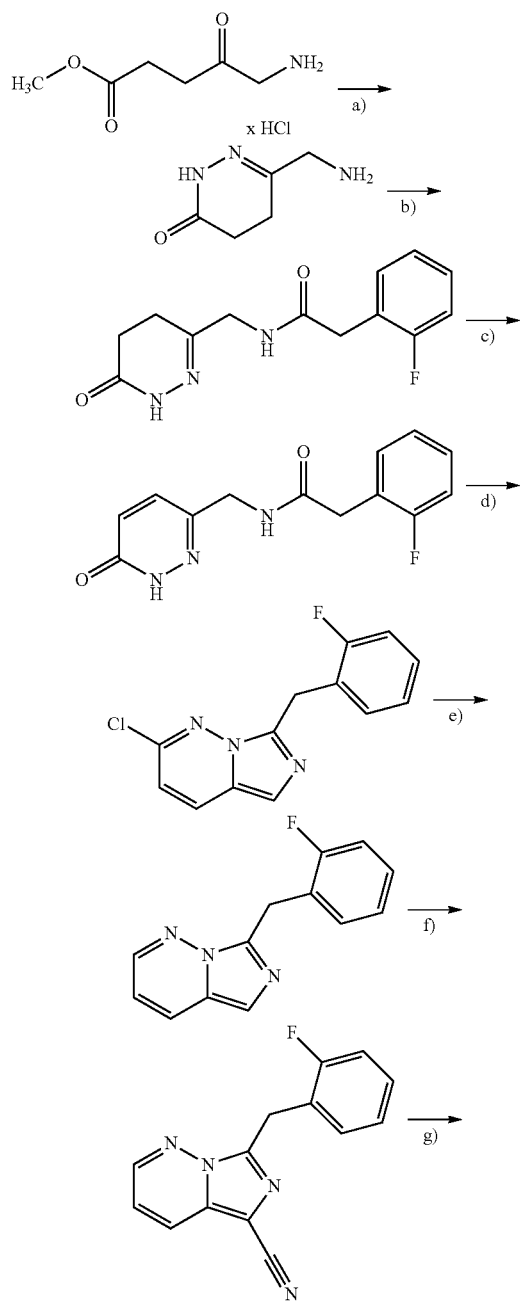

82
-continued

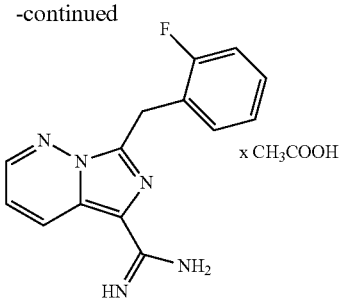

[a): hydrazine hydrate, triethylamine, ethanol, reflux; b): (2-fluorophenyl)acetyl chloride, triethylamine, acetonitrile; c): bromine, acetic acid, 50° C.; d): phosphoryl chloride, sulpholane, 100° C.; e): palladium on charcoal (5%), triethylamine, hydrogen, ethyl acetate; f): 1. N-bromosuccinimide, dichloromethane; 2. Copper(I) cyanide, DMSO, 170° C.; g): 1. Sodium methanolate, methanol, 2. NH₄Cl₄, acetic acid, reflux].

The compound of formula (VII) is known from the literature [cf. e.g. Winn M., *J. Med. Chem.* 1993, 36, 2676-7688; EP 634 413-A1; CN 1613849-A; EP 1626045-A1; WO 2009/018415], can be prepared by analogy with methods known from the literature or as shown in the following synthesis scheme (Scheme 7):

Scheme 7

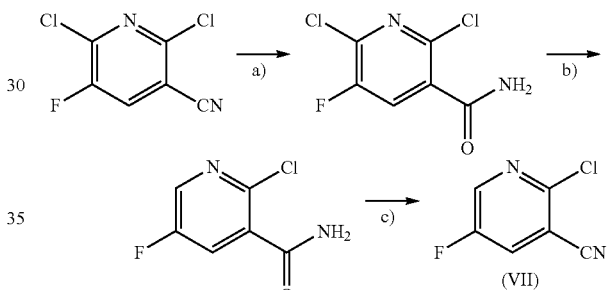

[a): sulphuric acid; b): zinc, methanol, glacial acetic acid; c): trifluoroacetic acid anhydride, dichloromethane].

The compounds of formula (IV) and (VI) are commercially available, known from the literature or can be prepared by analogy with methods known from the literature.

The compounds according to the invention act as potent stimulators of soluble guanylate cyclase and inhibitors of phosphodiesterase-5, possess valuable pharmacological properties, and have an improved therapeutic profile, for example with respect to their in-vivo properties and/or their pharmacokinetic behaviour and/or metabolic profile. They are therefore suitable for treating and/or preventing diseases in humans and animals.

The compounds according to the invention bring about vessel relaxation and inhibition of thrombocyte aggregation and lead to a lowering of blood pressure and to an increase in coronary blood flow. These effects are due to direct stimulation of soluble guanylate cyclase and an increase in intracellular cGMP. Moreover, the compounds according to the invention intensify the action of substances that raise the cGMP level, for example EDRF (endothelium-derived relaxing factor), NO donors, protoporphyrin IX, arachidonic acid or phenylhydrazine derivatives.

The compounds according to the invention are suitable for treating and/or preventing cardiovascular, pulmonary, thromboembolic and fibrotic diseases.

The compounds according to the invention can therefore be used in medicinal products for treating and/or preventing cardiovascular diseases, for example high blood pressure (hypertension), resistant hypertension, acute and chronic heart failure, coronary heart disease, stable and unstable angina pectoris, peripheral and cardiac vascular diseases, arrhythmias, disturbances of atrial and ventricular rhythm and conduction disturbances, for example atrioventricular blocks of degree I-III (AVB I-III), supraventricular tachyarrhythmia, atrial fibrillation, atrial flutter, ventricular fibrillation, ventricular flutter, ventricular tachyarrhythmia, torsade-de-pointes tachycardia, atrial and ventricular extrasystoles, AV-junction extrasystoles, sick-sinus syndrome, syncopes, AV-node reentry tachycardia, Wolff-Parkinson-White syndrome, acute coronary syndrome (ACS), autoimmune heart diseases (pericarditis, endocarditis, valvulitis, aortitis, cardiomyopathies), shock such as cardiogenic shock, septic shock and anaphylactic shock, aneurysms, Boxer cardiomyopathy (premature ventricular contraction (PVC)), for treating and/or preventing thromboembolic diseases and ischaemias such as myocardial ischaemia, myocardial infarction, stroke, cardiac hypertrophy, transient ischaemic attacks, preeclampsia, inflammatory cardiovascular diseases, spasms of the coronary arteries and peripheral arteries, development of oedema, for example pulmonary oedema, cerebral oedema, renal oedema or oedema due to heart failure, peripheral perfusion disturbances, reperfusion injury, arterial and venous thromboses, microalbuminuria, myocardial insufficiency, endothelial dysfunction, for preventing restenoses such as after thrombolysis therapies, percutaneous transluminal angioplasty (PTA), transluminal coronary angioplasty (PTCA), heart transplant and bypass operations, and micro- and macrovascular damage (vasculitis), increased level of fibrinogen and of low-density LDL and increased concentrations of plasminogen activator inhibitor 1 (PAI-1), and for treating and/or preventing erectile dysfunction and female sexual dysfunction.

In the sense of the present invention, the term heart failure comprises both acute and chronic manifestations of heart failure, as well as more specific or related forms of disease such as acute decompensated heart failure, right ventricular failure, left ventricular failure, total heart failure, ischaemic cardiomyopathy, dilatated cardiomyopathy, hypertrophic cardiomyopathy, idiopathic cardiomyopathy, congenital heart defects, heart failure with valvular defects, mitral valve stenosis, mitral valve insufficiency, aortic valve stenosis, aortic valve insufficiency, tricuspid stenosis, tricuspid insufficiency, pulmonary valve stenosis, pulmonary valve insufficiency, combined valvular defects, heart muscle inflammation (myocarditis), chronic myocarditis, acute myocarditis, viral myocarditis, diabetic heart failure, alcoholic cardiomyopathy, storage cardiomyopathies, diastolic heart failure and systolic heart failure and acute phases of exacerbation of existing chronic heart failure (worsening heart failure).

Furthermore, the compounds according to the invention can also be used for treating and/or preventing arteriosclerosis, disturbances of lipid metabolism, hypolipoproteinaemias, dyslipidaemias, hypertriglyceridaemias, hyperlipidaemias, hypercholesterolaemias, abetalipoproteinaemia, sitosterolaemia, xanthomatosis, Tangier disease, adiposity, obesity, and combined hyperlipidaemias and metabolic syndrome.

Moreover, the compounds according to the invention can be used for treating and/or preventing primary and secondary Raynaud phenomenon, microcirculation disturbances, claudication, peripheral and autonomic neuropathies, diabetic microangiopathies, diabetic retinopathy, diabetic limb ulcers, gangrene, CREST syndrome, erythematous disorders, onychomycosis, rheumatic diseases and for promoting wound healing.

Furthermore, the compounds according to the invention are suitable for treating urological diseases, for example benign prostatic syndrome (BPS), benign prostatic hyperplasia (BPH), benign prostatic enlargement (BPE), bladder outlet obstruction (BOO), lower urinary tract syndromes (LUTS, including feline urological syndrome (FUS)), diseases of the urogenital system including neurogenic overactive bladder (OAB) and (IC), urinary incontinence (UI) for example mixed, urge, stress, or overflow incontinence (MUI, UUI, SUI, OUI), pelvic pains, benign and malignant diseases of the organs of the male and female urogenital system.

Furthermore, the compounds according to the invention are suitable for treating and/or preventing kidney diseases, in particular acute and chronic renal insufficiency, and acute and chronic renal failure. In the sense of the present invention, the term renal insufficiency comprises both acute and chronic manifestations of renal insufficiency, as well as underlying or related kidney diseases such as renal hypoperfusion, intradialytic hypotension, obstructive uropathy, glomerulopathies, glomerulonephritis, acute glomerulonephritis, glomerulosclerosis, tubulointerstitial diseases, nephropathic diseases such as primary and congenital kidney disease, nephritis, immunological kidney diseases such as kidney transplant rejection, immune complex-induced kidney diseases, nephropathy induced by toxic substances, contrast medium-induced nephropathy, diabetic and non-diabetic nephropathy, pyelonephritis, renal cysts, nephrosclerosis, hypertensive nephrosclerosis and nephrotic syndrome, which can be characterized diagnostically for example by abnormally reduced creatinine and/or water excretion, abnormally increased blood concentrations of urea, nitrogen, potassium and/or creatinine, altered activity of renal enzymes such as e.g. glutamyl synthetase, altered urine osmolarity or urine volume, increased microalbuminuria, macroalbuminuria, lesions of glomeruli and arterioles, tubular dilatation, hyperphosphataemia and/or need for dialysis. The present invention also comprises the use of the compounds according to the invention for treating and/or preventing sequelae of renal insufficiency, for example pulmonary oedema, heart failure, uraemia, anaemia, electrolyte disturbances (e.g. hyperkalaemia, hyponatraemia) and disturbances in bone and carbohydrate metabolism.

Furthermore, the compounds according to the invention are also suitable for treating and/or preventing asthmatic diseases, pulmonary arterial hypertension (PAH) and other forms of pulmonary hypertension (PH), comprising pulmonary hypertension associated with left ventricular disease, HIV, sickle cell anaemia, thromboembolism (CTEPH), sarcoidosis, COPD or pulmonary fibrosis, chronic obstructive pulmonary disease (COPD), acute respiratory distress syndrome (ARDS), acute lung injury (ALI), alpha-1-antitrypsin deficiency (AATD), pulmonary fibrosis, pulmonary emphysema (e.g. smoking-induced pulmonary emphysema) and cystic fibrosis (CF).

The compounds described in the present invention are also active substances for combating diseases in the central nervous system that are characterized by disturbances of the NO/cGMP system. In particular, they are suitable for improving perception, capacity for concentration, capacity for learning or memory performance after cognitive disturbances, such as occur in particular in situations/diseases/syndromes such as mild cognitive impairment, age-related learning and memory disturbances, age-related memory loss, vascular dementia, head injury, stroke, post-stroke dementia, posttraumatic head injury, general disturbances of concentration, disturbances of concentration in children with learning and memory problems, Alzheimer's disease, Lewy body dementia, dementia with frontal lobe degeneration including Pick's syndrome, Parkinson's disease, progressive nuclear palsy, dementia with corticobasal degeneration, amyotrophic lateral sclerosis (ALS), Huntington's disease, demyelination, multiple sclerosis, thalamic degeneration, Creutzfeldt-Jakob dementia, HIV-dementia, schizophrenia with dementia or Korsakoff psychosis. They are also suitable for treating and/or preventing diseases of the central nervous system such as anxiety, tension and depression, CNS-related sexual dysfunctions and sleep disturbances and for controlling pathological eating disorders and use of luxury foods and addictive drugs.

Furthermore, the compounds according to the invention are also suitable for controlling cerebral perfusion and are effective agents for combating migraines. They are also suitable for preventing and combating the consequences of cerebral infarctions (apoplexia cerebri) such as stroke, cerebral ischaemias and head injury. The compounds according to the invention can also be used for combating pain states and tinnitus.

In addition, the compounds according to the invention possess anti-inflammatory action and can therefore be used as anti-inflammatory agents for treating and/or preventing sepsis (SIRS), multiple organ failure (MODS, MOF), inflammatory diseases of the kidney, chronic intestinal inflammations (IBD, Crohn's disease, UC), pancreatitis, peritonitis, rheumatoid diseases, inflammatory skin diseases and inflammatory eye diseases.

Moreover, the compounds according to the invention can also be used for treating and/or preventing autoimmune diseases.

Furthermore, the compounds according to the invention are suitable for treating and/or preventing fibrotic diseases of the internal organs, for example of the lung, heart, kidney, bone marrow and in particular of the liver, and dermatological fibroses and fibrotic diseases of the eye. In the sense of the present invention, the term fibrotic diseases comprises in particular the following terms: hepatic fibrosis, hepatic cirrhosis, pulmonary fibrosis, endomyocardial fibrosis, nephropathy, glomerulonephritis, interstitial renal fibrosis, fibrotic lesions as a consequence of diabetes, bone marrow fibrosis and similar fibrotic diseases, scleroderma, morphea, keloids, hypertrophic scars (including after surgery), naevi, diabetic retinopathy, proliferative vitreoretinopathy and connective tissue diseases (e.g. sarcoidosis).

Furthermore, the compounds according to the invention are suitable for combating postoperative scarring, e.g. as a result of glaucoma operations.

The compounds according to the invention can also be used cosmetically for ageing and keratinizing skin.

Moreover, the compounds according to the invention are suitable for treating and/or preventing hepatitis, neoplasms, osteoporosis, glaucoma and gastroparesis.

The present invention further relates to the use of the compounds according to the invention for treating and/or preventing diseases, in particular the aforementioned diseases.

The present invention further relates to the use of the compounds according to the invention for treating and/or preventing heart failure, angina pectoris, hypertension, pulmonary hypertension, ischaemias, vascular diseases, renal insufficiency, thromboembolic diseases, fibrotic diseases and arteriosclerosis.

The present invention further relates to the compounds according to the invention for use in a method of treating and/or preventing heart failure, angina pectoris, hypertension, pulmonary hypertension, ischaemias, vascular diseases, renal insufficiency, thromboembolic diseases, fibrotic diseases and arteriosclerosis.

The present invention further relates to the use of the compounds according to the invention for producing a medicinal product for treating and/or preventing diseases, in particular the aforementioned diseases.

The present invention further relates to the use of the compounds according to the invention for producing a medicinal product for treating and/or preventing heart failure, angina pectoris, hypertension, pulmonary hypertension, ischaemias, vascular diseases, renal insufficiency, thromboembolic diseases, fibrotic diseases and arteriosclerosis.

The present invention further relates to a method of treating and/or preventing diseases, in particular the aforementioned diseases, using an effective amount of at least one of the compounds according to the invention.

The present invention further relates to a method of treating and/or preventing heart failure, angina pectoris, hypertension, pulmonary hypertension, ischaemias, vascular diseases, renal insufficiency, thromboembolic diseases, fibrotic diseases and arteriosclerosis, using an effective amount of at least one of the compounds according to the invention.

The compounds according to the invention can be used alone or in combination with other active substances if necessary. The present invention further relates to medicinal products containing at least one of the compounds according to the invention and one or more further active substances, in particular for treating and/or preventing the aforementioned diseases. As suitable combination active substances, we may mention for example and preferably:

- organic nitrates and NO-donors, for example sodium nitroprusside, nitroglycerin, isosorbide mononitrate, isosorbide dinitrate, molsidomine or SIN-1, and inhalational NO;
- compounds that inhibit the degradation of cyclic guanosine monophosphate (cGMP), for example inhibitors of phosphodiesterases (PDE) 1, 2 and/or 5, in particular PDE-5 inhibitors such as sildenafil, vardenafil and tadalafil;
- antithrombotic agents, for example and preferably from the group of platelet aggregation inhibitors, anticoagulants or profibrinolytic substances;
- active substances for lowering blood pressure, for example and preferably from the group of calcium antagonists, angiotensin AII antagonists, ACE inhibitors, endothelin antagonists, renin inhibitors, alpha-blockers, beta-blockers, mineralocorticoid receptor antagonists and diuretics; and/or
- active substances that alter fat metabolism, for example and preferably from the group of thyroid receptor agonists, cholesterol synthesis inhibitors such as for example and preferably HMG-CoA-reductase or squalene synthesis inhibitors, ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbers, bile acid reabsorption inhibitors and lipoprotein(a) antagonists.

Antithrombotic agents are preferably to be understood as compounds from the group of platelet aggregation inhibitors, anticoagulants or profibrinolytic substances.

In a preferred embodiment of the invention, the compounds according to the invention are administered in combination with a platelet aggregation inhibitor, for example and preferably aspirin, clopidogrel, ticlopidine or dipyridamole.

In a preferred embodiment of the invention, the compounds according to the invention are administered in combination with a thrombin inhibitor, for example and preferably ximelagatran, dabigatran, melagatran, bivalirudin or Clexane.

In a preferred embodiment of the invention, the compounds according to the invention are administered in combination with a GPIIb/IIIa antagonist, for example and preferably tirofiban or abciximab.

In a preferred embodiment of the invention, the compounds according to the invention are administered in combination with a factor Xa inhibitor, for example and preferably rivaroxaban (BAY 59-7939), DU-176b, apixaban, otamixaban, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or a low molecular weight (LMW) heparin derivative.

In a preferred embodiment of the invention, the compounds according to the invention are administered in combination with a vitamin K antagonist, for example and preferably coumarin.

The agents for lowering blood pressure are preferably to be understood as compounds from the group of calcium antagonists, angiotensin AII antagonists, ACE inhibitors, endothelin antagonists, renin inhibitors, alpha-blockers, beta-blockers, mineralocorticoid-receptor antagonists and diuretics.

In a preferred embodiment of the invention, the compounds according to the invention are administered in combination with a calcium antagonist, for example and preferably nifedipine, amlodipine, verapamil or diltiazem.

In a preferred embodiment of the invention, the compounds according to the invention are administered in combination with an alpha-1-receptor blocker, for example and preferably prazosin.

In a preferred embodiment of the invention, the compounds according to the invention are administered in combination with a beta-blocker, for example and preferably propranolol, atenolol, timolol, pindolol, alprenolol, oxprenolol, penbutolol, bupranolol, metipranolol, nadolol, mepindolol, carazolol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an angiotensin AII antagonist, for example and preferably losartan, candesartan, valsartan, telmisartan or embursatan.

In a preferred embodiment of the invention, the compounds according to the invention are administered in combination with an ACE inhibitor, for example and preferably enalapril, captopril, lisinopril, ramipril, delapril, fosinopril, quinopril, perindopril or trandopril.

In a preferred embodiment of the invention, the compounds according to the invention are administered in combination with an endothelin antagonist, for example and preferably bosentan, darusentan, ambrisentan or sitaxsentan.

In a preferred embodiment of the invention, the compounds according to the invention are administered in combination with a renin inhibitor, for example and preferably aliskiren, SPP-600 or SPP-800.

In a preferred embodiment of the invention, the compounds according to the invention are administered in combination with a mineralocorticoid-receptor antagonist, for example and preferably spironolactone or eplerenone.

In a preferred embodiment of the invention, the compounds according to the invention are administered in combination with a loop diuretic, for example furosemide, torasemide, bumetanide and piretanide, with potassium-sparing diuretics for example amiloride and triamterene, with aldosterone antagonists, for example spironolactone, potassium canrenoate and eplerenone and thiazide diuretics, for example hydrochlorothiazide, chlorthalidone, xipamide, and indapamide.

Agents altering fat metabolism are preferably to be understood as compounds from the group of CETP inhibitors, thyroid receptor agonists, cholesterol synthesis inhibitors such as HMG-CoA-reductase or squalene synthesis inhibitors, the ACAT inhibitors, MTP inhibitors, PPAR-alpha, PPAR-gamma and/or PPAR-delta agonists, cholesterol-absorption inhibitors, polymeric bile acid adsorbers, bile acid reabsorption inhibitors, lipase inhibitors and the lipoprotein (a) antagonists.

In a preferred embodiment of the invention, the compounds according to the invention are administered in combination with a CETP inhibitor, for example and preferably dalcetrapib, BAY 60-5521, anacetrapib or CETP-vaccine (CETi-1).

In a preferred embodiment of the invention, the compounds according to the invention are administered in combination with a thyroid receptor agonist, for example and preferably D-thyroxin, 3,5,3'-triiodothyronin (T3), CGS 23425 or axitirome (CGS 26214).

In a preferred embodiment of the invention, the compounds according to the invention are administered in combination with a HMG-CoA-reductase inhibitor from the class of statins, for example and preferably lovastatin, simvastatin, pravastatin, fluvastatin, atorvastatin, rosuvastatin or pitavastatin.

In a preferred embodiment of the invention, the compounds according to the invention are administered in combination with a squalene synthesis inhibitor, for example and preferably BMS-188494 or TAK-475.

In a preferred embodiment of the invention, the compounds according to the invention are administered in combination with an ACAT inhibitor, for example and preferably avasimibe, melinamide, pactimibe, eflucimibe or SMP-797.

In a preferred embodiment of the invention, the compounds according to the invention are administered in combination with an MTP inhibitor, for example and preferably implitapide, BMS-201038, R-103757 or JTT-130.

In a preferred embodiment of the invention, the compounds according to the invention are administered in combination with a PPAR-gamma agonist, for example and preferably pioglitazone or rosiglitazone.

In a preferred embodiment of the invention, the compounds according to the invention are administered in combination with a PPAR-delta agonist, for example and preferably GW 501516 or BAY 68-5042.

In a preferred embodiment of the invention, the compounds according to the invention are administered in combination with a cholesterol-absorption inhibitor, for example and preferably ezetimibe, tiqueside or pamaqueside.

In a preferred embodiment of the invention, the compounds according to the invention are administered in combination with a lipase inhibitor, for example and preferably orlistat.

In a preferred embodiment of the invention, the compounds according to the invention are administered in combination with a polymeric bile acid adsorber, for example and preferably cholestyramine, colestipol, colesolvam, CholestaGel or colestimide.

In a preferred embodiment of the invention, the compounds according to the invention are administered in combination with a bile acid reabsorption inhibitor, for example and preferably ASBT(=IBAT) inhibitors, e.g. AZD-7806, S-8921, AK-105, BARI-1741, SC-435 or SC-635.

In a preferred embodiment of the invention, the compounds according to the invention are administered in combination with a lipoprotein(a) antagonist, for example and preferably gemcabene calcium (CI-1027) or nicotinic acid.

The present invention further relates to medicinal products that contain at least one compound according to the invention, usually together with one or more inert, non-toxic, pharmaceutically suitable excipients, and use thereof for the aforementioned purposes.

The compounds according to the invention can have systemic and/or local action. For this purpose they can be applied in a suitable way, e.g. by oral, parenteral, pulmonary, nasal, sublingual, lingual, buccal, rectal, dermal, transdermal, conjunctival, or otic administration or as implant or stent.

For these routes of application, the compounds according to the invention can be administered in suitable dosage forms.

Dosage forms functioning according to the prior art, for rapid and/or modified release of the compounds according to the invention, which contain the compounds according to the invention in crystalline and/or amorphized and/or dissolved form, e.g. tablets (uncoated or coated tablets, for example with enteric coatings or coatings with delayed dissolution or insoluble coatings, which control the release of the compound according to the invention), tablets or films/wafers that disintegrate rapidly in the oral cavity, films/lyophilizates, capsules (for example hard or soft gelatin capsules), sugar-coated pills, granules, pellets, powders, emulsions, suspensions, aerosols or solutions, are suitable for oral application.

Parenteral application can take place avoiding an absorption step (e.g. intravenous, intraarterial, intracardiac, intraspinal or intralumbar) or including absorption (e.g. intramuscular, subcutaneous, intracutaneous, percutaneous or intraperitoneal). Injection and infusion preparations in the form of solutions, suspensions, emulsions, lyophilizates or sterile powders are suitable, among others, as dosage forms for parenteral application.

Inhaled pharmaceutical forms (including powder inhalers, nebulizers), nasal drops, solutions or sprays, tablets, films/wafers or capsules for lingual, sublingual or buccal application, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, dusting powders, implants or stents for example are suitable for other routes of administration.

Oral or parenteral application is preferred, especially oral application.

The compounds according to the invention can be transformed to the aforementioned dosage forms. This can take place in a manner known per se by mixing with inert, non-toxic, pharmaceutically suitable excipients. These excipients include inter alia carriers (for example microcrystalline cellulose, lactose, mannitol), solvents (e.g. liquid polyethylene glycols), emulsifiers and dispersants or wetting agents (for example sodium dodecyl sulphate, polyoxysorbitan oleate), binders (for example polyvinylpyrrolidone), synthetic and natural polymers (for example albumin), stabilizers (e.g. antioxidants such as ascorbic acid), colorants (e.g. inorganic pigments, for example iron oxides) and taste and/or odour correctants.

In general, it has proved advantageous, in the case of parenteral application, to administer amounts of about 0.001 to 1 mg/kg, preferably about 0.01 to 0.5 mg/kg body weight to achieve effective results. For oral application, the dosage is about 0.001 to 2 mg/kg, preferably about 0.001 to 1 mg/kg body weight.

Nevertheless, it may optionally be necessary to deviate from the stated amounts, namely depending on body weight, route of application, individual response to the active substance, type of preparation and time point or interval when application takes place. Thus, in some cases it may be sufficient to use less than the aforementioned minimum amount, whereas in other cases the stated upper limit must be exceeded. When applying larger amounts, it may be advisable to distribute these in several individual doses throughout the day.

The following practical examples explain the invention. The invention is not limited to the examples.

The percentages in the following tests and examples are percentages by weight, unless stated otherwise; parts are parts by weight. Proportions of solvents, dilution ratios and concentrations for liquid/liquid solutions refer in each case to the volume.

A. EXAMPLES

Abbreviations and Acronyms:
aq. aqueous solution
calc. calculated
DCI direct chemical ionization (in MS)
DMF dimethylformamide
DMSO dimethylsulphoxide
of theor. of theoretical (referring to yield)
eq. equivalent(s)
ESI electrospray ionization (in MS)
Et ethyl
h hour(s)
HPLC high-performance liquid chromatography
HRMS high-resolution mass spectrometry
conc. concentrated
LC/MS liquid chromatography-coupled mass spectrometry
LiHMDS lithium hexamethyl disilazide
Me methyl
min minute(s)
MS mass spectrometry
NMR nuclear magnetic resonance spectrometry
Pd/C palladium on activated charcoal (10%)
Ph phenyl
qt quartet of triplet (NMR)
RT room temperature
$R_t$ retention time (in HPLC)
t-Bu tert.-butyl
TFA trifluoroacetic acid
THF tetrahydrofuran
UV ultraviolet spectrometry
v/v volume to volume ratio (of a solution)
XPHOS dicyclohexyl-(2',4',6'-triisopropylbiphenyl-2-yl)-phosphine
HPLC and LC/MS Methods:
Method 1 (LC-MS):
Instrument: Waters ACQUITY SQD UPLC system; column: Waters ACQUITY UPLC HSS T3 1.8 μ 50×1 mm; eluent A: 1 l water+0.25 ml 99% formic acid, eluent B: 1 l acetonitrile+0.25 ml 99% formic acid; gradient: 0.0 min 90% A→1.2 min 5% A→2.0 min 5% A, furnace: 50° C.; flow: 0.40 ml/min; UV-detection: 210-400 nm.
Method 2 (LC-MS):
Instrument type MS: Waters ZQ; instrument type HPLC: Agilent 1100 Series; UV DAD; column: Thermo Hypersil GOLD 3 μ 20 mm×4 mm; eluent A: 1 l water+0.5 ml 50% formic acid, eluent B: 1 l acetonitrile+0.5 ml 50% formic acid; gradient: 0.0 min 100% A→3.0 min 10% A→4.0 min 10% A, furnace: 55° C.; flow 2 ml/min; UV-detection: 210 nm.

Method 3 (LC-MS):

Instrument: Waters ACQUITY SQD UPLC system; column: Waters ACQUITY UPLC HSS T3 1.8 µ 30×2 mm; eluent A: 1 l water+0.25 ml 99% formic acid, eluent B: 1 l acetonitrile+0.25 ml 99% formic acid; gradient: 0.0 min 90% A→1.2 min 5% A→2.0 min 5% A, furnace: 50° C.; flow: 0.60 ml/min; UV-detection: 208-400 nm.

Method 4 (LC-MS):

Instrument: Micromass Quattro Premier with Waters UPLC ACQUITY; column: Thermo Hypersil GOLD 1.9 µ50×1 mm; eluent A: 1 l water+0.5 ml 50% formic acid, eluent B: 1 l acetonitrile+0.5 ml 50% formic acid; gradient: 0.0 min 97% A→0.5 min 97% A→3.2 min 5% A→4.0 min 5% A, furnace: 50° C.; flow: 0.3 ml/min; UV-detection: 210 nm.

Method 5 (LC-MS):

MS instrument: Waters SQD; HPLC instrument: Waters UPLC; column: Zorbax SB-Aq (Agilent), 50 mm×2.1 mm, 1.8 µm; eluent A: water+0.025% formic acid, eluent B: acetonitrile (ULC)+0.025% formic acid; gradient: 0.0 min 98% A-0.9 min 25% A-1.0 min 5% A-1.4 min 5% A-1.41 min 98% A-1.5 min 98% A; furnace: 40° C.; flow: 0.600 ml/min; UV-detection: DAD; 210 nm Method 6 (Prep. HPLC):

MS instrument: Waters, HPLC instrument: Waters (column Phenomenex Luna 5 µ C18(2) 100A, AXIA Tech. 50×21.2 mm, eluent A: water+0.05% formic acid, eluent B: methanol (ULC)+0.05% formic acid, with gradient, flow: 40 ml/min; UV-detection: DAD; 210-400 nm).

Method 7 (LC-MS):

MS instrument: Waters (Micromass) Quattro Micro; HPLC instrument: Agilent 1100 series; column: YMC-Triart C18 3 µ 50×3 mm; eluent A: 1 l water+0.01 mol ammonium carbonate, eluent B: 1 l acetonitrile; gradient: 0.0 min 100% A→2.75 min 5% A→4.5 min 5% A; furnace: 40° C.; flow: 1.25 ml/min; UV-detection: 210 nm.

Method 8 (LC-MS): Method: MCW_SQ-HSST3_long

Instrument: Waters ACQUITY SQD UPLC system; column: Waters ACQUITY UPLC HSS T3 1.8 µ 50×1 mm; eluent A: 1 l water+0.25 ml 99% formic acid, eluent B: 1 l acetonitrile+0.25 ml 99% formic acid; gradient: 0.0 min 95% A→6.0 min 5% A→7.5 min 5% A, furnace: 50° C.; flow: 0.35 ml/min; UV-detection: 210-400 nm.

Starting Compounds and Intermediates:

Example 1A 1-(2-Fluorobenzyl)-1H-pyrazolo[3,4-b]pyridine-3-carboximidamide hydrochloride

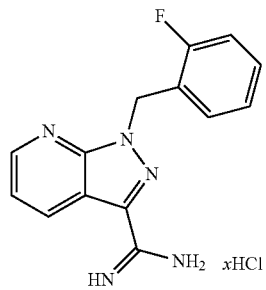 [SMILES: N=C(N)c1nn(Cc2ccccc2F)c2ncccc12]

The synthesis of this compound is described in WO 03/095451, example 6A.

Example 2A 2,6-Dichloro-5-fluoronicotinamide

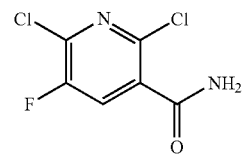 [SMILES: NC(=O)c1cc(F)c(Cl)nc1Cl]

A suspension of 25 g (130.90 mmol) of 2,6-dichloro-5-fluoro-3-cyanopyridine in conc. sulphuric acid (125 ml) was stirred for 1 h at 60-65° C. After cooling to RT, the flask contents were poured into ice water and extracted with ethyl acetate three times (100 ml each time). The combined organic phases were washed with water (100 ml) and then with saturated aqueous sodium hydrogen carbonate solution (100 ml), dried and concentrated in a rotary evaporator. The material obtained was dried under high vacuum.

Yield: 24.5 g (90% of theor.)

$^1$H-NMR (400 MHz, DMSO-d$_6$): δ=7.95 (br s, 1H), 8.11 (br s, 1H), 8.24 (d, 1H).

Example 3A

2-Chloro-5-fluoronicotinamide

44 g (210.58 mmol) of 2,6-dichloro-5-fluoronicotinamide was added at RT to a suspension of 21.9 g (335.35 mmol) of zinc in methanol (207 ml). Then acetic acid (18.5 ml) was added and it was heated under reflux for 24 h, with stirring. Then the flask contents were decanted from the zinc and ethyl acetate (414 ml) and saturated aqueous sodium hydrogen carbonate solution (414 ml) were added and stirred vigorously. Then it was filtered with suction on diatomaceous earth and washed again three times with ethyl acetate (517 ml each time). The organic phase was separated and the aqueous phase was washed with ethyl acetate (258 ml). The combined organic phases were washed once with saturated aqueous sodium hydrogen carbonate solution (414 ml), dried and concentrated by vacuum evaporation. Dichloromethane (388 ml) was added to the crystals thus obtained, and left to precipitate for 20 min. It was filtered with suction again and washed with diethyl ether and suction-dried.

Yield: 20.2 g (53% of theor.)

$^1$H-NMR (400 MHz, DMSO-d$_6$): δ=7.87 (br s, 1H), 7.99 (dd, 1H), 8.10 (br s, 1H), 8.52 (d, 1H).

Example 4A

2-Chloro-5-fluoronicotinonitrile

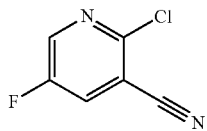

81.2 ml (582.25 mmol) of triethylamine was added to a suspension of 46.2 g (264.66 mmol) of 2-chloro-5-fluoronicotinamide in dichloromethane (783 ml) and cooled to 0° C. While stirring, 41.12 ml (291.13 mmol) of trifluoroacetic acid anhydride was slowly added dropwise and stirred for a further 1.5 h at 0° C. The reaction solution was then washed twice with saturated aqueous sodium hydrogen carbonate solution (391 ml each time), dried and concentrated by vacuum evaporation.

Yield: 42.1 g (90% of theor.).
$^{1}$H-NMR (400 MHz, DMSO-$d_6$): δ=8.66 (dd, 1H), 8.82 (d, 1H).

Example 5A

5-Fluoro-1H-pyrazolo[3,4-b]pyridin-3-amine

A suspension of 38.5 g (245.93 mmol) of 2-chloro-5-fluoronicotinonitrile in 1,2-ethanediol (380 ml) was prepared and then hydrazine hydrate (119.6 ml) was added. It was heated under reflux for 4 h, with stirring. On cooling, the product was precipitated. Water (380 ml) was added to the crystals and it was left to precipitate for 10 min at RT. Then the suspension was filtered with suction on a frit, and washed again with water (200 ml) and with cold (−10° C.) THF (200 ml). Drying over phosphorus pentoxide under high vacuum.

Yield: 22.8 g (61% of theor.)
$^{1}$H-NMR (400 MHz, DMSO-$d_6$): δ=5.54 (s, 2H), 7.96 (dd, 1H), 8.38 (m, 1H), 12.07(m, 1H).

Example 6A

5-Fluoro-3-iodo-1H-pyrazolo[3,4-b]pyridine

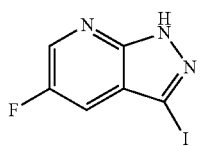 [SMILES: Fc1cnc2[nH]nc(I)c2c1]

10 g (65.75 mmol) of 5-fluoro-1H-pyrazolo[3,4-b]pyridin-3-amine was put in THF (329 ml) and cooled to 0° C. Then 16.65 ml (131.46 mmol) of boron trifluoride/diethyl ether complex was slowly added. The reaction mixture was cooled further to −10° C. Then a solution of 10.01 g (85.45 mmol) of isopentyl nitrite in THF (24.39 ml) was slowly added and stirred for a further 30 min. The mixture was diluted with cold diethyl ether (329 ml) and the resultant solid was filtered off. The resultant diazonium salt was added in portions to a cold (0° C.) solution of 12.81 g (85.45 mmol) of sodium iodide in acetone (329 ml) and the mixture was stirred for a further 30 min at RT. The reaction mixture was added to ice water (1.8 l) and was extracted twice with ethyl acetate (487 ml each time). The combined organic phases were washed with saturated aqueous sodium chloride solution (244 ml), dried, filtered and concentrated by evaporation. 12.1 g (86% purity, 60% of theor.) of the title compound was obtained as a solid. The raw product was reacted without further purification.

LC-MS (method 2): $R_t$=1.68 min
MS (ESIpos): m/z=264 [M+H]$^+$

Example 7A

5-Fluoro-1-(2-fluorobenzyl)-3-iodo-1H-pyrazolo[3,4-b]pyridine

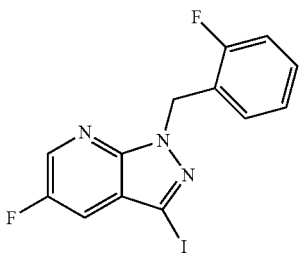 [SMILES: Fc1cnc2c(c1)c(I)nn2Cc1ccccc1F]

12.1 g (approx. 39.65 mmol) of the compound from example 6A was put in DMF (217 ml) and then 8.25 g (43.62 mmol) of 2-fluorobenzyl bromide and 14.21 g (43.62 mmol) of caesium carbonate were added. The mixture was stirred for two hours at RT. Then the reaction mixture was added to water (1.17 l) and was extracted twice with ethyl acetate (502 ml). The combined organic phases were washed with saturated aqueous sodium chloride solution (335 ml), dried, filtered and concentrated by evaporation. The residue was chromatographed on silica gel (solvent: petroleum ether/ethyl acetate 97:3) and the product fractions were concentrated by evaporation. 9.0 g (61% of theor.) of the title compound was obtained as a solid. The solid was taken up in ethyl acetate and washed with 10% aqueous sodium thiosulphate solution and then with saturated aqueous sodium chloride solution, dried and concentrated by evaporation.

LC-MS (method 2): $R_t$=2.57 min
MS (ESIpos): m/z=372 [M+H]$^+$
$^{1}$H-NMR (400 MHz, DMSO-$d_6$): δ=5.73 (s, 2H), 7.13-7.26 (m, 3H), 7.33-7.41 (m, 1H), 7.94 (dd, 1H), 8.69-8.73 (m, 1H).

Example 8A

Ethyl-5-fluoro-1-(2-fluorobenzyl)-1H-pyrazolo[3,4-b]pyridine-3-carboxylate

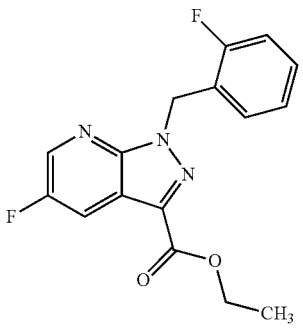 [SMILES: CCOC(=O)c1nn(Cc2ccccc2F)c2ncc(F)cc12]

13.487 g (51.228 mmol) of ethyl-5-amino-1-(2-fluorobenzyl)-1H-pyrazole-3-carboxylate (preparation described for example 20A in WO 00/06569) was put in 300 ml dioxane and 6 g (51.228 mmol) of 3-(dimethylamino)-2-fluoroacrylaldehyde (preparation described in *Justus Liebigs Annalen der Chemie* 1970; 99-107) was added at RT. Then 4.736 ml (61.473 mmol) of trifluoroacetic acid was added and the mixture was heated under reflux for 3 days, with stirring. After cooling, it was concentrated by vacuum evaporation and water and ethyl acetate were added to the residue. The phases were separated and the organic phase was washed twice with water. The combined aqueous phases were then extracted twice with ethyl acetate. The combined organic phases were dried over sodium sulphate, filtered and concentrated by vacuum evaporation. The residue (22 g) was then purified by silica gel chromatography (solvent: dichloromethane). 5.67 g (35% of theor.) of the title compound was obtained.

LC-MS (method 1): $R_t$=1.17 min
MS (ESIpos): m/z=318 [M+H]$^+$
$^1$H-NMR (400 MHz, DMSO-d$_6$): δ=1.37 (t, 3H), 4.40 (q, 2H), 5.86 (s, 2H), 7.15-7.27 (m, 3H), 7.36-7.41 (m, 1H), 8.25 (d, 1H), 8.78 (s br, 1H).

Example 9A

5-Fluoro-1-(2-fluorobenzyl)-1H-pyrazolo[3,4-b]pyridine-3-carboxamide

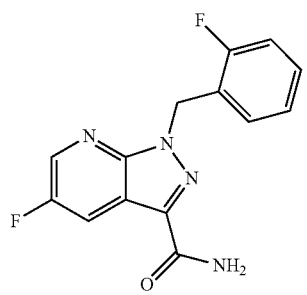 [SMILES: NC(=O)c1nn(Cc2ccccc2F)c2ncc(F)cc12]

1.00 g (3.152 mmol) of the compound obtained in example 8A was stirred in 10 ml of a 7N solution of ammonia in methanol at RT for three days. Then it was concentrated by vacuum evaporation. 908 mg (99% of theor.) of the title compound was obtained.

LC-MS (method 1): $R_t$=0.85 min
MS (ESIpos): m/z=289 [M+H]$^+$
$^1$H-NMR (400 MHz, DMSO-d$_6$): δ=5.87 (s, 2H), 7.12-7.26 (m, 3H), 7.34-7.40 (m, 1H), 7.60 (s br, 1H), 7.87 (s br, 1H), 8.28 (dd, 1H), 8.72 (dd, 1H).

Example 10A

5-Fluoro-1-(2-fluorobenzyl)-1H-pyrazolo[3,4-b]pyridine-3-carbonitrile

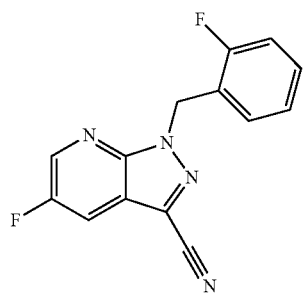 [SMILES: N#Cc1nn(Cc2ccccc2F)c2ncc(F)cc12]

Variant A:
A suspension of 16.03 g (43.19 mmol) of 5-fluoro-1-(2-fluorobenzyl)-3-iodo-1H-pyrazolo[3,4-b]pyridine (example 7A) and 4.25 g (47.51 mmol) of copper(I) cyanide was put in DMSO (120 ml) and stirred for 2 h at 150° C. After cooling, the flask contents were cooled to approx. 40° C., poured into a solution of conc ammonia water (90 ml) and water (500 ml), ethyl acetate (200 ml) was added and it was left to precipitate for a short time. The aqueous phase was separated and extracted two more times with ethyl acetate (200 ml each time). The combined organic phases were washed twice with 10% aqueous sodium chloride solution (100 ml each time), dried and concentrated by vacuum evaporation. The raw product was reacted without further purification.

Yield: 11.1 g (91% of theor.)

Variant B:
900 mg (3.122 mmol) of the compound obtained in example 9A was dissolved in THF (14 ml) and 0.646 ml (7.993 mmol) of pyridine was added. Then, while stirring, 1.129 ml (7.993 mmol) of trifluoroacetic acid anhydride was slowly added dropwise and then it was stirred overnight at RT.

Then the reaction mixture was poured into water and extracted three times with ethyl acetate. The combined organic phases were extracted with saturated aqueous sodium hydrogen carbonate solution and 1N hydrochloric acid and then washed with saturated aqueous sodium chloride solution. The organic phase was dried over sodium sulphate, filtered and concentrated by evaporation. 850 mg (99% of theor.) of the title compound was obtained.

LC-MS (method 1): $R_t$=1.06 min
MS (ESIpos): m/z=271 [M+H]$^+$
$^1$H-NMR (400 MHz, DMSO-d$_6$): δ=5.87 (s, 2H), 7.17-7.42 (m, 4H), 8.52 (dd, 1H), 8.87 (dd, 1H).

Example 11A

5-Fluoro-1-(2-fluorobenzyl)-1H-pyrazolo[3,4-b]pyridine-3-carboximidamide acetate

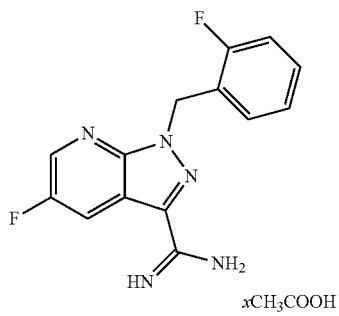 [SMILES: N=C(N)c1nn(Cc2ccccc2F)c2ncc(F)cc12]

11.1 g (41.07 mmol) of 5-fluoro-1-(2-fluorobenzyl)-1H-pyrazolo[3,4-b]pyridine-3-carbonitrile (example 10A) was added to 2.22 g (41.07 mmol) of sodium methanolate in methanol (270 ml) and stirred for 2 h at RT. Then 2.64 g (49.29 mmol) of ammonium chloride and acetic acid (9.17 ml) were added and it was heated under reflux overnight. Then the reaction mixture was evaporated to dryness and the residue was taken up in water (100 ml) and ethyl acetate (100 ml) and was adjusted to pH 10 with 2N sodium hydroxide solution. It was stirred vigorously for approx. 1 h at RT. The suspension obtained was filtered with suction and was washed with ethyl acetate (100 ml), water (100 ml) and again with ethyl acetate (100 ml). The residue is dried over phosphorus pentoxide under high vacuum.

Yield: 9.6 g (78% of theor.)
MS (ESIpos): m/z=288 [M+H]$^+$
$^1$H-NMR (400 MHz, DMSO-d$_6$): δ=1.85 (s, 3H), 5.80 (s, 2H), 7.14-7.25 (m, 3H), 7.36 (m, 1H), 8.42 (dd, 1H), 8.72 (dd, 1H).

Example 12A

Methyl-3,3-dicyano-2,2-dimethylpropanoate

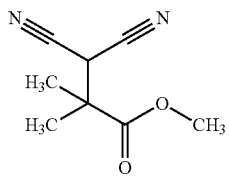

In THF (91 ml), 3 g (45.411 mmol) of malonic acid dinitrile was slowly added to 1.816 g (45.411 mmol) of sodium hydride (60% in mineral oil). Then 5.876 ml (45.411 mmol) of methyl-2-bromo-2-methylpropanoate was added and it was stirred overnight at RT. Then a further 5.876 ml (45.411 mmol) of methyl-2-bromo-2-methylpropanoate was added and it was heated overnight to 50° C. Then once again, 1.762 ml (13.623 mmol) of methyl-2-bromo-2-methylpropanoate was added and it was heated for a further 4 h to 50° C. Saturated aqueous sodium hydrogen carbonate solution was then added to the mixture and it was extracted three times with ethyl acetate. The combined organic phases were washed with saturated aqueous sodium chloride solution, dried over sodium sulphate, filtered and evaporated to dryness. 8.9 g of raw product was obtained, and was purified by silica gel chromatography (cyclohexane-ethyl acetate 4:1).

Yield: 6.47 g (85% of theor.)

$^1$H-NMR (400 MHz, DMSO-$d_6$): δ [ppm]=1.40 (s, 6H), 3.74 (s, 3H), 5.27 (s, 1H).

Example 13A

4-Amino-2-[1-(2-fluorobenzyl)-1H-pyrazolo[3,4-b]pyridin-3-yl]-5,5-dimethyl-5,7-dihydro-6H-pyrrolo[2,3-d]pyrimidin-6-one

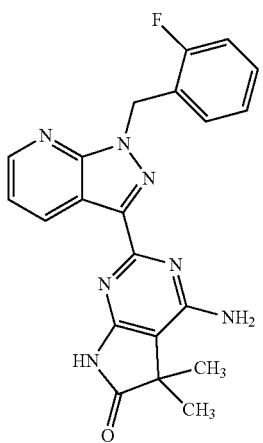 [SMILES: CC1(C)C(=O)Nc2nc(-c3nn(Cc4ccccc4F)c4ncccc34)nc(N)c21]

5.887 g (19.256 mmol) of example 1A was put in tert.-butanol (50 ml) and 2.593 g (23.107 mmol) of potassium tert.-butylate was added. Then 3.2 g (19.256 mmol) of example 12A in tert.-butanol (25 ml) was added dropwise and the mixture was heated under reflux overnight. Next day, a further 0.64 g (3.851 mmol) of example 12A was added and it was heated under reflux for another day. After cooling, a precipitate was filtered off, and was washed with diethyl ether. Then it was made into a slurry in water and filtered off once again and washed with diethyl ether. After drying under high vacuum, 6.65 g of the title compound was obtained (85% of theor.).

LC-MS (method 1): $R_t$=0.90 min; MS (ESIpos): m/z=404 [M+H]$^+$ $^1$H-NMR (400 MHz, DMSO-$d_6$): δ [ppm]=1.35 (s, 6H), 5.82 (s, 2H), 6.82 (br s, 2H), 7.14-7.25 (m, 3H), 7.33-7.40 (m, 2H), 8.63 (dd, 1H), 9.03 (dd, 1H), 10.98 (s br, 1H).

Example 14A

4-Amino-2-[5-fluoro-1-(2-fluorobenzyl)-1H-pyrazolo[3,4-b]pyridin-3-yl]-5,5-dimethyl-5,7-dihydro-6H-pyrrolo[2,3-d]pyrimidin-6-one

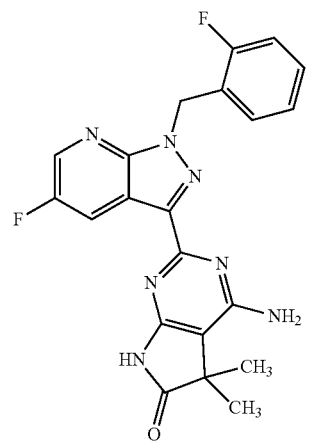 [SMILES: CC1(C)C(=O)Nc2nc(-c3nn(Cc4ccccc4F)c4ncc(F)cc34)nc(N)c21]

By analogy with the preparation of example 13A, 4.18 g (12.035 mmol) of example 11A was reacted with 2.20 g (13.239 mmol) of example 12A. 3.72 g of the title compound was obtained (73% of theor.).

LC-MS (method 1): $R_t$=0.98 min; MS (ESIpos): m/z=422 [M+H]$^+$ $^1$H-NMR (400 MHz, DMSO-$d_6$): δ [ppm]=1.34 (s, 6H), 5.81 (s, 2H), 6.85 (br s, 2H), 7.13-7.25 (m, 3H), 7.36 (m, 1H), 8.69 (dd, 1H), 8.84 (dd, 1H), 10.96 (s br, 1H).

Alternatively, example 73A can also be used instead of example 11A for production.

Example 15A

2-[1-(2-Fluorobenzyl)-1H-pyrazolo[3,4-b]pyridin-3-yl]-4-iodo-5,5-dimethyl-5,7-dihydro-6H-pyrrolo[2,3-d]pyrimidin-6-one

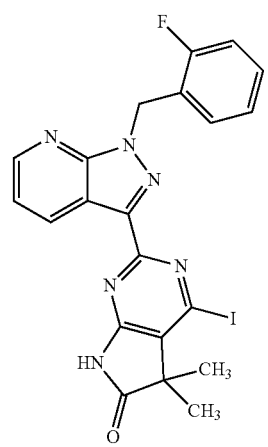 [SMILES: CC1(C)C(=O)Nc2nc(-c3nn(Cc4ccccc4F)c4ncccc34)nc(I)c21]

5.00 g (12.394 mmol) of example 13A was put in isopentyl nitrite (35.87 ml) and diiodomethane (1.16 mol, 93.71 ml) and heated for 12 h to 85° C. After cooling, the solids were filtered off, the filtrate was concentrated by evaporation and the residue was then purified by silica gel chromatography (solvent: first cyclohexane-dichloromethane gradient, then dichloromethane-methanol gradient). 5.50 g of the title compound was obtained (67% of theor.).

LC-MS (method 1): R$_t$=1.19 min; MS (ESIpos): m/z=515 [M+H]$^+$ $^1$H-NMR (400 MHz, DMSO-d$_6$): δ [ppm]=1.42 (s, 6H), 5.88 (s, 2H), 7.13-7.26 (m, 3H), 7.34-7.38 (m, 1H), 7.48 (dd, 1H), 8.69 (dd, 1H), 8.79 (dd, 1H), 11.78 (s br, 1H).

Example 16A

2-[5-Fluoro-1-(2-fluorobenzyl)-1H-pyrazolo[3,4-b]pyridin-3-yl]-4-iodo-5,5-dimethyl-5,7-dihydro-6H-pyrrolo[2,3-d]pyrimidin-6-one

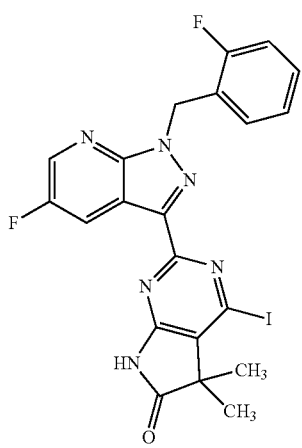 [SMILES: CC1(C)C(=O)Nc2nc(-c3nn(Cc4ccccc4F)c4ncc(F)cc34)nc(I)c21]

3.325 g (7.890 mmol) of example 14A was reacted on the analogy of example 15A. 3.65 g of the title compound was obtained (87% of theor., approx. 61% purity according to LC/MS).

LC-MS (method 1): R$_t$=1.26 min; MS (ESIpos): m/z=533 [M+H]$^+$ $^1$H-NMR (400 MHz, DMSO-d$_6$): δ [ppm]=1.42 (s, 6H), 5.87 (s, 2H), 7.14-7.26 (m, 3H), 7.37 (m, 1H), 8.48 (dd, 1H), 8.77 (dd, 1H), 11.76 (s br, 1H).

Improved Protocol for Larger Batches:

52.6 g (113.585 mmol, 91% purity) of example 14A was stirred in dioxane (239 ml) with 91.26 g (340.75 mmol) of diiodomethane and 39.91 g (340.75 mmol) of isopentyl nitrite for 2 h at 85° C. After concentration by evaporation, the residue was chromatographed on silica gel with dichloromethane:acetone (95:5) as eluent. 29.90 g of the title compound was obtained (49% of theor.).

Example 17A

5-Fluoro-1-[(3-fluoropyridin-2-yl)methyl]-3-iodo-1H-pyrazolo[3,4-b]pyridine

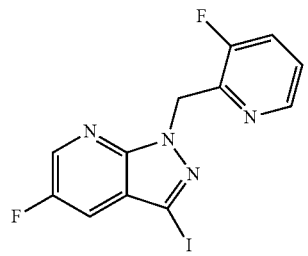 [SMILES: Fc1cnc2c(c1)c(I)nn2Cc1ncccc1F]

6.291 g (23.921 mmol) of 5-fluoro-3-iodo-1H-pyrazolo[3,4-b]pyridine and 8.573 g (26.313 mmol) of caesium carbonate were put in DMF (10 ml) and then 5.00 g (26.313 mmol) of 2-(bromomethyl)-3-fluoropyridine dissolved in DMF (20 ml) was added dropwise. The mixture was stirred overnight at RT. Then it was left to cool and was poured into 200 ml water. A precipitate was filtered off with suction, it was washed with water and dried overnight under high vacuum. 6.28 g (70% of theor.) of the title compound was obtained.

LC-MS (method 4): R$_t$=2.17 min

MS (ESIpos): m/z=373 [M+H]$^+$ $^1$H-NMR (400 MHz, DMSO-d$_6$): δ=5.88 (s, 2H), 7.42-7.46 (m, 1H), 7.77 (dd, 1H), 7.93 (dd, 1H), 8.27 (d, 1H), 8.67 (t, 1H).

Example 18A

5-Fluoro-1-[(3-fluoropyridin-2-yl)methyl]-1H-pyrazolo[3,4-b]pyridine-3-carbonitrile

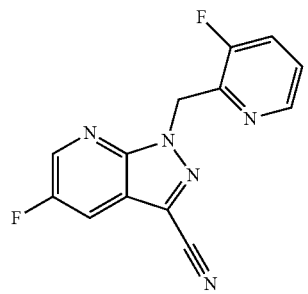 [SMILES: N#Cc1nn(Cc2ncccc2F)c2ncc(F)cc12]

6.280 g (16.876 mmol) of example 17A and 1.663 g (18.564 mmol) of copper(I) cyanide were put in DMSO (100 ml) and stirred for 3 h at 150° C. After cooling, the reaction mixture was filtered on Celite and washed with ethyl acetate.

The filtrate was extracted four times with saturated aqueous ammonium chloride solution and conc. ammonia water (3:1 v/v) and the organic phase was separated. This was then washed with saturated aqueous sodium chloride solution, dried over sodium sulphate, filtered and concentrated by vacuum evaporation. 3.97 g (86% of theor.) of the title compound was obtained.

LC-MS (method 1): $R_t$=0.92 min

MS (ESIpos): m/z=272 [M+H]$^+$ $^1$H-NMR (400 MHz, DMSO-d$_6$): δ=6.04 (s, 2H), 7.44-7.48 (m, 1H), 7.61 (t, 1H), 8.26 (d, 1H), 8.52 (dd, 1H), 8.83 (dd, 1H).

Example 19A

5-Fluoro-1-[(3-fluoropyridin-2-yl)methyl]-1H-pyrazolo[3,4-b]pyridine-3-carboximidamide acetate

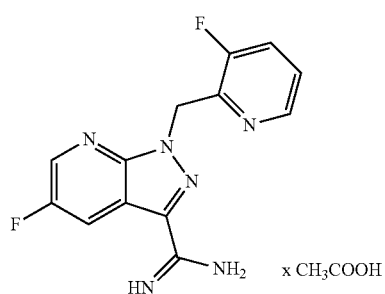

3.900 g (14.379 mmol) of example 18A in methanol (40 ml) was added to 777 mg (14.379 mmol) of sodium methanolate in methanol (20 ml) and stirred for 2 h at RT. Then 932 mg (17.255 mmol) of ammonium chloride and acetic acid (3.210 ml) were added and it was heated under reflux overnight. Then the reaction mixture was evaporated to dryness and ethyl acetate and 1N sodium hydroxide solution were added to the residue and stirred for 2 h at RT. Then a solid was filtered off, which was washed with ethyl acetate and water. The solid was dried overnight under high vacuum. 0.56 g (11% of theor.) of the title compound was obtained. The phases of the filtrate were separated, and the aqueous phase was extracted twice with ethyl acetate. The combined organic phases were dried over sodium sulphate and concentrated by evaporation. A further 1.86 g (14% of theor., 39% purity) of the title compound was obtained. The aqueous phase was also concentrated by evaporation, DMF was added to the residue and it was stirred for 30 min at RT. A precipitate was filtered off with suction, washed with DMF, the filtrate was concentrated by evaporation and dried overnight under high vacuum. A further 1.77 g (35% of theor.) of the title compound is obtained.

LC-MS (method 4): $R_t$=1.25 min

MS (ESIpos): m/z=289 [M+H]$^+$

Example 20A

4-Amino-2-{5-fluoro-1-[(3-fluoropyridin-2-yl)methyl]-1H-pyrazolo[3,4-b]pyridin-3-yl}-5,5-dimethyl-5,7-dihydro-6H-pyrrolo[2,3-d]pyrimidin-6-one

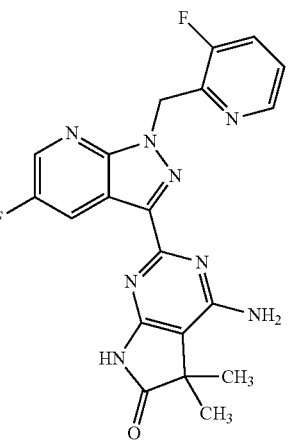

567 mg (1.628 mmol) of example 19A was put in tert.-butanol (10 ml) and 274 mg (2.442 mmol) of potassium tert.-butylate was added. Then 324 mg (1.953 mmol) of example 12A in tert.-butanol (5 ml) was added and the mixture was heated under reflux overnight. After cooling, water and ethanol were added to the reaction mixture, and it was stirred for 1 h. The resultant precipitate was filtered with suction and washed with a little ethanol. The solid was dried under high vacuum. 568 mg of the title compound was obtained (80% of theor.).

LC-MS (method 3): $R_t$=0.82 min; MS (ESIpos): m/z=423 [M+H]$^+$ $^1$H-NMR (400 MHz, DMSO-d$_6$): δ [ppm]=1.34 (s, 6H), 5.94 (s, 2H), 6.87 (br s, 2H), 7.42-7.46 (m, 1H), 7.75-7.80 (m, 1H), 8.27 (d, 1H), 8.67 (dd, 1H), 8.83 (dd, 1H), 10.95 (br s, 1H).

Example 21A

2-{5-Fluoro-1-[(3-fluoropyridin-2-yl)methyl]-1H-pyrazolo[3,4-b]pyridin-3-yl}-4-iodo-5,5-dimethyl-5,7-dihydro-6H-pyrrolo[2,3-d]pyrimidin-6-one

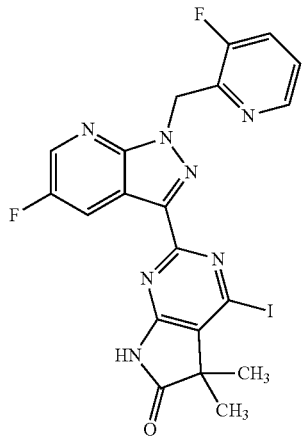 [SMILES: CC1(C)C(=O)Nc2nc(-c3nn(Cc4ncccc4F)c4ncc(F)cc34)nc(I)c21]

2.040 g (4.830 mmol) of example 20A was put in isopentyl nitrite (14 ml) and diiodomethane (37 ml) and heated for 1 h to 85° C. After cooling, a solid was filtered off, which was

Example 22A

2-[6-Chloro-3-(2,3,6-trifluorobenzyl)imidazo[1,5-a]pyridin-1-yl]-4-iodo-5,5-dimethyl-5,7-dihydro-6H-pyrrolo[2,3-d]pyrimidin-6-one

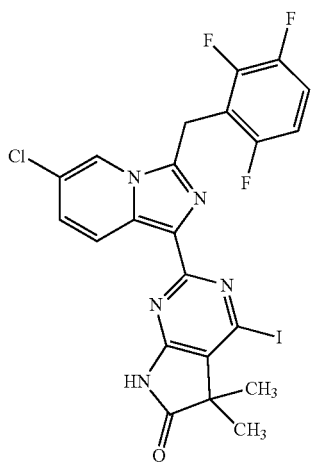 [SMILES: CC1(C)C(=O)Nc2nc(-c3nc(Cc4c(F)ccc(F)c4F)n4cc(Cl)ccc34)nc(I)c21]

556 mg (1.176 mmol) of 4-amino-2-[6-chloro-3-(2,3,6-trifluorobenzyl)imidazo[1,5-a]pyridin-1-yl]-5,5-dimethyl-5,7-dihydro-6H-pyrrolo[2,3-d]pyrimidin-6-one (described in WO 2010/065275) was put in 1,2-dimethoxyethane (14 ml), and 305 mg (1.176 mmol) of caesium iodide, 149 mg (0.588 mmol) of iodine and 67 mg (0.353 mmol) of copper(I) iodide were added at room temperature. Then isopentyl nitrite (0.933 ml) was added and it was heated overnight to 60° C. Next day, 305 mg (1.176 mmol) of caesium iodide, 149 mg (0.588 mmol) of iodine and 67 mg (0.353 mmol) of copper(I) iodide, and isopentyl nitrite (0.933 ml) were added again and it was heated for 3 days to 60° C. After cooling, it was combined with a smaller batch (starting from 50 mg 4-amino-2-[6-chloro-3-(2,3,6-trifluorobenzyl)imidazo[1,5-a]pyridin-1-yl]-5,5-dimethyl-5,7-dihydro-6H-pyrrolo[2,3-d]pyrimidin-6-one). It was extracted with ethyl acetate and saturated aqueous sodium thiosulphate and the phases were separated. The organic phase was extracted twice more with saturated aqueous sodium thiosulphate. Then the organic phase was washed with saturated aqueous sodium chloride solution, dried over sodium sulphate, filtered, concentrated by evaporation and the residue was purified by preparative HPLC (acetonitrile:water (+0.05% formic acid) gradient). 236 mg of the title compound was obtained (31% of theor.).

LC-MS (method 1): $R_t$=1.28 min; MS (ESIpos): m/z=584 [M+H]$^+$ $^1$H-NMR (400 MHz, DMSO-d$_6$): δ [ppm]=1.37 (s, 6H), 4.57 (s, 2H), 7.19-7.25 (m, 1H), 7.30 (dd, 1H), 7.48-7.56 (m, 1H), 8.43 (d, 1H), 8.87 (s, 1H), 11.58 (s, 1H).

In addition to the title compound, 27 mg (5% of theor., 90% purity) of 2-[6-chloro-3-(2,3,6-trifluorobenzyl)imidazo[1,5-a]pyridin-1-yl]-4-hydroxy-5,5-dimethyl-5,7-dihydro-6H-pyrrolo[2,3-d]pyrimidin-6-one was also obtained.

Example 23A 4-(Chloromethyl)-3-fluoropyridine hydrochloride

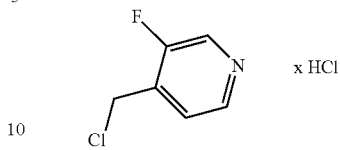

6.710 g (52.785 mmol) of (3-fluoropyridin-4-yl)methanol was put in 29 ml acetonitrile and heated to 50° C. Then a solution of 7.701 ml thionyl chloride in 14.5 ml acetonitrile was added dropwise and the reaction mixture was stirred for 4 h at 50° C. Then the reaction mixture was concentrated by evaporation and was co-distilled three times with dichloromethane. After drying under high vacuum, 10.27 g of the title compound was obtained, which was used in the next step without further purification.

Example 24A

5-Fluoro-1-[(3-fluoropyridin-4-yl)methyl]-3-iodo-1H-pyrazolo[3,4-b]pyridine

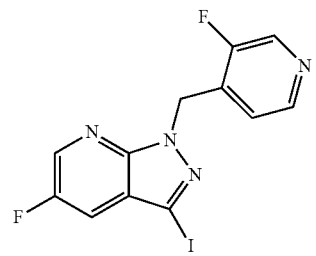 [SMILES: Fc1cnc2c(c1)c(I)nn2Cc1ccncc1F]

On the analogy of the specification in example 7A, 12.225 g (46.482 mmol) of 5-fluoro-3-iodo-1H-pyrazolo[3,4-b]pyridine was reacted with example 23A. 11.34 g (65% of theor.) of the title compound was obtained.

LC-MS (method 3): $R_t$=1.01 min
MS (ESIpos): m/z=373 [M+H]$^+$

Example 25A

5-Fluoro-1-[(3-fluoropyridin-4-yl)methyl]-1H-pyrazolo[3,4-b]pyridine-3-carbonitrile

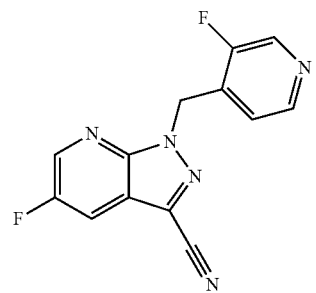 [SMILES: N#Cc1nn(Cc2ccncc2F)c2ncc(F)cc12]

On the analogy of the specification in example 10A, variant A, 11.340 g (30.474 mmol) of example 24A was reacted. 6.31 g (76% of theor.) of the title compound was obtained.

LC-MS (method 3): $R_t$=0.89 min
MS (ESIpos): m/z=272 [M+H]$^+$

Example 26A

5-Fluoro-1-[(3-fluoropyridin-4-yl)methyl]-1H-pyrazolo[3,4-b]pyridine-3-carboximidamide acetate

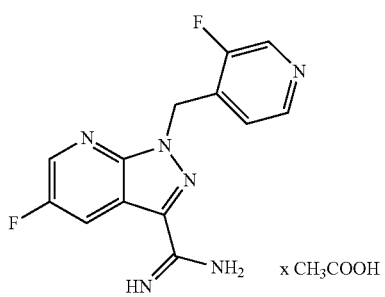 [SMILES: N=C(N)c1nn(Cc2ccncc2F)c2ncc(F)cc12]

On the analogy of the specification in example 11A, 6.310 g (23.264 mmol) of example 25A was reacted. 6.12 g (75% of theor.) of the title compound was obtained.
LC-MS (method 1): $R_t$=0.45 min
MS (ESIpos): m/z=289 [M+H]$^+$

Example 27A

4-Amino-2-{5-fluoro-1-[(3-fluoropyridin-4-yl)methyl]-1H-pyrazolo[3,4-b]pyridin-3-yl}-5,5-dimethyl-5,7-dihydro-6H-pyrrolo[2,3-d]pyrimidin-6-one

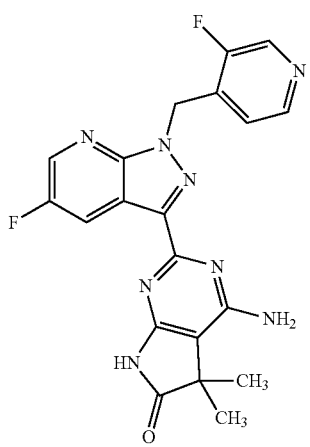 [SMILES: CC1(C)C(=O)Nc2nc(-c3nn(Cc4ccncc4F)c4ncc(F)cc34)nc(N)c21]

On the analogy of the specification in example 13A, 3.050 g (8.756 mmol) of example 26A was reacted. Purification by preparative silica gel chromatography (dichloromethane: methanol gradient). 528 mg of the title compound was obtained (14% of theor.).
LC-MS (method 1): $R_t$=0.80 min; MS (ESIpos): m/z=423 [M+H]$^+$
$^1$H-NMR (400 MHz, DMSO-d$_6$): δ [ppm]=1.35 (s, 6H), 5.90 (s, 2H), 6.89 (br s, 2H), 7.11 (t, 1H), 8.35 (d, 1H), 8.59 (d, 1H), 8.70 (dd, 1H), 8.87 (dd, 1H), 10.99 (br s, 1H).

Example 28A

2-{5-Fluoro-1-[(3-fluoropyridin-4-yl)methyl]-1H-pyrazolo[3,4-b]pyridin-3-yl}-4-iodo-5,5-dimethyl-5,7-dihydro-6H-pyrrolo[2,3-d]pyrimidin-6-one

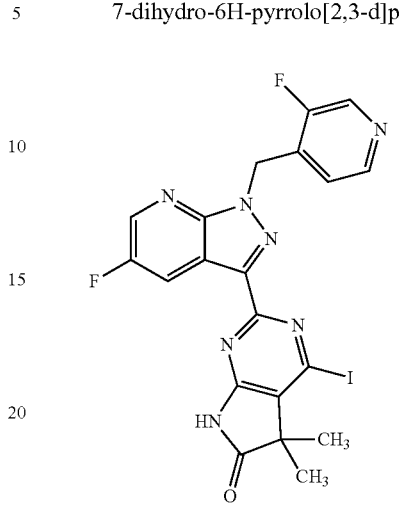

On the analogy of the specification in example 21A, 527 mg (1.248 mmol) of example 27A was reacted. 395 mg of the title compound was obtained (39% of theor., 66% purity). The raw compound was used in the next steps without further purification.
LC-MS (method 3): $R_t$=1.09 min; MS (ESIpos): m/z=534 [M+H]$^+$

Example 29A 1,4,5,6-Tetrahydrocyclopenta[c]pyrazole-3-carbonitrile

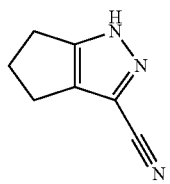

Preparation of the compound is described in: *Org. Process Res. Dev.* 2009, 13, 543.

Example 30A 1-(2-Fluorobenzyl)-1,4,5,6-tetrahydrocyclopenta[c]pyrazole-3-carbonitrile

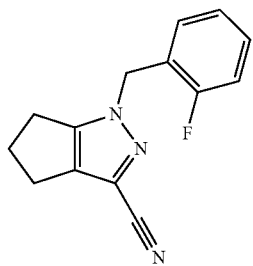 [SMILES: N#Cc1nn(Cc2ccccc2F)c2c1CCC2]

10.320 g (77.50 mmol) of 1,4,5,6-tetrahydrocyclopenta[c]pyrazole-3-carbonitrile was dissolved in 100 ml DMF, 30.304 g (93.01 mmol) of caesium carbonate and 16.116 g (85.26 mmol) of 2-fluorobenzyl bromide were added and it was stirred at RT overnight. The reaction mixture was concentrated by evaporation and taken up in dichloromethane and water was added. The organic phase was separated and the aqueous phase was extracted twice with dichloromethane. The combined organic phases were washed with saturated aqueous sodium chloride solution, filtered on a silicone filter and concentrated by evaporation. The residue was purified by silica-gel flash chromatography (eluent: hexane/ethyl acetate, gradient). 11.37 g (60% of theor.) of the target compound was obtained.

$^1$H-NMR (400 MHz, DMSO-$d_6$): δ [ppm]=2.59-2.64 (m, 4H), 5.33 (s, 2H), 7.15-7.23 (m, 2H), 7.27-7.33 (m, 1H), 7.36-7.43 (m, 1H).

Example 31A 1-(2-Fluorobenzyl)-1,4,5,6-tetrahydrocyclopenta[c]pyrazole-3-carboximidamide

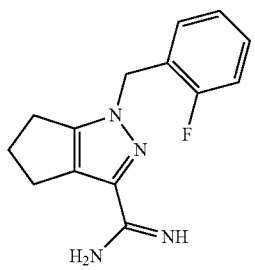 [SMILES: N=C(N)c1nn(Cc2ccccc2F)c2c1CCC2]

Under nitrogen atmosphere, 3.600 g (14.92 mmol) of 1-(2-fluorobenzyl)-1,4,5,6-tetrahydrocyclopenta[c]pyrazole-3-carbonitrile was dissolved in 37 ml of absolute methanol. 1.306 g (24.17 mmol) of sodium methylate was added and it was stirred for 4 h at RT. 1.452 g (24.17 mmol) of acetic acid and 1.197 g (22.38 mmol) of ammonium chloride were added and the suspension was stirred overnight at 50° C. The reaction mixture was concentrated by evaporation and the residue was suspended in 100 ml water and 25 ml 1N hydrochloric acid. The mixture was extracted with dichloromethane. The aqueous phase was made basic (pH=12) with 2N sodium hydroxide solution and extracted three times with a mixture of dichloromethane/methanol (v/v=8:2). The combined organic phases were dried over sodium sulphate, concentrated by evaporation, toluene was added and again evaporated to dryness. 1.94 g (50% of theor.) of the target compound was obtained.

LC-MS (method 7): $R_t$=2.52 min; MS (ESIpos): m/z=259 [M+H]$^+$

Example 32A

4-Amino-2-[1-(2-fluorobenzyl)-1,4,5,6-tetrahydrocyclopenta[c]pyrazol-3-yl]-5,5-dimethyl-5,7-dihydro-6H-pyrrolo[2,3-d]pyrimidin-6-one

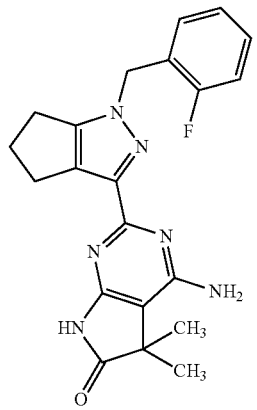 [SMILES: CC1(C)C(=O)Nc2nc(-c3nn(Cc4ccccc4F)c4c3CCC4)nc(N)c21]

300 mg (1.15 mmol) of 1-(2-fluorobenzyl)-1,4,5,6-tetrahydrocyclopenta[c]pyrazole-3-carboximidamide was dissolved with 2 ml tert.-butanol, 287 mg (1.38 mmol) of methyl-3,3-dicyano-2,2-dimethylpropanoate in 2 ml tert.-butanol and 181 mg (1.61 mmol) of potassium tert.-butylate was added and it was heated under reflux for 72 h. It was evaporated to dryness and the residue was mixed with water/isopropanol (v/v=3:1). The solid was filtered off and dried under high vacuum. 385 mg (80% of theor.) of the target compound was obtained.

LC-MS (method 1): $R_t$=0.83 min; MS (ESIpos): m/z=393 [M+H]$^+$

Example 33A

2-[1-(2-Fluorobenzyl)-1,4,5,6-tetrahydrocyclopenta[c]pyrazol-3-yl]-4-iodo-5,5-dimethyl-5,7-dihydro-6H-pyrrolo[2,3-d]pyrimidin-6-one

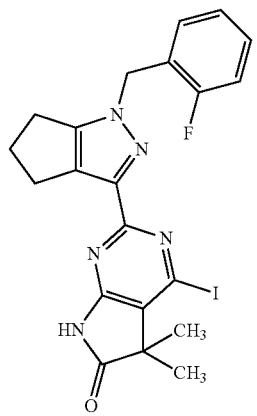 [SMILES: CC1(C)C(=O)Nc2nc(-c3nn(Cc4ccccc4F)c4c3CCC4)nc(I)c21]

285 mg (0.68 mmol) of 4-amino-2-[1-(2-fluorobenzyl)-1,4,5,6-tetrahydrocyclopenta[c]pyrazol-3-yl]-5,5-dimethyl-5,7-dihydro-6H-pyrrolo[2,3-c]pyrimidin-6-one was put in absolute dimethoxyethane and 800 mg (6.83 mmol) of isopentyl nitrite, 87 mg (0.34 mmol) of iodine, 39 mg (0.21 mmol) of copper (I) iodide and 177 mg (0.68 mmol) of caesium iodide were added. The mixture was stirred for 40 min at 100° C. The mixture was concentrated in a rotary evaporator, the residue was taken up in dichloromethane and was washed with 5% aqueous sodium thiosulphate solution and saturated aqueous sodium chloride solution. The organic phase was dried over sodium sulphate, concentrated by evaporation and purified by preparative HPLC (eluent: acetonitrile/water with 0.1% formic acid, gradient 20:80→100:0). 148 mg (40% of theor.) of the target compound was obtained.

LC-MS (method 1): $R_t$=1.23 min; MS (ESIpos): m/z=504 [M+H]$^+$

Example 34A 1-(2-Bromophenyl)-2-(2-fluorophenyl)ethanone

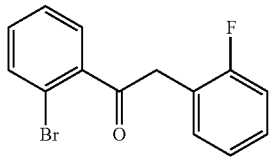 [SMILES: O=C(Cc1ccccc1F)c1ccccc1Br]

15.0 g (69.8 mmol) of 2-methyl bromobenzoate and 11.8 g (76.7 mmol) of 2-fluorophenylacetic acid were put in THF (278 ml) under argon atmosphere at −70° C. and 174 ml of a 1M solution of sodium hexamethyldisilazane in THF was added dropwise in the space of 20 min. The reaction mixture was heated to 0° C., stirred for 30 min at this temperature and 1N hydrochloric acid (278 ml) was added. After 1 h of vigorous stirring with evolution of gas ($CO_2$ cleavage), the reaction mixture was extracted with ethyl acetate (500 ml). The organic phase was washed twice with saturated aqueous sodium hydrogen carbonate solution, once with water and once with saturated aqueous sodium chloride solution. After drying and removal of the solvent in the rotary evaporator, 16.8 g of residue was obtained (55% purity). The residue was dissolved in THF (140 ml), 1N sodium hydroxide solution (70 ml) was added and it was stirred for 4 h at RT, in order to saponify excess ester. The THF was removed in the rotary evaporator, the aqueous phase was extracted with diethyl ether and the organic phase was washed with saturated aqueous sodium hydrogen carbonate solution and saturated aqueous sodium chloride solution. After drying and removal of the solvent, 12.2 g of residue was obtained (approx. 80% purity). The residue was dissolved in THF (100 ml), 1N sodium hydroxide solution (40 ml) was added and it was stirred overnight at RT. The THF was removed in the rotary evaporator, the aqueous phase was extracted with diethyl ether and the organic phase was washed with saturated aqueous sodium hydrogen carbonate solution and saturated aqueous sodium chloride solution. After drying and removal of the solvent, 7.90 g (37% of theor.) of the title compound was isolated.

$^1$H-NMR (400 MHz, DMSO-$d_6$): δ [ppm]=4.35 (s, 2H), 7.14-7.22 (m, 2H), 7.30-7.39 (m, 2H), 7.41-7.47 (m, 1H), 7.49-7.55 (m, 1H), 7.70-7.78 (m, 2H).

Example 35A

2-[1-(2-Bromophenyl)-2-(2-fluorophenyl)ethylidene]hydrazinecarboximidamide

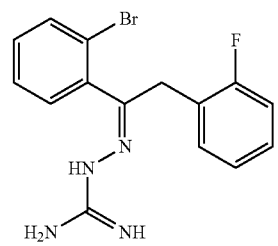 [SMILES: N=C(N)N/N=C(/Cc1ccccc1F)c1ccccc1Br]

7.80 g (26.6 mmol) of example 34A and 5.88 g (53.2 mmol) of aminoguanidine hydrochloride were put in ethylene glycol (193 ml) and 8.50 g (59.9 mmol) of boron trifluoride/diethyl ether complex was added. The reaction mixture was heated for 2 h at 120° C. on a distillation bridge. After cooling, again 5.88 g (53.2 mmol) of aminoguanidine hydrochloride and 8.50 g (59.9 mmol) of boron trifluoride/diethyl ether complex were added and it was stirred for 3 h at 120° C. After cooling, water (750 ml) was added and it was adjusted to pH 11-12 with 1N sodium hydroxide solution. After crystals began to form, 300 g ice was added, it was stirred for 5 min and the solid was then filtered off. The residue was washed first with water, then with pentane, and dried under vacuum. 8.30 g (87% of theor.) of the title compound was obtained.

LC-MS (method 1): $R_t$=0.78 min; MS (ESIpos): m/z (Br-isotope 1+2)=349+351 [M+H]$^+$ Example 36A 3-(2-Fluorobenzyl)-1H-indazole-1-carboximidamide

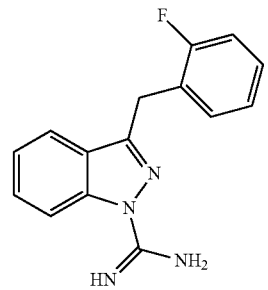 [SMILES: N=C(N)n1nc(Cc2ccccc2F)c2ccccc21]

320 ml of N-methylpyrrolidone was heated to 140° C., 8.20 g (23.5 mmol) of example 35A and 4.47 g (23.5 mmol) of copper(I) iodide were added and it was stirred for 14 min at 170° bath temperature. The reaction mixture was then added slowly to 1 L of ice water and concentrated aqueous ammonia solution (350 mL) was added. After stirring for 5 minutes, 1 L of ethyl acetate was added and the mixture was stirred for 10 min. The aqueous phase was extracted once with ethyl acetate and the combined organic phases were washed with water three times. After drying and removal of the solvent in the rotary evaporator, 7.10 g (74% of theor., 66% purity) of the title compound was obtained. The raw product was reacted further without purification.

LC-MS (method 1): $R_t$=0.68 min; MS (ESIpos): m/z=269 [M+H]$^+$

Example 37A

4-Amino-2-[3-(2-fluorobenzyl)-1H-indazol-1-yl]-5,5-dimethyl-5,7-dihydro-6H-pyrrolo[2,3-d]pyrimidin-6-one

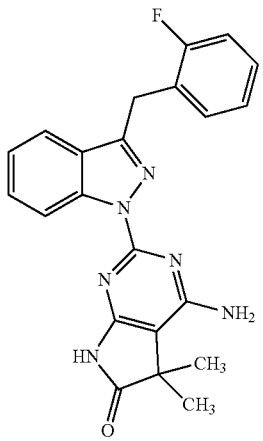 [SMILES: CC1(C)C(=O)Nc2nc(-n3nc(Cc4ccccc4F)c4ccccc43)nc(N)c21]

7.00 g (approx. 17.2 mmol, 66% purity) of the raw product from example 36A and 5.72 g (34.4 mmol) of example 12A were put in tert.-butanol (77.0 ml) and 3.29 g (29.3 mmol) of potassium tert.-butylate was added. The reaction mixture was heated under reflux for 18 h. After cooling, the reaction mixture was diluted with ethyl acetate and washed with approx. 7% aqueous ammonium chloride solution. The organic phase was washed with saturated aqueous sodium chloride solution, dried and the solvent was removed in the rotary evaporator. The residue was purified chromatographically on 600 ml silica gel with cyclohexane/ethyl acetate 2:3. 2.20 g (29% of theor.) of the title compound was obtained as a solid.

LC-MS (method 4): $R_t$=2.19 min; MS (ESIpos): m/z=403 [M+H]$^+$ $^1$H-NMR (400 MHz, DMSO-d$_6$): δ [ppm]=1.35 (s, 6H), 4.39 (s, 2H), 6.97 (br s, 2H), 7.11-7.18 (m, 1H), 7.21 (d, 1H), 7.24-7.33 (m, 2H), 7.36 (t, 1H), 7.50 (t, 1H), 7.70 (d, 1H), 8.82 (d, 1H), 11.10 (s, 1H).

Example 38A

2-[3-(2-Fluorobenzyl)-1H-indazol-1-yl]-4-iodo-5,5-dimethyl-5,7-dihydro-6H-pyrrolo[2,3-d]pyrimidin-6-one

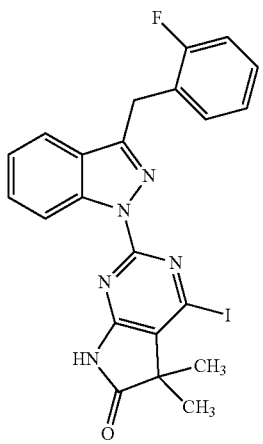 [SMILES: CC1(C)C(=O)Nc2nc(-n3nc(Cc4ccccc4F)c4ccccc43)nc(I)c21]

500 mg (1.242 mmol) of example 37A was put in isopentyl nitrite (3.552 ml) and diiodomethane (9.430 ml) and heated overnight to 85° C. After cooling, the reaction mixture was filtered on silica gel (dichloromethane:methanol gradient) and concentrated by evaporation. Dichloromethane and methanol were added to the residue and it was stirred for 10 min at room temperature. The solid that formed was filtered off and then washed with dichloromethane and methanol. The filtrate was concentrated by evaporation. Methanol and acetonitrile were then added to this residue. A precipitate formed again, which was filtered with suction and was washed again with acetonitrile. After drying under high vacuum, 127 mg of the title compound was obtained (18% of theor.). The filtrate was concentrated by evaporation, thus obtaining a further 334 mg of the title compound at 57% purity (30% of theor.).

LC-MS (method 1): $R_t$=1.31 min; MS (ESIpos): m/z=514 [M+H]$^+$ $^1$H-NMR (400 MHz, DMSO-d$_6$): δ [ppm]=1.42 (s, 6H), 4.43 (s, 2H), 7.13-7.23 (m, 2H), 7.29-7.41 (m, 3H), 7.62 (t, 1H), 7.74 (d, 1H), 8.58 (d, 1H), 11.89 (s, 1H).

In addition to the title compound, 57 mg (9% of theor., 86% purity) of 2-[3-(2-fluorobenzyl)-1H-indazol-1-yl]-4-hydroxy-5,5-dimethyl-5,7-dihydro-6H-pyrrolo[2,3-d]pyrimidin-6-one (example 22) was obtained.

Example 39A 1-(2-Bromo-5-fluorophenyl)-2-(2-fluorophenyl)ethanone

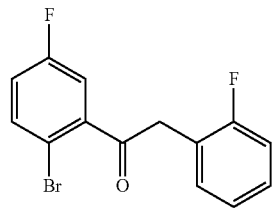 [SMILES: O=C(Cc1ccccc1F)c1cc(F)ccc1Br]

15.0 g (63.1 mmol) of 2-bromo-5-methyl fluorobenzoate and 11.7 g (75.7 mmol) of 2-fluorophenylacetic acid were put in THF (278 ml) under argon atmosphere at −70° C. and a 1M solution of sodium hexamethyldisilazane in THF (158 ml) was added dropwise in the space of 20 min. The reaction mixture was stirred at this temperature for 30 min, heated to 0° C., stirred for a further 30 min at 0° C. and then 1N hydrochloric acid (251 ml) was added. After stirring vigorously for 1 h with evolution of gas (CO$_2$ cleavage), the reaction mixture was extracted with ethyl acetate (700 ml). The organic phase was washed twice with saturated aqueous sodium hydrogen carbonate solution, once with water and once with saturated aqueous sodium chloride solution. After drying and removal of the solvent in the rotary evaporator, 16.9 g of residue was obtained (50% purity). The residue was dissolved in THF (200 ml), 1N sodium hydroxide solution (100 ml) was added and it was stirred overnight at RT. The THF was removed in the rotary evaporator, the aqueous phase was extracted with diethyl ether and the organic phase was washed with saturated aqueous sodium hydrogen carbonate solution and saturated aqueous sodium chloride solution. After drying and removal of the solvent in the rotary evaporator, 9.10 g (42% of theor.) of the title compound was isolated.

$^1$H-NMR (400 MHz, DMSO-d$_6$): δ [ppm]=4.36 (s, 2H), 7.14-7.24 (m, 2H), 7.30-7.39 (m, 3H), 7.71-7.80 (m, 2H).

Example 40A

2-[1-(2-Bromo-5-fluorophenyl)-2-(2-fluorophenyl)ethylidene]hydrazinecarboximidamide

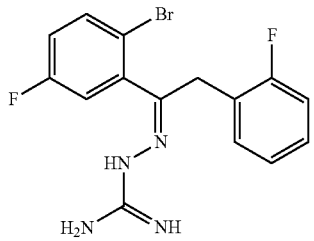 [SMILES: N=C(N)N/N=C(/Cc1ccccc1F)c1cc(F)ccc1Br]

9.00 g (28.9 mmol) of example 39A and 6.40 g (58.9 mmol) of aminoguanidine hydrochloride were put in ethylene glycol (207 ml) and 9.24 g (65.1 mmol) of boron trifluoride/diethyl ether complex was added. The reaction mixture was heated for 2 h at 120° C. on a distillation bridge. After cooling, 6.40 g (58.9 mmol) of aminoguanidine hydrochloride and 9.24 g (65.1 mmol) of boron trifluoride/diethyl ether complex were added again and it was stirred for 3 h at 120° C. After cooling, the reaction mixture was slowly added to water (800 ml) and was adjusted to pH 11-12 with 1N sodium hydroxide solution. After a precipitate started to form, 300 g ice was added and it was stirred for 15 min Owing to the sticky nature of the precipitate, the water was decanted off and the residue was precipitated twice more, with 200 ml water each time. The sticky precipitate was dissolved in diethyl ether, washed with water, the organic phase was dried, the solvent was removed in the rotary evaporator and 6.00 g (54% of theor.) of the title compound was isolated as a foam.

LC-MS (method 1): $R_t$=0.80 min; MS (ESIpos): m/z=367+369 [M+H]$^+$

Example 41A

5-Fluoro-3-(2-fluorobenzyl)-1H-indazole-1-carboximidamide

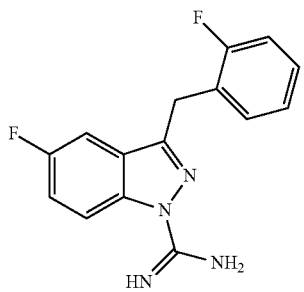 [SMILES: N=C(N)n1nc(Cc2ccccc2F)c2cc(F)ccc21]

222 ml of N-methylpyrrolidone was heated to 140° C., 6.00 g (16.3 mmol) of example 40A and 3.11 g (16.3 mmol) of copper(I) iodide were added and it was stirred for 14 min at 170° C. bath temperature. The reaction mixture was then added slowly to 700 ml ice water, and concentrated aqueous ammonia solution (230 mL) was added. After stirring for 5 minutes, 700 ml ethyl acetate was added and it was stirred for 10 min. The aqueous phase was extracted with ethyl acetate once more and the combined organic phases were washed with water three times. After drying and removal of the solvent in the rotary evaporator, 6.00 g (64% of theor., 50% purity) of product was obtained. The raw product was reacted further without purification.

LC-MS (method 3): $R_t$=1.60 min; MS (ESIpos): m/z=287 [M+H]$^+$

Example 42A

4-Amino-2-[5-fluoro-3-(2-fluorobenzyl)-1H-indazol-1-yl]-5,5-dimethyl-5,7-dihydro-6H-pyrrolo[2,3-d]pyrimidin-6-one

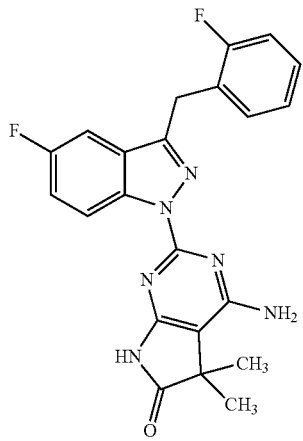 [SMILES: CC1(C)C(=O)Nc2nc(-n3nc(Cc4ccccc4F)c4cc(F)ccc43)nc(N)c21]

6.00 g (approx. 10.5 mmol, 50% purity) of the raw product from example 41A and 5.22 g (31.4 mmol) of example 12A were put in tert.-butanol (46.0 ml) and 2.00 g (17.8 mmol) of potassium tert.-butylate was added. The reaction mixture was heated under reflux for 18 h. After cooling, it was diluted with ethyl acetate and was extracted with approx. 7% aqueous ammonium chloride solution. The organic phase was washed with saturated aqueous sodium chloride solution, dried and the solvent was removed in the rotary evaporator. The residue was purified by chromatography on 600 ml silica gel with cyclohexane/ethyl acetate 2:3. The product-containing fractions were concentrated by evaporation and mixed with approx. 20 ml diethyl ether, filtered with suction and washed with diethyl ether. 1.80 g (37% of theor.) of the title compound was obtained as a solid.

LC-MS (method 1): $R_t$=1.00 min; MS (ESIpos): m/z=421 [M+H]$^+$

Example 43A

2-[5-Fluoro-3-(2-fluorobenzyl)-1H-indazol-1-yl]-4-iodo-5,5-dimethyl-5,7-dihydro-6H-pyrrolo[2,3-d]pyrimidin-6-one

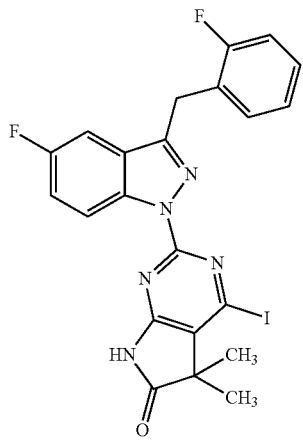 [SMILES: CC1(C)C(=O)Nc2nc(-n3nc(Cc4ccccc4F)c4cc(F)ccc43)nc(I)c21]

500 mg (1.189 mmol) of example 42A was put in isopentyl nitrite (3.40 ml) and diiodomethane (9.027 ml) and heated overnight to 85° C. After cooling, it was filtered on silica gel (dichloromethane:methanol gradient) and concentrated by evaporation. The residue was purified by preparative HPLC (acetonitrile:water (+0.05% formic acid) gradient). 274 mg of the title compound was obtained (43% of theor.).

LC-MS (method 1): $R_t$=1.33 min; MS (ESIpos): m/z=532 [M+H]$^+$ $^1$H-NMR (400 MHz, DMSO-d$_6$): δ [ppm]=1.41 (s, 6H), 4.41 (s, 2H), 7.14-7.23 (m, 2H), 7.29-7.35 (m, 1H), 7.39-7.43 (ddd, 1H), 7.52-7.61 (m, 2H), 8.58 (d, 1H), 11.91 (s, 1H).

In addition to the title compound, 72 mg (14% of theor., 83% purity) of 2-[5-fluoro-3-(2-fluorobenzyl)-1H-indazol-1-yl]-4-hydroxy-5,5-dimethyl-5,7-dihydro-6H-pyrrolo[2,3-d]pyrimidin-6-one (example 31) was obtained.

Example 44A

Ethyl-8-(2-fluorobenzyl)imidazo[1,5-a]pyrimidine-6-carboxylate

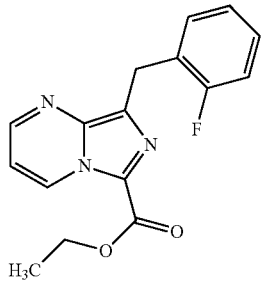 [SMILES: CCOC(=O)c1nc(Cc2ccccc2F)c2ncccn12]

Preparation of the compound is described in: US 2010/29653, Page 19, example 10A.

Example 45A 8-(2-Fluorobenzyl)imidazo[1,5-a]pyrimidine-6-carboxamide

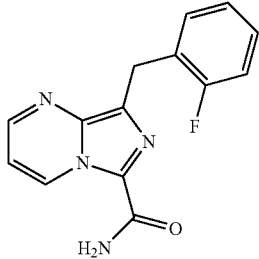 [SMILES: NC(=O)c1nc(Cc2ccccc2F)c2ncccn12]

8.200 g (27.40 mmol) of ethyl-8-(2-fluorobenzyl)imidazo[1,5-a]pyrimidine-6-carboxylate was distributed in 8 microwave vessels. Each vessel was charged with 10 ml of 7N solution of ammonia in methanol and stirred for 80 min at 150° C. in the microwave. After cooling, the contents of the vessels were combined, the resultant precipitate was filtered with suction, washed with a little methanol and dried under high vacuum. 8.42 g (quant.) of the target compound was obtained.

LC-MS (method 1) $R_t$=0.76 min; MS (ESIpos): m/z=271 [M+H]$^+$

Example 46A 8-(2-Fluorobenzyl)imidazo[1,5-a]pyrimidine-6-carbonitrile

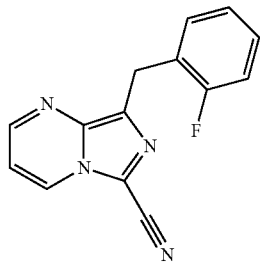 [SMILES: N#Cc1nc(Cc2ccccc2F)c2ncccn12]

150 ml of phosphoryl chloride was added to 9.100 g (33.67 mmol) of 8-(2-fluorobenzyl)imidazo[1,5-a]pyrimidine-6-carboxamide and it was stirred for 2 h at 120° C. The reaction mixture was concentrated in the rotary evaporator and the residue was mixed with water. The solid was filtered with suction, washed with a little water and dried under high vacuum. 8.02 g (92% of theor.) of the target compound was obtained.

LC-MS (method 1) $R_t$=0.92 min; MS (ESIpos): m/z=253 [M+H]$^+$

Example 47A 8-(2-Fluorobenzyl)imidazo[1,5-a]pyrimidine-6-carboximidamide

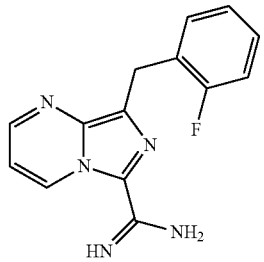 [SMILES: N=C(N)c1nc(Cc2ccccc2F)c2ncccn12]

Under argon atmosphere, 6.98 g (32.30 mmol) of sodium methylate (25% solution in methanol) was put in 50 ml methanol and 8.000 g (30.76 mmol) of 8-(2-fluorobenzyl)imidazo[1,5-a]pyrimidine-6-carbonitrile dissolved in 40 ml of absolute methanol was added. The reaction mixture was stirred for 1 h at RT. 7.205 g (119.98 mmol) of acetic acid and 1.975 g (36.92 mmol) of ammonium chloride were added and the mixture was stirred for 2 h at 50° C. The reaction mixture was concentrated by evaporation and the residue was distributed between 150 ml water and 100 ml ethyl acetate. The aqueous phase was made basic (pH=10) with 2N sodium hydroxide solution and the phases were stirred for 1 h at RT. Water was added and it was extracted three times with ethyl acetate. The combined organic phases were dried over sodium sulphate, concentrated by evaporation and the residue was dried under high vacuum. 7.53 g (purity 73%, 66% of theor.) of the target compound was obtained.

LC-MS (method 1) $R_t$=0.56 min; MS (ESIpos): m/z=270 [M+H]$^+$

Example 48A

4-Amino-2-[8-(2-fluorobenzyl)imidazo[1,5-a]pyrimidin-6-yl]-5,5-dimethyl-5,7-dihydro-6H-pyrrolo[2,3-c]pyrimidin-6-one

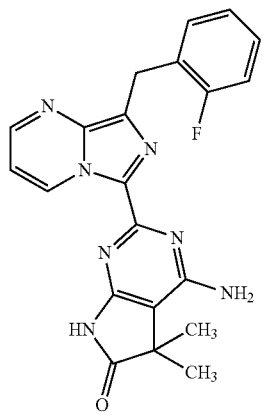 [SMILES: CC1(C)C(=O)Nc2nc(-c3nc(Cc4ccccc4F)c4ncccn34)nc(N)c21]

4.000 g (purity 73%, 10.84 mmol) of 8-(2-fluorobenzyl)imidazo[1,5-a]pyrimidine-6-carboximidamide was put in 25 ml tert.-butanol, 2.162 g (13.01 mmol) of methyl-3,3-dicyano-2,2-dimethylpropanoate dissolved in 25 ml tert.-butanol and 1.703 g (15.18 mmol) of potassium tert.-butylate were added and it was heated under reflux for 18 h. A further 1.802 g (10.84 mmol) of methyl-3,3-dicyano-2,2-dimethylpropanoate was added and it was boiled under reflux for 5 h. It was evaporated to dryness and the residue was mixed with water/isopropanol (v/v=4:1). The solid was filtered off and was mixed with methanol and diethyl ether. It was filtered with suction and the residue was dried under high vacuum. 1.90 g (purity 90%, 39% of theor.) of the target compound was obtained.

LC-MS (method 1): $R_t$=0.84 min; MS (ESIpos): m/z=404 [M+H]$^+$

Example 49A

2-[8-(2-Fluorobenzyl)imidazo[1,5-a]pyrimidin-6-yl]-4-iodo-5,5-dimethyl-5,7-dihydro-6H-pyrrolo[2,3-d]pyrimidin-6-one

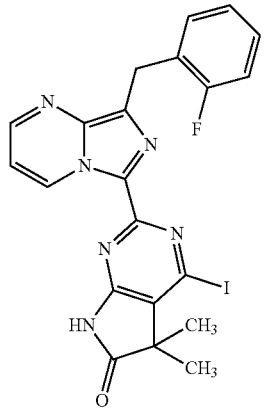 [SMILES: CC1(C)C(=O)Nc2nc(-c3nc(Cc4ccccc4F)c4ncccn34)nc(I)c21]

1.500 g (3.35 mmol) of 4-amino-2-[8-(2-fluorobenzyl)imidazo[1,5-a]pyrimidin-6-yl]-5,5-dimethyl-5,7-dihydro-6H-pyrrolo[2,3-d]pyrimidin-6-one was suspended in 6.00 ml (44.56 mmol) of isopentyl nitrite and 4.00 ml (49.66 mmol) of diiodomethane and it was stirred for 2d at 85° C. 4.00 ml isopentyl nitrite and 5 ml NMP were added and the solution was stirred for 4 h at 85° C. The mixture was concentrated by evaporation in the rotary evaporator except the NMP and was purified by preparative HPLC (eluent: acetonitrile/water with 0.1% formic acid, gradient 20:80→100:0). 928 mg (purity 69%, 37% of theor.) of the target compound was obtained.

LC-MS (method 1): $R_t$=1.11 min; MS (ESIpos): m/z=515 [M+H]$^+$

Example 50A

5-Fluoro-6-methyl-1H-pyrazolo[3,4-b]pyridin-3-amine

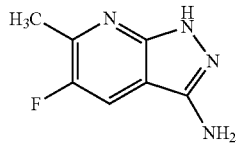

58 g (340.027 mmol) of 2-chloro-5-fluoro-6-methylnicotinonitrile (preparation described in WO2007/41052, example U-2, page 80) was put in 1,2-ethanediol (580 ml) and then hydrazine hydrate (24.813 ml) and 56.091 ml (340.027 mmol) of diisopropyl ethylamine were added. The reaction mixture was heated with stirring for 16 h to 80° C. and then for 66 h to 120° C. After cooling, water (2.5 l) and ethyl acetate (2.5 l) were added and it was filtered with suction. The solid obtained was dried. 28.4 g (47% of theor.) of the target compound was obtained.

LC-MS (method 7): $R_t$=1.77 min; MS (ESIpos): m/z=167 [M+H]$^+$

Example 51A

5-Fluoro-3-iodo-6-methyl-1H-pyrazolo[3,4-b]pyridine

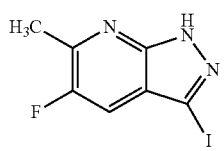

28 g (168.513 mmol) of example 50A was reacted, on the analogy of example 6A. After silica gel chromatography (cyclohexane:ethyl acetate 9:1), 14.9 g (31% of theor.) of the title compound was obtained.

LC-MS (method 1): $R_t$=0.84 min; MS (ESIpos): m/z=278 [M+H]$^+$

Example 52A

5-Fluoro-1-(2-fluorobenzyl)-3-iodo-6-methyl-1H-pyrazolo[3,4-b]pyridine

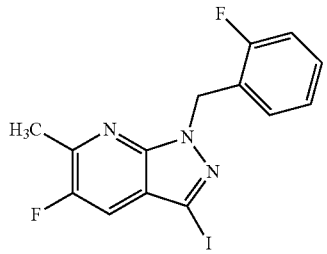 [SMILES: Cc1nc2c(cc1F)c(I)nn2Cc1ccccc1F]

13 g (46.925 mmol) of example 51A was reacted, on the analogy of example 7A. After silica gel chromatography (cyclohexane:ethyl acetate gradient), 8.4 g (43% of theor.) of the title compound was obtained.

LC-MS (method 1): $R_t$=1.32 min; MS (ESIpos): m/z=386 [M+H]$^+$

Example 53A

5-Fluoro-1-(2-fluorobenzyl)-6-methyl-1H-pyrazolo[3,4-b]pyridine-3-carbonitrile

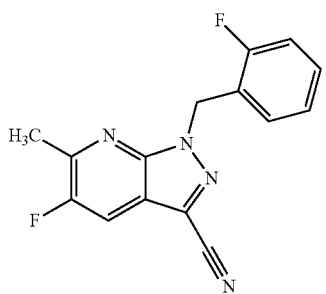 [SMILES: Cc1nc2c(cc1F)c(C#N)nn2Cc1ccccc1F]

9.3 g (24.146 mmol) of example 52A was reacted, on the analogy of example 10A, variant A. After silica gel chromatography (cyclohexane:ethyl acetate gradient), 5.7 g (80% of theor.) of the title compound was obtained.

LC-MS (method 1): $R_t$=1.20 min; MS (ESIpos): m/z=285 [M+H]$^+$

Example 54A

5-Fluoro-1-(2-fluorobenzyl)-6-methyl-1H-pyrazolo[3,4-b]pyridine-3-carboximidamide acetate

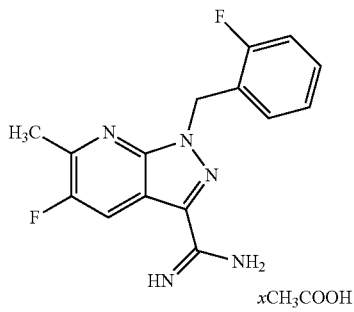 [SMILES: Cc1nc2c(cc1F)c(C(=N)N)nn2Cc1ccccc1F]

5.7 g (18.908 mmol, approx. 95%) of example 53A was reacted, on the analogy of example 11A. 6.6 g (96% of theor.) of the title compound was obtained.

LC-MS (method 1): $R_t$=0.66 min; MS (ESIpos): m/z=302 [M+H]$^+$

Example 55A

4-Amino-2-[5-fluoro-1-(2-fluorobenzyl)-6-methyl-1H-pyrazolo[3,4-b]pyridin-3-yl]-5,5-dimethyl-5,7-dihydro-6H-pyrrolo[2,3-d]pyrimidin-6-one

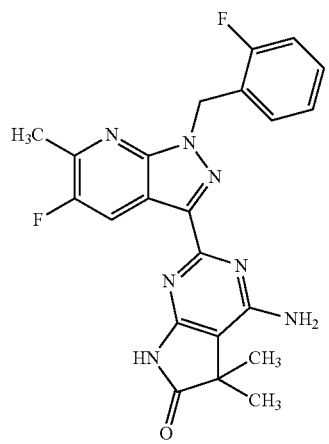 [SMILES: Cc1nc2c(cc1F)c(-c1nc(N)c3c(n1)NC(=O)C3(C)C)nn2Cc1ccccc1F]

1 g (2.767 mmol) of example 54A was reacted, on the analogy of example 13A. 971 mg (80% of theor.) of the title compound was obtained.

LC-MS (method 1): $R_t$=1.05 min; MS (ESIpos): m/z=436 [M+H]$^+$

Example 56A

2-[5-Fluoro-1-(2-fluorobenzyl)-6-methyl-1H-pyrazolo[3,4-b]pyridin-3-yl]-4-iodo-5,5-dimethyl-5,7-dihydro-6H-pyrrolo[2,3-d]pyrimidin-6-one

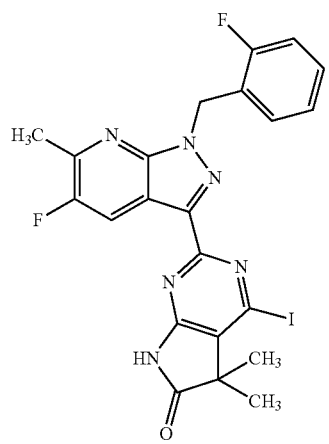 [SMILES: Cc1nc2c(cc1F)c(-c1nc(I)c3c(n1)NC(=O)C3(C)C)nn2Cc1ccccc1F]

960 mg (2.205 mmol) of example 55A was reacted, on the analogy of example 15A. 749 mg (62% of theor., 84% purity) of the title compound was obtained.

LC-MS (method 1): $R_t$=1.35 min; MS (ESIpos): m/z=547 [M+H]$^+$.

In addition to the title compound, 99 mg (10% of theor.) of 2-[5-fluoro-1-(2-fluorobenzyl)-6-methyl-1H-pyrazolo[3,4-b]pyridin-3-yl]-4-hydroxy-5,5-dimethyl-5,7-dihydro-6H-pyrrolo[2,3-c]pyrimidin-6-one was obtained in this batch.

Example 57A

4'-Amino-2'-[5-fluoro-1-(2-fluorobenzyl)-1H-pyrazolo[3,4-b]pyridin-3-yl]-4,5-dihydrospiro[furan-3,5'-pyrrolo[2,3-c]pyrimidin]-6'(7'H)-one

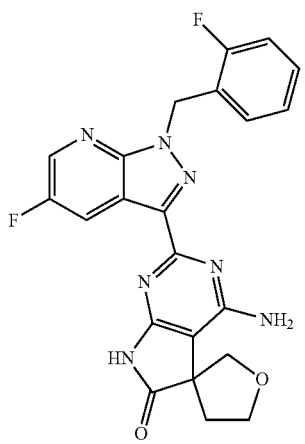 [SMILES: Nc1nc(-c2nn(Cc3ccccc3F)c3ncc(F)cc23)nc2c1C1(CCOC1)C(=O)N2]

1.505 g (4.650 mmol) of example 73A was reacted, on the analogy of example 13A, with 0.903 g (4.650 mmol) of methyl-3-(dicyanomethyl)tetrahydrofuran-3-carboxylate (described in WO 2012/004259, example 12A, page 42). 178 mg (8% of theor.) of the title compound was obtained.

LC-MS (method 1): $R_t$=0.99 min; MS (ESIpos): m/z=450 [M+H]$^+$

Example 58A

2'-[5-Fluoro-1-(2-fluorobenzyl)-1H-pyrazolo[3,4-b]pyridin-3-yl]-4'-iodo-4,5-dihydrospiro[furan-3,5'-pyrrolo[2,3-d]pyrimidin]-6'(7'H)-one

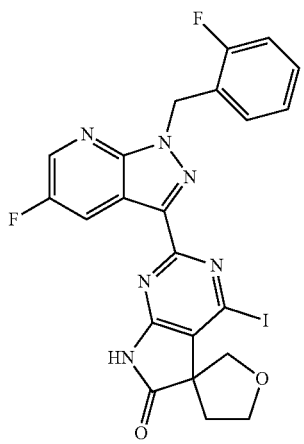 [SMILES: O=C1Nc2nc(-c3nn(Cc4ccccc4F)c4ncc(F)cc34)nc(I)c2C12CCOC2]

155 mg (0.345 mmol) of example 57A was reacted, on the analogy of WO 2012/004258, example 57A, page 97-98. 86 mg (44% of theor.) of the title compound was obtained.

LC-MS (method 1): $R_t$=1.16 min; MS (ESIpos): m/z=561 [M+H]$^+$

Example 59A

Ethyl-4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidine-5-carboxylate

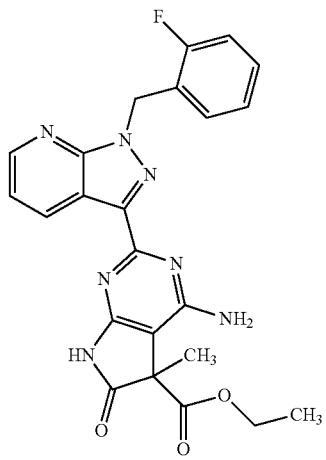 [SMILES: CCOC(=O)C1(C)C(=O)Nc2nc(-c3nn(Cc4ccccc4F)c4ncccc34)nc(N)c21]

4.687 g (15.329 mmol) of example 1A was put in tert.-butanol (120 ml) and 3.069 g (30.659 mmol) of potassium hydrogen carbonate was added. Then 4.2 g (17.629 mmol) of diethyl-(dicyanomethyl)(methyl)malonate was added and the mixture was heated for 5 h to 85° C. Then water was added, it was stirred for 30 min at room temperature and then a solid was filtered with suction. This was washed with a little diethyl ether. After drying under high vacuum, 6.20 g of the title compound was obtained (87% of theor.).

LC-MS (method 1): $R_t$=0.95 min; MS (ESIpos): m/z=462 [M+H]$^+$

Example 60A

Ethyl-2-[1-(2-fluorobenzyl)-1H-pyrazolo[3,4-b]pyridin-3-yl]-4-iodo-5-methyl-6-oxo-6,7-dihydro-5H-pyrrolo[2,3-c]pyrimidine-5-carboxylate

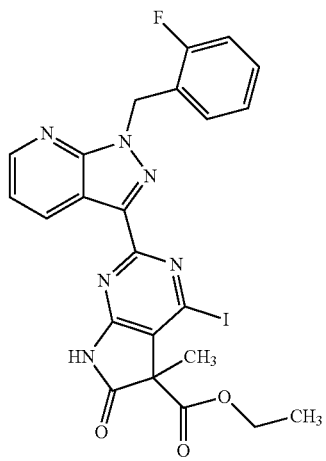 [SMILES: CCOC(=O)C1(C)C(=O)Nc2nc(-c3nn(Cc4ccccc4F)c4ncccc34)nc(I)c21]

1.00 g (2.167 mmol) of example 59A was reacted, on the analogy of the specification in example 15A. 0.887 g of the title compound was obtained (71% of theor.).

LC-MS (method 1): $R_t$=1.22 min; MS (ESIpos): m/z=573 [M+H]$^+$

In addition to the title compound, 173 mg (17% of theor.) of ethyl-2-[1-(2-fluorobenzyl)-1H-pyrazolo[3,4-b]pyridin-3-yl]-4-hydroxy-5-methyl-6-oxo-6,7-dihydro-5H-pyrrolo[2,3-d]pyrimidine-5-carboxylate (example 101) was obtained.

Example 61A tert.-Butyl-(1-{2-[1-(2-fluorobenzyl)-1H-pyrazolo[3,4-b]pyridin-3-yl]-5,5-dimethyl-6-oxo-6,7-dihydro-5H-pyrrolo[2,3-d]pyrimidin-4-yl}pyrrolidin-3-yl)carbamate (racemate)

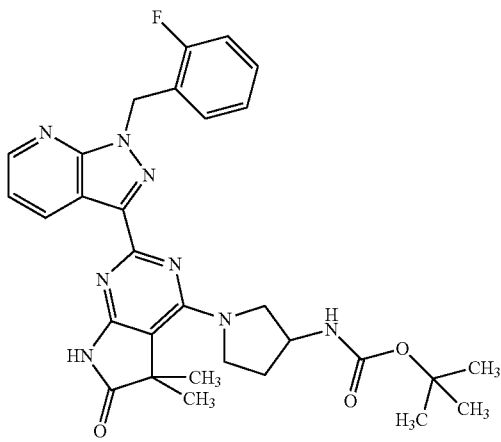 [SMILES: CC(C)(C)OC(=O)NC1CCN(c2nc(-c3nn(Cc4ccccc4F)c4ncccc34)nc3c2C(C)(C)C(=O)N3)C1]

150 mg (0.21 mmol, purity approx. 71%) of 2-[1-(2-fluorobenzyl)-1H-pyrazolo[3,4-b]pyridin-3-yl]-4-iodo-5,5-dimethyl-5,7-dihydro-6H-pyrrolo[2,3-d]pyrimidin-6-one (example 15A) was dissolved, in a reaction vessel suitable for a microwave, in 1-methyl-2-pyrrolidone (3.1 ml), and 0.22 ml (1.24 mmol) of N,N-diisopropyl ethylamine and 154 mg (0.83 mmol) of tert.-butyl-pyrrolidin-3-ylcarbamate were added. Then the reaction vessel was sealed with a septum and was heated for 6 h at 150° C. in the microwave. After cooling, water was added to the reaction mixture, and trifluoroacetic acid extracted three times with dichloromethane. The combined organic phases were dried over sodium sulphate, filtered and concentrated by evaporation. The residue was purified by preparative HPLC (acetonitrile:water (+0.1% trifluoroacetic acid) gradient). 69 mg of the title compound was obtained (59% of theor.).

LC-MS (method 1): $R_t$=1.17 min; MS (EIpos): m/z=573 [M+H]$^+$.

Example 62A tert.-Butyl-(1-{2-[1-(2-fluorobenzyl)-1H-pyrazolo[3,4-b]pyridin-3-yl]-5,5-dimethyl-6-oxo-6,7-dihydro-5H-pyrrolo[2,3-d]pyrimidin-4-yl}azetidin-3-yl)carbamate

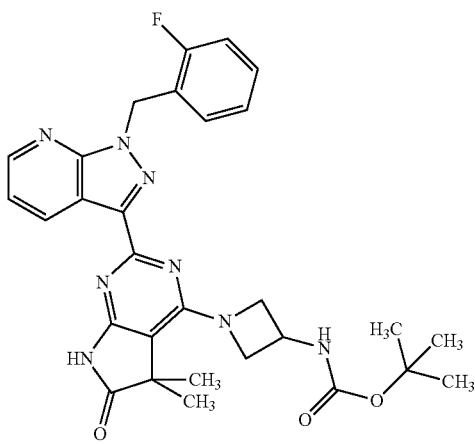 [SMILES: CC(C)(C)OC(=O)NC1CN(c2nc(-c3nn(Cc4ccccc4F)c4ncccc34)nc3c2C(C)(C)C(=O)N3)C1]

150 mg (0.21 mmol, purity approx. 71%) of 2-[1-(2-fluorobenzyl)-1H-pyrazolo[3,4-b]pyridin-3-yl]-4-iodo-5,5-dimethyl-5,7-dihydro-6H-pyrrolo[2,3-d]pyrimidin-6-one (example 15A) was dissolved, in a reaction vessel suitable for a microwave, in 1-methyl-2-pyrrolidone (3.1 ml), and 0.22 ml (1.24 mmol) of N,N-diisopropyl ethylamine and 143 mg (0.83 mmol) of tert.-butyl-azetidin-3-ylcarbamate were added. Then the reaction vessel was sealed with a septum and heated for 8 h at 150° C. in the microwave. Then 0.15 ml (0.82 mmol) of N,N-diisopropyl ethylamine and 107 mg (0.62 mmol) of tert.-butyl-azetidin-3-ylcarbamate were added again and the reaction mixture was heated for 3 h at 150° C. in the microwave. After cooling, water was added to the reaction mixture and it was purified by preparative HPLC (acetonitrile:water (+0.1% trifluoroacetic acid) gradient). 81 mg of the title compound was obtained (64% of theor.; purity 91%).

LC-MS (method 1): $R_t$=1.15 min; MS (EIpos): m/z=559 [M+H]$^+$.

Example 63A

4-Chloro-6-methyl-1H-pyrazolo[3,4-d]pyrimidine

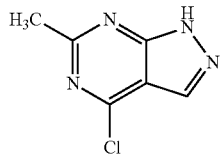

This compound was prepared according to a modified specification from: C. C. Cheng, R. K. Robins, *J. Org. Chem.* 1958, 23, 191.

4.878 g (33.2 mmol) of 6-methyl-1H-pyrazolo[3,4-d]pyrimidin-4-ol (*J. Org. Chem.* 1958, 23, 191) was put in 50 ml toluene, 15.5 ml (165.8 mmol) of phosphoryl chloride and 12.7 ml (72.9 mmol) of diisopropyl ethylamine were added and it was stirred for 1 h at 80° C. It was concentrated by evaporation and distributed between ethyl acetate and 1 M hydrochloric acid. The organic phase was dried over sodium sulphate and concentrated by evaporation. The residue (4.464 g, 92% purity, 73% of theor.) was processed further without purification.

LC-MS (method 1): $R_t$=0.53 min; MS (ESIpos): m/z=169 (M+H)$^+$

Example 64A

6-Methyl-1H-pyrazolo[3,4-d]pyrimidine

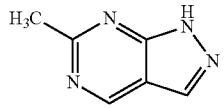

4.464 g (approx. 24.28 mmol, purity 92%) of 4-chloro-6-methyl-1H-pyrazolo[3,4-d]pyrimidine was dissolved in 180 ml dioxane and 2.948 g (29.14 mmol) of triethylamine and 5.629 g of 20% palladium hydroxide on charcoal were added and it was hydrogenated at 3 bar hydrogen pressure and RT for 2 days. 100 ml ethyl acetate, 2.948 g (29.14 mmol) of triethylamine and 2.000 g of 20% palladium hydroxide on charcoal were added. The mixture was hydrogenated with hydrogen at 3 bar hydrogen pressure and RT for 3 h. The reaction mixture was filtered on Celite, washed with a little dioxane/ethyl acetate and the filtrate was concentrated in the rotary evaporator. 2.180 g (purity 73%, 49% of theor.) of the target compound was obtained.

LC-MS (method 4): $R_t$=0.40 min; MS (ESIpos): m/z=135 (M+H)$^+$

Example 65A

3-Iodo-6-methyl-1H-pyrazolo[3,4-d]pyrimidine

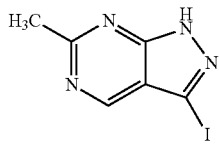

2.180 g (purity 73%, approx. 11.82 mmol) of 6-methyl-1H-pyrazolo[3,4-d]pyrimidine and 3.987 g (17.72 mmol) of N-iodosuccinimide were dissolved in 30 ml DMF and heated for 2 h at 80° C. After cooling, the mixture was concentrated in the rotary evaporator and the residue was mixed with dichloromethane, filtered with suction and dried under high vacuum. 7.950 g (approx. 38% purity) of the target compound was obtained.

LC-MS (method 1): $R_t$=0.52 min; MS (ESIpos): m/z=261 (M+H)$^+$

Example 66A 1-(2-Fluorobenzyl)-3-iodo-6-methyl-1H-pyrazolo[3,4-d]pyrimidine

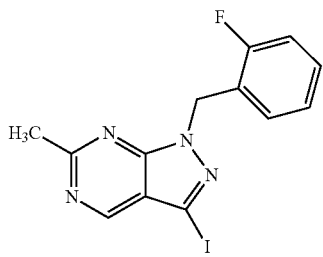 [SMILES: Cc1ncc2c(I)nn(Cc3ccccc3F)c2n1]

7.950 g (13.76 mmol) of 3-iodo-6-methyl-1H-pyrazolo[3,4-d]pyrimidine and 4.930 g (15.13 mmol) of caesium carbonate were put in 20 ml DMF and 2.860 g (15.13 mmol) of 2-fluorobenzyl bromide dissolved in 5 ml DMF was added. The reaction mixture was stirred overnight at RT, diluted with 100 ml water and extracted with ethyl acetate. The organic phase was dried over sodium sulphate and concentrated in a rotary evaporator. The residue was purified by preparative HPLC (eluent: acetonitrile/water, gradient 30:70→95:5). 1.030 g of the target compound was obtained (20% of theor.).

LC-MS (method 4): $R_t$=2.27 min; MS (ESIpos): m/z=369 (M+H)$^+$

Example 67A 1-(2-Fluorobenzyl)-6-methyl-1H-pyrazolo[3,4-d]pyrimidine-3-carbonitrile

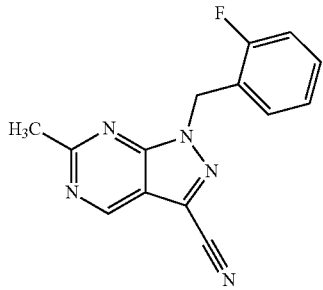 [SMILES: Cc1ncc2c(C#N)nn(Cc3ccccc3F)c2n1]

1.485 g (4.03 mmol) of 1-(2-fluorobenzyl)-3-iodo-6-methyl-1H-pyrazolo[3,4-d]pyrimidine and 397 mg (4.44 mmol) of copper(I) cyanide were put in 11 ml of absolute DMSO and heated for 2 h at 150° C. After cooling, the reaction mixture was filtered on Celite and then washed with ethyl acetate and THF. The organic phase was washed with 25% aqueous ammonia solution, saturated aqueous ammonium chloride solution and saturated aqueous sodium chloride solution, dried over sodium sulphate and concentrated in a rotary evaporator. 994 mg (purity 81%, 75% of theor.) of the target compound was obtained.

LC-MS (method 1): $R_t$=0.96 min; MS (ESIpos): m/z=268 (M+H)$^+$

Example 68A 1-(2-Fluorobenzyl)-6-methyl-1H-pyrazolo[3,4-d]pyrimidine-3-carboximidamide

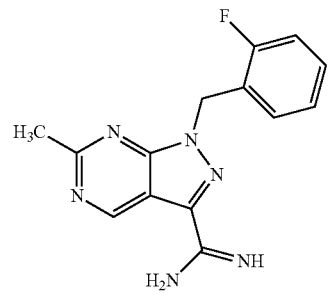 [SMILES: Cc1ncc2c(C(=N)N)nn(Cc3ccccc3F)c2n1]

Under an argon atmosphere, 994 mg (purity 81%, approx. 3.01 mmol) of 1-(2-fluorobenzyl)-6-methyl-1H-pyrazolo[3,4-d]pyrimidine-3-carbonitrile was dissolved in 15 ml of absolute methanol. 209 mg (3.72 mmol) of sodium methylate was added and it was stirred for 1 h at RT. Then a further 31 mg (0.56 mmol) of sodium methylate was added and it was stirred for 15 min at RT. 871 mg (14.50 mmol) of acetic acid and 489 mg (4.46 mmol) of ammonium chloride were added and the mixture was stirred for 45 min at 45° C. The reaction mixture was concentrated by evaporation, the residue was mixed with 1N sodium hydroxide solution, the precipitate was filtered with suction and dried under high vacuum. 918 mg (purity 91%, 97% of theor.) of the target compound was obtained.

LC-MS (method 2) $R_t$=0.53 min; MS (ESIpos): m/z=285 (M+H)$^+$ $^1$H-NMR (400 MHz, DMSO-$d_6$): δ [ppm]=2.75 (s, 3H), 5.65-5.73 (m, 1H), 5.71 (s, 2H), 7.10-7.18 (m, 2H), 7.19-7.29 (m, 1H), 7.33-7.43 (m, 1H), 9.51 (s, 1H).

Example 69A

4-Amino-2-[1-(2-fluorobenzyl)-6-methyl-1H-pyrazolo[3,4-d]pyrimidin-3-yl]-5,5-dimethyl-5,7-dihydro-6H-pyrrolo[2,3-d]pyrimidin-6-one

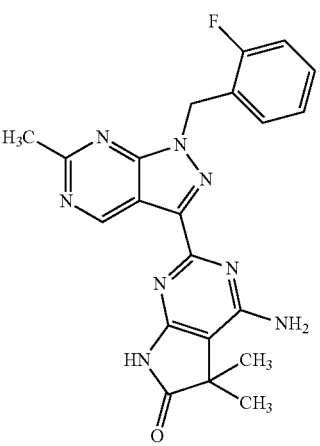 [SMILES: Cc1ncc2c(-c3nc(N)c4c(n3)NC(=O)C4(C)C)nn(Cc3ccccc3F)c2n1]

3 ml tert.-butanol, a solution of 146 mg (0.70 mmol) of methyl-3,3-dicyano-2,2-dimethylpropanoate in 1.5 ml tert.-butanol and 94 mg (0.84 mmol) of potassium tert.-butylate were added to 200 mg (0.70 mmol) of 1-(2-fluorobenzyl)-6-methyl-1H-pyrazolo[3,4-d]pyrimidine-3-carboximidamide and it was heated under reflux for 48 h. Water was added and the precipitate was filtered off. The filtrate was extracted with dichloromethane, the organic phase was dried over sodium sulphate and concentrated in a rotary evaporator. The residue was mixed with water/ethanol. The solid was filtered off and dried under high vacuum. 102 mg (34% of theor.) of the target compound was obtained.

LC-MS (method 1): $R_t$=0.81 min; MS (ESIpos): m/z=419 $(M+H)^+$

Example 70A

2-[1-(2-Fluorobenzyl)-6-methyl-1H-pyrazolo[3,4-d]pyrimidin-3-yl]-4-iodo-5,5-dimethyl-5,7-dihydro-6H-pyrrolo[2,3-d]pyrimidin-6-one

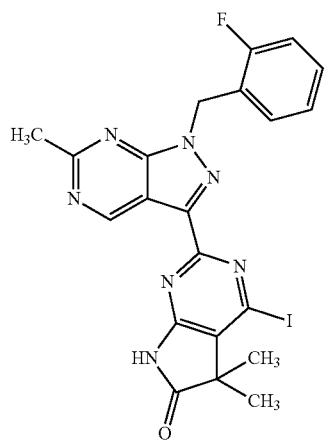 [SMILES: Cc1ncc2c(-c3nc(I)c4c(n3)NC(=O)C4(C)C)nn(Cc3ccccc3F)c2n1]

3.770 g (14.08 mmol) of diiodomethane and 411 mg (3.51 mmol) of isopentyl nitrite were added to 70 mg (0.17 mmol) of 4-amino-2-[1-(2-fluorobenzyl)-6-methyl-1H-pyrazolo[3,4-d]pyrimidin-3-yl]-5,5-dimethyl-5,7-dihydro-6H-pyrrolo[2,3-d]pyrimidin-6-one. The mixture was stirred for 8 h at 85° C. After cooling, it was diluted with acetonitrile and the mixture was purified by preparative HPLC (eluent: acetonitrile/water, gradient 30:70→95:5). 35 mg (24% of theor.) of the target compound was obtained.

LC-MS (method 4): $R_t$=2.37 min; MS (ESIpos): m/z=530 $(M+H)^+$

In addition, 10 mg (14% of theor.) of 2-[1-(2-fluorobenzyl)-6-methyl-1H-pyrazolo[3,4-d]pyrimidin-3-yl]-4-hydroxy-5,5-dimethyl-5,7-dihydro-6H-pyrrolo[2,3-d]pyrimidin-6-one was obtained.

Example 71A

4-Amino-2-[1-(2,3-difluorobenzyl)-5-fluoro-1H-pyrazolo[3,4-b]pyridin-3-yl]-5,5-dimethyl-5,7-dihydro-6H-pyrrolo[2,3-d]pyrimidin-6-one

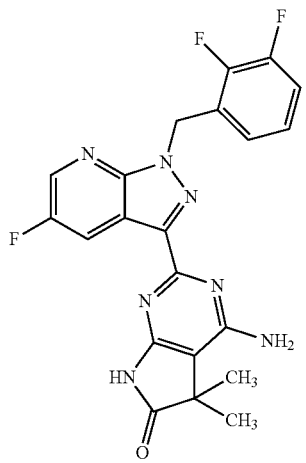 [SMILES: CC1(C)C(=O)Nc2nc(-c3nn(Cc4cccc(F)c4F)c4ncc(F)cc34)nc(N)c21]

On the analogy of the preparation of example 13A, 5.00 g (13.687 mmol) of 1-(2,3-difluorobenzyl)-5-fluoro-1H-pyrazolo[3,4-b]pyridine-3-carboximidamide acetate (example 64A from WO 2012/004258, Page 102-103) was reacted. 5.13 g of the title compound was obtained (85% of theor.).

LC-MS (method 1) $R_t$=0.97 min; MS (ESIpos): m/z=440 $[M+H]^+$

Example 72A

2-[1-(2,3-Difluorobenzyl)-5-fluoro-1H-pyrazolo[3,4-b]pyridin-3-yl]-4-iodo-5,5-dimethyl-5,7-dihydro-6H-pyrrolo[2,3-d]pyrimidin-6-one

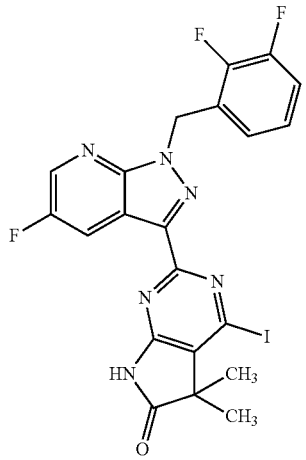 [SMILES: CC1(C)C(=O)Nc2nc(-c3nn(Cc4cccc(F)c4F)c4ncc(F)cc34)nc(I)c21]

On the analogy of the preparation of example 16A, 5.11 g (11.629 mmol) of example 71A was reacted. 2.39 g of the title compound was obtained (85% of theor.).

LC-MS (method 1) $R_t$=1.25 min; MS (ESIpos): m/z=551 $[M+H]^+$

In addition to the title compound, 660 mg (12% of theor.) of 2-[1-(2,3-difluorobenzyl)-5-fluoro-1H-pyrazolo[3,4-b]pyridin-3-yl]-4-hydroxy-5,5-dimethyl-5,7-dihydro-6H-pyrrolo[2,3-d]pyrimidin-6-one (example 116) was obtained.

Example 73A

5-Fluoro-1-(2-fluorobenzyl)-1H-pyrazolo[3,4-b]pyridine-3-carboximidamide hydrochloride

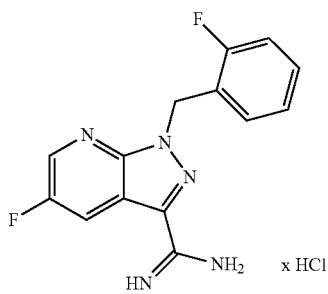 [SMILES: N=C(N)c1nn(Cc2ccccc2F)c2ncc(F)cc12]

406.0 g (1.50 mol) of the compound from example 10A was suspended in 2.08 L ethanol. Then 54.1 g (0.30 mol) of sodium methanolate in methanol (30%) was added and it was stirred overnight at room temperature. 88.4 g (1.65 mol) of ammonium chloride was added, it was heated to 65° C. and stirred for 3.5 h at 65° C. The solvents were distilled off and the residue was stirred overnight with 1.6 L ethyl acetate. The precipitated solid was filtered with suction, washed twice with 140 ml ethyl acetate each time and dried in a vacuum drying cabinet at 50° C. under a gentle nitrogen stream. 441.4 g (90.7% of theor.) of the title compound was obtained.

MS (ESIpos): m/z=288 (M+H)$^+$ $^1$H-NMR (400 MHz, DMSO-d$_6$): δ=5.90 (s, 2H), 7.15-7.20 (m, 1H), 7.22-7.28 (m, 1H), 7.29-7.35 (m, 1H), 7.36-7.43 (m, 1H), 8.48 (dd, 1H), 8.86 (dd, 1H), 9.35 (br s, 3H) ppm.

PRACTICAL EXAMPLES

Example 1

2-[1-(2-Fluorobenzyl)-1H-pyrazolo[3,4-b]pyridin-3-yl]-4-methoxy-5,5-dimethyl-5,7-dihydro-6H-pyrrolo[2,3-d]pyrimidin-6-one

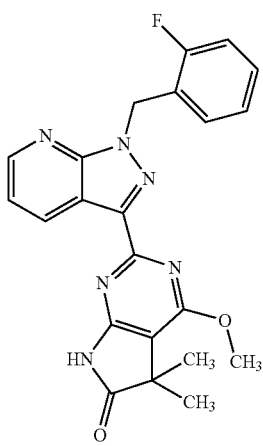 [SMILES: COc1nc(-c2nn(Cc3ccccc3F)c3ncccc23)nc2c1C(C)(C)C(=O)N2]

Methanol (3 ml), 126 mg (0.389 mmol) of caesium carbonate, 3.7 mg (0.019 mmol) of copper(I) iodide and 9 mg (0.039 mmol) of 3,4,7,8-tetramethyl-1,10-phenanthroline were added to 100 mg (0.194 mmol) of example 15A in a reaction vessel suitable for a microwave. It was rinsed with argon under ultrasonic treatment for 5 min and then sealed with a suitable septum. Then it was heated in the microwave in 3 cycles, in each case for 2 h at 140° C. After cooling, the reaction mixture was filtered, concentrated by evaporation and the residue was purified by preparative HPLC (acetonitrile:water (+0.05% formic acid) gradient). 32 mg of the title compound was obtained (39% of theor.).

LC-MS (method 1): R$_t$=1.08 min; MS (EIpos): m/z=419 [M+H]$^+$.

$^1$H-NMR (400 MHz, DMSO-d$_6$): δ [ppm]=1.35 (s, 6H), 4.15 (s, 3H), 5.87 (s, 2H), 7.13-7.26 (m, 3H), 7.34-7.38 (m, 1H), 7.45 (dd, 1H), 8.68 (dd, 1H), 8.91 (dd, 1H), 11.44 (s br, 1H).

Example 2

2-[5-Fluoro-1-(2-fluorobenzyl)-1H-pyrazolo[3,4-b]pyridin-3-yl]-4-[(2-hydroxyethyl)amino]-5,5-dimethyl-5,7-dihydro-6H-pyrrolo[2,3-d]pyrimidin-6-one

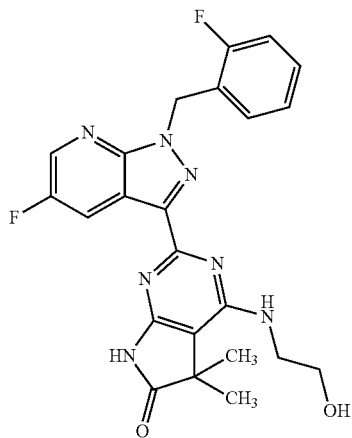 [SMILES: CC1(C)C(=O)Nc2nc(-c3nn(Cc4ccccc4F)c4ncc(F)cc34)nc(NCCO)c21]

In a reaction vessel suitable for a microwave, 100 mg (0.115 mmol, approx. 61% purity) of example 16A was dissolved in 1-methyl-2-pyrrolidone (2 ml) and 0.75 ml aminoethanol was added. Then it was sealed with a corresponding septum and was heated in the microwave for 5 h at 150° C. After cooling, the reaction mixture was purified by preparative HPLC (acetonitrile:water (+0.05% formic acid) gradient). 68 mg of the title compound was obtained (100% of theor., 94% purity according to LC/MS).

LC-MS (method 3): R$_t$=0.94 min; MS (EIpos): m/z=466 [M+H]$^+$.

$^1$H-NMR (400 MHz, DMSO-d$_6$): δ [ppm]=1.36 (s, 6H), 3.29 (s, signal superimposed with water signal, 2H), 3.64 (s, 2H), 4.82 (t, 1H), 5.83 (s, 2H), 6.65 (t br, 1H), 7.13-7.25 (m, 3H), 7.33-7.39 (m, 1H), 8.55 (dd, 1H), 8.71 (dd, 1H), 11.00 (s br, 1H).

Example 3

4-[(2-Amino-2-methylpropyl)amino]-2-[5-fluoro-1-(2-fluorobenzyl)-1H-pyrazolo[3,4-b]pyridin-3-yl]-5,5-dimethyl-5,7-dihydro-6H-pyrrolo[2,3-d]pyrimidin-6-one

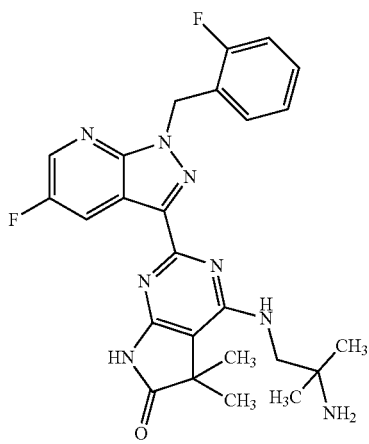

100 mg (0.115 mmol, approx. 61% purity) of example 16A was dissolved in 1-methyl-2-pyrrolidone (2 ml) in a reaction vessel suitable for a microwave and 0.75 ml 2-methylpropane-1,2-diamine was added. Then it was sealed with a corresponding septum and it was heated in the microwave at 150° C. for 3 h. After cooling, the reaction mixture was purified by preparative HPLC (acetonitrile:water (+0.05% formic acid) gradient). 57 mg of the title compound was obtained (100% of theor.).

LC-MS (method 3): $R_t$=0.82 min; MS (EIpos): m/z=493 [M+H]$^+$.

$^1$H-NMR (400 MHz, DMSO-d$_6$): δ [ppm]=1.21 (s, 6H), 1.41 (s, 6H), 3.67 (signal superimposed with water signal probably 2H), 5.84 (s, 2H), 6.98 (m br, 1H), 7.15 (t, 1H), 7.20-7.26 (m, 2H), 7.34-7.39 (m, 1H), 8.56 (dd, 1H), 8.73 (dd, 1H), signals for —NH—C=O and —NH$_2$ not observed.

Example 4

2-[5-Fluoro-1-(2-fluorobenzyl)-1H-pyrazolo[3,4-b]pyridin-3-yl]-4-[(2-hydroxy-2-methylpropyl)amino]-5,5-dimethyl-5,7-dihydro-6H-pyrrolo[2,3-d]pyrimidin-6-one

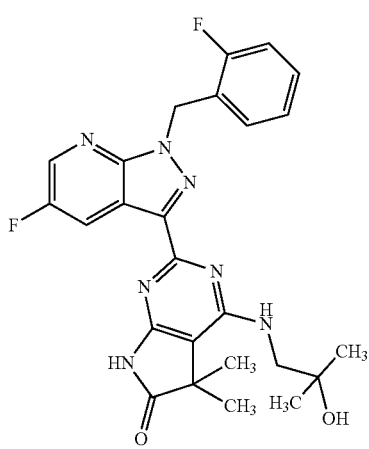 [SMILES: CC(C)(O)CNc1nc(-c2nn(Cc3ccccc3F)c3ncc(F)cc23)nc2c1C(C)(C)C(=O)N2]

100 mg (0.115 mmol, approx. 61% purity) of example 16A was dissolved in 1-methyl-2-pyrrolidone (2 ml) in a reaction vessel suitable for a microwave and 0.5 ml of 1-amino-2-methylpropan-2-ol was added. Then it was sealed with a corresponding septum and it was heated in the microwave at 150° C. for 3 h. After cooling, the reaction mixture was purified by preparative HPLC (acetonitrile:water (+0.05% formic acid) gradient). 56 mg of the title compound was obtained (100% of theor.).

LC-MS (method 1): $R_t$=1.06 min; MS (EIpos): m/z=494 [M+H]$^+$.

$^1$H-NMR (400 MHz, DMSO-d$_6$): δ [ppm]=1.15 (s, 6H), 1.39 (s, 6H), 3.60 (d, 2H), 4.76 (s, 1H), 5.82 (s, 2H), 6.41 (t, 1H), 7.15 (t, 1H), 7.20-7.26 (m, 2H), 7.34-7.39 (m, 1H), 8.64 (dd, 1H), 8.72 (dd, 1H), 11.06 (s br, 1H).

Example 5

2-[5-Fluoro-1-(2-fluorobenzyl)-1H-pyrazolo[3,4-b]pyridin-3-yl]-5,5-dimethyl-4-[(3,3,3-trifluoropropyl)amino]-5,7-dihydro-6H-pyrrolo[2,3-d]pyrimidin-6-one

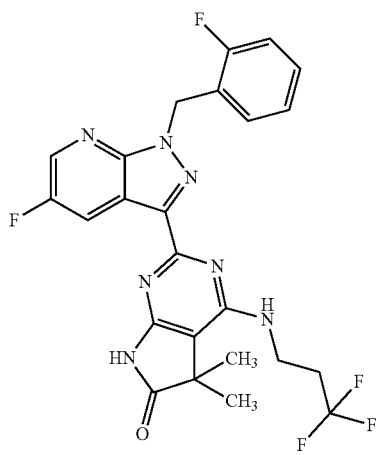 [SMILES: CC1(C)C(=O)Nc2nc(-c3nn(Cc4ccccc4F)c4ncc(F)cc34)nc(NCCC(F)(F)F)c21]

100 mg (0.115 mmol, approx. 61% purity) of example 16A was dissolved in 1-methyl-2-pyrrolidone (2 ml) in a reaction vessel suitable for a microwave and 0.5 ml of 3,3,3-trifluoropropyl-1-amine was added. Then it was sealed with a corresponding septum and it was heated in the microwave at 150° C. for 3 h. After cooling, the reaction mixture was purified by preparative HPLC (acetonitrile:water (+0.05% formic acid) gradient). 60 mg of the title compound was obtained (100% of theor.).

LC-MS (method 1): $R_t$=1.21 min; MS (EIpos): m/z=518 [M+H]$^+$.

$^1$H-NMR (400 MHz, DMSO-d$_6$): δ [ppm]=1.35 (s, 6H), 2.64-2.71 (m, 2H), 3.82 (q, 2H), 5.83 (s, 2H), 6.88 (t, 1H), 7.15 (t, 1H), 7.20-7.25 (m, 2H), 7.34-7.40 (m, 1H), 8.48 (dd, 1H), 8.72 (dd, 1H), 11.10 (s, 1H).

Example 6

4-[(2-Amino-3,3,3-trifluoropropyl)amino]-2-[5-fluoro-1-(2-fluorobenzyl)-1H-pyrazolo[3,4-b]pyridin-3-yl]-5,5-dimethyl-5,7-dihydro-6H-pyrrolo[2,3-d]pyrimidin-6-one

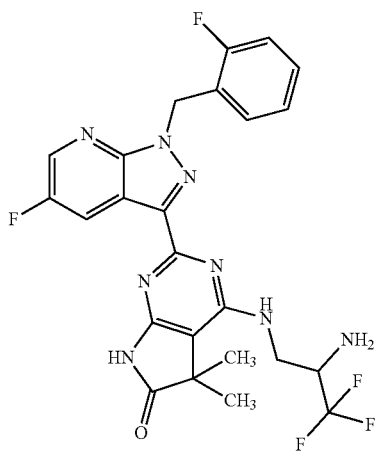 [SMILES: CC1(C)C(=O)Nc2nc(-c3nn(Cc4ccccc4F)c4ncc(F)cc34)nc(NCC(N)C(F)(F)F)c21]

100 mg (0.115 mmol, approx. 61% purity) of example 16A was suspended in 1-methyl-2-pyrrolidone (2 ml) in a reaction vessel suitable for a microwave, and 1 ml diisopropyl ethylamine and then 300 mg (1.492 mmol) of 1-(trifluoromethyl)ethylene-1,2-diamin-dihydrochloride were added. Then it was sealed with a corresponding septum and it was heated in the microwave at 150° C. for 3 h. After cooling, the reaction mixture was purified by preparative HPLC (acetonitrile:water (+0.05% formic acid) gradient). 5.7 mg of the title compound was obtained (9% of theor.).

LC-MS (method 1): $R_t$=0.98 min; MS (EIpos): m/z=534 [M+H]$^+$.

$^1$H-NMR (400 MHz, DMSO-d$_6$): δ [ppm]=1.37 (d, 6H), 3.47-3.45 (m, 1H), 3.62-3.73 (m, 1H), 3.94-4.00 (m, 1H), 5.83 (s, 2H), 6.82 (t, 1H), 7.15 (t, 1H), 7.20-7.26 (m, 2H), 7.34-7.39 (m, 1H), 8.56 (dd, 1H), 8.72 (br d, 1H), 11.11 (br s, 1H), —NH$_2$ not observed

Example 7

4-[(2,2-Difluoroethyl)amino]-2-[5-fluoro-1-(2-fluorobenzyl)-1H-pyrazolo[3,4-b]pyridin-3-yl]-5,5-dimethyl-5,7-dihydro-6H-pyrrolo[2,3-d]pyrimidin-6-one

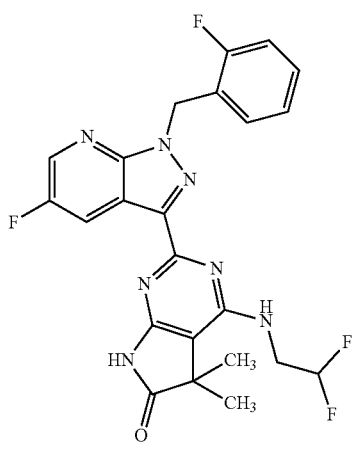 [SMILES: CC1(C)C(=O)Nc2nc(-c3nn(Cc4ccccc4F)c4ncc(F)cc34)nc(NCC(F)F)c21]

100 mg (0.115 mmol, approx. 61% purity) of example 16A was dissolved in 1-methyl-2-pyrrolidone (2 ml) in a reaction vessel suitable for a microwave and 0.5 ml of 2,2-difluoroethylamine was added. Then it was sealed with a corresponding septum and it was heated in the microwave at 150° C. for 3 h. After cooling, the reaction mixture was purified by preparative HPLC (acetonitrile:water (+0.05% formic acid) gradient). 30 mg of the title compound was obtained (55% of theor., 100%).

LC-MS (method 1): $R_t$=1.15 min; MS (EIpos): m/z=486 [M+H]$^+$.

$^1$H-NMR (400 MHz, DMSO-d$_6$): δ [ppm]=1.37(s, 6H), 3.91-4.00 (m, 2H), 5.83 (s, 2H), 6.13-6.43 (m, 1H), 7.04 (t, 1H), 7.15 (dd, 1H), 7.20-7.25 (m, 2H), 7.34-7.39 (m, 1H), 8.46 (dd, 1H), 8.72 (dd, 1H), 11.13 (s, 1H).

Example 8

4-(3-Fluoroazetidin-1-yl)-2-[5-fluoro-1-(2-fluorobenzyl)-1H-pyrazolo[3,4-b]pyridin-3-yl]-5,5-dimethyl-5,7-dihydro-6H-pyrrolo[2,3-d]pyrimidin-6-one

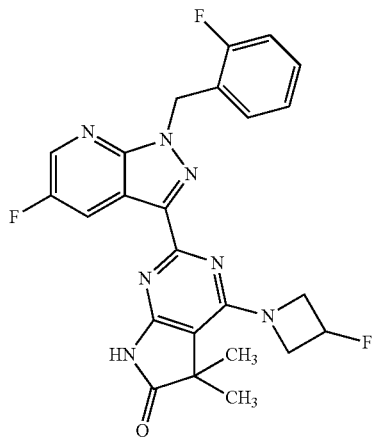 [SMILES: CC1(C)C(=O)Nc2nc(-c3nn(Cc4ccccc4F)c4ncc(F)cc34)nc(N3CC(F)C3)c21]

100 mg (0.115 mmol, approx. 61% purity) of example 16A was dissolved in 1-methyl-2-pyrrolidone (2 ml) in a reaction vessel suitable for a microwave, and 0.314 ml (1.800 mmol) of N,N-diisopropyl ethylamine and 200 mg (1.793 mmol) of 3-fluoroazetidine hydrochloride were added. Then it was sealed with a corresponding septum and it was heated in the microwave at 150° C. for 3 h. After cooling, the reaction mixture was purified by preparative HPLC (acetonitrile:water (+0.05% formic acid) gradient). 22 mg of the title compound was obtained (41% of theor.).

LC-MS (method 1): $R_t$=1.19 min; MS (EIpos): m/z=480 [M+H]$^+$.

$^1$H-NMR (400 MHz, DMSO-d$_6$): δ [ppm]=1.35 (s, 6H), 4.34-4.42 (m, 2H), 4.63-4.73 (m, 2H), 5.48-5.66 (m, 1H), 5.84 (s, 2H), 7.13-7.25 (m, 3H), 7.34-7.40 (m, 1H), 8.52 (dd, 1H), 8.73 (dd, 1H), 11.27 (s, 1H).

Example 9

4-[(Dicyclopropylmethyl)amino]-2-[5-fluoro-1-(2-fluorobenzyl)-1H-pyrazolo[3,4-b]pyridin-3-yl]-5,5-dimethyl-5,7-dihydro-6H-pyrrolo[2,3-d]pyrimidin-6-one

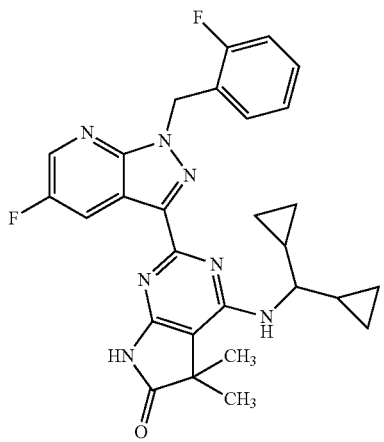 [SMILES: CC1(C)C(=O)Nc2nc(-c3nn(Cc4ccccc4F)c4ncc(F)cc34)nc(NC(C3CC3)C3CC3)c21]

100 mg (0.115 mmol, approx. 61% purity) of example 16A was dissolved in 1-methyl-2-pyrrolidone (2 ml) in a reaction vessel suitable for a microwave and 0.5 ml of dicyclopropylmethylamine was added. Then it was sealed with a corresponding septum and it was heated in the microwave at 150° C. for 3 h. After cooling, the reaction mixture was purified by preparative HPLC (acetonitrile:water (+0.05% formic acid) gradient). 25 mg of the title compound was obtained (42% of theor.).

LC-MS (method 1): $R_t$=1.34 min; MS (EIpos): m/z=516 [M+H]$^+$.

$^1$H-NMR (400 MHz, DMSO-d$_6$): δ [ppm]=0.28-0.41 (m, 6H), 0.49-0.58 (m, 2H), 1.25-1.34 (m, 2H), 1.40 (s, 6H), 3.49 (dd, 1H), 5.81 (s, 2H), 6.40 (d, 1H), 7.14 (t, 1H), 7.20-7.24 (m, 2H), 7.34-7.39 (m, 1H), 8.37 (dd, 1H), 8.72 (m, 1H), 11.02 (s br, 1H).

Example 10

4-[(Cyclopropylmethyl)amino]-2-[5-fluoro-1-(2-fluorobenzyl)-1H-pyrazolo[3,4-b]pyridin-3-yl]-5,5-dimethyl-5,7-dihydro-6H-pyrrolo[2,3-d]pyrimidin-6-one

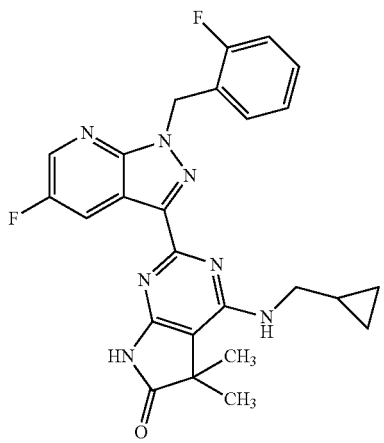 [SMILES: CC1(C)C(=O)Nc2nc(-c3nn(Cc4ccccc4F)c4ncc(F)cc34)nc(NCC3CC3)c21]

100 mg (0.115 mmol, approx. 61% purity) of example 16A was dissolved in 1-methyl-2-pyrrolidone (2 ml) in a reaction vessel suitable for a microwave and 0.5 ml of aminomethyl-cyclopropane was added. Then it was sealed with a corresponding septum and it was heated in the microwave at 150° C. for 3 h. After cooling, the reaction mixture was purified by preparative HPLC (acetonitrile:water (+0.05% formic acid) gradient). 45 mg of the title compound was obtained (82% of theor.).

LC-MS (method 1): $R_t$=1.22 min; MS (EIpos): m/z=476 [M+H]$^+$.

$^1$H-NMR (400 MHz, DMSO-d$_6$): δ [ppm]=0.31-0.34 (m, 2H), 0.42-0.46 (m, 2H), 1.21-1.26 (m, 1H), 1.37 (s, 6H), 3.45 (t, 2H), 5.83 (s, 2H), 6.88 (t, 1H), 7.15 (t, 1H), 7.21-7.25 (m, 2H), 7.34-7.39 (m, 1H), 8.57 (dd, 1H), 8.72 (m, 1H), 11.02 (s br, 1H).

Example 11

2-[5-Fluoro-1-(2-fluorobenzyl)-1H-pyrazolo[3,4-b]pyridin-3-yl]-5,5-dimethyl-4-[(2,2,2-trifluoroethyl)amino]-5,7-dihydro-6H-pyrrolo[2,3-d]pyrimidin-6-one

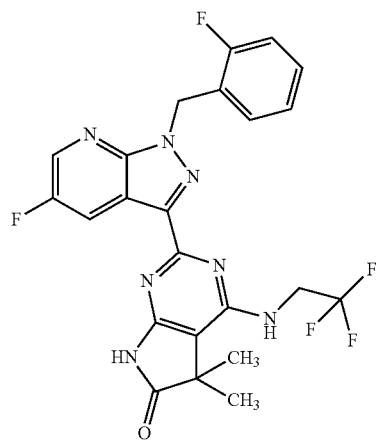 [SMILES: CC1(C)C(=O)Nc2nc(-c3nn(Cc4ccccc4F)c4ncc(F)cc34)nc(NCC(F)(F)F)c21]

100 mg (0.115 mmol, approx. 61% purity) of example 16A was dissolved in 1-methyl-2-pyrrolidone (2 ml) in a reaction vessel suitable for a microwave and 1 ml of 2,2,2-trifluoroethylamine was added. Then it was sealed with a corresponding septum and heated in the microwave at 150° C. for 20 h. After cooling, the reaction mixture was purified by preparative HPLC (acetonitrile:water (+0.05% formic acid) gradient). 35 mg of the title compound was obtained (61% of theor.).

LC-MS (method 1): $R_t$=1.12 min; MS (EIpos): m/z=504 [M+H]$^+$.

$^1$H-NMR (400 MHz, DMSO-d$_6$): δ [ppm]=1.39 (s, 6H), 4.35-4.43 (m, 2H), 5.84 (s, 2H), 7.15 (t, 1H), 7.20-7.25 (m, 3H), 7.34-7.40 (m, 1H), 8.46 (dd, 1H), 8.73 (m, 1H), 11.22 (s br, 1H).

Example 12

2-{5-Fluoro-1-[(3-fluoropyridin-2-yl)methyl]-1H-pyrazolo[3,4-b]pyridin-3-yl}-5,5-dimethyl-4-[(3,3,3-trifluoropropyl)amino]-5,7-dihydro-6H-pyrrolo[2,3-d]pyrimidin-6-one

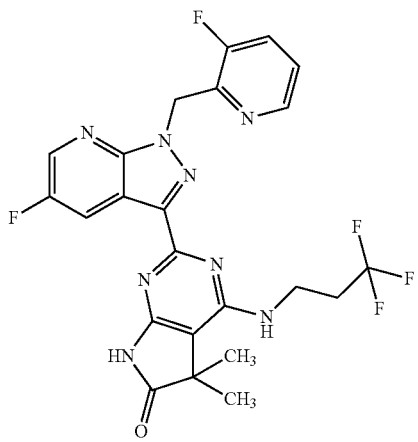 [SMILES: CC1(C)C(=O)Nc2nc(-c3nn(Cc4ncccc4F)c4ncc(F)cc34)nc(NCCC(F)(F)F)c21]

350 mg (0.361 mmol, approx. 55% purity) of example 21A was dissolved in 1-methyl-2-pyrrolidone (4 ml) in a reaction vessel suitable for a microwave and 1.2 ml of 3,3,3-trifluoropropyl-1-amine was added. Then it was sealed with a corresponding septum and it was heated in the microwave at 150° C. for 3 h. After cooling, the reaction mixture was purified by preparative HPLC (acetonitrile:water (+0.05% formic acid) gradient). 108 mg of the title compound was obtained (57% of theor.).

LC-MS (method 1): $R_t$=1.08 min; MS (EIpos): m/z=519 [M+H]$^+$.

$^1$H-NMR (400 MHz, DMSO-d$_6$): δ [ppm]=1.35 (s, 6H), 2.62-2.72 (m, 2H), 3.82 (q, 2H), 5.96 (s, 2H), 6.82 (t, 1H), 7.42-7.45 (m, 1H), 7.76 (t, 1H), 8.27 (d, 1H), 8.48 (dd, 1H), 8.67 (br s, 1H), 11.03 (s, 1H).

Example 13

2-[6-Chloro-3-(2,3,6-trifluorobenzyl)imidazo[1,5-a]pyridin-1-yl]-5,5-dimethyl-4-[(3,3,3-trifluoropropyl)amino]-5,7-dihydro-6H-pyrrolo[2,3-d]pyrimidin-6-one

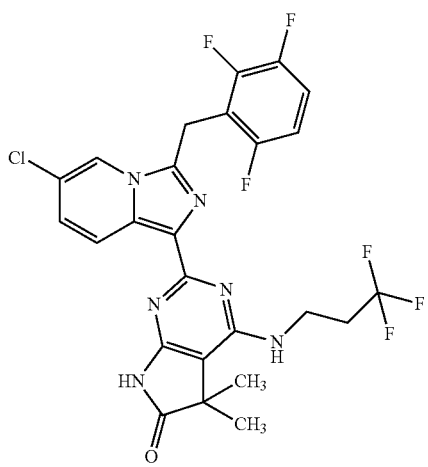 [SMILES: CC1(C)C(=O)Nc2nc(-c3nc(Cc4c(F)ccc(F)c4F)n4cc(Cl)ccc34)nc(NCCC(F)(F)F)c21]

128 mg (0.219 mmol) of example 22A was dissolved in 1-methyl-2-pyrrolidone (2.334 ml) in a reaction vessel suitable for a microwave and 0.584 ml of 3,3,3-trifluoropropyl-1-amine was added. Then it was sealed with a corresponding septum and it was heated in the microwave at 150° C. for 3 h. After cooling, the reaction mixture was purified by preparative HPLC (acetonitrile:water (+0.05% formic acid) gradient). 57 mg of the title compound was obtained (46% of theor.).

LC-MS (method 1): $R_t$=1.21 min; MS (EIpos): m/z=569 [M+H]$^+$.

$^1$H-NMR (400 MHz, DMSO-d$_6$): δ [ppm]=1.31 (s, 6H), 2.62-2.71 (m, 2H), 3.73 (q, 2H), 4.53 (s, 2H), 6.69 (t, 1H), 7.05 (dd, 1H), 7.17-7.24 (m, 1H), 7.46-7.55 (m, 1H), 8.42 (d, 1H), 8.80 (s, 1H), 10.91 (s, 1H).

Example 14

2-{5-Fluoro-1-[(3-fluoropyridin-2-yl)methyl]-1H-pyrazolo[3,4-b]pyridin-3-yl}-5,5-dimethyl-4-[(3,3,3-trifluoropropyl)amino]-5,7-dihydro-6H-pyrrolo[2,3-d]pyrimidin-6-one

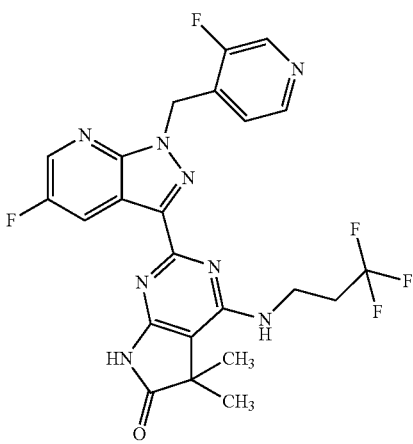 [SMILES: CC1(C)C(=O)Nc2nc(-c3nn(Cc4ccncc4F)c4ncc(F)cc34)nc(NCCC(F)(F)F)c21]

150 mg (0.186 mmol, approx. 66% purity) of the compound obtained in example 28A was dissolved in 1-methyl-2-pyrrolidone (3.6 ml) in a reaction vessel suitable for a microwave and 0.9 ml of 3,3,3-trifluoropropyl-1-amine was added. Then it was sealed with a corresponding septum and it was heated in the microwave at 150° C. for 3 h. After cooling, the reaction mixture was purified by preparative HPLC (acetonitrile:water (+0.05% formic acid) gradient). 33 mg of the title compound was obtained (34% of theor.).

LC-MS (method 1): $R_t$=1.00 min; MS (EIpos): m/z=519 [M+H]$^+$.

$^1$H-NMR (400 MHz, DMSO-d$_6$): δ [ppm]=1.36 (s, 6H), 2.61-2.74 (m, 2H), 3.82 (q, 2H), 5.92 (s, 2H), 6.89 (t, 1H), 7.13 (t, 1H), 8.35 (d, 1H), 8.50 (dd, 1H), 8.59 (d, 1H), 8.73 (dd, 1H), 11.10 (s, 1H).

Example 15

4-(3-Fluoroazetidin-1-yl)-2-{5-fluoro-1-[(3-fluoro-pyridin-2-yl)methyl]-1H-pyrazolo[3,4-b]pyridin-3-yl}-5,5-dimethyl-5,7-dihydro-6H-pyrrolo[2,3-d]pyrimidin-6-one

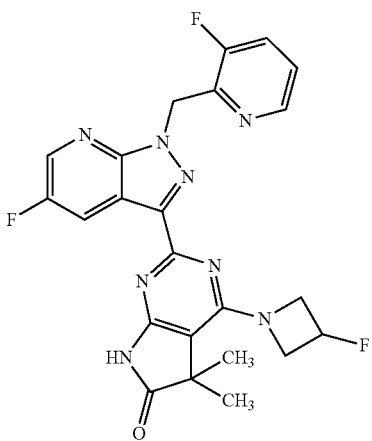 [SMILES: CC1(C)C(=O)Nc2nc(-c3nn(Cc4ncccc4F)c4ncc(F)cc34)nc(N3CC(F)C3)c21]

150 mg (0.155 mmol, approx. 55% purity) of the compound obtained in example 21A was dissolved in 1-methyl-2-pyrrolidone (2.7 ml) in a reaction vessel suitable for a microwave, and 0.423 ml (2.430 mmol) of N,N-diisopropyl ethylamine and 270 mg (2.420 mmol) of 3-fluoroazetidine hydrochloride were added. Then it was sealed with a corresponding septum and it was heated in the microwave at 150° C. for 3 h. After cooling, the reaction mixture was purified by preparative HPLC (acetonitrile:water (+0.05% formic acid) gradient). 30 mg of the title compound was obtained (40% of theor.).

LC-MS (method 1): $R_t$=0.97 min; MS (EIpos): m/z=481 [M+H]$^+$.

$^1$H-NMR (400 MHz, DMSO-$d_6$): δ [ppm]=1.35 (s, 6H), 4.34-4.42 (m, 2H), 4.63-4.73 (m, 2H), 5.48-5.65 (m, 1H), 5.98 (s, 2H), 7.41-7.45 (m, 1H), 7.74-7.79 (m, 1H), 8.24-8.28 (m, 1H), 8.52 (dd, 1H), 8.68 (dd, 1H), 11.22 (s, 1H).

Example 16

2-{5-Fluoro-1-[(3-fluoropyridin-2-yl)methyl]-1H-pyrazolo[3,4-b]pyridin-3-yl}-5,5-dimethyl-4-[(2,2,2-trifluoroethyl)amino]-5,7-dihydro-6H-pyrrolo[2,3-d]pyrimidin-6-one

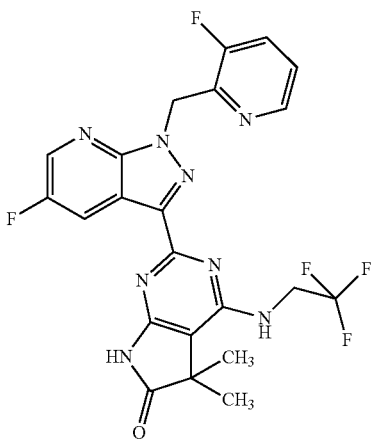 [SMILES: CC1(C)C(=O)Nc2nc(-c3nn(Cc4ncccc4F)c4ncc(F)cc34)nc(NCC(F)(F)F)c21]

150 mg (0.155 mmol, approx. 55% purity) of the compound obtained in example 21A was dissolved in 1-methyl-2-pyrrolidone (2.7 ml) in a reaction vessel suitable for a microwave and 0.675 ml 2,2,2-trifluoroethylamine was added. Then it was sealed with a corresponding septum and heated in the microwave at 150° C. for 21 h. After cooling, the reaction mixture was purified by preparative HPLC (acetonitrile:water (+0.05% formic acid) gradient). 31 mg of the title compound was obtained (39% of theor.).

LC-MS (method 1): $R_t$=0.99 min; MS (EIpos): m/z=505 [M+H]$^+$.

$^1$H-NMR (400 MHz, DMSO-$d_6$): δ [ppm]=1.39 (s, 6H), 4.35-4.44 (m, 2H), 5.98 (s, 2H), 7.19 (t, 1H), 7.41-7.45 (m, 1H), 7.74-7.79 (m, 1H), 8.24-8.28 (m, 1H), 8.46 (dd, 1H), 8.68 (dd, 1H), 11.16 (s br, 1H).

Example 17

4-[(Cyclopropylmethyl)amino]-2-{5-fluoro-1-[(3-fluoropyridin-2-yl)methyl]-1H-pyrazolo[3,4-b]pyridin-3-yl}-5,5-dimethyl-5,7-dihydro-6H-pyrrolo[2,3-d]pyrimidin-6-one

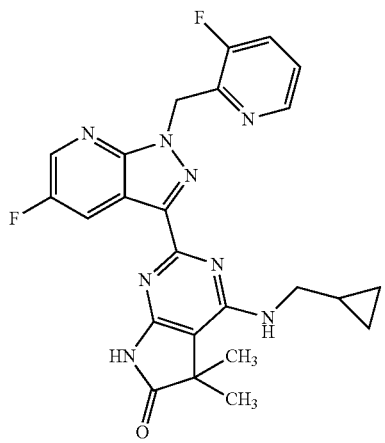 [SMILES: CC1(C)C(=O)Nc2nc(-c3nn(Cc4ncccc4F)c4ncc(F)cc34)nc(NCC3CC3)c21]

200 mg (0.206 mmol, approx. 55% purity) of the compound obtained in example 21A was dissolved in 1-methyl-2-pyrrolidone (4 ml) in a reaction vessel suitable for a microwave and 1 ml of aminomethylcyclopropane was added. Then it was sealed with a corresponding septum and it was heated in the microwave at 150° C. for 3 h. After cooling, the reaction mixture was purified by preparative HPLC (acetonitrile:water (+0.05% formic acid) gradient). 64 mg of the title compound was obtained (65% of theor.).

LC-MS (method 1): $R_t$=1.09 min; MS (EIpos): m/z=477 [M+H]$^+$.

$^1$H-NMR (400 MHz, DMSO-$d_6$): δ [ppm]=0.30-0.33 (m, 2H), 0.42-0.46 (m, 2H), 1.21-1.27 (m, 1H), 1.37 (s, 6H), 3.46 (t, 2H), 5.96 (s, 2H), 6.78-6.85 (m, 1H), 7.41-7.45 (m, 1H), 7.76 (t, 1H), 8.24-8.28 (m, 1H), 8.57 (dd, 1H), 8.67 (dd, 1H), 10.95 (s br, 1H).

Example 18

2-[5-Fluoro-1-(2-fluorobenzyl)-1H-pyrazolo[3,4-b]pyridin-3-yl]-5,5-dimethyl-4-[(4,4,4-trifluorobutyl)amino]-5,7-dihydro-6H-pyrrolo[2,3-d]pyrimidin-6-one

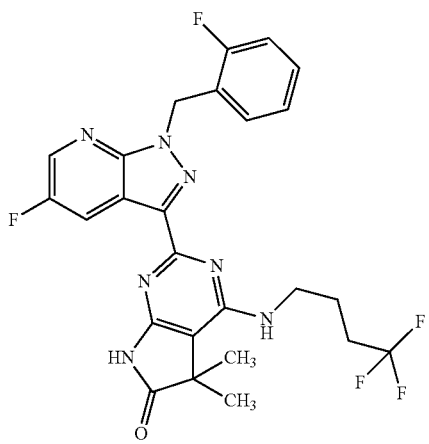 [SMILES: CC1(C)C(=O)Nc2nc(-c3nn(Cc4ccccc4F)c4ncc(F)cc34)nc(NCCCC(F)(F)F)c21]

150 mg (0.186 mmol, approx. 66% purity) of the compound obtained in example 16A was dissolved in 1-methyl-2-pyrrolidone (3 ml) in a reaction vessel suitable for a microwave and 0.4 ml of 4,4,4-trifluorobutylamine was added. Then it was sealed with a corresponding septum and it was heated in the microwave at 150° C. for 3 h. After cooling, the reaction mixture was purified by preparative HPLC (acetonitrile:water (+0.05% formic acid) gradient). 47 mg of the title compound was obtained (48% of theor.).

LC-MS (method 1): $R_t$=1.19 min; MS (EIpos): m/z=532 [M+H]$^+$.

$^1$H-NMR (400 MHz, DMSO-d$_6$): δ [ppm]=1.37 (s, 6H), 1.87-1.94 (m, 2H), 2.30-2.43 (m, 2H), 3.63 (q, 2H), 5.83 (s, 2H), 6.81 (t, 1H), 7.12-7.17 (m, 1H), 7.21-7.25 (m, 2H), 7.34-7.39 (m, 1H), 8.47 (dd, 1H), 8.72 (dd, 1H), 11.04 (s, 1H).

Example 19

2-[1-(2-Fluorobenzyl)-1,4,5,6-tetrahydrocyclopenta[c]pyrazol-3-yl]-5,5-dimethyl-4-[(2,2,2-trifluoroethyl)amino]-5,7-dihydro-6H-pyrrolo[2,3-d]pyrimidin-6-one

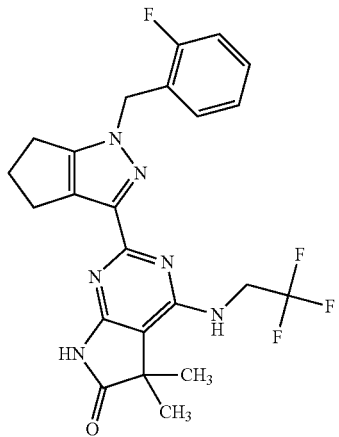 [SMILES: CC1(C)C(=O)Nc2nc(-c3nn(Cc4ccccc4F)c4c3CCC4)nc(NCC(F)(F)F)c21]

50 mg (0.09 mmol) of 2-[1-(2-fluorobenzyl)-1,4,5,6-tetrahydrocyclopenta[c]pyrazol-3-yl]-4-iodo-5,5-dimethyl-5,7-dihydro-6H-pyrrolo[2,3-d]pyrimidin-6-one (example 33A) was dissolved in 1 ml of absolute NMP and 336 mg (3.70 mmol) of 2,2,2-trifluoroethanamine was added. The mixture was heated in the microwave for 2 h at 150° C., 18 h at 150° C., 2 h at 160° C., 2 h at 170° C. and 5 h at 170° C. The reaction solution was filtered and purified by preparative HPLC (eluent: acetonitrile/water with 0.1% formic acid, gradient 20:80→100:0). 18 mg (purity 88%, 36% of theor.) of the target compound was obtained.

LC-MS (method 1): $R_t$=1.09 min; MS (ESIpos): m/z=475 [M+H]$^+$ $^1$H-NMR (400 MHz, DMSO-d$_6$): δ [ppm]=1.34 (s, 6H), 2.64 (t, 2H), 2.79 (t, 2H), 4.24-4.32 (m, 2H), 5.30 (s, 2H), 7.01 (t, 1H), 7.18-7.28 (m, 3H), 7.36-7.42 (m, 1H), 11.01 (s, 1H).

Example 20

2-[1-(2-Fluorobenzyl)-1,4,5,6-tetrahydrocyclopenta[c]pyrazol-3-yl]-5,5-dimethyl-4-[(3,3,3-trifluoropropyl)amino]-5,7-dihydro-6H-pyrrolo[2,3-d]pyrimidin-6-one

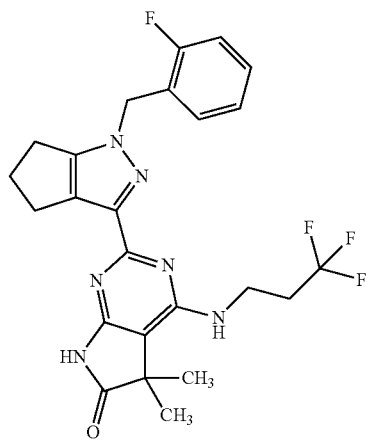 [SMILES: CC1(C)C(=O)Nc2nc(-c3nn(Cc4ccccc4F)c4c3CCC4)nc(NCCC(F)(F)F)c21]

40 mg (0.07 mmol) of 2-[1-(2-fluorobenzyl)-1,4,5,6-tetrahydrocyclopenta[c]pyrazol-3-yl]-4-iodo-5,5-dimethyl-5,7-dihydro-6H-pyrrolo[2,3-d]pyrimidin-6-one (example 33A) was dissolved in 1 ml of absolute NMP and 334 mg (2.96 mmol) of 3,3,3-trifluoropropan-1-amine was added. The mixture was heated in the microwave for 2 h at 150° C. and 1 h at 150° C. The reaction solution was filtered and purified by preparative HPLC (eluent: acetonitrile/water with 0.1% hydrochloric acid, gradient 20:80→100:0). 27 mg (purity 93%, 70% of theor.) of the target compound was obtained.

LC-MS (method 1): $R_t$=1.17 min; MS (ESIpos): m/z=489 [M+H]$^+$ $^1$H-NMR (400 MHz, DMSO-d$_6$): δ [ppm]=1.32 (s, 6H), 2.57-2.67 (m, 4H), 2.80 (t, 2H), 3.68-3.73 (m, 2H), 5.32 (s, 2H), 6.85 (s br, 1H), 7.19-7.29 (m, 3H), 7.37-7.42 (m, 1H), 10.93 (s, 1H).

Example 21

4-(3-Ethyl-2-oxoimidazolidin-1-yl)-2-[1-(2-fluorobenzyl)-1H-pyrazolo[3,4-b]pyridin-3-yl]-5,5-dimethyl-5,7-dihydro-6H-pyrrolo[2,3-d]pyrimidin-6-one

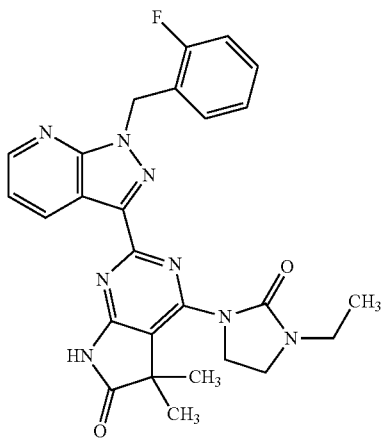 [SMILES: CCN1CCN(c2nc(-c3nn(Cc4ccccc4F)c4ncccc34)nc3c2C(C)(C)C(=O)N3)C1=O]

Under argon atmosphere, 150 mg (purity 62%, 0.18 mmol) of 2-[1-(2-fluorobenzyl)-1H-pyrazolo[3,4-b]pyridin-3-yl]-4-iodo-5,5-dimethyl-5,7-dihydro-6H-pyrrolo[2,3-d]pyrimidin-6-one (example 15A) was suspended in 2 ml of absolute acetonitrile and 413 mg (3.62 mmol) of 1-ethylimidazolidin-2-one, 118 mg (0.36 mmol) of caesium carbonate, 5 mg (0.04 mmol) of copper(I) oxide and 20 mg (0.15 mmol) of 2-hydroxybenzaldehyde-oxime were added. The mixture was heated in the microwave for 1 h at 200° C. The reaction solution was filtered and purified by preparative HPLC (eluent: acetonitrile/water, gradient 20:80→100:0). 35 mg (purity 91%, 35% of theor.) of the target compound was obtained.

LC-MS (method 1): $R_t$=1.03 min; MS (ESIpos): m/z=501 [M+H]$^+$ $^1$H-NMR (400 MHz, DMSO-d$_6$): δ [ppm]=1.13 (t, 3H), 1.41 (s, 6H), 3.28 (q, 2H), 3.57 (t, 2H), 3.97 (t, 2H), 5.87 (s, 2H), 7.12-7.25 (m, 3H), 7.34-7.38 (m, 1H), 7.44 (dd, 1H), 8.67 (dd, 1H), 8.83 (dd, 1H), 11.63 (s, 1H).

Example 22

2-[3-(2-Fluorobenzyl)-1H-indazol-1-yl]-4-hydroxy-5,5-dimethyl-5,7-dihydro-6H-pyrrolo[2,3-d]pyrimidin-6-one

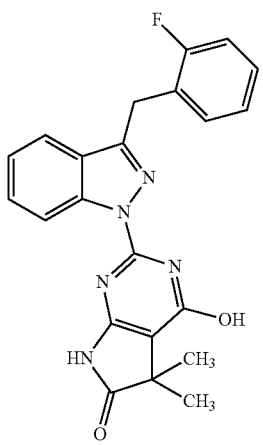 [SMILES: CC1(C)C(=O)Nc2nc(-n3nc(Cc4ccccc4F)c4ccccc43)nc(O)c21]

The title compound was obtained as a side component in the experiment for example 38A. Yield: 57 mg (9% of theor., 86% purity)

LC-MS (method 1): $R_t$=1.03 min; MS (ESIpos): m/z=404 [M+H]$^+$ $^1$H-NMR (400 MHz, DMSO-d$_6$): δ [ppm]=1.33 (s, 6H), 4.42 (s, 2H), 7.13-7.23 (m, 2H), 7.28-7.44 (m, 3H), 7.57-7.61 (m, 1H), 7.73 (d, 1H), 3H cannot be ascribed definitely.

Example 23

4-(3,5-Dimethyl-1H-pyrazol-1-yl)-2-[1-(2-fluorobenzyl)-1H-pyrazolo[3,4-b]pyridin-3-yl]-5,5-dimethyl-5,7-dihydro-6H-pyrrolo[2,3-d]pyrimidin-6-one

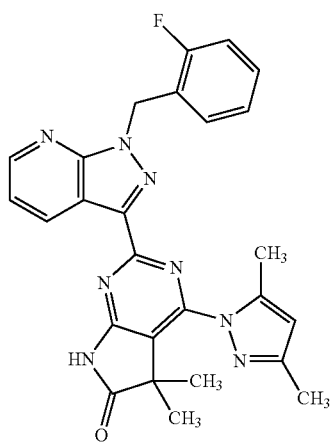 [SMILES: Cc1cc(C)n(-c2nc(-c3nn(Cc4ccccc4F)c4ncccc34)nc3c2C(C)(C)C(=O)N3)n1]

Under argon atmosphere, 150 mg (purity 62%, 0.18 mmol) of 2-[1-(2-fluorobenzyl)-1H-pyrazolo[3,4-b]pyridin-3-yl]-4-iodo-5,5-dimethyl-5,7-dihydro-6H-pyrrolo[2,3-d]pyrimidin-6-one (example 15A) was suspended in 2 ml of absolute acetonitrile, and 26 mg (0.27 mmol) of 3,5-dimethyl-1H-pyrazole, 118 mg (0.36 mmol) of caesium carbonate, 5 mg (0.04 mmol) of copper(I) oxide and 20 mg (0.15 mmol) of 2-hydroxybenzaldehyde-oxime were added. The mixture was heated in the microwave for 1 h at 150° C. Then 346 mg (3.62 mmol) of 3,5-dimethyl-1H-pyrazole was added and the mixture was heated in the microwave for 45 min at 200° C. The reaction solution was filtered and purified by preparative HPLC (eluent: acetonitrile/water, gradient 20:80→100:0). 20 mg (23% of theor.) of the target compound was obtained.

LC-MS (method 1): $R_t$=1.23 min; MS (ESIpos): m/z=483 [M+H]$^+$ $^1$H-NMR (400 MHz, DMSO-d$_6$): δ [ppm]=1.43 (s, 6H), 2.27 (s, 3H), 2.53 (s, 3H), 5.87 (s, 2H), 6.22 (s, 1H), 7.16 (t, 1H), 7.21-7.30 (m, 2H), 7.35-7.39 (m, 1H), 7.46 (dd, 1H), 8.69 (dd, 1H), 8.79 (dd, 1H), 11.76 (s, 1H).

Example 24

2-[1-(2-Fluorobenzyl)-1H-pyrazolo[3,4-b]pyridin-3-yl]-4-(3-fluoro-2-oxopyridin-1(2H)-yl)-5,5-dimethyl-5,7-dihydro-6H-pyrrolo[2,3-d]pyrimidin-6-one

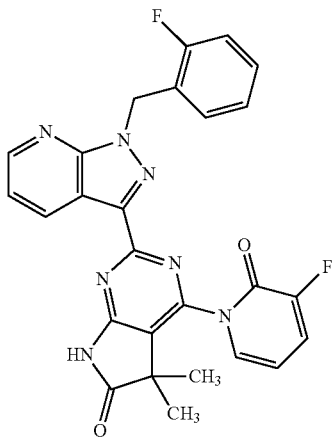 [SMILES: CC1(C)C(=O)Nc2nc(-c3nn(Cc4ccccc4F)c4ncccc34)nc(-n3cccc(F)c3=O)c21]

Under argon atmosphere, 200 mg (purity 62%, 0.24 mmol) of 2-[1-(2-fluorobenzyl)-1H-pyrazolo[3,4-b]pyridin-3-yl]-4-iodo-5,5-dimethyl-5,7-dihydro-6H-pyrrolo[2,3-d]pyrimidin-6-one (example 15A) was suspended in 2.5 ml of absolute acetonitrile, and 545 mg (4.82 mmol) of 3-fluoropyridin-2-ol, 157 mg (0.48 mmol) of caesium carbonate, 7 mg (0.05 mmol) of copper(I) oxide and 20 mg (0.15 mmol) of 2-hydroxybenzaldehyde-oxime were added. The mixture was heated in the microwave for 1 h at 200° C. The reaction solution was filtered and purified by preparative HPLC (eluent: acetonitrile/water, gradient 20:80→100:0). 20 mg (23% of theor.) of the target compound was obtained.

LC-MS (method 1): $R_t$=1.11 min; MS (ESIpos): m/z=500 [M+H]$^+$ $^1$H-NMR (400 MHz, DMSO-d$_6$): δ [ppm]=1.49 (s, 6H), 5.81 (s, 2H), 7.10-7.23 (m, 4H), 7.32-7.38 (m, 1H), 7.61-7.65 (m, 2H), 8.07-8.12 (m, 1H), 8.36 (dd, 1H), 8.59 (dd, 1H), 11.75 (s, 1H).

Example 25

2-[1-(2-Fluorobenzyl)-1H-pyrazolo[3,4-b]pyridin-3-yl]-5,5-dimethyl-4-[2-oxo-4-(trifluoromethyl)pyrrolidin-1-yl]-5,7-dihydro-6H-pyrrolo[2,3-d]pyrimidin-6-one

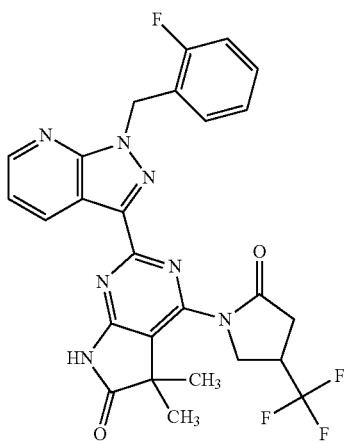 [SMILES: CC1(C)C(=O)Nc2nc(-c3nn(Cc4ccccc4F)c4ncccc34)nc(N3CC(C(F)(F)F)CC3=O)c21]

Under argon atmosphere, 200 mg (purity 62%, 0.24 mmol) of 2-[1-(2-fluorobenzyl)-1H-pyrazolo[3,4-b]pyridin-3-yl]-4-iodo-5,5-dimethyl-5,7-dihydro-6H-pyrrolo[2,3-d]pyrimidin-6-one (example 15A) was suspended in 2.5 ml of absolute acetonitrile, and 738 mg (4.82 mmol) of 4-(trifluoromethyl)pyrrolidin-2-one, 157 mg (0.48 mmol) of caesium carbonate, 7 mg (0.05 mmol) of copper(I) oxide and 26 mg (0.19 mmol) of 2-hydroxybenzaldehyde-oxime were added. The mixture was heated in the microwave for 1 h at 200° C. The reaction solution was filtered and purified by preparative HPLC (eluent: acetonitrile/water with 0.1% formic acid, gradient 20:80→100:0). 26 mg (19% of theor.) of the target compound was obtained.

LC-MS (method 1): $R_t$=1.02 min; MS (ESIpos): m/z=540 [M+H]$^+$ $^1$H-NMR (400 MHz, DMSO-d$_6$): δ [ppm]=1.32 (s, 3H), 1.36 (s, 3H), 2.70 (dd, 1H), 3.08 (dd, 1H), 3.67-3.75 (m, 1H), 3.87(dd, 1H), 4.32 (dd, 1H), 5.88 (s, 2H), 7.14 (t, 1H), 7.16-7.25 (m, 2H), 7.34-7.38 (m, 1H), 7.45 (dd, 1H), 8.69 (dd, 1H), 8.84 (dd, 1H), 11.83 (s, 1H).

Example 26

2-[1-(2-Fluorobenzyl)-1H-pyrazolo[3,4-b]pyridin-3-yl]-4-(4-hydroxy-1H-pyrazol-1-yl)-5,5-dimethyl-5,7-dihydro-6H-pyrrolo[2,3-d]pyrimidin-6-one

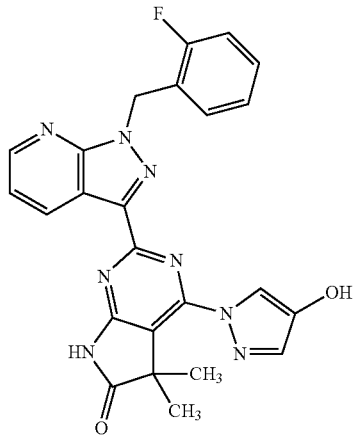 [SMILES: CC1(C)C(=O)Nc2nc(-c3nn(Cc4ccccc4F)c4ncccc34)nc(-n3cc(O)cn3)c21]

Under an argon atmosphere, 150 mg (purity 62%, 0.18 mmol) of 2-[1-(2-fluorobenzyl)-1H-pyrazolo[3,4-b]pyridin-3-yl]-4-iodo-5,5-dimethyl-5,7-dihydro-6H-pyrrolo[2,3-d]pyrimidin-6-one (example 15A) was suspended in 2 ml of absolute acetonitrile, and 304 mg (3.62 mmol) of 1H-pyrazol-4-ol, 118 mg (0.36 mmol) of caesium carbonate, 5 mg (0.04 mmol) of copper(I) oxide and 20 mg (0.15 mmol) of 2-hydroxybenzaldehyde-oxime were added. The mixture was heated in the microwave for 1 h at 200° C. The reaction solution was filtered and purified by preparative HPLC (eluent: acetonitrile/water with 0.1% formic acid, gradient 20:80→100:0). 20 mg (24% of theor.) of the target compound was obtained.

LC-MS (method 1): $R_t$=1.03 min; MS (ESIpos): m/z=471 [M+H]$^+$ $^1$H-NMR (400 MHz, DMSO-d$_6$): δ [ppm]=1.59 (s, 6H), 5.89 (s, 2H), 7.15 (t, 1H), 7.22-7.25 (m, 2H), 7.35-7.39 (m, 1H), 7.51 (dd, 1H), 7.72 (s, 1H), 8.25 (s, 1H), 8.71 (dd, 1H), 8.87 (dd, 1H), 9.37 (s, 1H), 11.75 (s br, 1H).

In addition, 2-[1-(2-fluorobenzyl)-1H-pyrazolo[3,4-b]pyridin-3-yl]-5,5-dimethyl-4-(1H-pyrazol-4-yloxy)-5,7-dihy dro-6H-pyrrolo[2,3-d]pyrimidin-6-one was obtained in this batch (see example 27).

Example 27

2-[1-(2-Fluorobenzyl)-1H-pyrazolo[3,4-b]pyridin-3-yl]-5,5-dimethyl-4-(1H-pyrazol-4-yloxy)-5,7-dihydro-6H-pyrrolo[2,3-d]pyrimidin-6-one

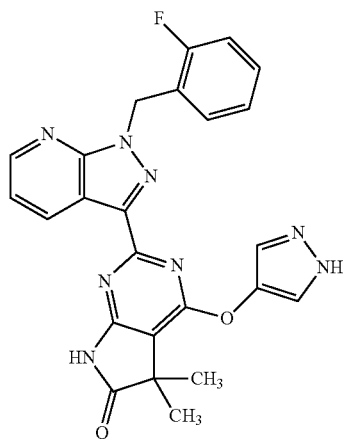 [SMILES: CC1(C)C(=O)Nc2nc(-c3nn(Cc4ccccc4F)c4ncccc34)nc(Oc3cn[nH]c3)c21]

Formed during the preparation in example 26 (see example 26). 20 mg (23% of theor.) of the target compound was obtained.

LC-MS (method 1): $R_t$=0.94 min; MS (ESIpos): m/z=471 [M+H]$^+$ $^1$H-NMR (400 MHz, DMSO-d$_6$): δ [ppm]=1.45 (s, 6H), 5.83 (s, 2H), 7.14 (t, 1H), 7.19-7.25 (m, 3H), 7.33-7.38 (m, 1H), 7.67 (s br, 1H), 8.00 (s br, 1H), 8.22 (d, 1H), 8.62 (dd, 1H), 11.57 (s, 1H), 12.92 (s br, 1H).

Example 28

2-[1-(2-Fluorobenzyl)-1H-pyrazolo[3,4-b]pyridin-3-yl]-4-[3-(1-hydroxyethyl)-1H-pyrazol-1-yl]-5,5-dimethyl-5,7-dihydro-6H-pyrrolo[2,3-d]pyrimidin-6-one

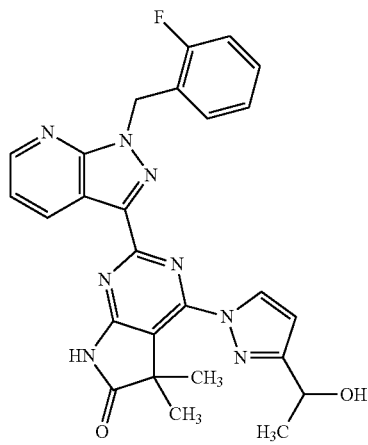 [SMILES: CC(O)c1ccn(-c2nc(-c3nn(Cc4ccccc4F)c4ncccc34)nc3c2C(C)(C)C(=O)N3)n1]

Under argon atmosphere, 150 mg (purity 62%, 0.18 mmol) of 2-[1-(2-fluorobenzyl)-1H-pyrazolo[3,4-b]pyridin-3-yl]-4-iodo-5,5-dimethyl-5,7-dihydro-6H-pyrrolo[2,3-d]pyrimidin-6-one (example 15A) was suspended in 2 ml of absolute acetonitrile, and 405 mg (3.62 mmol) of 1-(1H-pyrazol-3-yl)ethanol, 118 mg (0.36 mmol) of caesium carbonate, 5 mg (0.04 mmol) of copper(I) oxide and 20 mg (0.15 mmol) of 2-hydroxybenzaldehyde-oxime were added. The mixture was heated in the microwave for 1 h at 200° C. The reaction solution was filtered and purified by preparative HPLC (eluent: acetonitrile/water with 0.1% formic acid, gradient 20:80→100:0). 20 mg (24% of theor.) of the target compound was obtained.

LC-MS (method 1): $R_t$=0.96 min; MS (ESIpos): m/z=499 [M+H]$^+$ $^1$H-NMR (400 MHz, DMSO-d$_6$): δ [ppm]=1.38 (s, 3H), 1.40 (s, 3H), 1.86 (d, 3H), 5.66 (q, 1H), 5.84 (s, 2H), 6.20 (d, 1H), 7.13 (t, 1H), 7.20-7.38 (m, 3H), 7.41 (dd, 1H), 7.63 (s, 1H), 8.28 (d, 1H), 8.69 (dd, 1H), 12.63 (s br, 2H).

Example 29

2-[1-(2-Fluorobenzyl)-1H-pyrazolo[3,4-b]pyridin-3-yl]-5,5-dimethyl-4-[4-(trifluoromethyl)-1H-pyrazol-1-yl]-5,7-dihydro-6H-pyrrolo[2,3-d]pyrimidin-6-one

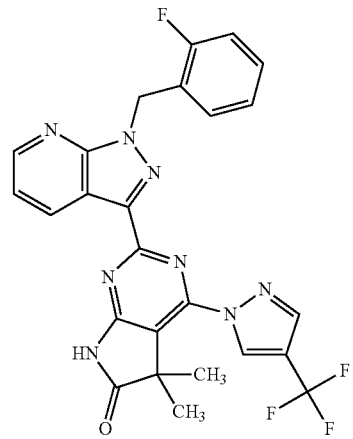 [SMILES: CC1(C)C(=O)Nc2nc(-c3nn(Cc4ccccc4F)c4ncccc34)nc(-n3cc(C(F)(F)F)cn3)c21]

Under argon atmosphere, 200 mg (purity 62%, 0.24 mmol) of 2-[1-(2-fluorobenzyl)-1H-pyrazolo[3,4-b]pyridin-3-yl]-4-iodo-5,5-dimethyl-5,7-dihydro-6H-pyrrolo[2,3-d]pyrimidin-6-one (example 15A) was suspended in 2.5 ml of absolute acetonitrile, and 656 mg (4.82 mmol) of 4-(trifluoromethyl)-1H-pyrazole, 157 mg (0.48 mmol) of caesium carbonate, 7 mg (0.05 mmol) of copper(I) oxide and 26 mg (0.19 mmol) of 2-hydroxybenzaldehyde-oxime were added. The mixture was heated in the microwave for 1 h at 200° C. The reaction solution was filtered and purified by preparative HPLC (eluent: acetonitrile/water with 0.1% formic acid, gradient 20:80→100:0). 85 mg (63% of theor.) of the target compound was obtained.

LC-MS (method 1): $R_t$=1.33 min; MS (ESIpos): m/z=523 [M+H]$^+$ $^1$H-NMR (400 MHz, DMSO-d$_6$): δ [ppm]=1.56 (s, 6H), 5.91 (s, 2H), 7.15 (t, 1H), 7.20-7.25 (m, 2H), 7.34-7.39 (m, 1H), 7.52 (dd, 1H), 8.51 (s, 1H), 8.71 (dd, 1H), 8.92 (dd, 1H), 9.30 (s, 1H), 11.99 (s, 1H).

Example 30

2-[1-(2-Fluorobenzyl)-1H-pyrazolo[3,4-b]pyridin-3-yl]-5,5-dimethyl-4-[3-(trifluoromethyl)-1H-pyrazol-1-yl]-5,7-dihydro-6H-pyrrolo[2,3-d]pyrimidin-6-one

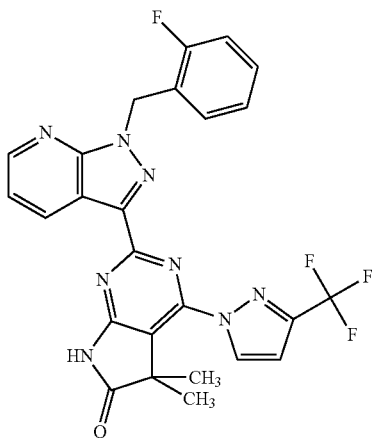 [SMILES: CC1(C)C(=O)Nc2nc(-c3nn(Cc4ccccc4F)c4ncccc34)nc(-n3ccc(C(F)(F)F)n3)c21]

Under argon atmosphere, 200 mg (purity 62%, 0.24 mmol) of 2-[1-(2-fluorobenzyl)-1H-pyrazolo[3,4-b]pyridin-3-yl]-4-iodo-5,5-dimethyl-5,7-dihydro-6H-pyrrolo[2,3-d]pyrimidin-6-one (example 15A) was suspended in 2.5 ml of absolute acetonitrile, and 656 mg (4.82 mmol) of 3-(trifluoromethyl)-1H-pyrazole, 157 mg (0.48 mmol) of caesium carbonate, 7 mg (0.05 mmol) of copper(I) oxide and 26 mg (0.19 mmol) of 2-hydroxybenzaldehyde-oxime were added. The mixture was heated in the microwave for 1 h at 200° C. The reaction solution was filtered and purified by preparative HPLC (eluent: acetonitrile/water with 0.1% formic acid, gradient 20:80→100:0). 41 mg (33% of theor.) of the target compound was obtained.

LC-MS (method 1): $R_t$=1.32 min; MS (ESIpos): m/z=523 [M+H]$^+$ $^1$H-NMR (400 MHz, DMSO-d$_6$): δ [ppm]=1.55 (s, 6H), 5.90 (s, 2H), 7.15 (t, 1H), 7.21-7.25 (m, 3H), 7.35-7.39 (m, 1H), 7.50 (dd, 1H), 8.72 (dd, 1H), 8.93 (dd, 1H), 9.05 (s, 1H), 12.02 (s, 1H).

Example 31

2-[5-Fluoro-3-(2-fluorobenzyl)-1H-indazol-1-yl]-4-hydroxy-5,5-dimethyl-5,7-dihydro-6H-pyrrolo[2,3-d]pyrimidin-6-one

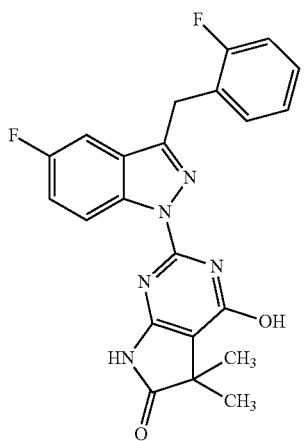 [SMILES: CC1(C)C(=O)Nc2nc(-n3nc(Cc4ccccc4F)c4cc(F)ccc43)nc(O)c21]

The title compound was obtained as a side component in the experiment for example 43A. Yield: 72 mg (14% of theor., 83% purity).

LC-MS (method 1): $R_t$=1.33 min; MS (ESIpos): m/z=422 [M+H]$^+$ $^1$H-NMR (400 MHz, DMSO-d$_6$): δ [ppm]=1.33 (s, 6H), 4.40 (s, 2H), 7.14-7.23 (m, 2H), 7.27-7.34 (m, 1H), 7.42 (t, 1H), 7.49-7.58 (m, 2H), 8.75 (s br, 1H), 11.31 (s br, 1H), 12.37 (s br, 1H).

Example 32

2-[1-(2-Fluorobenzyl)-1H-pyrazolo[3,4-b]pyridin-3-yl]-5,5-dimethyl-4-[2-(trifluoromethyl)morpholin-4-yl]-5,7-dihydro-6H-pyrrolo[2,3-d]pyrimidin-6-one

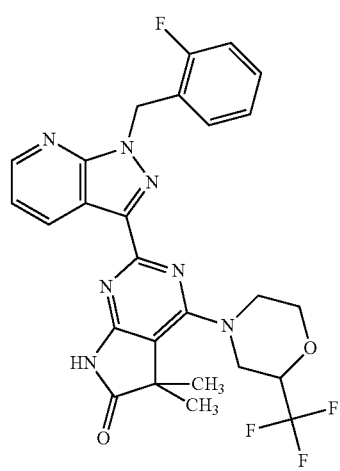 [SMILES: CC1(C)C(=O)Nc2nc(-c3nn(Cc4ccccc4F)c4ncccc34)nc(N3CCOC(C(F)(F)F)C3)c21]

Under argon atmosphere, 200 mg (purity 62%, 0.24 mmol) of 2-[1-(2-fluorobenzyl)-1H-pyrazolo[3,4-b]pyridin-3-yl]-4-iodo-5,5-dimethyl-5,7-dihydro-6H-pyrrolo[2,3-d]pyrimidin-6-one (example 15A) was put in 4 ml of absolute NMP, and 924 mg (4.82 mmol) of 2-(trifluoromethyl)morpholine and 623 mg (4.82 mmol) of N,N-diisopropyl ethylamine were added. The mixture was heated in the microwave at 150° C. for 5 h. The reaction solution was filtered and purified by preparative HPLC (eluent: acetonitrile/water with 0.1% formic acid, gradient 20:80→100:0). 60 mg (46% of theor.) of the target compound was obtained.

LC-MS (method 1): $R_t$=1.16 min; MS (ESIpos): m/z=542 [M+H]$^+$ $^1$H-NMR (400 MHz, DMSO-d$_6$): δ [ppm]=1.43 (s, 6H), 3.36-3.42 (m, 1H), 3.80 (dt, 1H), 4.13 (dd, 2H), 4.43-4.51 (m, 2H), 5.85 (s, 2H), 7.14 (t, 1H), 7.18-7.24 (m, 2H), 7.34-7.38 (m, 1H), 7.40 (dd, 1H), 8.66 (dd, 1H), 8.75 (dd, 1H), 11.41 (s, 1H).

Example 33

2-[1-(2-Fluorobenzyl)-1H-pyrazolo[3,4-b]pyridin-3-yl]-5,5-dimethyl-4-[3-(trifluoromethyl)pyrrolidin-1-yl]-5,7-dihydro-6H-pyrrolo[2,3-d]pyrimidin-6-one

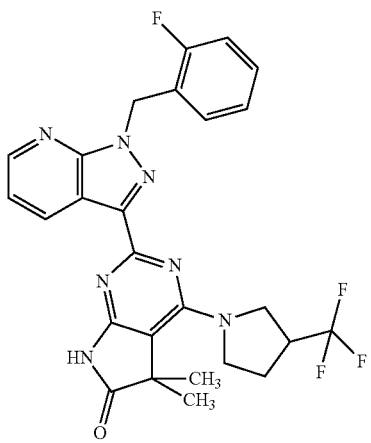 [SMILES: CC1(C)C(=O)Nc2nc(-c3nn(Cc4ccccc4F)c4ncccc34)nc(N3CCC(C(F)(F)F)C3)c21]

Under an argon atmosphere, 200 mg (purity 62%, 0.24 mmol) of 2-[1-(2-fluorobenzyl)-1H-pyrazolo[3,4-b]pyridin-3-yl]-4-iodo-5,5-dimethyl-5,7-dihydro-6H-pyrrolo[2,3-d]pyrimidin-6-one (example 15A) was put in 4 ml of absolute NMP and 671 mg (4.82 mmol) of 3-(trifluoromethyl)pyrrolidine was added. The mixture was heated in the microwave at 150° C. for 5 h. The reaction solution was filtered and purified by preparative HPLC (eluent: acetonitrile/water with 0.1% formic acid, gradient 20:80→100:0). 65 mg (49% of theor.) of the target compound was obtained.

LC-MS (method 1): $R_t$=1.21 min; MS (ESIpos): m/z=526 [M+H]$^+$ $^1$H-NMR (400 MHz, DMSO-d$_6$): δ [ppm]=1.42 (s, 3H), 1.43 (s, 3H), 2.15-2.23 (m, 1H), 2.32-2.41 (m, 1H), 3.38-3.48 (m, 1H), 3.79-3.94 (m, 3H), 4.07 (dd, 1H), 5.84 (s, 2H), 7.12-7.25 (m, 3H), 7.33-7.39 (m, 1H), 7.42 (dd, 1H), 8.65 (dd, 1H), 8.81 (dd, 1H), 11.29 (s, 1H).

Example 34

2-[5-Fluoro-3-(2-fluorobenzyl)-1H-indazol-1-yl]-5,5-dimethyl-4-(3,3,3-trifluoropropoxy)-5,7-dihydro-6H-pyrrolo[2,3-d]pyrimidin-6-one

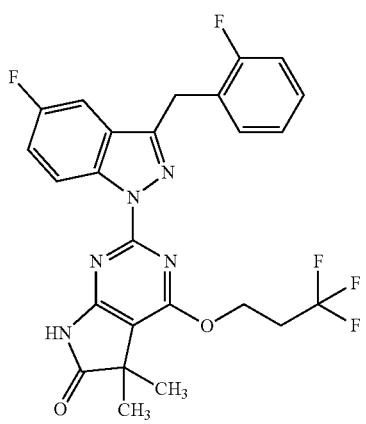 [SMILES: CC1(C)C(=O)Nc2nc(-n3nc(Cc4ccccc4F)c4cc(F)ccc43)nc(OCCC(F)(F)F)c21]

Under argon, 80 mg (0.19 mmol) of the compound from example 31 was largely dissolved in 2 ml THF, 32.5 mg (0.29 mmol) of 3,3,3-trifluoropropan-1-ol, 75 mg (0.29 mmol) of triphenyl phosphine and 56 µl (0.29 mmol) of diisopropyl azodicarboxylate were added and it was stirred for 3 d at RT. A further 11 mg (0.01 mmol) of 3,3,3-trifluoropropan-1-ol, 25 mg (0.01 mmol) of triphenyl phosphine and 19 µl (0.01 mmol) of diisopropyl azodicarboxylate were added and it was stirred for 1 d at RT. The reaction mixture was concentrated by evaporation and the residue was purified by preparative HPLC (Reprosil C18, gradient of acetonitrile/0.01% aq. formic acid). Yield: 48 mg (49% of theor.)

LC-MS (method 1): $R_t$=1.32 min; MS (ESIpos): m/z=518 [M+H]$^+$ $^1$H-NMR (500 MHz, DMSO-d$_6$): δ [ppm]=1.34 (s, 6H), 2.82-3.00 (m, 2H), 4.40 (s, 2H), 4.75 (t, 2H), 7.11-7.24 (m, 2H), 7.26-7.32 (m, 1H), 7.37-7.50 (m, 2H), 7.53-7.62 (m, 1H), 8.60 (dd, 1H), 11.53 (br s, 1H).

Example 35

2-[3-(2-Fluorobenzyl)-1H-indazol-1-yl]-5,5-dimethyl-4-[(3,3,3-trifluoropropyl)amino]-5,7-dihydro-6H-pyrrolo[2,3-d]pyrimidin-6-one

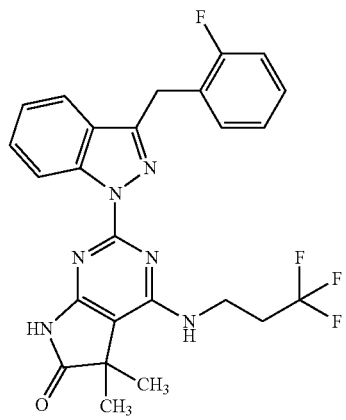 [SMILES: CC1(C)C(=O)Nc2nc(-n3nc(Cc4ccccc4F)c4ccccc43)nc(NCCC(F)(F)F)c21]

60 mg (0.12 mmol) of the compound from example 38A was dissolved in 1.2 ml NMP and after adding 0.3 ml of 3,3,3-trifluoropropylamine in a sealed microwave vessel, it was heated in the microwave at 150° C. for 3 h. The reaction mixture was purified by preparative HPLC (Reprosil C18, gradient of acetonitrile/0.01% aq. formic acid). Yield: 38 mg (65% of theor.)

LC-MS (method 1): $R_t$=1.26 min; MS (ESIpos): m/z=499 [M+H]$^+$ $^1$H-NMR (400 MHz, DMSO-d$_6$): δ [ppm]=1.36 (s, 6H), 2.58-2.80 (m, 2H), 3.80 (q, 2H), 4.40 (s, 2H), 6.98 (t, 1H), 7.09-7.24 (m, 2H), 7.25-7.33 (m, 2H), 7.38 (t, 1H), 7.50 (t, 1H), 7.74 (d, 1H), 8.59 (d, 1H), 11.19 (s, 1H).

The compounds listed in Table 3 were prepared on the analogy of example 35:

TABLE 3

| Example No. | Structure | Educts; yield | Analysis |
|---|---|---|---|
| 36 | 4-[(cyclopropylmethyl)amino]-2-[3-(2-fluorobenzyl)-1H-indazol-1-yl]-5,5-dimethyl-5,7-dihydro-6H-pyrrolo[2,3-d]pyrimidin-6-one | Example 38A, cyclopropylmethylamine; 77% of theor. | LC-MS (method 1): $R_t$ = 1.27 min; MS (ESIpos): m/z = 457 [M + H]$^+$<br>$^1$H-NMR (500 MHz, DMSO-$d_6$): δ [ppm] = 0.29-0.36 (m, 2H), 0.39-0.48 (m, 2H), 1.15-1.28 (m, 1H), 1.38 (s, 6H), 3.38-3.50 (m, 2H), 4.39 (s, 2H), 6.85-6.95 (m, 1H), 7.10-7.22 (m, 2H), 7.23-7.33 (m, 2H), 7.34-7.41 (m, 1H), 7.50-7.58 (m, 1H), 7.72 (dd, 1H), 8.67 (dd, 1H), 11.08 (s, 1H). |
| 37 | 2-[5-fluoro-3-(2-fluorobenzyl)-1H-indazol-1-yl]-5,5-dimethyl-4-[(3,3,3-trifluoropropyl)amino]-5,7-dihydro-6H-pyrrolo[2,3-d]pyrimidin-6-one | Example 43A, 3,3,3-trifluoropropylamine, 82% of theor. | LC-MS (method 1): $R_t$ = 1.27 min; MS (ESIpos): m/z = 517 [M + H]$^+$<br>$^1$H-NMR (500 MHz, DMSO-$d_6$): δ [ppm] = 1.36 (s, 6H), 2.60-2.75 (m, 2H), 3.78 (q, 2H), 4.38 (s, 2H), 6.96 (t, 1H), 7.12-7.22 (m, 2H), 7.27-7.44 (m, 3H), 7.54 (dd, 1H), 8.55-8.64 (m, 1H), 11.16 (s, 1H). |

TABLE 3-continued

| Example No. | Structure | Educts; yield | Analysis |
|---|---|---|---|
| 38 | 4-[(cyclopropylmethyl)amino]-2-[5-fluoro-3-(2-fluorobenzyl)-1H-indazol-1-yl]-5,5-dimethyl-5,7-dihydro-6H-pyrrolo[2,3-d]pyrimidin-6-one | Example 43A, cyclopentyl-methylamine; 74% of theor. | LC-MS (method 1): $R_t$ = 1.29 min; MS (ESIpos): m/z = 475 $[M + H]^+$<br>$^1$H-NMR (500 MHz, DMSO-$d_6$): δ [ppm] = 0.27-0.35 (m, 2H), 0.38-0.47 (m, 2H), 1.15-1.27 (m, 1H), 3.43 (t, 2H), 4.38 (s, 2H), 6.87-6.97 (m, 1H), 7.10-7.23 (m, 2H), 7.26-7.34 (m, 1H), 7.36-7.48 (m, 2H), 7.53 (d, 1H), 8.67 (dd, 1H), 11.09 (br s, 1H). |

Example 39

2-[8-(2-Fluorobenzyl)imidazo[1,5-a]pyrimidin-6-yl]-5,5-dimethyl-4-[(3,3,3-trifluoropropyl)amino]-5,7-dihydro-6H-pyrrolo[2,3-d]pyrimidin-6-one

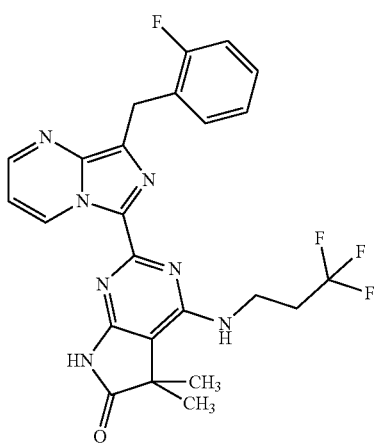 [SMILES: CC1(C)C(=O)Nc2nc(-c3nc(Cc4ccccc4F)c4ncccn34)nc(NCCC(F)(F)F)c21]

Under an argon atmosphere, 200 mg (purity 69%, 0.27 mmol) of 2-[8-(2-fluorobenzyl) imidazo[1,5-a]pyrimidin-6-yl]-4-iodo-5,5-dimethyl-5,7-dihydro-6H-pyrrolo[2,3-d]pyrimidin-6-one (example 52A) was suspended in 3.2 ml of absolute NMP and 607 mg (5.37 mmol) of 3,3,3-trifluoropropan-1-amine was added. The mixture was stirred for 1.5 h at 150° C. in the microwave. The reaction solution was filtered and purified by preparative HPLC (eluent: acetonitrile/water with 0.1% hydrochloric acid, gradient 20:80→100:0). 41 mg (31% of theor.) of the target compound was obtained.

LC-MS (method 1): $R_t$=1.09 min; MS (ESIpos): m/z=500 $[M+H]^+$ $^1$H-NMR (400 MHz, DMSO-$d_6$): δ [ppm]=1.35 (s, 6H), 2.62-2.74 (m, 2H), 3.77 (q, 2H), 4.33 (s, 2H), 6.87 (t, 1H), 6.96 (dd. 1H), 7.07-7.17 (m, 2H), 7.22-7.27 (m, 1H), 7.32 (t, 1H), 8.34 (d, 1H), 9.83 (d, 1H), 11.10 (s, 1H).

Example 40

2-[1-(2-Fluorobenzyl)-1H-pyrazolo[3,4-b]pyridin-3-yl]-5,5-dimethyl-4-{[(1-methyl-1H-pyrazol-5-yl)methyl]amino}-5,7-dihydro-6H-pyrrolo[2,3-d]pyrimidin-6-one

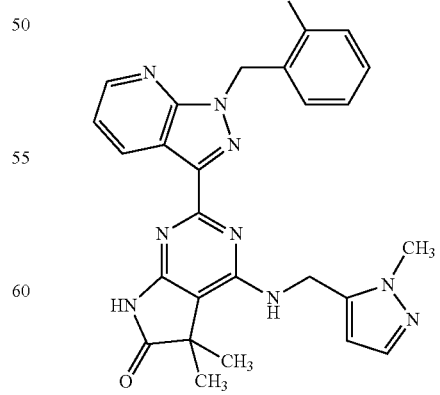

111.1 mg (1.0 mmol) of 1-(1-methyl-1H-pyrazol-5-yl)methanamine was put in a vial of a microwave reactor block and a solution of 51.4 mg (100 μmol) of 2-[1-(2-fluorobenzyl)-1H-pyrazolo[3,4-b]pyridin-3-yl]-4-iodo-5,5-dimethyl-5,7-dihydro-6H-pyrrolo[2,3-d]pyrimidin-6-one (example 15A) in 0.6 ml of 1-methyl-2-pyrrolidinone was added. Then the reactor block was sealed and was irradiated for 6 h with microwaves, in order to reach and maintain a temperature of the mixture of 170° C. After cooling, it was purified by preparative LC-MS (method 6). The product-containing fractions were concentrated by evaporation by means of a centrifugal dryer under vacuum. The residue of the individual fractions was in each case dissolved in 0.6 ml DMSO and combined. Then the solvent was evaporated completely in the centrifugal dryer. 32.7 mg (61% of theor.) of the target product was obtained.

LC-MS (method 5): $R_t$=1.07 min;

MS (ESIpos): m/z=498 [M+H]$^+$, purity: 93%

The compounds listed in Table 4 were prepared on the analogy of example 40.

TABLE 4

| Example No. | Structure<br>Yield (% of theor.) | Name | Analytical data |
| --- | --- | --- | --- |
| 41 | 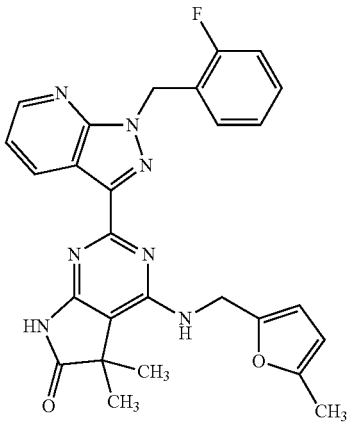<br>27.1 mg (51% of theor.) | 2-[1-(2-fluorobenzyl)-1H-pyrazolo[3,4-b]pyridin-3-yl]-5,5-dimethyl-4-{[(5-methylfuran-2-yl)methyl]amino}-5,7-dihydro-6H-pyrrolo[2,3-d]pyrimidin-6-one | LC/MS (method 5):<br>$R_t$ = 1.19 min<br>MS (ESIpos):<br>m/z = 498 [M + H]$^+$<br>Purity: 94% |
| 42 | 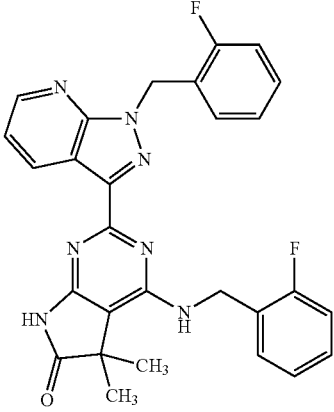<br>14.5 mg (28% of theor.) | 4-[(2-fluorobenzyl)amino]-2-[1-(2-fluorobenzyl)-1H-pyrazolo[3,4-b]pyridin-3-yl]-5,5-dimethyl-5,7-dihydro-6H-pyrrolo[2,3-d]pyrimidin-6-one | LC/MS (method 5.):<br>$R_t$ = 1.20 min<br>MS (ESIpos):<br>m/z = 512 [M + H]$^+$ |

TABLE 4-continued

| Example No. | Structure Yield (% of theor.) | Name | Analytical data |
|---|---|---|---|
| 43 | 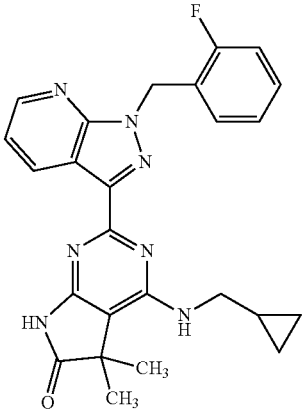<br>11.3 mg (25% of theor.) | 4-[(cyclopropylmethyl)amino]-2-[1-(2-fluorobenzyl)-1H-pyrazolo[3,4-b]pyridin-3-yl]-5,5-dimethyl-5,7-dihydro-6H-pyrrolo[2,3-d]pyrimidin-6-one | LC/MS (method 5.):<br>$R_t$ = 1.19 min<br>MS (ESIpos):<br>m/z = 458 [M + H]$^+$ |
| 44 | 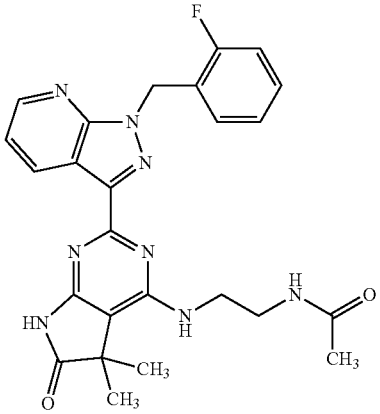<br>10.5 mg (21% of theor.) | N-[2-({2-[1-(2-fluorobenzyl)-1H-pyrazolo[3,4-b]pyridin-3-yl]-5,5-dimethyl-6-oxo-6,7-dihydro-5H-pyrrolo[2,3-d]pyrimidin-4-yl}amino)ethyl]acetamide | LC/MS (method 5.):<br>$R_t$ = 0.99 min<br>MS (ESIpos):<br>m/z = 489 [M + H]$^+$ |
| 45 | 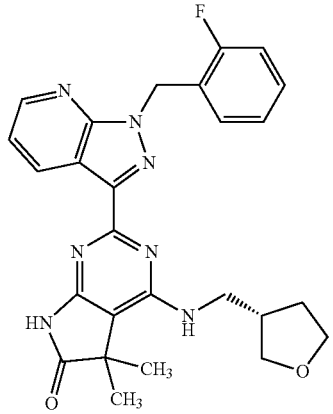<br>28.1 mg (58% of theor.) | 2-[1-(2-fluorobenzyl)-1H-pyrazolo[3,4-b]pyridin-3-yl]-5,5-dimethyl-4-[(tetrahydrofuran-3-ylmethyl)amino]-5,7-dihydro-6H-pyrrolo[2,3-d]pyrimidin-6-one | LC/MS (method 5.):<br>$R_t$ = 1.11 min<br>MS (ESIpos):<br>m/z = 488 [M + H]$^+$ |

TABLE 4-continued

| Example No. | Structure Yield (% of theor.) | Name | Analytical data |
|---|---|---|---|
| 46 | 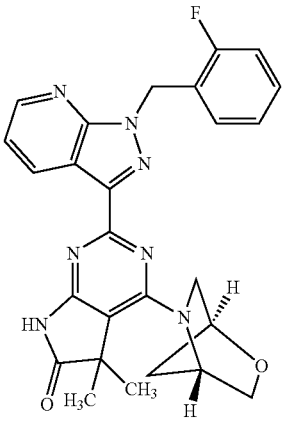<br>2 mg (4% of theor.) | 2-[1-(2-fluorobenzyl)-1H-pyrazolo[3,4-b]pyridin-3-yl]-5,5-dimethyl-4-[(1S,4S)-2-oxa-5-azabicyclo[2.2.1]hept-5-yl]-5,7-dihydro-6H-pyrrolo[2,3-d]pyrimidin-6-one | LC/MS (method 5.):<br>$R_t$ = 1.10 min<br>MS (ESIpos):<br>m/z = 486 [M + H]$^+$<br>Purity: 92% |
| 47 | 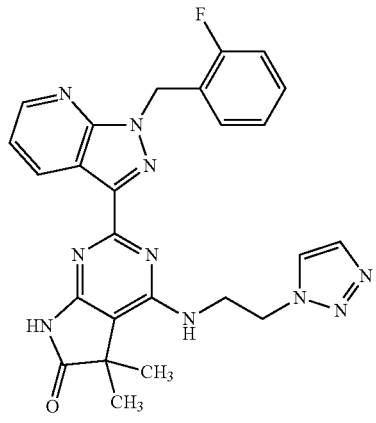<br>28.2 mg (52% of theor.) | 2-[1-(2-fluorobenzyl)-1H-pyrazolo[3,4-b]pyridin-3-yl]-5,5-dimethyl-4-{[2-(1H-1,2,3-triazol-1-yl)ethyl]amino}-5,7-dihydro-6H-pyrrolo[2,3-d]pyrimidin-6-one | LC/MS (method 5.):<br>$R_t$ = 1.02 min<br>MS (ESIpos):<br>m/z = 499 [M + H]$^+$<br>Purity: 92% |
| 48 | 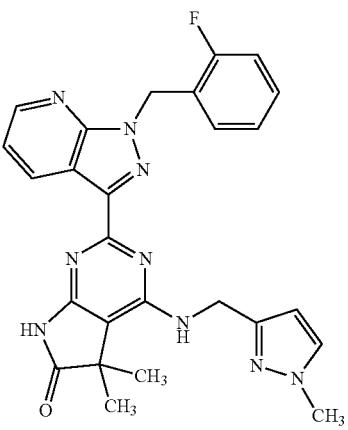<br>11.4 mg (17% of theor.) | 2-[1-(2-fluorobenzyl)-1H-pyrazolo[3,4-b]pyridin-3-yl]-5,5-dimethyl-4-{[(1-methyl-1H-pyrazol-3-yl)methyl]amino}-5,7-dihydro-6H-pyrrolo[2,3-d]pyrimidin-6-one | LC/MS (method 5.):<br>$R_t$ = 1.05 min<br>MS (ESIpos):<br>m/z = 498 [M + H]$^+$<br>Purity: 76% |

TABLE 4-continued

| Example No. | Structure Yield (% of theor.) | Name | Analytical data |
|---|---|---|---|
| 49 | 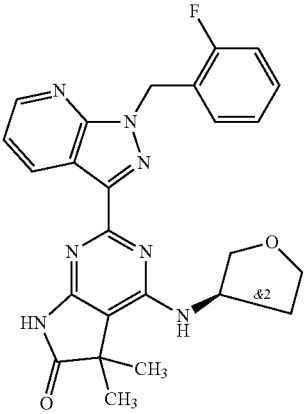<br>1.3 mg (3% of theor.) | 2-[1-(2-fluorobenzyl)-1H-pyrazolo[3,4-b]pyridin-3-yl]-5,5-dimethyl-4-(tetrahydrofuran-3-ylamino)-5,7-dihydro-6H-pyrrolo[2,3-d]pyrimidin-6-one | LC/MS (method 5.):<br>$R_t$ = 0.79 min<br>MS (ESIpos):<br>m/z = 474 [M + H]$^+$ |
| 50 | 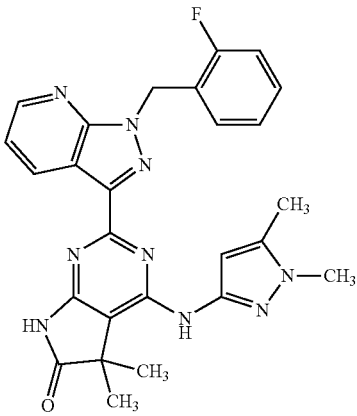<br>9.1 mg (17% of theor.) | 4-[(1,5-dimethyl-1H-pyrazol-3-yl)amino]-2-[1-(2-fluorobenzyl)-1H-pyrazolo[3,4-b]pyridin-3-yl]-5,5-dimethyl-5,7-dihydro-6H-pyrrolo[2,3-d]pyrimidin-6-one | LC/MS (method 5.):<br>$R_t$ = 1.08 min<br>MS (ESIpos):<br>m/z = 498 [M + H]$^+$<br>Purity: 95% |
| 51 | 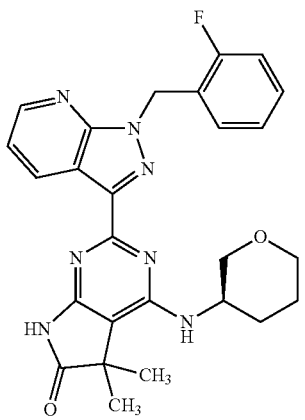<br>2.0 mg (4% of theor.) | 2-[1-(2-fluorobenzyl)-1H-pyrazolo[3,4-b]pyridin-3-yl]-5,5-dimethyl-4-(tetrahydro-2H-pyran-3-ylamino)-5,7-dihydro-6H-pyrrolo[2,3-d]pyrimidin-6-one | LC/MS (method 5.):<br>$R_t$ = 1.14 min<br>MS (ESIpos):<br>m/z = 488 [M + H]$^+$<br>Purity: 95% |

TABLE 4-continued

| Example No. | Structure Yield (% of theor.) | Name | Analytical data |
|---|---|---|---|
| 52 | 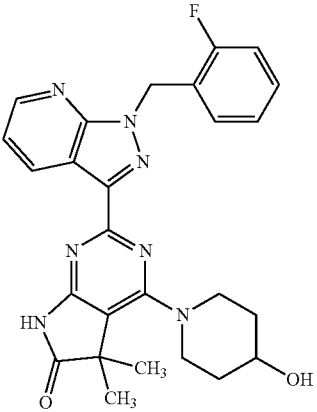<br>17.8 mg (37% of theor.) | 2-[1-(2-fluorobenzyl)-1H-pyrazolo[3,4-b]pyridin-3-yl]-4-(4-hydroxypiperidin-1-yl)-5,5-dimethyl-5,7-dihydro-6H-pyrrolo[2,3-d]pyrimidin-6-one | LC/MS (method 5.):<br>$R_t$ = 1.04 min<br>MS (ESIpos):<br>m/z = 488 [M + H]$^+$ |
| 53 | 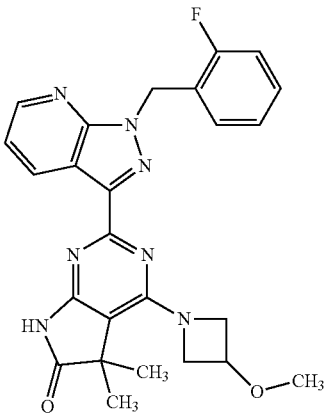<br>6.3 mg (11% of theor.) | 2-[1-(2-fluorobenzyl)-1H-pyrazolo[3,4-b]pyridin-3-yl]-4-(3-methoxyazetidin-1-yl)-5,5-dimethyl-5,7-dihydro-6H-pyrrolo[2,3-d]pyrimidin-6-one | LC/MS (method 5.):<br>$R_t$ = 0.82 min<br>MS (ESIpos):<br>m/z = 474 [M + H]$^+$<br>Purity: 83% |
| 54 | 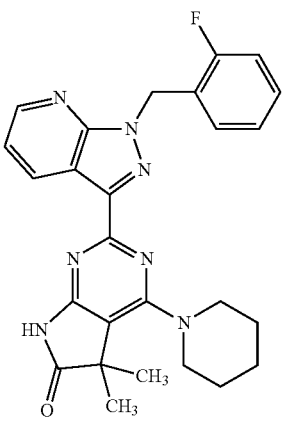<br>0.5 mg (1% of theor.) | 2-[1-(2-fluorobenzyl)-1H-pyrazolo[3,4-b]pyridin-3-yl]-5,5-dimethyl-4-(piperidin-1-yl)-5,7-dihydro-6H-pyrrolo[2,3-d]pyrimidin-6-one | LC/MS (method 5.):<br>$R_t$ = 1.26 min<br>MS (ESIpos):<br>m/z = 472 [M + H]$^+$<br>Purity: 95% |

TABLE 4-continued

| Example No. | Structure Yield (% of theor.) | Name | Analytical data |
|---|---|---|---|
| 55 | 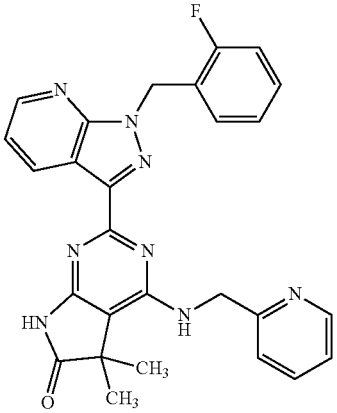<br>26.7 mg (49% of theor.) | 2-[1-(2-fluorobenzyl)-1H-pyrazolo[3,4-b]pyridin-3-yl]-5,5-dimethyl-4-[(pyridin-2-ylmethyl)amino]-5,7-dihydro-6H-pyrrolo[2,3-d]pyrimidin-6-one | LC/MS (method 5.):<br>$R_t$ = 0.95 min<br>MS (ESIpos):<br>m/z = 495 [M + H]$^+$<br>Purity: 91% |
| 56 | 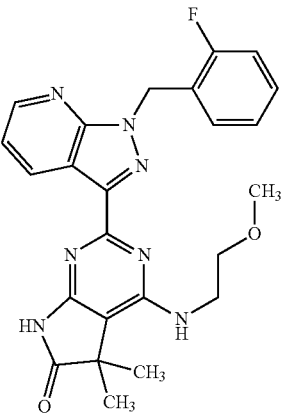<br>6.0 mg (12% of theor.) | 2-[1-(2-fluorobenzyl)-1H-pyrazolo[3,4-b]pyridin-3-yl]-4-[(2-methoxyethyl)amino]-5,5-dimethyl-5,7-dihydro-6H-pyrrolo[2,3-d]pyrimidin-6-one | LC/MS (method 5.):<br>$R_t$ = 1.09 min<br>MS (ESIpos):<br>m/z = 462 [M + H]$^+$<br>Purity: 94% |
| 57 | 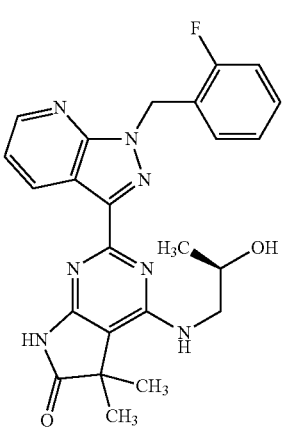<br>24.2 mg (50% of theor.) | 2-[1-(2-fluorobenzyl)-1H-pyrazolo[3,4-b]pyridin-3-yl]-4-[(2-hydroxypropyl)amino]-5,5-dimethyl-5,7-dihydro-6H-pyrrolo[2,3-d]pyrimidin-6-one | LC/MS (method 5.):<br>$R_t$ = 1.01 min<br>MS (ESIpos):<br>m/z = 461 (M + H]$^+$<br>Purity: 95% |

TABLE 4-continued

| Example No. | Structure Yield (% of theor.) | Name | Analytical data |
|---|---|---|---|
| 58 | 25.6 mg (51% of theor.) | 2-[1-(2-fluorobenzyl)-1H-pyrazolo[3,4-b]pyridin-3-yl]-5,5-dimethyl-4-{[2-(1H-pyrazol-1-yl)ethyl]amino}-5,7-dihydro-6H-pyrrolo[2,3-d]pyrimidin-6-one | LC/MS (method 5.): $R_t$ = 1.08 min MS (ESIpos): m/z = 498 [M + H]$^+$ |
| 59 | 26.5 mg (51% of theor.) | 2-[1-(2-fluorobenzyl)-1H-pyrazolo[3,4-b]pyridin-3-yl]-5,5-dimethyl-4-{[(1-methyl-1H-pyrazol-4-yl)methyl]amino}-5,7-dihydro-6H-pyrrolo[2,3-d]pyrimidin-6-one | LC/MS (method 5.): $R_t$ = 1.07 min MS (ESIpos): m/z = 498 [M + H]$^+$ |
| 60 | 22.6 mg (45% of theor.) | 2-[1-(2-fluorobenzyl)-1H-pyrazolo[3,4-b]pyridin-3-yl]-5,5-dimethyl-4-{[(1-methyl-1H-imidazol-2-yl)methyl]amino}-5,7-dihydro-6H-pyrrolo[2,3-d]pyrimidin-6-one | LC/MS (method 5.): $R_t$ = 0.79 min MS (ESIpos): m/z = 498 [M + H]$^+$ |

TABLE 4-continued

| Example No. | Structure Yield (% of theor.) | Name | Analytical data |
|---|---|---|---|
| 61 | 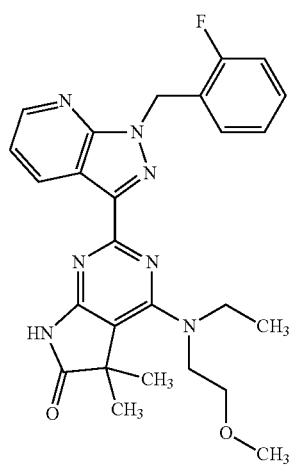<br>1.5 mg (3% of theor.) | 4-[ethyl(2-methoxyethyl)amino]-2-[1-(2-fluorobenzyl)-1H-pyrazolo[3,4-b]pyridin-3-yl]-5,5-dimethyl-5,7-dihydro-6H-pyrrolo[2,3-d]pyrimidin-6-one | LC/MS (method 5.):<br>$R_t$ = 1.19 min<br>MS (ESIpos):<br>m/z = 490 [M + H]$^+$ |
| 62 | 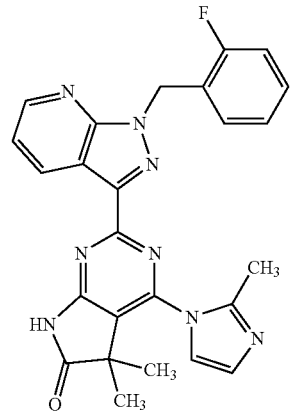<br>10.6 mg (23% of theor.) | 2-[1-(2-fluorobenzyl)-1H-pyrazolo[3,4-b]pyridin-3-yl]-5,5-dimethyl-4-(2-methyl-1H-imidazol-1-yl)-5,7-dihydro-6H-pyrrolo[2,3-d]pyrimidin-6-one | LC/MS (method 5.):<br>$R_t$ = 0.83 min<br>MS (ESIpos):<br>m/z = 469 [M + H]$^+$ |
| 63 | 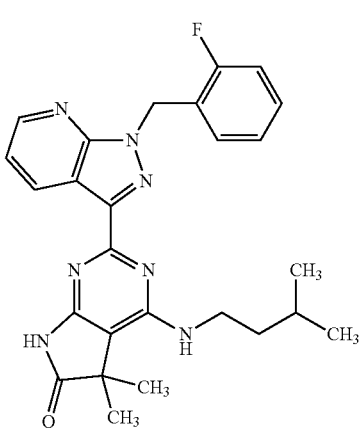<br>23.7 mg (50% of theor.) | 2-[1-(2-fluorobenzyl)-1H-pyrazolo[3,4-b]pyridin-3-yl]-5,5-dimethyl-4-[(3-methylbutyl)amino]-5,7-dihydro-6H-pyrrolo[2,3-d]pyrimidin-6-one | LC/MS (method 5.):<br>$R_t$ = 1.25 min<br>MS (ESIpos):<br>m/z = 474 [M + H]$^+$ |

TABLE 4-continued

| Example No. | Structure Yield (% of theor.) | Name | Analytical data |
|---|---|---|---|
| 64 | 11.3 mg (25% of theor.) | 2-[1-(2-fluorobenzyl)-1H-pyrazolo[3,4-b]pyridin-3-yl]-5,5-dimethyl-4-(pyrrolidin-1-yl)-5,7-dihydro-6H-pyrrolo[2,3-d]pyrimidin-6-one | LC/MS (method 5.):<br>$R_t$ = 1.32 min<br>MS (ESIpos):<br>m/z = 458 [M + H]$^+$ |
| 65 | 7.6 mg (16% of theor.) | 2-[1-(2-fluorobenzyl)-1H-pyrazolo[3,4-b]pyridin-3-yl]-5,5-dimethyl-4-(pyridin-3-ylamino)-5,7-dihydro-6H-pyrrolo[2,3-d]pyrimidin-6-one | LC/MS (method 5.):<br>$R_t$ = 0.78 min<br>MS (ESIpos):<br>m/z = 481 [M + H]$^+$ |
| 66 | 24.0 mg (44% of theor.) | 2-[1-(2-fluorobenzyl)-1H-pyrazolo[3,4-b]pyridin-3-yl]-5,5-dimethyl-4-{[(5-oxopyrrolidin-3-yl)methyl]amino}-5,7-dihydro-6H-pyrrolo[2,3-d]pyrimidin-6-one | LC/MS (method 5.):<br>$R_t$ = 0.98 min<br>MS (ESIpos):<br>m/z = 501 [M + H]$^+$<br>Purity: 91% |

TABLE 4-continued

| Example No. | Structure Yield (% of theor.) | Name | Analytical data |
|---|---|---|---|
| 67 | 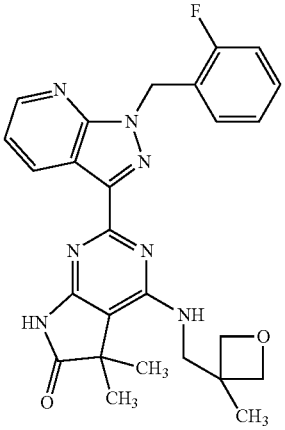<br>4.4 mg (9% of theor.) | 2-[1-(2-fluorobenzyl)-1H-pyrazolo[3,4-b]pyridin-3-yl]-5,5-dimethyl-4-{[(3-methyloxetan-3-yl)methyl]amino}-5,7-dihydro-6H-pyrrolo[2,3-d]pyrimidin-6-one | LC/MS (method 5.):<br>$R_t$ = 1.07 min<br>MS (ESIpos):<br>m/z = 488 [M + H]$^+$<br>Purity: 87% |
| 68 | 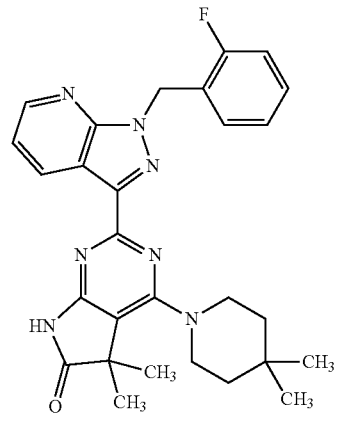<br>6.6 mg (12% of theor.) | 4-(4,4-dimethylpiperidin-1-yl)-2-[1-(2-fluorobenzyl)-1H-pyrazolo[3,4-b]pyridin-3-yl]-5,5-dimethyl-5,7-dihydro-6H-pyrrolo[2,3-d]pyrimidin-6-one | LC/MS (method 5.):<br>$R_t$ = 1.31 min<br>MS (ESIpos):<br>m/z = 500 [M + H]$^+$<br>Purity: 93% |
| 69 | 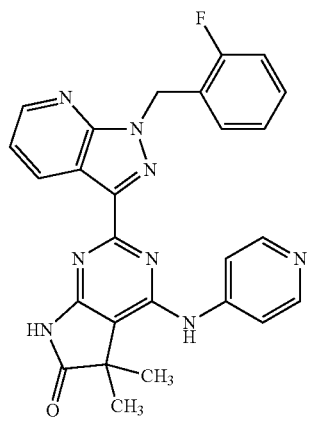<br>3.7 mg (7% of theor.) | 2-[1-(2-fluorobenzyl)-1H-pyrazolo[3,4-b]pyridin-3-yl]-5,5-dimethyl-4-(pyridin-4-ylamino)-5,7-dihydro-6H-pyrrolo[2,3-d]pyrimidin-6-one | LC/MS (method 5.):<br>$R_t$ = 0.79 min<br>MS (ESIpos):<br>m/z = 481 [M + H]$^+$<br>Purity: 90% |

TABLE 4-continued

| Example No. | Structure Yield (% of theor.) | Name | Analytical data |
|---|---|---|---|
| 70 | 17.3 mg (36% of theor.) | 2-[1-(2-fluorobenzyl)-1H-pyrazolo[3,4-b]pyridin-3-yl]-5,5-dimethyl-4-(4-methylpiperazin-1-yl)-5,7-dihydro-6H-pyrrolo[2,3-d]pyrimidin-6-one | LC/MS (method 5.): $R_t$ = 0.75 min MS (ESIpos): m/z = 487 [M + H]$^+$ |
| 71 | 20.3 mg (41% of theor.) | 4-[(3-ethoxypropyl)amino]-2-[1-(2-fluorobenzyl)-1H-pyrazolo[3,4-b]pyridin-3-yl]-5,5-dimethyl-5,7-dihydro-6H-pyrrolo[2,3-d]pyrimidin-6-one | LC/MS (method 5.): $R_t$ = 1.17 min MS (ESIpos): m/z = 490 [M + H]$^+$ |
| 72 | 17.3 mg (37% of theor.) | 2-[1-(2-fluorobenzyl)-1H-pyrazolo[3,4-b]pyridin-3-yl]-5,5-dimethyl-4-(morpholin-4-yl)-5,7-dihydro-6H-pyrrolo[2,3-d]pyrimidin-6-one | LC/MS (method 5.): $R_t$ = 1.13 min MS (ESIpos): m/z = 474 [M + H]$^+$ |

TABLE 4-continued

| Example No. | Structure Yield (% of theor.) | Name | Analytical data |
|---|---|---|---|
| 73 | 2.5 mg (5% of theor.) | N³-{2-[1-(2-fluorobenzyl)-1H-pyrazolo[3,4-b]pyridin-3-yl]-5,5-dimethyl-6-oxo-6,7-dihydro-5H-pyrrolo[2,3-d]pyrimidin-4-yl}-beta-alaninamide | LC/MS (method 5.):<br>R$_t$ = 0.94 min<br>MS (ESIpos):<br>m/z = 475 [M + H]⁺ |
| 74 | 27.9 mg (59% of theor.) | 2-[1-(2-fluorobenzyl)-1H-pyrazolo[3,4-b]pyridin-3-yl]-4-[(3-methoxypropyl)amino]-5,5-dimethyl-5,7-dihydro-6H-pyrrolo[2,3-d]pyrimidin-6-one | LC/MS (method 5.):<br>R$_t$ = 1.14 min<br>MS (ESIpos):<br>m/z = 476 [M + H]⁺ |
| 75 | 2.1 mg (4% of theor.) | 2-[1-(2-fluorobenzyl)-1H-pyrazolo[3,4-b]pyridin-3-yl]-4-[(2-methoxyethyl)(methyl)amino]-5,5-dimethyl-5,7-dihydro-6H-pyrrolo[2,3-d]pyrimidin-6-one | LC/MS (method 5.):<br>R$_t$ = 1.15 min<br>MS (ESIpos):<br>m/z = 476 [M + H]⁺ |

TABLE 4-continued

| Example No. | Structure Yield (% of theor.) | Name | Analytical data |
|---|---|---|---|
| 76 | 7.7 mg (16% of theor.) | 4-(3,3-difluoropyrrolidin-1-yl)-2-[1-(2-fluorobenzyl)-1H-pyrazolo[3,4-b]pyridin-3-yl]-5,5-dimethyl-5,7-dihydro-6H-pyrrolo[2,3-d]pyrimidin-6-one | LC/MS (method 5.): $R_t$ = 1.19 min MS (ESIpos): m/z = 494 [M + H]$^+$ |
| 77 | 1.0 mg (2% of theor.) | 4-[(4-fluorobenzyl)amino]-2-[1-(2-fluorobenzyl)-1H-pyrazolo[3,4-b]pyridin-3-yl]-5,5-dimethyl-5,7-dihydro-6H-pyrrolo[2,3-d]pyrimidin-6-one | LC/MS (method 5.): $R_t$ = 1.19 min MS (ESIpos): m/z = 512 [M + H]$^+$ |
| 78 | 28.0 mg (55% of theor.) | 4-[(3-fluorobenzyl)amino]-2-[1-(2-fluorobenzyl)-1H-pyrazolo[3,4-b]pyridin-3-yl]-5,5-dimethyl-5,7-dihydro-6H-pyrrolo[2,3-d]pyrimidin-6-one | LC/MS (method 5.): $R_t$ = 1.20 min MS (ESIpos): m/z = 512 [M + H]$^+$ |

TABLE 4-continued

| Example No. | Structure Yield (% of theor.) | Name | Analytical data |
| --- | --- | --- | --- |
| 79 | 0.6 mg (1% of theor.) | N₂-{2-[1-(2-fluorobenzyl)-1H-pyrazolo[3,4-b]pyridin-3-yl]-5,5-dimethyl-6-oxo-6,7-dihydro-5H-pyrrolo[2,3-d]pyrimidin-4-yl}-L-alaninamide | LC/MS (method 5.):<br>$R_t$ = 0.96 min<br>MS (ESIpos):<br>m/z = 475 [M + H]⁺<br>Purity: 94% |
| 80 | 0.8 mg (2% of theor.) | 4-[(cyclopentylmethyl)amino]-2-[1-(2-fluorobenzyl)-1H-pyrazolo[3,4-b]pyridin-3-yl]-5,5-dimethyl-5,7-dihydro-6H-pyrrolo[2,3-d]pyrimidin-6-one | LC/MS (method 5.):<br>$R_t$ = 1.27 min<br>MS (ESIpos):<br>m/z = 486 [M + H]⁺ |
| 81 | 21.3 mg (39% of theor.) | 2-[1-(2-fluorobenzyl)-1H-pyrazolo[3,4-b]pyridin-3-yl]-5,5-dimethyl-4-[(2-oxopiperidin-3-yl)amino]-5,7-dihydro-6H-pyrrolo[2,3-d]pyrimidin-6-one | LC/MS (method 5.):<br>$R_t$ = 1.01 min<br>MS (ESIpos):<br>m/z = 501 [M + H]⁺<br>Purity: 92% |

TABLE 4-continued

| Example No. | Structure Yield (% of theor.) | Name | Analytical data |
|---|---|---|---|
| 82 | 0.8 mg (2% of theor.) | 2-[1-(2-fluorobenzyl)-1H-pyrazolo[3,4-b]pyridin-3-yl]-5,5-dimethyl-4-(3-oxopiperazin-1-yl)-5,7-dihydro-6H-pyrrolo[2,3-d]pyrimidin-6-one | LC/MS (method 5.):<br>$R_t$ = 0.98 min<br>MS (ESIpos):<br>m/z = 487 [M + H]$^+$ |
| 83 | 24.3 mg (49% of theor.) | 4-(benzylamino)-2-[1-(2-fluorobenzyl)-1H-pyrazolo[3,4-b]pyridin-3-yl]-5,5-dimethyl-5,7-dihydro-6H-pyrrolo[2,3-d]pyrimidin-6-one | LC/MS (method 5.):<br>$R_t$ = 1.20 min<br>MS (ESIpos):<br>m/z = 494 [M + H]$^+$ |
| 84 | 22.9 mg (46% of theor.) | 2-[1-(2-fluorobenzyl)-1H-pyrazolo[3,4-b]pyridin-3-yl]-5,5-dimethyl-4-[(pyridin-3-ylmethyl)amino]-5,7-dihydro-6H-pyrrolo[2,3-d]pyrimidin-6-one | LC/MS (method 5.):<br>$R_t$ = 0.91 min<br>MS (ESIpos):<br>m/z = 495 [M + H]$^+$ |

TABLE 4-continued

| Example No. | Structure Yield (% of theor.) | Name | Analytical data |
|---|---|---|---|
| 85 | 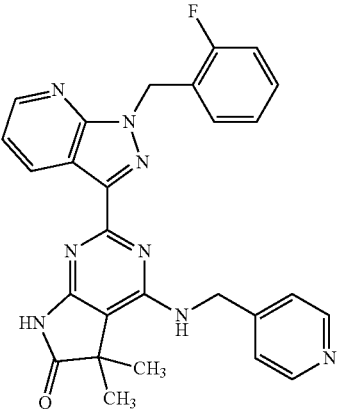 16.5 mg (33% of theor.) | 2-[1-(2-fluorobenzyl)-1H-pyrazolo[3,4-b]pyridin-3-yl]-5,5-dimethyl-4-[(pyridin-4-ylmethyl)amino]-5,7-dihydro-6H-pyrrolo[2,3-d]pyrimidin-6-one | LC/MS (method 5.): $R_t$ = 0.87 min MS (ESIpos): m/z = 495 [M + H]$^+$ |
| 86 | 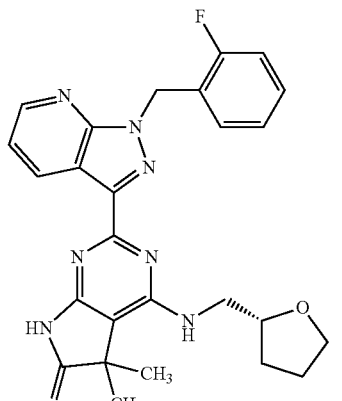 23.2 mg (48% of theor.) | 2-[1-(2-fluorobenzyl)-1H-pyrazolo[3,4-b]pyridin-3-yl]-5,5-dimethyl-4-[(tetrahydrofuran-2-ylmethyl)amino]-5,7-dihydro-6H-pyrrolo[2,3-d]pyrimidin-6-one | LC/MS (method 5.): $R_t$ = 1.12 min MS (ESIpos): m/z = 488 [M + H]$^+$ |
| 87 | 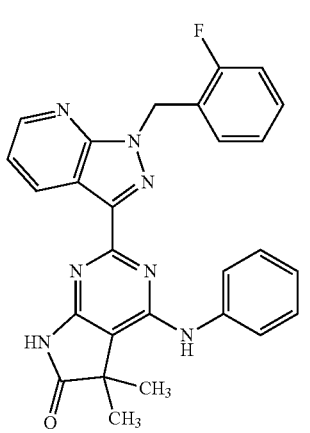 17.6 mg (37% of theor.) | 2-[1-(2-fluorobenzyl)-1H-pyrazolo[3,4-b]pyridin-3-yl]-5,5-dimethyl-4-(phenylamino)-5,7-dihydro-6H-pyrrolo[2,3-d]pyrimidin-6-one | LC/MS (method 5.): $R_t$ = 1.21 min MS (ESIpos): m/z = 480 [M + H]$^+$ |

Example 88

4-{[(1R)-1-Cyclopropylethyl]amino}-2-[5-fluoro-1-(2-fluorobenzyl)-1H-pyrazolo[3,4-b]pyridin-3-yl]-5,5-dimethyl-5,7-dihydro-6H-pyrrolo[2,3-d]pyrimidin-6-one

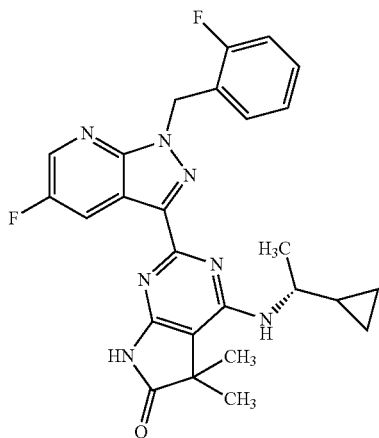 [SMILES: C[C@@H](Nc1nc(-c2nn(Cc3ccccc3F)c3ncc(F)cc23)nc2c1C(C)(C)C(=O)N2)C1CC1]

150 mg (0.186 mmol, approx. 66% purity) of example 16A was dissolved in 1-methyl-2-pyrrolidone (3.5 ml) in a reaction vessel suitable for a microwave, and 0.5 ml of (R)-1-cyclopropylethylamine was added. Then it was sealed with a corresponding septum and it was heated in the microwave at 150° C. for 3 h. After cooling, the reaction mixture was purified by preparative HPLC (acetonitrile:water: water+1% trifluoroacetic acid—(70:24:6). 54 mg of the title compound was obtained (59% of theor.).

LC-MS (method 1): $R_t$=1.29 min; MS (EIpos): m/z=490 [M+H]$^+$.

$^1$H-NMR (400 MHz, DMSO-d$_6$): δ [ppm]=0.19-0.25 (m, 1H), 0.35-0.41 (m, 2H), 0.48-0.53 (m, 1H), 1.13-1.21 (m, 1H), 1.35 (d, 3H), 1.39 (2s, 6H), 4.00-4.06 (m, 1H), 5.82 (s, 2H), 6.29 (d, 1H), 7.12-7.16 (m, 1H), 7.19-7.24 (m, 2H), 7.33-7.39 (m, 1H), 8.42 (dd, 1H), 8.71 (dd, 1H), 10.99 (s, 1H).

Example 89

4-{[(1S)-1-Cyclopropylethyl]amino}-2-[5-fluoro-1-(2-fluorobenzyl)-1H-pyrazolo[3,4-b]pyridin-3-yl]-5,5-dimethyl-5,7-dihydro-6H-pyrrolo[2,3-d]pyrimidin-6-one

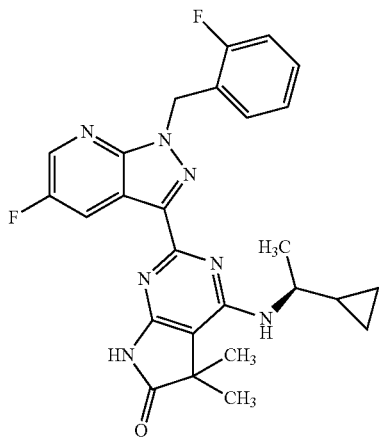 [SMILES: C[C@H](Nc1nc(-c2nn(Cc3ccccc3F)c3ncc(F)cc23)nc2c1C(C)(C)C(=O)N2)C1CC1]

150 mg (0.186 mmol, approx. 66% purity) of example 16A was dissolved in 1-methyl-2-pyrrolidone (3.5 ml) in a reaction vessel suitable for a microwave and 0.5 ml of (S)-1-cyclopropylethylamine was added. Then it was sealed with a corresponding septum and it was heated in the microwave at 150° C. for 3 h. After cooling, the reaction mixture was purified by preparative HPLC (acetonitrile:water:water+1% trifluoroacetic acid (70:24:6). 69 mg of the title compound was obtained (75% of theor.).

LC-MS (method 1): $R_t$=1.29 min; MS (EIpos): m/z=490 [M+H]$^+$.

$^1$H-NMR (400 MHz, DMSO-d$_6$): δ [ppm]=0.19-0.25 (m, 1H), 0.35-0.41 (m, 2H), 0.48-0.53 (m, 1H), 1.13-1.21 (m, 1H), 1.35 (d, 3H), 1.39 (2s, 6H), 4.00-4.06 (m, 1H), 5.82 (s, 2H), 6.29 (d, 1H), 7.12-7.16 (m, 1H), 7.19-7.24 (m, 2H), 7.33-7.39 (m, 1H), 8.42 (dd, 1H), 8.71 (dd, 1H), 10.99 (s, 1H).

Example 90

2-[5-Fluoro-1-(2-fluorobenzyl)-6-methyl-1H-pyrazolo[3,4-b]pyridin-3-yl]-5,5-dimethyl-4-[(3,3,3-trifluoropropyl)amino]-5,7-dihydro-6H-pyrrolo[2,3-d]pyrimidin-6-one

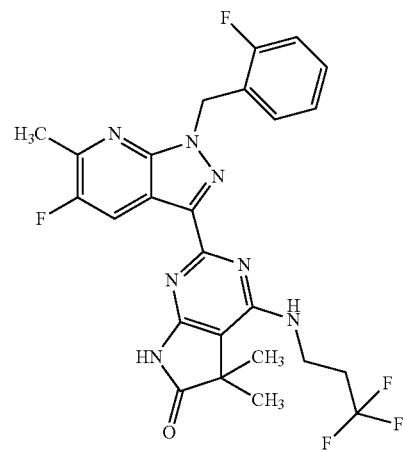 [SMILES: Cc1nc2c(cc1F)c(-c1nc(NCCC(F)(F)F)c3c(n1)NC(=O)C3(C)C)nn2Cc1ccccc1F]

150 mg (0.231 mmol, approx. 84% purity) of example 53A was dissolved in 1-methyl-2-pyrrolidone (3 ml) in a reaction vessel suitable for a microwave and 1 ml of 3,3,3-trifluoropropyl-1-amine was added. Then it was sealed with a corresponding septum and it was heated in the microwave at 150° C. for 3 h. After cooling, the reaction mixture was purified by preparative HPLC (acetonitrile:water (+0.05% formic acid) gradient). 89 mg of the title compound was obtained (73% of theor.).

LC-MS (method 1): $R_t$=1.27 min; MS (EIpos): m/z=532 [M+H]$^+$.

$^1$H-NMR (400 MHz, DMSO-d$_6$): δ [ppm]=1.35 (s, 6H), 2.62 (d, 3H), 2.64-2.73 (m, 2H), 3.81 (q, 2H), 5.78 (s, 2H), 6.84 (t, 1H), 7.12-7.25 (m, 3H), 7.33-7.39 (m, 1H), 8.36 (d, 1H), 11.05 (s br, 1H).

Example 91

2-[1-(2-Fluorobenzyl)-1H-pyrazolo[3,4-b]pyridin-3-yl]-5,5-dimethyl-4-[2-oxo-5-(trifluoromethyl)piperidin-1-yl]-5,7-dihydro-6H-pyrrolo[2,3-d]pyrimidin-6-one

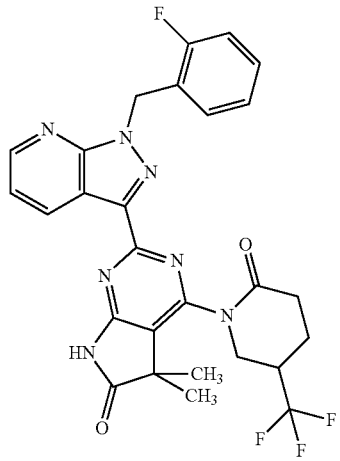 [SMILES: CC1(C)C(=O)Nc2nc(-c3nn(Cc4ccccc4F)c4ncccc34)nc(N3CC(C(F)(F)F)CCC3=O)c21]

Under argon atmosphere, 200 mg (purity 62%, 0.24 mmol) of 2-[1-(2-fluorobenzyl)-1H-pyrazolo[3,4-b]pyridin-3-yl]-4-iodo-5,5-dimethyl-5,7-dihydro-6H-pyrrolo[2,3-d]pyrimidin-6-one (example 15A) was suspended in 2.5 ml of absolute acetonitrile, and 806 mg (4.82 mmol) of 5-(trifluoromethyl)piperidin-2-one, 157 mg (0.48 mmol) of caesium carbonate, 7 mg (0.05 mmol) of copper(I) oxide and 26 mg (0.19 mmol) of 2-hydroxybenzaldehyde-oxime were added. The mixture was heated in the microwave for 1 h at 200° C. The reaction solution was filtered and purified by preparative HPLC (eluent: acetonitrile/water, gradient 20:80→100:0). 15 mg (11% of theor.) of the target compound was obtained.

LC-MS (method 1): $R_t$=1.07 min; MS (ESIpos): m/z=554 [M+H]$^+$ $^1$H-NMR (400 MHz, DMSO-d$_6$): δ [ppm]=1.31 (d, 6H), 1.41 (s, 6H), 2.05-2.24 (m, 2H), 2.59-2.78 (m, 3H), 3.76-3.87 (m, 2H), 5.89 (s, 2H), 7.12-7.18 (m, 2H), 7.23 (t, 1H), 7.33-7.38 (m, 1H), 7.46 (dd, 1H), 8.69 (d, 1H), 8.87 (d, 1H), 11.82 (s, 1H).

Example 92

2-[1-(2-Fluorobenzyl)-1H-pyrazolo[3,4-b]pyridin-3-yl]-5,5-dimethyl-4-(2-methyl-3-oxopiperazin-1-yl)-5,7-dihydro-6H-pyrrolo[2,3-d]pyrimidin-6-one

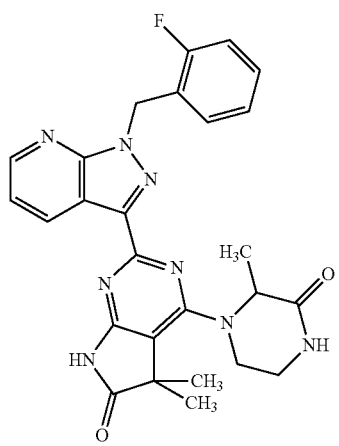 [SMILES: CC1C(=O)NCCN1c1nc(-c2nn(Cc3ccccc3F)c3ncccc23)nc2c1C(C)(C)C(=O)N2]

Under argon atmosphere, 200 mg (purity 62%, 0.24 mmol) of 2-[1-(2-fluorobenzyl)-1H-pyrazolo[3,4-b]pyridin-3-yl]-4-iodo-5,5-dimethyl-5,7-dihydro-6H-pyrrolo[2,3-d]pyrimidin-6-one (example 15A) was suspended in 4 ml of absolute 1-methyl-2-pyrrolidone and 550 mg (4.82 mmol) of 3-methylpiperazin-2-one was added. The mixture was heated in the microwave for 3 h at 150° C. and for 3 h at 220° C. After cooling, the reaction mixture was purified by preparative HPLC (eluent: acetonitrile/water, gradient 20:80→100:0). 61 mg (purity 100%, 50% of theor.) of the target compound was obtained.

LC-MS (method 8): $R_t$=2.55 min; MS (ESIpos): m/z=501 [M+H]$^+$ $^1$H-NMR (400 MHz, DMSO-d$_6$): δ [ppm]=1.42-1.45 (m, 9H), 3.54-3.61 (m, 1H), 4.13-4.18 (m, 1H), 4.97 (q, 1H), 5.86 (s, 2H), 7.12-7.25 (m, 3H), 7.33-7.39 (m, 1H), 7.45 (dd, 1H), 8.09 (s, 1H), 8.67 (dd, 1H), 8.76 (dd, 1H), 11.40 (s br, 1H).

Example 93

4-(1,1-Dioxidothiomorpholin-4-yl)-2-[1-(2-fluorobenzyl)-1H-pyrazolo[3,4-b]pyridin-3-yl]-5,5-dimethyl-5,7-dihydro-6H-pyrrolo[2,3-d]pyrimidin-6-one

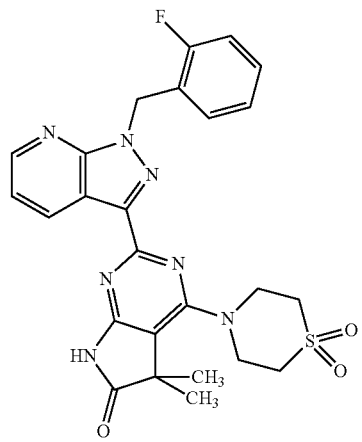 [SMILES: CC1(C)C(=O)Nc2nc(-c3nn(Cc4ccccc4F)c4ncccc34)nc(N3CCS(=O)(=O)CC3)c21]

Under argon atmosphere, 200 mg (purity 62%, 0.24 mmol) of 2-[1-(2-fluorobenzyl)-1H-pyrazolo[3,4-b]pyridin-3-yl]-4-iodo-5,5-dimethyl-5,7-dihydro-6H-pyrrolo[2,3-d]pyrimidin-6-one (example 15A) was suspended in 4 ml of absolute 1-methyl-2-pyrrolidone and 652 mg (4.82 mmol) of thiomorpholine-1,1-dioxide was added. The mixture was heated in the microwave for 3 h at 150° C. and 1 h at 200° C. After cooling, the reaction mixture was purified by preparative HPLC (eluent: acetonitrile/water with 0.1% formic acid, gradient 20:80→100:0). 72 mg (57% of theor.) of the target compound was obtained.

LC-MS (method 1): $R_t$=0.96 min; MS (ESIpos): m/z=522 [M+H]$^+$ $^1$H-NMR (400 MHz, DMSO-d$_6$): δ [ppm]=1.43 (s, 6H), 3.36-3.39 (m, 4H), 4.14-4.17 (m, 4H), 5.85 (s, 2H), 7.11-7.25 (m, 3H), 7.33-7.39 (m, 1H), 7.44 (dd, 1H), 8.66-8.71 (m, 2H), 11.45 (s, 1H).

Example 94

N-(1-{2-[1-(2-Fluorobenzyl)-1H-pyrazolo[3,4-b]pyridin-3-yl]-5,5-dimethyl-6-oxo-6,7-dihydro-5H-pyrrolo[2,3-d]pyrimidin-4-yl}pyrrolidin-3-yl)acetamide

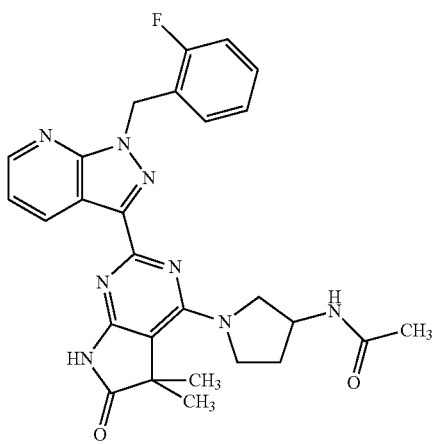 [SMILES: CC(=O)NC1CCN(c2nc(-c3nn(Cc4ccccc4F)c4ncccc34)nc3c2C(C)(C)C(=O)N3)C1]

Under argon atmosphere, 200 mg (purity 62%, 0.24 mmol) of 2-[1-(2-fluorobenzyl)-1H-pyrazolo[3,4-b]pyridin-3-yl]-4-iodo-5,5-dimethyl-5,7-dihydro-6H-pyrrolo[2,3-d]pyrimidin-6-one (example 15A) was suspended in 4 ml of absolute 1-methyl-2-pyrrolidone and 618 mg (4.82 mmol) of N-(pyrrolidin-3-yl)acetamide was added. The mixture was heated in the microwave at 150° C. for 3 h. After cooling, the reaction mixture was purified by preparative HPLC (eluent: acetonitrile/water with 0.1% formic acid, gradient 20:80→100:0). 122 mg (98% of theor.) of the target compound was obtained.

LC-MS (method 1): $R_t$=0.91 min; MS (ESIpos): m/z=515 [M+H]$^+$ $^1$H-NMR (400 MHz, DMSO-d$_6$): δ [ppm]=1.42 (s, 6H), 1.83 (s, 3H), 1.90-2.01 (m, 1H), 2.17-2.25 (m, 1H), 3.65 (dd, 1H), 3.81-3.97 (m, 3H), 4.33-4.40 (m, 1H), 5.84 (s, 2H), 7.12-7.25 (m, 3H), 7.32-7.40 (m, 1H), 7.43 (dd, 1H), 8.22 (d, 1H), 8.65 (dd, 1H), 8.86 (dd, 1H), 11.21 (s, 1H).

Example 95

2-[1-(2-Fluorobenzyl)-1H-pyrazolo[3,4-b]pyridin-3-yl]-4-[(trans-4-hydroxycyclohexyl)amino]-5,5-dimethyl-5,7-dihydro-6H-pyrrolo[2,3-d]pyrimidin-6-one

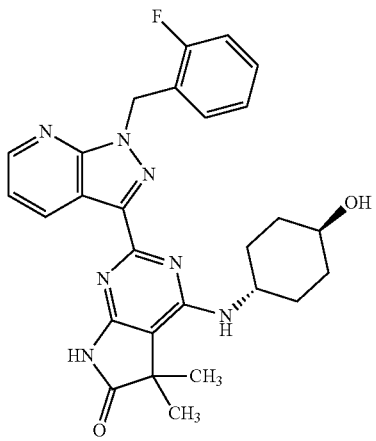 [SMILES: CC1(C)C(=O)Nc2nc(-c3nn(Cc4ccccc4F)c4ncccc34)nc(N[C@H]3CC[C@H](O)CC3)c21]

Under argon atmosphere, 200 mg (purity 62%, 0.24 mmol) of 2-[1-(2-fluorobenzyl)-1H-pyrazolo[3,4-b]pyridin-3-yl]-4-iodo-5,5-dimethyl-5,7-dihydro-6H-pyrrolo[2,3-d]pyrimidin-6-one (example 15A) was suspended in 4 ml of absolute 1-methyl-2-pyrrolidone and 555 mg (4.82 mmol) of trans-4-aminocyclohexanol was added. The mixture was heated in the microwave at 150° C. for 3 h. After cooling, the reaction mixture was purified by preparative HPLC (eluent: acetonitrile/water with 0.1% formic acid, gradient 20:80→100:0). 91 mg (73% of theor.) of the target compound was obtained.

LC-MS (method 1): $R_t$=0.92 min; MS (ESIpos): m/z=502 [M+H]$^+$ $^1$H-NMR (400 MHz, DMSO-d$_6$): δ [ppm]=1.31-1.41 (m, 2H), 1.36 (s, 6H), 1.49-1.58 (m, 2H), 1.91-1.98 (m, 4H), 3.42-3.51 (m, 1H), 4.12-4.22 (m, 1H), 4.61 (d, 1H), 5.83 (s, 2H), 6.15 (d, 1H), 7.12-7.25 (m, 3H), 7.33-7.38 (m, 1H), 7.41 (dd, 1H), 8.66 (dd, 1H), 8.80 (dd, 1H), 11.21 (s, 1H).

Example 96

2-[5-Fluoro-1-(2-fluorobenzyl)-1H-pyrazolo[3,4-b]pyridin-3-yl]-5,5-dimethyl-4-[(3,3,3-trifluoro-2-hydroxypropyl)amino]-5,7-dihydro-6H-pyrrolo[2,3-d]pyrimidin-6-one

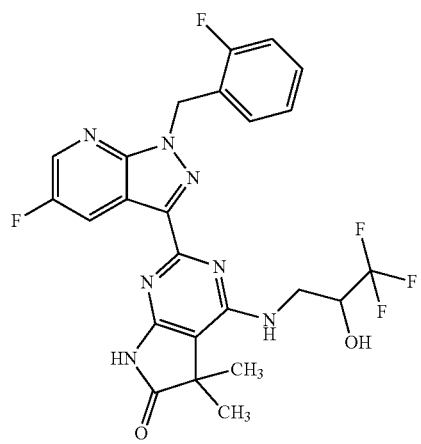 [SMILES: CC1(C)C(=O)Nc2nc(-c3nn(Cc4ccccc4F)c4ncc(F)cc34)nc(NCC(O)C(F)(F)F)c21]

300 mg (0.372 mmol, purity 66%) of example 16A was dissolved in 1-methyl-2-pyrrolidone (5 ml) in a reaction vessel suitable for a microwave and 300 mg (2.324 mmol) of 3-amino-1,1,1-trifluoro-2-propanol was added. Then it was sealed with a corresponding septum and heated twice in the microwave at 150° C. for 3 h. After cooling, the reaction mixture was purified by preparative HPLC (acetonitrile:water (+0.05% formic acid) gradient). 164 mg of the title compound was obtained (83% of theor.)

LC-MS (method 1): Rt=1.12 min; MS (EIpos): m/z=534 [M+H]$^+$.

Separation into Enantiomers:

164 mg of the racemate obtained was separated into the enantiomers by preparative HPLC (solvent: ((iso-hexane:ethanol+0.2% trifluoroacetic acid+1% water) 80/20), wavelength: 210 nM on chiral phase (Daicel Chiralpak OZ-H (HPLC), 5 μM 250×20 mm)

Example 96-1 (Enantiomer 1)

Yield: 42 mg ee=99% (analytical HPLC: (solvent: (iso-hexane:ethanol 80/20)+0.2% trifluoroacetic acid+1% water on chiral phase (Chiralcel OZ-H, 5 μM 250*4.6 mm)

$R_t$=5.004 min

¹H-NMR (400 MHz, DMSO-d₆): δ [ppm]=1.36 (s, 3H), 1.37 (s, 3H), 3.61-3.68 (m, 1H), 3.91-3.97 (m, 1H), 4.32-4.42 (m, 1H), 5.82 (s, 2H), 6.56 (d, 1H), 6.90 (t, 1H), 7.13-7.26 (m, 3H), 7.34-7.39 (m, 1H), 8.53 (dd, 1H), 8.71 (dd, 1H), 11.05 (br s, 1H).

Example 96-2 (Enantiomer 2)

Yield: 31 mg ee=96% (analytical HPLC: (solvent: (iso-hexane:ethanol 80/20)+0.2% trifluoroacetic acid+1% water on chiral phase (Chiralcel OZ-H, 5 µM 250*4.6 mm)

R$_t$=5.044 min

Example 97

4-{[(2,2-Difluorocyclopropyl)methyl]amino}-2-[5-fluoro-1-(2-fluorobenzyl)-1H-pyrazolo[3,4-b]pyridin-3-yl]-5,5-dimethyl-5,7-dihydro-6H-pyrrolo[2,3-d]pyrimidin-6-one

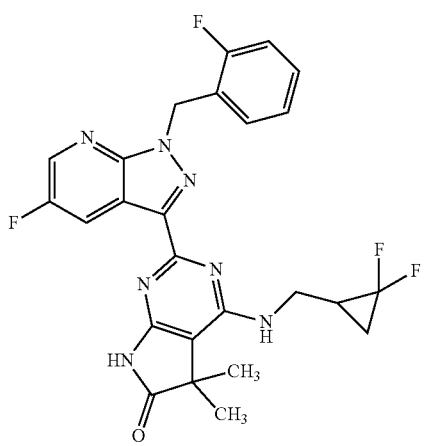 [SMILES: CC1(C)C(=O)Nc2nc(-c3nn(Cc4ccccc4F)c4ncc(F)cc34)nc(NCC3CC3(F)F)c21]

100 mg (0.115 mmol, purity 61%) of example 16A was dissolved in 1-methyl-2-pyrrolidone (3 ml) in a reaction vessel suitable for a microwave and 164 mg (1.146 mmol) of 2,2-difluorocyclopropylmethylamine hydrochloride and 0.24 ml (1.375 mmol) of N,N-diisopropyl ethylamine were added. Then the reaction vessel was sealed with a septum and was heated in the microwave at 150° C. for 12 h. After cooling, the reaction mixture was purified by preparative HPLC (acetonitrile:water (+0.05% formic acid) gradient). 21 mg of the title compound was obtained (35% of theor.).

LC-MS (method 1): R$_t$=1.20 min; MS (EIpos): m/z=512 [M+H]⁺.

¹H-NMR (400 MHz, DMSO-d₆): δ [ppm]=1.37 (s, 6H), 1.42-1.50 (m, 1H), 1.53-1.61 (m, 1H), 2.12-2.22 (m, 1H), 3.57-3.63 (m, 1H), 3.73-3.79 (m, 1H), 5.83 (s, 2H), 6.98 (t, 1H), 7.13-7.17 (m, 1H), 7.20-7.26 (m, 2H), 7.34-7.39 (m, 1H), 8.51 (dd, 1H), 8.72 (dd, 1H), 11.06 (s, 1H).

Example 98

2-[5-Fluoro-1-(2-fluorobenzyl)-1H-pyrazolo[3,4-b]pyridin-3-yl]-4-{[(1-hydroxycyclopropyl)methyl]amino}-5,5-dimethyl-5,7-dihydro-6H-pyrrolo[2,3-d]pyrimidin-6-one

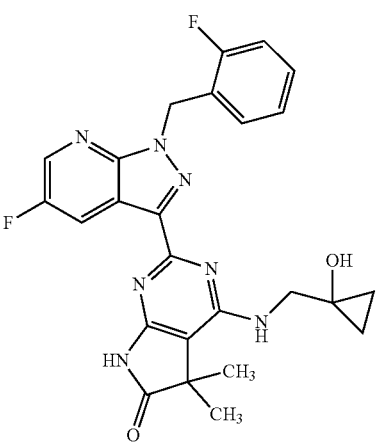 [SMILES: CC1(C)C(=O)Nc2nc(-c3nn(Cc4ccccc4F)c4ncc(F)cc34)nc(NCC3(O)CC3)c21]

200 mg (0.376 mmol) of example 16A was dissolved in 1-methyl-2-pyrrolidone (3 ml) in a reaction vessel suitable for a microwave and 98 mg (1.127 mmol) of 1-(aminomethyl)-cyclopropanol was added. Then the reaction vessel was sealed with a septum and heated in the microwave at 150° C. for 12 h. After cooling, the reaction mixture was purified by preparative HPLC (acetonitrile:water (+0.05% formic acid) gradient). 56 mg of the title compound was obtained (31% of theor.).

LC-MS (method 1) R$_t$=1.07 min; MS (EIpos): m/z=492 [M+H]⁺.

¹H-NMR (400 MHz, DMSO-d₆): δ [ppm]=0.56-0.63 (m, 4H), 1.37 (s, 6H), 3.77-3.79 (m, 2H), 5.54 (s, 1H), 5.82 (s, 2H), 6.58 (m, 1H), 7.12-7.16 (m, 1H), 7.20-7.25 (m, 2H), 7.34-7.39 (m, 1H), 8.60 (dd, 1H), 8.71 (dd, 1H), 11.02 (s, 1H).

Example 99

4-{[(2,2-Dimethylcyclopropyl)methyl]amino}-2-[5-fluoro-1-(2-fluorobenzyl)-1H-pyrazolo[3,4-b]pyridin-3-yl]-5,5-dimethyl-5,7-dihydro-6H-pyrrolo[2,3-d]pyrimidin-6-one

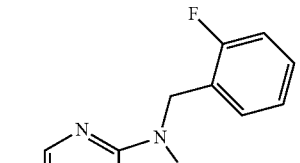
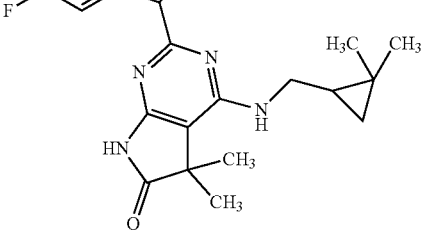

200 mg (0.376 mmol) of example 16A was dissolved in a reaction vessel suitable for a microwave in 1-methyl-2-pyrrolidone (3 ml) and 254 mg (1.879 mmol) of 1-(2,2-dimethylcyclopropyl)methanamine hydrochloride and 0.393 ml (2.254 mmol) of N,N-diisopropyl ethylamine were added. Then it was sealed with a corresponding septum and it was heated in the microwave at 150° C. for 3 h. After cooling, the reaction mixture was purified by preparative HPLC (acetonitrile:water (+0.05% formic acid) gradient). 64 mg of the title compound was obtained (33% of theor.).

LC-MS (method 1) R$_t$=1.38 min; MS (EIpos): m/z=504 [M+H]$^+$.

$^1$H-NMR (400 MHz, DMSO-d$_6$): δ [ppm]=0.24 (dd, 1H), 0.43 (dd, 1H), 1.02 (s, 3H), 1.08-1.15 (m, 1H), 1.17 (s, 3H), 1.37 (s, 6H), 3.30-3.41 (m, 1H), 3.70-3.76 (m, 1H), 5.82 (s, 2H), 6.81 (t, 1H), 7.13-7.17 (m, 1H), 7.20-7.26 (m, 2H), 7.34-7.39 (m, 1H), 8.58 (dd, 1H), 8.72 (dd, 1H), 11.01 (s, 1H).

Example 100

2'-[5-Fluoro-1-(2-fluorobenzyl)-1H-pyrazolo[3,4-b]pyridin-3-yl]-4'-[(3,3,3-trifluoropropyl)amino]-4,5-dihydrospiro[furan-3,5'-pyrrolo[2,3-d]pyrimidin]-6'(7'H)-one

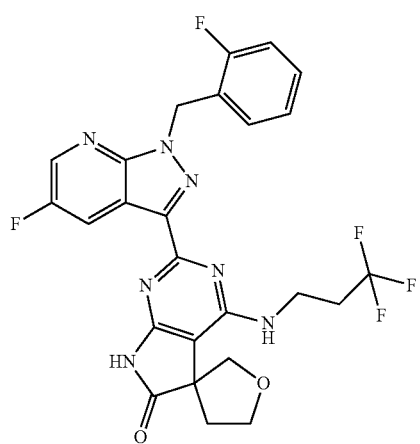 [SMILES: O=C1Nc2nc(-c3nn(Cc4ccccc4F)c4ncc(F)cc34)nc(NCCC(F)(F)F)c2C12CCOC2]

84 mg (0.150 mmol) of example 58A was dissolved in 1-methyl-2-pyrrolidone (3 ml) in a reaction vessel suitable for a microwave and 112 mg (0.750 mmol) of 3,3,3-trifluoropropyl-1-amine hydrochloride and 0.157 ml (0.900 mmol) of N,N-diisopropyl ethylamine were added. Then the reaction vessel was sealed with a septum and was heated in the microwave at 150° C. for 3 h. After cooling, the reaction mixture was purified by preparative HPLC (acetonitrile:water (+0.05% formic acid) gradient). 27 mg of the title compound was obtained (33% of theor.).

LC-MS (method 1): R$_t$=1.23 min; MS (EIpos): m/z=546 [M+H]$^+$.

$^1$H-NMR (400 MHz, DMSO-d$_6$): δ [ppm]=2.19-2.29 (m, 2H), 2.63-2.75 (m, 2H), 3.70 (d, 1H), 3.79-3.95 (m, 3H), 4.09 (d, 1H), 4.26-4.32 (m, 1H), 5.84 (s, 2H), 6.41(t, 1H), 7.13-7.17 (m, 1H), 7.21-7.28 (m, 2H), 7.34-7.39 (m, 1H), 8.48 (dd, 1H), 8.73 (dd, 1H), 11.24 (s, 1H).

Example 101

Ethyl-2-[1-(2-fluorobenzyl)-1H-pyrazolo[3,4-b]pyridin-3-yl]-4-hydroxy-5-methyl-6-oxo-6,7-dihydro-5H-pyrrolo[2,3-d]pyrimidine-5-carboxylate

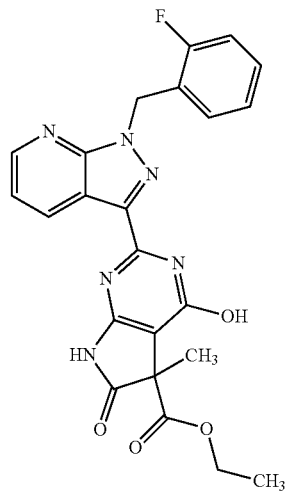 [SMILES: CCOC(=O)C1(C)C(=O)Nc2nc(-c3nn(Cc4ccccc4F)c4ncccc34)nc(O)c21]

1.00 g (2.167 mmol) of example 59A was reacted on the analogy of the specification in example 15A. 173 mg (17% of theor.) of the title compound and 0.887 g of ethyl-2-[1-(2-fluorobenzyl)-1H-pyrazolo[3,4-b]pyridin-3-yl]-4-iodo-5-methyl-6-oxo-6,7-dihydro-5H-pyrrolo[2,3-d]pyrimidine-5-carboxylate (example 60A) were obtained.

LC-MS (method 1): R$_t$=0.96 min; MS (EIpos): m/z=462 [M+H]$^+$.

$^1$H-NMR (400 MHz, DMSO-d$_6$): δ [ppm]=1.09 (t, 3H), 1.55 (s, 3H), 4.10 (q, 2H), 5.87 (s, 2H), 7.13-7.17 (m, 1H), 7.21-7.26 (m, 1H), 7.36-7.40 (m, 2H), 7.50 (dd, 1H), 8.73-8.78 (m, 2H), 11.48 (br s, 1H), 12.72 (br s, 1H).

Example 102

2-[5-Fluoro-1-(2-fluorobenzyl)-1H-pyrazolo[3,4-b]pyridin-3-yl]-4-hydroxy-5,5-dimethyl-5,7-dihydro-6H-pyrrolo[2,3-d]pyrimidin-6-one

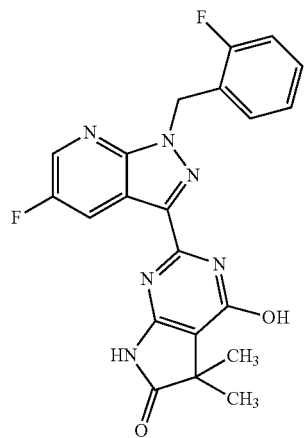 [SMILES: CC1(C)C(=O)Nc2nc(-c3nn(Cc4ccccc4F)c4ncc(F)cc34)nc(O)c21]

200 mg (0.376 mmol) of example 16A was dissolved in 3 ml water and 3 ml tetrahydrofuran in a reaction vessel suitable for a microwave, the reaction vessel was sealed with a septum and was heated in the microwave for 1 h at 140° C. Then 1.127 ml (1.127 mmol) of 1M sodium hydroxide solution was added and it was heated in the microwave for a further 14 h at

Example 103

4-(4,4-Difluoropiperidin-1-yl)-2-[5-fluoro-1-(2-fluorobenzyl)-1H-pyrazolo[3,4-b]pyridin-3-yl]-5,5-dimethyl-5,7-dihydro-6H-pyrrolo[2,3-d]pyrimidin-6-one

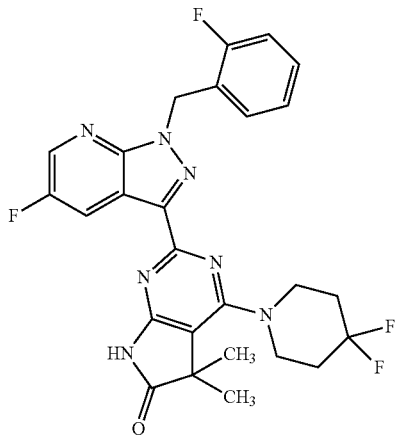 [SMILES: CC1(C)C(=O)Nc2nc(-c3nn(Cc4ccccc4F)c4ncc(F)cc34)nc(N3CCC(F)(F)CC3)c21]

100 mg (0.18 mmol) of 2-[5-fluoro-1-(2-fluorobenzyl)-1H-pyrazolo[3,4-b]pyridin-3-yl]-4-iodo-5,5-dimethyl-5,7-dihydro-6H-pyrrolo[2,3-d]pyrimidin-6-one (example 16A) was dissolved in 1-methyl-2-pyrrolidone (3.1 ml) in a reaction vessel suitable for a microwave, and 0.19 ml (1.07 mmol) of N,N-diisopropyl ethylamine and 140 mg (0.89 mmol) of 4,4-difluoropiperidine hydrochloride were added. Then the reaction vessel was sealed with a septum and was heated in the microwave for 5 h at 150° C. Then the same amounts of N,N-diisopropyl ethylamine and 4,4-difluoropiperidine hydrochloride were added again to the reaction solution and the reaction mixture was stirred for 6 h at 150° C. in the microwave. Water was added to the reaction mixture, the precipitated solid was stirred for 30 min at room temperature and then filtered off. The precipitated solid was stirred with 1 ml acetonitrile, the solid was filtered off and was washed with 0.5 ml acetonitrile. 63 mg of the target compound (64% of theor.) was obtained.

LC-MS (method 1): $R_t$=1.29 min; MS (EIpos): m/z=526 [M+H]$^+$.

$^1$H-NMR (400 MHz, DMSO-d$_6$): δ [ppm]=1.44 (s, 6H), 2.10-2.23 (m, 4H), 3.79-3.90 (m, 4H), 5.84 (s, 2H), 7.10-7.28 (m, 3H), 7.32-7.40 (m, 1H), 8.42-8.48 (m, 1H), 8.70-8.76 (m, 1H), 11.35 (s, 1H).

Example 104

2-[5-Fluoro-1-(2-fluorobenzyl)-1H-pyrazolo[3,4-b]pyridin-3-yl]-4-(3-hydroxyazetidin-1-yl)-5,5-dimethyl-5,7-dihydro-6H-pyrrolo[2,3-d]pyrimidin-6-one

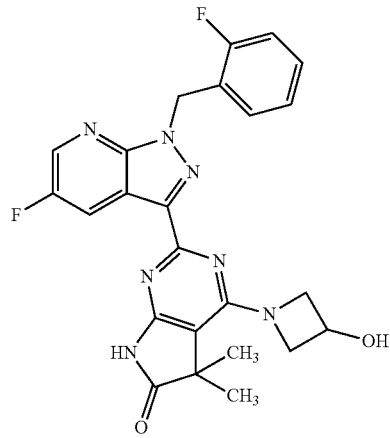 [SMILES: CC1(C)C(=O)Nc2nc(-c3nn(Cc4ccccc4F)c4ncc(F)cc34)nc(N3CC(O)C3)c21]

100 mg (0.18 mmol, approx. 95% purity) of 2-[5-fluoro-1-(2-fluorobenzyl)-1H-pyrazolo[3,4-b]pyridin-3-yl]-4-iodo-5,5-dimethyl-5,7-dihydro-6H-pyrrolo[2,3-d]pyrimidin-6-one (example 16A) was dissolved in 1-methyl-2-pyrrolidone (3.1 ml) in a reaction vessel suitable for a microwave, and 0.19 ml (1.07 mmol) of N,N-diisopropyl ethylamine and 97 mg (0.89 mmol) of azetidin-3-ol hydrochloride were added. Then the reaction vessel was sealed with a septum and was heated in the microwave at 150° C. for 3 h. After cooling, water/trifluoroacetic acid was added to the reaction mixture and the resultant solid was filtered off. The filtrate was purified by preparative HPLC (acetonitrile:water (+0.1% trifluoroacetic acid) gradient). 19 mg of the title compound was obtained (21% of theor.; purity 93%).

LC-MS (method 1): $R_t$=1.01 min; MS (EIpos): m/z=478 [M+H]$^+$.

$^1$H-NMR (400 MHz, DMSO-d$_6$): δ [ppm]=1.34 (s, 6H), 4.03-4.09 (m, 2H), 4.50-4.57 (m, 2H), 4.62-4.69 (m, 1H), 5.83 (s, 2H), 7.15 (t, 1H), 7.19-7.26 (m, 2H), 7.33-7.40 (m, 1H), 8.53 (dd, 1H), 8.71-8.73 (m, 1H), 11.19 (s, 1H).

Example 105

2-[1-(2-Fluorobenzyl)-1H-pyrazolo[3,4-b]pyridin-3-yl]-5,5-dimethyl-4-[3-(pyrrolidin-1-yl)azetidin-1-yl]-5,7-dihydro-6H-pyrrolo[2,3-d]pyrimidin-6-one

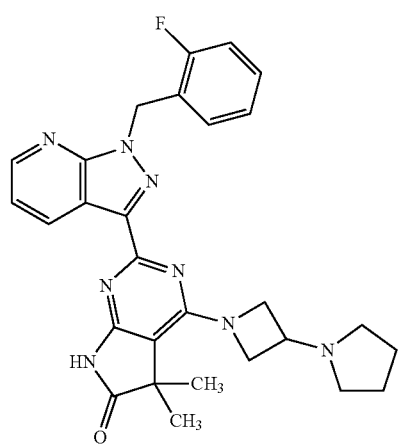 [SMILES: CC1(C)C(=O)Nc2nc(-c3nn(Cc4ccccc4F)c4ncccc34)nc(N3CC(N4CCCC4)C3)c21]

150 mg (0.21 mmol, purity approx. 71%) of 2-[1-(2-fluorobenzyl)-1H-pyrazolo[3,4-b]pyridin-3-yl]-4-iodo-5,5-dimethyl-5,7-dihydro-6H-pyrrolo[2,3-d]pyrimidin-6-one (example 15A) was dissolved in 1-methyl-2-pyrrolidone (3.1 ml) in a reaction vessel suitable for a microwave, and 0.29 ml (1.66 mmol) of N,N-diisopropyl ethylamine and 165 mg (0.83 mmol) of 1-(azetidin-3-yl)pyrrolidine-dihydrochloride were added. Then the reaction vessel was sealed with a septum and heated in the microwave at 150° C. for 6 h. After cooling, water was added to the reaction mixture. It was stirred for 30 min and filtered to remove the resultant solid. The filtrate was purified by preparative HPLC (acetonitrile:water (+0.1% trifluoroacetic acid) gradient). The product fraction was dissolved in dichloromethane and was washed twice with saturated aqueous sodium hydrogen carbonate solution. The organic phase was dried over sodium sulphate, filtered and concentrated by evaporation. 52 mg of the title compound was obtained (46% of theor.; purity 94%).

LC-MS (method 1): $R_t$=0.71 min; MS (EIpos): m/z=513 [M+H]$^+$.

$^1$H-NMR (400 MHz, DMSO-d$_6$): δ [ppm]=1.34 (s, 6H), 1.70-1.79 (m, 4H), 2.48-2.57 (m, masked by the DMSO signal), 3.41-3.51 (m, 1H), 4.10-4.18 (m, 2H), 4.37-4.43 (m, 2H), 5.83 (s, 2H), 7.10-7.28 (m, 3H), 7.31-7.46 (m, 2H), 8.62-8.66 (m, 1H), 8.85-8.89 (m, 1H), 11.20 (s, 1H).

Example 106

4-(3-Aminopyrrolidin-1-yl)-2-[1-(2-fluorobenzyl)-1H-pyrazolo[3,4-b]pyridin-3-yl]-5,5-dimethyl-5,7-dihydro-6H-pyrrolo[2,3-d]pyrimidin-6-one (racemate)

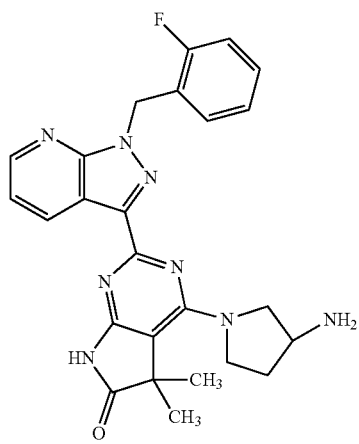 [SMILES: CC1(C)C(=O)Nc2nc(-c3nn(Cc4ccccc4F)c4ncccc34)nc(N3CCC(N)C3)c21]

0.71 ml of a 2N solution of hydrogen chloride in diethyl ether was added to 81 mg (0.24 mmol) of tert.-butyl-(1-{2-[1-(2-fluorobenzyl)-1H-pyrazolo[3,4-b]pyridin-3-yl]-5,5-dimethyl-6-oxo-6,7-dihydro-5H-pyrrolo[2,3-d]pyrimidin-4-yl}pyrrolidin-3-yl)carbamate (racemate, example 61A) and it was stirred for 4 h at room temperature. The reaction solution was concentrated and was purified by preparative HPLC (acetonitrile/water (+0.1% trifluoroacetic acid) gradient). The concentrated fractions were dissolved in dichloromethane and washed twice with saturated aqueous sodium hydrogen carbonate solution. The combined aqueous phases were extracted twice with dichloromethane. The combined organic phases were dried over sodium sulphate, filtered and concentrated by evaporation. 37 mg (55% of theor.) of the target compound was obtained.

LC-MS (method 1): $R_t$=0.73 min; MS (ESIpos): m/z=473 [M+H]$^+$ $^1$H-NMR (400 MHz, DMSO-d$_6$): δ [ppm]=1.42 (s, 6H), 1.70-1.79 (m, 1H), 2.06-2.16 (m, 1H), 3.39-3.45 (m, 1H), 3.58-3.63 (m, 1H), 3.73-3.82 (m, 1H), 3.83-3.94 (m, 2H), 5.83 (s, 2H), 7.10-7.26 (m, 3H), 7.31-7.39 (m, 1H), 7.42 (dd, 1H), 8.65 (dd, 1H), 8.88 (dd, 1H), 11.29 (br s, 1H).

Example 107

4-(3-Aminoazetidin-1-yl)-2-[1-(2-fluorobenzyl)-1H-pyrazolo[3,4-b]pyridin-3-yl]-5,5-dimethyl-5,7-dihydro-6H-pyrrolo[2,3-d]pyrimidin-6-one

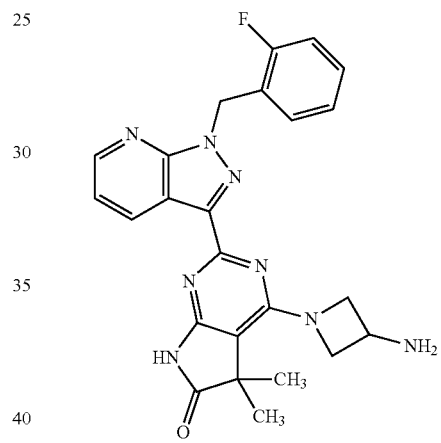

0.66 ml of a 2N solution of hydrogen chloride in diethyl ether was added to 81 mg (0.13 mmol; purity 91%) of tert.-butyl-(1-[2-[1-(2-fluorobenzyl)-1H-pyrazolo[3,4-b]pyridin-3-yl]-5,5-dimethyl-6-oxo-6,7-dihydro-5H-pyrrolo[2,3-d]pyrimidin-4-yl]azetidin-3-yl)carbamate (example 62A) and it was stirred for 4 h at room temperature. The reaction solution was concentrated by evaporation and purified twice by preparative HPLC (acetonitrile/water (+0.1% trifluoroacetic acid) gradient). The concentrated fractions were dissolved in dichloromethane and washed twice with saturated aqueous sodium hydrogen carbonate solution. The combined aqueous phases were extracted twice with dichloromethane. The combined organic phases were dried over sodium sulphate, filtered and concentrated by evaporation. 31 mg (49% of theor.) of the target compound was obtained.

LC-MS (method 1): $R_t$=0.71 min; MS (ESIpos): m/z=459 [M+H]$^+$ $^1$H-NMR (400 MHz, DMSO-d$_6$): δ [ppm]=1.33 (s, 6H), 2.22 (br s, 2H), 3.83-3.98 (m, 3H), 4.46 (t, 2H), 5.82 (s, 2H), 7.10-7.27 (m, 3H), 7.31-7.38 (m, 1H), 7.42 (dd, 1H), 8.65 (dd, 1H), 8.88 (dd, 1H), 11.18 (s, 1H).

Example 108

2-[1-(2-Fluorobenzyl)-6-methyl-1H-pyrazolo[3,4-d]pyrimidin-3-yl]-5,5-dimethyl-4-[(3,3,3-trifluoropropyl)amino]-5,7-dihydro-6H-pyrrolo[2,3-d]pyrimidin-6-one

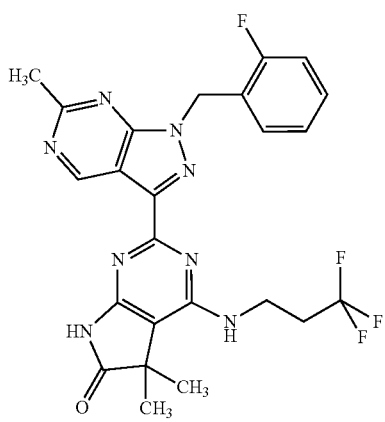 [SMILES: Cc1ncc2c(-c3nc(NCCC(F)(F)F)c4c(n3)NC(=O)C4(C)C)nn(Cc3ccccc3F)c2n1]

The title compound was prepared similarly to the specification for example 35 starting from 100 mg (0.16 mmol) of example 70A and 372 mg (3.29 mmol) of 3,3,3-trifluoropropylamine.

Yield: 38 mg (44% of theor.)

LC-MS (method 1): $R_t$=1.11 min; MS (ESIpos): m/z=515 [M+H]$^+$ $^1$H-NMR (400 MHz, DMSO-d$_6$): δ [ppm]=1.37 (s, 6H), 2.59-2.74 (m, 2H), 2.78 (s, 3H), 3.83 (q, 2H), 5.75 (s, 2H), 6.89 (t, 1H), 7.10-7.29 (m, 3H), 7.32-7.43 (m, 1H), 9.65 (s, 1H), 11.11 (s, 1H).

Example 109

2-[1-(2-Fluorobenzyl)-1H-pyrazolo[3,4-b]pyridin-3-yl]-4-hydroxy-5,5-dimethyl-5,7-dihydro-6H-pyrrolo[2,3-d]pyrimidin-6-one

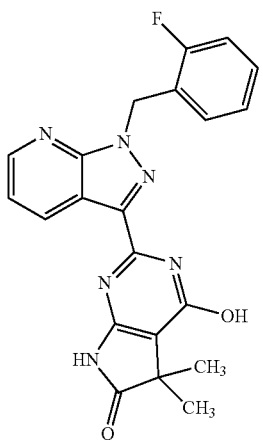 [SMILES: CC1(C)C(=O)Nc2nc(-c3nn(Cc4ccccc4F)c4ncccc34)nc(O)c21]

6.0 g (14.87 mmol) of example 13A was dissolved in 60 ml of trifluoroacetic acid (heating) and cooled in an ice bath. While stirring, 6.7 ml of water and then, in small portions within 1 h, 1.54 g (22.3 mmol) of sodium nitrite, were added. Then the reaction mixture was poured into 250 ml water and the resultant precipitate was filtered with suction. The solid was left to precipitate in 50 ml water (adjusted to pH 6 with conc. sodium hydrogen carbonate solution), filtered with suction again, washed with water and dried. Yield: 5.75 g (94% of theor.)

LC-MS (method 1): $R_t$=0.92 min; MS (ESIpos): m/z=405 [M+H]$^+$ $^1$H-NMR (400 MHz, DMSO-d$_6$): δ [ppm]=1.33 (s, 6H), 5.86 (s, 2H), 7.16 (t, 1H), 7.23 (t, 1H), 7.28-7.41 (m, 2H), 7.49 (dd, 1H), 8.61-8.85 (m, 2H), 11.11 (s, 1H), 12.12 (br s, 0.2H), 12.44 (br s, 0.8H).

Example 110

2-[1-(2,3-Difluorobenzyl)-5-fluoro-1H-pyrazolo[3,4-b]pyridin-3-yl]-5,5-dimethyl-4-(3,3,3-trifluoropropoxy)-5,7-dihydro-6H-pyrrolo[2,3-d]pyrimidin-6-one

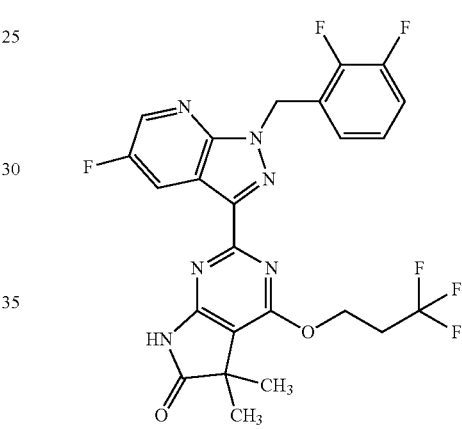

Under argon, 80 mg (0.18 mmol) of the compound from example 116 was dissolved in 2 ml THF and 0.4 ml DMF, and 31 mg (0.27 mmol) of 3,3,3-trifluoropropan-1-ol, 71.5 mg (0.27 mmol) of triphenyl phosphine and 57 μl (0.27 mmol) of 94% diisopropyl azodicarboxylate were added and it was stirred overnight at RT. A further 71.5 mg (0.27 mmol) of triphenyl phosphine was added and it was treated for 15 min in the ultrasonic bath, then a further 57.5 μl (0.27 mmol) of 94% diisopropyl azodicarboxylate was added dropwise and it was stirred overnight at RT. Then 31 mg (0.27 mmol) of 3,3,3-trifluoropropan-1-ol and 71.5 mg (0.27 mmol) of triphenyl phosphine were added, it was treated for 15 min in the ultrasonic bath, 57.5 μl (0.27 mmol) of 94% diisopropyl azodicarboxylate was added and it was stirred overnight at RT. The reaction mixture was purified by preparative HPLC (Chromatorex C18, gradient of acetonitrile/0.01% aq. formic acid). Yield: 41 mg (42% of theor.)

LC-MS (method 1): $R_t$=1.46 min; MS (ESIpos): m/z=633 [M+H]$^+$ $^1$H-NMR (400 MHz, DMSO-d$_6$): δ [ppm]=1.35 (s, 6H), 2.93 (qt, 2H), 4.79 (t, 2H), 5.92 (s, 2H), 7.01-7.10 (m, 1H), 7.18 (t, 1H), 7.34-7.46 (m, 1H), 8.55 (dd, 1H), 8.76 (dd, 1H), 11.45 (s, 1H).

Example 111

2-[1-(2-Fluorobenzyl)-1H-pyrazolo[3,4-b]pyridin-3-yl]-5,5-dimethyl-4-propoxy-5,7-dihydro-6H-pyrrolo[2,3-d]pyrimidin-6-one

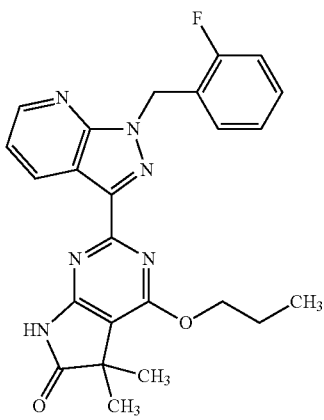 [SMILES: CCCOc1nc(-c2nn(Cc3ccccc3F)c3ncccc23)nc2c1C(C)(C)C(=O)N2]

Under argon, 80 mg (0.20 mmol) of the compound from example 109, 13 mg (16 µl, 0.22 mmol) of n-propanol and 57 mg (0.22 mmol) of triphenyl phosphine were suspended in 0.8 ml THF, mixed for 10 min in the ultrasonic bath and finally 44 mg (43 µl, 0.22 mmol) of diisopropyl azodicarboxylate was added and it was stirred for 1 h at RT. The reaction mixture was purified by preparative HPLC (Reprosil C18, gradient of acetonitrile/0.01% aq. formic acid). Yield: 48 mg (55% of theor.)

LC-MS (method 1): $R_t$=1.28 min; MS (ESIpos): m/z=447 [M+H]$^+$ $^1$H-NMR (400 MHz, DMSO-d$_6$): δ [ppm]=1.05 (t, 3H), 1.36 (s, 6H), 1.77-1.91 (m, 2H), 4.54 (t, 2H), 5.86 (s, 2H), 7.11-7.27 (m, 3H), 7.32-7.40 (m, 1H), 7.45 (dd, 1H), 8.68 (dd, 1H), 8.85 (dd, 1H), 11.39 (s, 1H).

Example 112

4-Ethoxy-2-[1-(2-fluorobenzyl)-1H-pyrazolo[3,4-b]pyridin-3-yl]-5,5-dimethyl-5,7-dihydro-6H-pyrrolo[2,3-d]pyrimidin-6-one

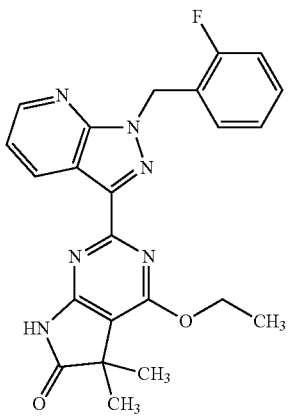 [SMILES: CCOc1nc(-c2nn(Cc3ccccc3F)c3ncccc23)nc2c1C(C)(C)C(=O)N2]

Similarly to the specification for example 111, 150 mg (0.37 mmol) of example 109, 24 µl (0.41 mmol) of ethanol and 107 mg (0.41 mmol) of triphenyl phosphine were mixed in 1.5 ml THF for 10 min in the ultrasonic bath, 82.5 mg (0.41 mmol) of diisopropyl azodicarboxylate was added and it was stirred overnight at RT. Then a further 24 µl (0.41 mmol) of ethanol and 107 mg (0.41 mmol) of triphenyl phosphine were added, mixed for 5 min in the ultrasonic bath, 82.5 mg (0.41 mmol) of diisopropyl azodicarboxylate was added and it was stirred for approx. 30 min at RT. The reaction mixture was purified by preparative HPLC (Reprosil C18, gradient of acetonitrile/0.01% aq. formic acid). Yield: 25 mg (16% of theor.).

LC-MS (method 1): $R_t$=1.21 min; MS (ESIpos): m/z=433 [M+H]$^+$ $^1$H-NMR (400 MHz, DMSO-d$_6$): δ [ppm]=1.35 (s, 6H), 1.43 (t, 3H), 4.62 (q, 2H), 5.86 (s, 2H), 7.09-7.27 (m, 3H), 7.31-7.40 (m, 1H), 7.45 (dd, 1H), 8.68 (dd, 1H), 8.85 (dd, 1H), 11.39 (s, 1H).

Example 113

4-(Cyclopropylmethoxy)-2-[1-(2-fluorobenzyl)-1H-pyrazolo[3,4-b]pyridin-3-yl]-5,5-dimethyl-5,7-dihydro-6H-pyrrolo[2,3-d]pyrimidin-6-one

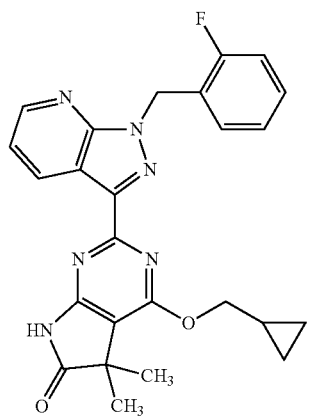 [SMILES: CC1(C)C(=O)Nc2nc(-c3nn(Cc4ccccc4F)c4ncccc34)nc(OCC3CC3)c21]

Similarly to the specification for example 111, 200 mg (0.50 mmol) of example 109, 39 mg (0.54 mmol) of cyclopropanemethanol and 143 mg (0.54 mmol) of triphenyl phosphine were mixed in 2 ml THF for 10 min in the ultrasonic bath, 110 mg (0.11 ml, 0.54 mmol) of diisopropyl azodicarboxylate was added and it was stirred overnight at RT. Then a further 14 mg (0.19 mmol) of cyclopropanemethanol, 48 mg (0.18 mmol) of triphenyl phosphine and 35 ml (0.17 mmol) of diisopropyl azodicarboxylate were added and it was stirred for 1.5 h at RT. The reaction mixture was purified by preparative HPLC (Chromatorex C18, gradient of acetonitrile/0.01% aq. formic acid). Yield: 52 mg (23% of theor.)

LC-MS (method 1): $R_t$=1.27 min; MS (ESIpos): m/z=459 [M+H]$^+$ $^1$H-NMR (400 MHz, DMSO-d$_6$): δ [ppm]=0.40-0.48 (m, 2H), 0.55-0.64 (m, 2H), 1.27-1.43 (m, 7H), 4.44 (d, 2H), 5.86 (s, 2H), 7.09-7.28 (m, 3H), 7.31-7.41 (m, 1H), 7.47 (dd, 1H), 8.68 (dd, 1H), 8.84 (dd, 1H), 11.41 (s, 1H).

Example 114

2-[3-(2-Fluorobenzyl)-1H-pyrazolo[4,3-b]pyridin-1-yl]-5,5-dimethyl-4-(3,3,3-trifluoropropoxy)-5,7-dihydro-6H-pyrrolo[2,3-d]pyrimidin-6-one

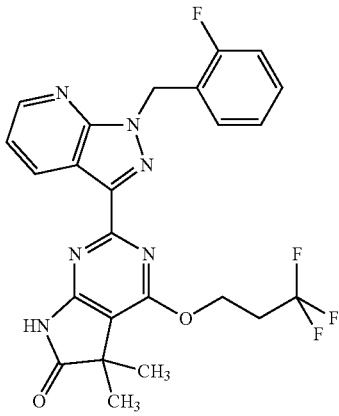 [SMILES: CC1(C)C(=O)Nc2nc(-c3nn(Cc4ccccc4F)c4ncccc34)nc(OCCC(F)(F)F)c21]

Under argon, 57 mg (0.22 mmol) of triphenyl phosphine was dissolved in 1.5 ml THF, 43 μl (0.22 mmol) of diisopropyl azodicarboxylate and 25 mg (0.22 mmol) of 3,3,3-trifluoropropan-1-ol were added and it was stirred for 10 min. Then a suspension of 80 mg of example 109 in 0.5 ml DMF, which had been treated for 3 min in the ultrasonic bath, was added and the reaction mixture was stirred overnight at RT (solution). A further 57 mg (0.22 mmol) of triphenyl phosphine was added, the mixture was treated for 10 min in the ultrasonic bath, then a further 43 μl (0.22 mmol) of diisopropyl azodicarboxylate was added and it was stirred overnight. Then a further 25 mg (0.22 mmol) of 3,3,3-trifluoropropan-1-ol and 57 mg (0.22 mmol) of triphenyl phosphine were added, the reaction mixture was treated for 10 min in the ultrasonic bath, then 43 μl (0.22 mmol) of diisopropyl azodicarboxylate was added and it was stirred for another night at RT. The reaction mixture was purified by preparative HPLC (Reprosil C18, gradient of acetonitrile/0.01% aq. formic acid). Yield: 37 mg (37% of theor.)

LC-MS (method 1): $R_t$=1.21 min; MS (ESIpos): m/z=501 [M+H]$^+$ $^1$H-NMR (400 MHz, DMSO-d$_6$): δ [ppm]=1.35 (s, 6H), 2.92 (qt, 2H), 4.79 (t, 2H), 5.87 (s, 2H), 7.11-7.27 (m, 3H), 7.32-7.41 (m, 1H), 7.45 (dd, 1H), 8.68 (dd, 1H), 8.86 (dd, 1H), 11.45 (s, 1H).

Example 115

2-[1-(2-Fluorobenzyl)-1H-pyrazolo[3,4-b]pyridin-3-yl]-5,5-dimethyl-4-(2,2,2-trifluoroethoxy)-5,7-dihydro-6H-pyrrolo[2,3-d]pyrimidin-6-one

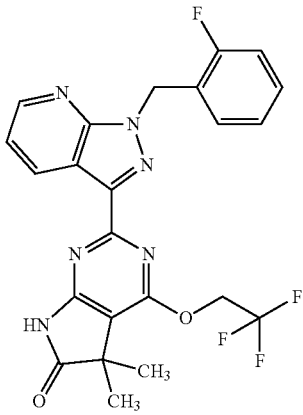 [SMILES: CC1(C)C(=O)Nc2nc(-c3nn(Cc4ccccc4F)c4ncccc34)nc(OCC(F)(F)F)c21]

177 mg (0.54 mmol) of caesium carbonate and 114 mg (0.54 mmol) of 2,2,2-trifluoroethyl iodide were added to a suspension of 200 mg (0.5 mmol) of the compound from example 109 in DMF (1.97 ml) and it was stirred overnight at RT. Then it was heated in the microwave to 120° C. for 1 h. The reaction mixture was purified by preparative HPLC (Chromatorex C18, gradient of acetonitrile/0.01% aq. formic acid). Yield: 14.5 mg (6% of theor.).

LC-MS (method 1): $R_t$=1.20 min; MS (ESIpos): m/z=487 [M+H]$^+$ $^1$H-NMR (400 MHz, DMSO-d$_6$): δ [ppm]=1.36 (s, 6H), 5.30 (q, 2H), 5.88 (s, 2H), 7.10-7.28 (m, 3H), 7.32-7.41 (m, 1H), 7.48 (dd, 1H), 8.69 (dd, 1H), 8.89 (dd, 1H), 11.61 (s, 1H).

Example 116

2-[1-(2,3-Difluorobenzyl)-5-fluoro-1H-pyrazolo[3,4-b]pyridin-3-yl]-4-hydroxy-5,5-dimethyl-5,7-dihydro-6H-pyrrolo[2,3-d]pyrimidin-6-one

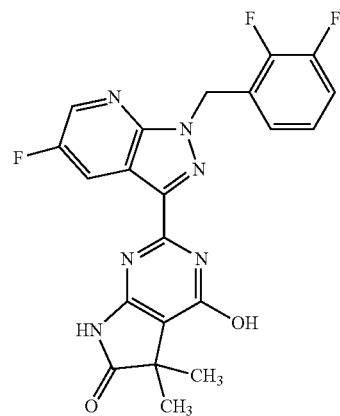 [SMILES: CC1(C)C(=O)Nc2nc(-c3nn(Cc4cccc(F)c4F)c4ncc(F)cc34)nc(O)c21]

On the analogy of the preparation of example 16A, 5.11 g (11.629 mmol) of example 69A was reacted. 660 mg (12% of theor.) of the title compound and 2.39 g of 2-[1-(2,3-difluorobenzyl)-5-fluoro-1H-pyrazolo[3,4-b]pyridin-3-yl]-4-iodo-5,5-dimethyl-5,7-dihydro-6H-pyrrolo[2,3-d]pyrimidin-6-one (example 70A) were obtained.

LC-MS (method 1): $R_t$=0.98 min; MS (ESIpos): m/z=441 [M+H]$^+$ $^1$H-NMR (400 MHz, DMSO-d$_6$): δ [ppm]=1.33 (s, 6H), 5.89 (s, 2H), 7.15-7.20 (m, 2H), 7.37-7.45 (m, 1H), 8.58 (br s, 1H), 8.79 (s, 1H), 11.08 (br s, 1H), 12.58 (br s, 1H).

Example 117

2-[1-(2-Fluorobenzyl)-1H-pyrazolo[3,4-b]pyridin-3-yl]-4-(2-hydroxyethoxy)-5,5-dimethyl-5,7-dihydro-6H-pyrrolo[2,3-d]pyrimidin-6-one

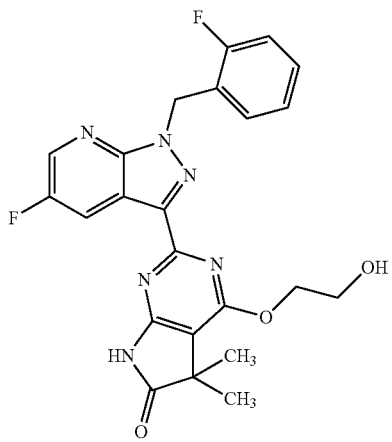 [SMILES: CC1(C)C(=O)Nc2nc(-c3nn(Cc4ccccc4F)c4ncc(F)cc34)nc(OCCO)c21]

Similarly to example 1, 100 mg (0.19 mmol) of example 15A, 121 mg (1.94 mmol) of ethylene glycol, 9 mg (0.039 mmol) of 3,4,7,8-tetramethyl-1,10-phenanthroline, 3.7 mg (0.019 mmol) of copper(I) iodide and 126 mg (0.39 mmol) of caesium carbonate in 3 ml toluene were heated in the microwave in 4 cycles for in each case 2 h at 140° C. Yield: 24 mg (28% of theor.)

LC-MS (method 1): $R_t$=0.94 min; MS (EIpos): m/z=449 [M+H]$^+$.

$^1$H-NMR (400 MHz, DMSO-$d_6$): δ [ppm]=1.37 (s, 6H), 3.82 (q, 2H), 4.58 (t, 2H), 4.94 (t, 1H), 5.86 (s, 2H), 7.10-7.27 (m, 3H), 7.32-7.40 (m, 1H), 7.45 (dd, 1H), 8.68 (dd, 1H), 8.86 (dd, 1H), 11.41 (s, 1H).

B. Assessment of Pharmacological Efficacy

The following abbreviations are used in the following:
BSA bovine serum albumin
EDTA ethylenediaminetetraacetic acid
μCi microcurie
Tris Tris(hydroxymethyl)-aminomethane The pharmacological action of the compounds according to the invention can be demonstrated in the following assays:

B-1. Vessel-relaxing Action in vitro

Rabbits are stunned with a blow on the back of the neck and exsanguinated. The aorta is removed, freed from adhering tissue, separated into rings with a width of 1.5 mm, and placed individually, with preloading, in 5-ml organ baths with carbogen-gassed Krebs-Henseleit solution at 37° C. with the following composition (mM in each case): sodium chloride: 119; potassium chloride: 4.8; calcium chloride dihydrate: 1; magnesium sulphate heptahydrate: 1.4; potassium dihydrogen phosphate: 1.2; sodium hydrogen carbonate: 25; glucose: 10. The contraction force is recorded with Statham UC2 cells, amplified and digitized via an A/D converter (DAS-1802 HC, Keithley Instruments Munich) and recorded in parallel on a continuous-line recorder. To produce contraction, phenylephrine is added to the bath cumulatively in increasing concentration. After several control cycles, the test substance is added in increasing dosage in each subsequent pass and the level of contraction is compared with the level of contraction reached in the immediately preceding pass. This is used for calculating the concentration that is required to reduce the level of the control value by 50% ($IC_{50}$ value). The standard application volume is 5 μl, and the proportion of DMSO in the bath solution corresponds to 0.1%.

Representative $IC_{50}$ values for the compounds according to the invention are shown in the following table (Table 1):

TABLE 1

| Example No. | $IC_{50}$ [nM] |
|---|---|
| 1 | 114 |
| 2 | 54 |
| 3 | 469 |
| 4 | 62 |
| 5 | 285 |
| 6 | 680 |
| 7 | 200 |
| 8 | 309 |
| 9 | 21000 |
| 10 | 552 |
| 11 | 663 |
| 12 | 631 |
| 13 | 4970 |
| 14 | 1030 |
| 15 | 453 |
| 16 | 126 |
| 17 | 200 |
| 18 | 2720 |
| 19 | 1280 |
| 20 | 1870 |
| 21 | 100 |
| 22 | 530 |
| 23 | 2864 |
| 24 | 573 |
| 25 | 501 |
| 26 | 674 |
| 27 | 1470 |
| 28 | 98 |
| 29 | 11400 |
| 30 | >10000 |
| 31 | 142 |
| 32 | 9160 |
| 33 | 696 |
| 34 | 6150 |
| 35 | >10000 |
| 36 | 5490 |
| 37 | 3870 |
| 38 | 10000 |
| 39 | 618 |
| 88 | 1670 |
| 89 | 3880 |
| 90 | 3072 |
| 91 | 517 |
| 92 | 520 |
| 93 | 984 |
| 94 | 277 |
| 95 | 228 |
| 96-1 | 1468 |
| 96-2 | 601 |
| 97 | 1350 |
| 98 | 214 |
| 99 | 10000 |
| 100 | 4758 |
| 102 | 156 |
| 103 | 551 |
| 104 | 482 |
| 105 | 478 |
| 106 | 1454 |
| 107 | 700 |
| 108 | 444 |
| 109 | 81 |
| 110 | 10000 |
| 111 | 1620 |
| 112 | 1620 |
| 113 | 1960 |
| 114 | 1600 |
| 115 | 1634 |
| 117 | 38 |

B-2. Action on Recombinant Guanylate Cyclase Reporter Cell Line

The cellular action of the compounds according to the invention is determined on a recombinant guanylate cyclase reporter cell line, as described in F. Wunder et al., *Anal. Biochem.* 339, 104-112 (2005).

Representative values (MEC=minimal effective concentration) for the compounds according to the invention are shown in the following table (Table 2):

TABLE 2

| Example | MEC [μm] |
|---|---|
| 1 | 0.1 |
| 2 | 0.3 |
| 3 | 3.0 |
| 4 | 0.1 |
| 5 | 0.03 |
| 6 | 0.1 |
| 7 | 0.1 |
| 8 | 0.3 |
| 9 | 0.1 |
| 10 | 0.3 |
| 11 | 0.3 |
| 12 | 0.1 |
| 13 | 0.1 |
| 14 | 0.3 |
| 15 | 1.0 |
| 16 | 0.1 |
| 17 | 0.1 |
| 18 | 0.03 |
| 19 | 0.3 |
| 20 | 0.3 |
| 21 | 0.03 |
| 22 | 0.03 |
| 23 | 0.1 |
| 24 | 0.1 |
| 25 | 0.1 |
| 26 | 0.03 |
| 27 | 0.1 |
| 28 | 0.3 |
| 29 | 1.0 |
| 30 | 1.0 |
| 31 | 0.01 |
| 32 | 1.0 |
| 33 | 0.3 |
| 34 | 1.0 |
| 35 | 0.3 |
| 36 | 0.3 |
| 37 | 0.3 |
| 38 | 0.3 |
| 39 | 0.1 |
| 40 | 0.1 |
| 41 | 0.01 |
| 42 | 0.1 |
| 43 | 0.03 |
| 44 | 0.1 |
| 45 | 0.1 |
| 46 | 0.1 |
| 47 | 0.1 |
| 48 | 0.1 |
| 49 | 0.3 |
| 50 | 0.1 |
| 51 | 0.03 |
| 52 | 0.01 |
| 53 | 3.0 |
| 54 | 0.03 |
| 55 | 0.03 |
| 56 | 0.03 |
| 57 | 0.1 |
| 58 | 0.03 |
| 59 | 0.1 |
| 60 | 0.3 |
| 61 | 0.03 |
| 62 | 0.1 |
| 63 | 0.03 |
| 64 | 0.1 |
| 65 | 0.1 |
| 66 | 0.1 |
| 67 | 0.03 |
| 68 | 0.1 |
| 69 | 0.3 |
| 70 | 0.03 |
| 71 | 0.01 |
| 72 | 0.1 |
| 73 | 0.3 |
| 74 | 0.01 |
| 75 | 0.03 |
| 76 | 0.03 |
| 77 | 0.1 |
| 78 | 0.03 |
| 79 | 0.1 |
| 80 | 0.03 |
| 81 | 0.03 |
| 82 | 0.1 |
| 83 | 0.03 |
| 84 | 0.1 |
| 85 | 0.3 |
| 86 | 0.01 |
| 87 | 0.03 |
| 88 | 0.1 |
| 89 | 0.03 |
| 90 | 0.3 |
| 91 | 0.03 |
| 92 | 0.3 |
| 93 | 0.3 |
| 94 | 0.1 |
| 95 | 0.1 |
| 96-1 | 0.1 |
| 96-2 | 0.01 |
| 97 | 0.1 |
| 98 | 0.01 |
| 99 | 0.3 |
| 100 | 0.3 |
| 101 | 0.03 |
| 102 | 1 |
| 103 | 1 |
| 104 | 0.1 |
| 105 | 0.3 |
| 106 | 1 |
| 107 | 1 |
| 108 | 0.3 |
| 109 | 0.03 |
| 110 | 1.0 |
| 111 | 0.3 |
| 112 | 0.1 |
| 113 | 0.1 |
| 114 | 0.3 |
| 115 | 0.3 |
| 116 | 0.03 |
| 117 | 0.03 |

B-3. Radiotelemetric Blood Pressure Measurement on Awake, Spontaneously Hypertensive Rats The blood pressure measurement on awake rats described below uses a commercially available telemetry system from the company DATA SCIENCES INTERNATIONAL DSI, USA.

The system consists of 3 main components:
- implantable transmitter (Physiotel® Telemetry Transmitter)
- receiver (Physiotel® Receiver), which are connected via a multiplexer (DSI Data Exchange Matrix) to a
- data acquisition computer.

The telemetry system provides continuous acquisition of blood pressure, heart rate and body movement on awake animals in their usual living space.

Animal Material

The investigations are carried out on adult female, spontaneously hypertensive rats (SHR Okamoto) with a body weight of >200 g. SHR/NCrl from Okamoto Kyoto School of Medicine, 1963 were crossed from male Wistar Kyoto rats with greatly increased blood pressure and females with slightly raised blood pressure and were delivered in F13 to the U.S. National Institutes of Health.

After transmitter implantation, the experimental animals are kept individually in Makrolon cages, type 3. They have free access to standard feed and water.

The day-night rhythm in the testing laboratory is alternated by the room lighting at 06:00 hours in the morning and at 19:00 hours in the evening.

Transmitter Implantation

The TA11 PA—C40 telemetry transmitters used are implanted surgically in the experimental animals under aseptic conditions at least 14 days before the first test. The animals provided with this instrumentation can be used again after the wound has healed and the implant has become incorporated.

For implantation, the fasting animals are anaesthetized with pentobarbital (Nembutal, Sanofi: 50 mg/kg i.p.) and are shaved and disinfected on a wide area of the abdomen. After opening the abdominal cavity along the linea alba, the liquid-filled measuring catheter of the system is inserted above the bifurcation in the cranial direction into the aorta descendens and secured with tissue adhesive (VetBonD™, 3M). The transmitter housing is fixed intraperitoneally on the abdominal wall musculature and the wound is closed layer by layer.

Postoperatively, an antibiotic is administered to prevent infection (Tardomyocel COMP Bayer 1 ml/kg s.c.)

Substances and Solutions

Unless described otherwise, the test substances are in each case administered orally by stomach tube to a group of animals (n=6). Corresponding to an application volume of 5 ml/kg body weight, the test substances are dissolved in suitable solvent mixtures or suspended in 0.5% Tylose.

A group of animals treated with solvents is used as control.

Test Procedure

The present telemetry measuring device is configured for 24 animals. Each test is recorded under a test number (test year month day).

The instrumented rats living in the unit are each assigned their own receiving antenna (1010 Receiver, DSI).

The implanted transmitters can be activated from outside by an in-built magnetic switch. They are switched to transmission at the start of the tests. The signals emitted can be recorded online by a data acquisition system (Dataquest™ A.R.T. for WINDOWS, DSI) and processed appropriately. The data are saved in each case to a folder opened for this, which bears the test number.

In the standard procedure, the following are measured, in each case for 10 seconds:
systolic blood pressure (SBP)
diastolic blood pressure (DBP)
mean arterial pressure (MAP)
heart rate (HR)
activity (ACT).

Recording of the measured values is repeated at 5-minute intervals under computer control. The source data recorded as absolute value are corrected in the diagram with the currently measured barometric pressure (Ambient Pressure Reference Monitor; APR-1) and saved in individual data. Further technical details can be found in the extensive documentation of the manufacturer (DSI).

Unless described otherwise, the test substances are administered on the test day at 09.00 hours. Following application, the parameters described above are measured for 24 hours.

Evaluation

After the end of the test, the individual data recorded are sorted with the analysis software (DATAQUEST™ A. R.T.™ ANALYSIS). The 2 hours before application are taken as the blank value here, so that the selected data set comprises the period from 07:00 hours on the test day to 09:00 hours on the next day.

The data are smoothed for a pre-settable time by mean value determination (15-minute average) and transferred as text file to a storage medium. The pre-sorted and compressed measured values are transferred to Excel templates and presented as tables. The data recorded are saved per test day in a specific folder, which bears the test number. Results and test protocols are filed in folders, sorted in paper form by numbers.

Literature

Klaus Witte, Kai Hu, Johanna Swiatek, Claudia Müssig, Georg Ertl and Björn Lemmer: Experimental heart failure in rats: effects on cardiovascular circadian rhythms and on myocardial β-adrenergic signaling. Cardiovasc Res 47 (2): 203-405, 2000; Kozo Okamoto: Spontaneous hypertension in rats. Int Rev Exp Pathol 7: 227-270, 1969; Maarten van den Buuse: Circadian Rhythms of Blood Pressure, Heart Rate, and Locomotor Activity in Spontaneously Hypertensive Rats as Measured with Radio-Telemetry. Physiology & Behavior 55(4): 783-787, 1994

B-4. Determination of Pharmacokinetic Parameters after Intravenous and Oral Administration The pharmacokinetic parameters of the compounds according to the invention are determined in male CD-1 mice, male Wistar rats and female beagles. Intravenous administration takes place in mice and rats using a species-specific plasma/DMSO formulation and in dogs using a water/PEG400/ethanol formulation. Oral administration of the dissolved substance by stomach tube is carried out in all species on the basis of a water/PEG400/ethanol formulation. To simplify collection of blood, prior to administration of the substance the rats are fitted with a silicone catheter in the right vena jugularis externa. The operation is performed at least one day before the test under isoflurane anaesthesia and with administration of an analgesic (atropine/Rimadyl (3/1) 0.1 mL s.c.). Blood collection (as a rule more than 10 time points) takes place in a time window that includes terminal time points from at least 24 to max. 72 hours after administration of the substance. On collection, the blood is led into heparinized tubes. Then the blood plasma is obtained by centrifugation and optionally stored at −20° C. until further processing.

An internal standard (which can also be a chemically unrelated substance) is added to the samples of the compounds according to the invention, the calibration samples and the qualifiers and then protein precipitation is carried out using acetonitrile in excess. After adding a buffer solution, which is suitable for the LC conditions, and then vortexing, centrifugation is carried out at 1000 g. The supernatant is measured by LC-MS/MS using C18-reversed-phase columns and variable eluent mixtures. The substances are quantified on the basis of the peak heights or areas from extracted ion chromatograms of specific selected ion monitoring experiments.

The pharmacokinetic parameters such as AUC, $C_{max}$, $t_{1/2}$ (terminal half-life), MRT (mean residence time) and CL (clearance) are calculated from the plasma concentration-time curves obtained by means of validated pharmacokinetics software.

As substance quantification takes place in plasma, the blood/plasma distribution of the substance must be determined for appropriate adjustment of the pharmacokinetic parameters. For this, a defined amount of the substance in heparinized whole blood of the corresponding species is incubated for 20 min in the tumbling roller mixer. After centrifugation at 1000 g, the concentration of the plasma is measured (by LC-MS/MS; see above) and the $C_{blood}/C_{plasma}$ value is determined by finding the quotient.

B-5. Investigation of Metabolism

To determine the metabolism profile of the compounds according to the invention, these are incubated with recombinant human cytochrome P450 (CYP) enzymes, liver microsomes or with primary fresh hepatocytes of various animal species (e.g. rat, dog) as well as of human origin, in order to obtain and compare information on hepatic phase I and phase II metabolism that is as complete as possible and on the enzymes involved in metabolism.

The compounds according to the invention were incubated at a concentration of about 0.1-10 µM. For this, stock solutions of the compounds according to the invention with a concentration of 0.01-1 mM were prepared in acetonitrile, and then pipetted at 1:100 dilution into the incubation preparation. The liver microsomes and recombinant enzymes were incubated at 37° C. in 50 mM potassium phosphate buffer pH 7.4 with and without NADPH-generating system, consisting of 1 mM $NADP^+$, 10 mM glucose-6-phosphate and 1 unit of glucose-6-phosphate dehydrogenase. Primary hepatocytes were also incubated at 37° C. in suspension in Williams E medium. After an incubation time of 0-4 h, the incubation assays were stopped with acetonitrile (final concentration approx. 30%) and the protein was centrifuged off at approx. 15000×g. The samples stopped in this way were either analysed directly or were stored at −20° C. until analysis.

The analysis takes place by high-performance liquid chromatography with ultraviolet and mass-spectrometry detection (HPLC-UV-MS/MS). For this, the supernatants of the incubation samples are chromatographed with suitable C18-reversed-phase columns and variable eluent mixtures of acetonitrile and 10 mM aqueous ammonium formate solution or 0.05% formic acid. The UV chromatograms in conjunction with mass-spectrometry data serve for identification, structure elucidation and quantitative estimation of the metabolites, and the quantitative metabolic decrease of the compound according to the invention in the incubation assays.

B-6. Inhibition of Human Phosphodiesterase 5 (PDE-5)

PDE-5 preparations are obtained from human platelets by lysis (Microfluidizer®, 800 bar, 3 passages), followed by centrifugation (75000 g, 60 min, 4° C.) and ion-exchange chromatography of the supernatant on a Mono Q 10/10 column (linear sodium chloride gradient, elution with a 0.2-0.3M solution of sodium chloride in buffer (20 mM Hepes pH 7.2, 2 mM magnesium chloride). Fractions that have PDE-5 activity are combined (PDE-5 preparation) and stored at −80° C.

For determining their in-vitro action on human PDE-5, the test substances are dissolved in 100% DMSO and serial dilutions are prepared. Typically, dilution series (1:3) from 200 µM to 0.091 µM are prepared (resultant final concentrations in the test: 4 µM to 0.0018 µM). In each case 2 µL of the diluted solutions of the substance are put in the wells of microtitre plates (Isoplate-96/200W; Perkin-Elmer). Then 50 µL of a dilution of the PDE-5 preparation described above is added. The dilution of the PDE-5 preparation is selected so that during subsequent incubation less than 70% of the substrate is reacted (typical dilution: 1:100; dilution buffer: 50 mM Tris/hydrochloric acid pH 7.5, 8.3 mM magnesium chloride, 1.7 mM EDTA, 0.2% BSA). The substrate [8-$^3$H]cyclic guanosine-3',5'-monophosphate (1 µCi/µL; Perkin-Elmer) is diluted 1:2000 with assay buffer (50 mM Tris/hydrochloric acid pH 7.5, 8.3 mM magnesium chloride, 1.7 mM EDTA) to a concentration of 0.0005 µCi/µL. The enzyme reaction is finally started by adding 50 µL (0.025 µCi) of the diluted substrate. The test preparations are incubated for 60 min at room temperature and the reaction is stopped by adding 25 µL of a suspension of 18 mg/mL of Yttrium Scintillation Proximity Beads in water (phosphodiesterase beads for SPA assays, RPNQ 0150, Perkin-Elmer). The microtitre plates are sealed with film and left to stand for 60 min at room temperature. Then the plates are measured for 30 s per well in a Microbeta scintillation counter (Perkin-Elmer). $IC_{50}$ values are determined on the basis of the graphs plotted of the substance concentration versus the percentage PDE-5 inhibition.

Representative $IC_{50}$ values for the compounds according to the invention are presented in the following table (Table 3):

TABLE 3

| Example No. | $IC_{50}$ [nM] |
|---|---|
| 1 | 140 |
| 2 | 8.0 |
| 3 | 46 |
| 4 | 6.0 |
| 5 | 130 |
| 6 | 120 |
| 7 | 110 |
| 8 | 400 |
| 9 | 230 |
| 10 | 52 |
| 11 | 48 |
| 12 | 50 |
| 13 | 80 |
| 14 | 130 |
| 15 | 430 |
| 16 | 13 |
| 17 | 24 |
| 18 | 120 |
| 19 | 280 |
| 20 | 900 |
| 21 | 400 |
| 22 | 580 |
| 23 | 1600 |
| 24 | 100 |
| 25 | 320 |
| 26 | 12 |
| 27 | 4.0 |
| 28 | 110 |
| 29 | >4000 |
| 30 | >4000 |
| 31 | 500 |
| 32 | 720 |
| 33 | 570 |
| 34 | 550 |
| 35 | 110 |
| 36 | 89 |
| 37 | 100 |
| 38 | 41 |
| 39 | 88 |
| 40 | 11 |
| 41 | 170 |
| 42 | 120 |
| 43 | 410 |
| 44 | 86 |
| 45 | 78 |
| 46 | 35 |
| 47 | 83 |
| 48 | 54 |
| 49 | |
| 50 | 40 |
| 51 | 5.0 |
| 52 | 34 |
| 53 | 150 |
| 54 | |
| 55 | 130 |

TABLE 3-continued

| Example No. | IC$_{50}$ [nM] |
|---|---|
| 56 | 34 |
| 57 | 16 |
| 58 | 270 |
| 59 | 8.0 |
| 60 | 430 |
| 61 | 100 |
| 62 | 480 |
| 63 | 230 |
| 64 | 980 |
| 65 | 430 |
| 66 | 16 |
| 67 | |
| 68 | 35 |
| 69 | 46 |
| 70 | 80 |
| 71 | 42 |
| 72 | 110 |
| 73 | 16 |
| 74 | 110 |
| 75 | 210 |
| 76 | 130 |
| 77 | |
| 78 | 330 |
| 79 | |
| 80 | |
| 81 | 290 |
| 82 | |
| 83 | 230 |
| 84 | 19 |
| 85 | 4.2 |
| 86 | 330 |
| 87 | 210 |
| 88 | 150 |
| 89 | 82 |
| 90 | 230 |
| 91 | 600 |
| 92 | 170 |
| 93 | 120 |
| 94 | 140 |
| 95 | 4.0 |
| 96-1 | 150 |
| 96-2 | 26 |
| 97 | 63 |
| 98 | 4.0 |
| 99 | 440 |
| 100 | 2800 |
| 101 | 870 |
| 102 | 74 |
| 103 | 400 |
| 104 | 80 |
| 105 | 980 |
| 106 | 12 |
| 107 | 100 |
| 108 | 25 |
| 109 | 50 |
| 110 | 840 |
| 111 | 320 |
| 112 | 210 |
| 113 | 120 |
| 114 | 200 |
| 115 | 250 |
| 116 | 83 |
| 117 | 52 |

B-7. Determination of the Organ-protective Effects in the Long-term Test on Rats The organ-protective effects of the sGC stimulators were demonstrated in a therapeutically relevant "low nitric oxide (NO)/high renin" hypertension model in rats. The study was carried out on the basis of the recent publication (Sharkovska Y, Kalk P, Lawrenz B, Godes M, Hoffmann L S, Wellkisch K, Geschka S, Relle K, Hocher B, Stasch J P. NO-independent stimulation of soluble guanylate cyclase reduces target organ damage in low- and high-renin models of hypertension. J. Hypertension. 2010; 28: 1666-1675). In this, renin-transgenic rats (TGR(mRen2)27), which were administered the NO-synthase inhibitor L-NAME in the drinking water, were treated simultaneously with an sGC stimulator or vehicle for several weeks. Haemodynamic and renal parameters were determined during the treatment period. At the end of the long-term study, organ protection (kidney, lung, heart, aorta) was demonstrated by histopathological investigations, biomarkers, expression analyses and cardiovascular plasma parameters.

C. Practical Examples of Pharmaceutical Compositions

The compounds according to the invention can be transformed as follows into pharmaceutical preparations:

Tablet:

Composition:

100 mg of the compound according to the invention, 50 mg lactose (monohydrate), 50 mg maize starch (native), 10 mg polyvinylpyrrolidone (PVP 25) (from BASF, Ludwigshafen, Germany) and 2 mg magnesium stearate.

Tablet weight 212 mg, diameter 8 mm, radius of convexity 12 mm

Production:

The mixture of compound according to the invention, lactose and starch is granulated with a 5% solution (w/w) of PVP in water. After drying, the granules are mixed with the magnesium stearate for 5 minutes. This mixture is compressed with a usual tablet press (see above for tablet format). A pressing force of 15 kN is used as a guide value for compression.

Oral Suspension:

Composition:

1000 mg of the compound according to the invention, 1000 mg ethanol (96%), 400 mg Rhodigel® (xanthan gum from the company FMC, Pennsylvania, USA) and 99 g water.

An individual dose of 100 mg of the compound according to the invention corresponds to 10 ml of oral suspension.

Production:

The Rhodigel is suspended in ethanol, and the compound according to the invention is added to the suspension. Water is added while stirring. It is stirred for approx. 6 h, until swelling of the Rhodigel has ceased.

Oral Solution:

Composition:

500 mg of the compound according to the invention, 2.5 g polysorbate and 97 g polyethylene glycol 400. An individual dose of 100 mg of the compound according to the invention corresponds to 20 g of oral solution.

Production:

The compound according to the invention is suspended in a mixture of polyethylene glycol and polysorbate, with stirring. Stirring is continued until the compound according to the invention has dissolved completely.

i.v. Solution:

The compound according to the invention is dissolved at a concentration below the saturation solubility in a physiologically compatible solvent (e.g. isotonic saline, glucose solution 5% and/or PEG 400 solution 30%). The solution is sterile-filtered and filled in sterile and pyrogen-free injection containers.

The invention claimed is:
1. A compound of general formula (I)

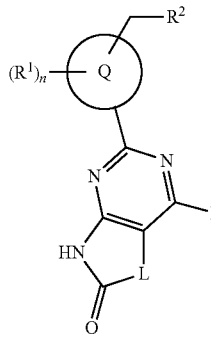

in which
L stands for a group $\#^1$—$CR^{7A}R^{7B}$-$\#^2$,
wherein
$\#^1$ stands for the point of attachment to the carbonyl group,
$\#^2$ stands for the point of attachment to the pyrimidine ring,
$R^{7A}$ stands for hydrogen, fluorine, $(C_1$-$C_4)$-alkyl, hydroxyl or amino,
in which $(C_1$-$C_4)$-alkyl can be substituted with 1 to 3 substituents selected independently of one another from the group fluorine, trifluoromethyl, hydroxy, hydroxycarbonyl, $(C_1$-$C_4)$-alkoxycarbonyl and amino,
$R^{7B}$ stands for hydrogen, fluorine, difluoromethyl, trifluoromethyl, $(C_1$-$C_6)$-alkyl, $(C_1$-$C_4)$-alkoxycarbonylamino, cyano, $(C_3$-$C_7)$-cycloalkyl, difluoromethoxy, trifluoromethoxy, phenyl or a group of formula -M-$R^{13}$,
in which $(C_1$-$C_6)$-alkyl can be substituted with 1 to 3 substituents selected independently of one another from the group fluorine, cyano, trifluoromethyl, $(C_3$-$C_7)$-cycloalkyl, hydroxy, difluoromethoxy, trifluoromethoxy, $(C_1$-$C_4)$-alkoxy, hydroxycarbonyl, $(C_1$-$C_4)$-alkoxycarbonyl and amino,
and in which
M stands for a bond or $(C_1$-$C_4)$-alkanediyl,
$R^{13}$ stands for —(C=O)$_r$—OR$^{14}$, —(C=O)$_r$—NR$^{14}$R$^{15}$, —C(=S)—NR$^{14}$R$^{15}$, —NR$^{14}$—(C=O)—R$^{17}$, —NR$^{14}$—(C=O)—NR$^{15}$R$^{16}$, —NR$^{14}$—SO$_2$—NR$^{15}$R$^{16}$, —NR$^{14}$—SO$_2$—R$^{17}$, —S(O)$_s$—R$^{17}$, —SO$_2$—NR$^{14}$R$^{15}$, 4- to 7-membered heterocyclyl, phenyl or 5- or 6-membered heteroaryl,
in which
r denotes the number 0 or 1,
s denotes the number 0, 1 or 2,
$R^{14}$, $R^{15}$ and $R^{16}$ each stand, independently of one another, for hydrogen, $(C_1$-$C_6)$-alkyl, $(C_3$-$C_8)$-cycloalkyl, 4- to 7-membered heterocyclyl, phenyl or 5- or 6-membered heteroaryl,
or
$R^{14}$ and $R^{15}$ form, together with the respective atom(s) to which they are bound, a 4- to 7-membered heterocycle, in which for its part the 4- to 7-membered heterocycle can be substituted with 1 or 2 substituents selected independently of one another from the group cyano, trifluoromethyl, $(C_1$-$C_6)$-alkyl, hydroxy, oxo, $(C_1$-$C_6)$-alkoxy, trifluoromethoxy, $(C_1$-$C_6)$-alkoxycarbonyl, amino, mono-$(C_1$-$C_6)$-alkylamino and di$(C_1$-$C_6)$-alkylamino,
or
$R^{15}$ and $R^{16}$ form, together with the respective atom(s) to which they are bound, a 4- to 7-membered heterocycle,
in which for its part the 4- to 7-membered heterocycle can be substituted with 1 or 2 substituents selected independently of one another from the group cyano, trifluoromethyl, $(C_1$-$C_6)$-alkyl, hydroxy, oxo, $(C_1$-$C_6)$-alkoxy, trifluoromethoxy, $(C_1$-$C_6)$-alkoxycarbonyl, amino, mono-$(C_1$-$C_6)$-alkylamino and di$(C_1$-$C_6)$-alkylamino,
$R^{17}$ stands for $(C_1$-$C_6)$-alkyl or $(C_3$-$C_7)$-cycloalkyl,
or
$R^{14}$ and $R^{17}$ form, together with the respective atom(s) to which they are bound, a 4- to 7-membered heterocycle,
in which for its part the 4- to 7-membered heterocycle can be substituted with 1 or 2 substituents selected independently of one another from the group cyano, trifluoromethyl, $(C_1$-$C_6)$-alkyl, hydroxy, oxo, $(C_1$-$C_6)$-alkoxy, trifluoromethoxy, $(C_1$-$C_6)$-alkoxycarbonyl, amino, mono-$(C_1$-$C_6)$-alkylamino and di$(C_1$-$C_6)$-alkylamino,
and
in which for their part the 4- to 7-membered heterocyclyl, phenyl and 5- or 6-membered heteroaryl can be substituted with 1 to 3 substituents selected independently of one another from the group halogen, cyano, difluoromethyl, trifluoromethyl, $(C_1$-$C_6)$-alkyl, $(C_3$-$C_7)$-cycloalkyl, hydroxy, oxo, thiooxo and $(C_1$-$C_4)$-alkoxy,
and
in which the aforementioned $(C_1$-$C_4)$-alkyl, $(C_1$-$C_6)$-alkyl, $(C_3$-$C_8)$-cycloalkyl, $(C_3$-$C_7)$-cycloalkyl and 4- to 7-membered heterocyclyl groups, unless stated otherwise, can in each case be further substituted independently of one another with 1 to 3 substituents selected independently of one another from the group fluorine, difluoromethyl, trifluoromethyl, $(C_1$-$C_4)$-alkyl, $(C_3$-$C_7)$-cycloalkyl, hydroxy, difluoromethoxy, trifluoromethoxy, $(C_1$-$C_4)$-alkoxy, hydroxycarbonyl, $(C_1$-$C_4)$-alkoxycarbonyl, amino, phenyl, 4- to 7-membered heterocyclyl and 5- or 6-membered heteroaryl,
or
$R^{7A}$ and $R^{7B}$ together with the carbon atom to which they are bound, form a $(C_2$-$C_4)$-alkenyl group, an oxo group, a 3- to 6-membered carbocycle or a 4- to 7-membered heterocycle,
in which the 3- to 6-membered carbocycle and the 4- to 7-membered heterocycle can be substituted with 1 or 2 substituents selected independently of one another from the group fluorine and $(C_1$-$C_4)$-alkyl,
the ring Q stands for a nitrogen-containing 8- or 9-membered heteroaryl,
$R^3$ stands for —OR$^4$ or —NR$^5$R$^6$, wherein $R^4$ stands for hydrogen, $(C_1\text{-}C_6)$-alkyl, $(C_3\text{-}C_7)$-cycloalkyl, 4- to 7-membered heterocyclyl, phenyl or 5- or 6-membered heteroaryl, in which $(C_1\text{-}C_6)$-alkyl, $(C_3\text{-}C_7)$-cycloalkyl, 4- to 7-membered heterocyclyl, phenyl and 5- or 6-membered heteroaryl can be substituted with 1 to 3 substituents selected independently of one another from the group fluorine, difluoromethyl, trifluoromethyl, $(C_1\text{-}C_6)$-alkyl, $(C_3\text{-}C_6)$-cycloalkyl, difluoromethoxy, trifluoromethoxy, Oxo, —(C=O)$_{PO}$R$^9$, —C(=O)$_p$—NR$^9$R$^{10}$, —NR$^9$—(C=O)—R$^{10}$, —NR$^9$—(C=O)—OR$^{10}$, —NR$^9$—(C=O)—NR$^{10}$R$^{11}$, —NR$^9$—SO$_2$—R$^{10}$, —S(O)$_q$—R$^{12}$ and —SO$_2$—NR$^9$R$^{10}$, in which p denotes the number 0 or 1, q denotes the number 0, 1 or 2, $R^9$, $R^{10}$ and $R^{11}$ each stand, independently of one another, for hydrogen, $(C_1\text{-}C_6)$-alkyl or $(C_3\text{-}C_8)$-cycloalkyl, in which $(C_1\text{-}C_6)$-alkyl for its part can be substituted with 1 or 2 substituents selected independently of one another from the group fluorine, difluoromethyl, trifluoromethyl, hydroxy, $(C_1\text{-}C_6)$-alkoxy, difluoromethoxy, trifluoromethoxy, $(C_1\text{-}C_6)$-alkoxycarbonyl, amino, mono-$(C_1\text{-}C_6)$-alkylamino, di$(C_1\text{-}C_6)$-alkylamino and 4- to 7-membered heterocyclyl, or $R^9$ and $R^{10}$ form, together with the respective atom(s) to which they are bound, a 4- to 7-membered heterocycle, in which for its part the 4- to 7-membered heterocycle can be substituted with 1 or 2 substituents selected independently of one another from the group fluorine, trifluoromethyl, $(C_1\text{-}C_6)$-alkyl, hydroxy, oxo, $(C_1\text{-}C_6)$-alkoxy, trifluoromethoxy, $(C_1\text{-}C_6)$-alkoxycarbonyl, amino, mono-$(C_1\text{-}C_6)$-alkylamino and di$(C_1\text{-}C_6)$-alkylamino, or $R^{10}$ and $R^{11}$ form, together with the respective atom(s) to which they are bound, a 4- to 7-membered heterocycle, in which for its part the 4- to 7-membered heterocycle can be substituted with 1 or 2 substituents selected independently of one another from the group fluorine, trifluoromethyl, $(C_1\text{-}C_6)$-alkyl, hydroxy, oxo, $(C_1\text{-}C_6)$-alkoxy, trifluoromethoxy, $(C_1\text{-}C_6)$-alkoxycarbonyl, amino, mono-$(C_1\text{-}C_6)$-alkylamino and di$(C_1\text{-}C_6)$-alkylamino, and in which $R^{12}$ stands for $(C_1\text{-}C_6)$-alkyl or $(C_3\text{-}C_7)$-cycloalkyl, and in which the aforementioned $(C_1\text{-}C_4)$-alkyl, $(C_1\text{-}C_6)$-alkyl, $(C_3\text{-}C_8)$-cycloalkyl, $(C_3\text{-}C_7)$-cycloalkyl and 4- to 7-membered heterocyclyl groups, unless stated otherwise, can in each case be further substituted independently of one another with 1 to 3 substituents selected independently of one another from the group fluorine, difluoromethyl, trifluoromethyl, $(C_1\text{-}C_4)$-alkyl, $(C_3\text{-}C_7)$-cycloalkyl, hydroxy, difluoromethoxy, trifluoromethoxy, $(C_1\text{-}C_4)$-alkoxy, hydroxycarbonyl, $(C_1\text{-}C_4)$-alkoxycarbonyl, amino, phenyl, 4- to 7-membered heterocyclyl and 5- or 6-membered heteroaryl, $R^5$ stands for hydrogen or $(C_1\text{-}C_4)$-alkyl, $R^6$ stands for $(C_1\text{-}C_6)$-alkyl, $(C_3\text{-}C_7)$-cycloalkyl, 4- to 7-membered heterocyclyl, phenyl or 5- or 6-membered heteroaryl, in which $(C_1\text{-}C_6)$-alkyl, $(C_3\text{-}C_7)$-cycloalkyl, 4- to 7-membered heterocyclyl, phenyl and 5- or 6-membered heteroaryl can be substituted with 1 to 3 substituents selected independently of one another from the group fluorine, difluoromethyl, trifluoromethyl, $(C_1\text{-}C_6)$-alkyl, $(C_3\text{-}C_7)$-cycloalkyl, difluoromethoxy, trifluoromethoxy, oxo, —(C=O)$_p$—OR$^9$, —(C=O)$_p$—NR$^9$R$^{10}$, —NR$^9$—(C=O)—R$^{10}$, —NR$^9$—(C=O)—OR$^{10}$, —NR$^9$—(C=O)—NR$^{10}$R$^{11}$, —NR$^9$—SO$_2$—R$^{10}$, —S(O)$_q$—R$^{12}$, —SO$_2$—NR$^9$R$^{10}$, phenyl, 4- to 7-membered heterocyclyl and 5- or 6-membered heteroaryl, in which p denotes the number 0 or 1, q denotes the number 0, 1 or 2, $R^9$, $R^{10}$ and $R^{11}$ each stand, independently of one another, for hydrogen, $(C_1\text{-}C_6)$-alkyl or $(C_3\text{-}C_8)$-cycloalkyl, in which $(C_1\text{-}C_6)$-alkyl for its part can be substituted with 1 to 3 substituents selected independently of one another from the group fluorine, difluoromethyl, trifluoromethyl, $(C_3\text{-}C_7)$-cycloalkyl, difluoromethoxy, trifluoromethoxy and $(C_1\text{-}C_4)$-alkoxy, or $R^9$ and $R^{10}$ form, together with the respective atom(s) to which they are bound, a 4- to 7-membered heterocycle, in which for its part the 4- to 7-membered heterocycle can be substituted with 1 or 2 substituents selected independently of one another from the group fluorine, cyano, trifluoromethyl, $(C_1\text{-}C_6)$-alkyl, hydroxy, oxo, $(C_1\text{-}C_6)$-alkoxy, trifluoromethoxy, $(C_1\text{-}C_6)$-alkoxycarbonyl, amino, mono-$(C_1\text{-}C_6)$-alkylamino and di$(C_1\text{-}C_6)$-alkylamino, or $R^{10}$ and $R^{11}$ form, together with the respective atom(s) to which they are bound, a 4- to 7-membered heterocycle, in which for its part the 4- to 7-membered heterocycle can be substituted with 1 or 2 substituents selected independently of one another from the group cyano, trifluoromethyl, $(C_1\text{-}C_6)$-alkyl, hydroxy, oxo, $(C_1\text{-}C_6)$-alkoxy, trifluoromethoxy, $(C_1\text{-}C_6)$-alkoxycarbonyl, amino, mono-$(C_1\text{-}C_6)$-alkylamino and di$(C_1\text{-}C_6)$-alkylamino, in which $R^{12}$ stands for $(C_1\text{-}C_6)$-alkyl or $(C_3\text{-}C_7)$-cycloalkyl, and in which phenyl, 4- to 7-membered heterocyclyl and 5- or 6-membered heteroaryl for their part can be substituted with 1 to substituents selected independently of one another from the group halogen, cyano, difluoromethyl, trifluoromethyl, $(C_1\text{-}C_4)$-alkyl, $(C_3\text{-}C_7)$-cycloalkyl, hydroxy, oxo, difluoromethoxy, trifluoromethoxy and $(C_1\text{-}C_4)$-alkoxy, or $R^5$ and $R^6$ form, together with the nitrogen atom to which they are bound, a 4- to 7-membered heterocycle or a 5- or 6-membered heteroaryl, in which the 4- to 7-membered heterocycle and the 5- or 6-membered heteroaryl can be substituted with 1 to 3 substituents selected independently of one another from the group fluorine, cyano, difluoromethyl, trifluoromethyl, $(C_1\text{-}C_6)$-alkyl, $(C_3\text{-}C_7)$-cycloalkyl, hydroxy, oxo, $(C_1-C_6)$-alkoxy, difluoromethoxy, trifluoromethoxy, $(C_1-C_6)$-alkoxycarbonyl, $(C_1-C_6)$-alkylcarbonylamino, amino, mono-$(C_1-C_6)$-alkylamino, di$(C_1-C_6)$-alkylamino and 4- to 7-membered heterocyclyl, and in which the aforementioned $(C_1-C_4)$-alkyl, $(C_1-C_6)$-alkyl, $(C_3-C_8)$-cycloalkyl, $(C_3-C_7)$-cycloalkyl and 4- to 7-membered heterocyclyl groups, unless stated otherwise, can in each case be further substituted independently of one another with 1 to 3 substituents selected independently of one another from the group fluorine, difluoromethyl, trifluoromethyl, $C_1-C_4$)-alkyl, $(C_3-C_7)$-cycloalkyl, hydroxy, difluoromethoxy, trifluoromethoxy, $(C_1-C_4)$-alkoxy, hydroxycarbonyl, $(C_1-C_4)$-alkoxycarbonyl, amino, phenyl, 4- to 7-membered heterocyclyl and 5- or 6-membered heteroaryl, $R^1$ stands for fluorine, chlorine, cyano, difluoromethyl, trifluoromethyl, $(C_1-C_4)$-alkyl, $(C_3-C_7)$-cycloalkyl or $(C_1-C_4)$-alkoxy, n stands for a number 0, 1 or 2, $R^2$ stands for trifluoromethyl, $(C_1-C_6)$-alkyl, $(C_3-C_8)$-cycloalkyl, phenyl or 5- or 6-membered heteroaryl, wherein $(C_1-C_6)$-alkyl is substituted with a substituent selected from the group difluoromethyl and trifluoromethyl, wherein $(C_1-C_6)$-alkyl can be substituted with 1 to 3 fluorine substituents, wherein $(C_3-C_8)$-cycloalkyl can be substituted with 1 or 2 substituents selected independently of one another from the group fluorine, methyl and methoxy, wherein phenyl is substituted with 1 to 3 fluorine substituents, wherein phenyl can be substituted with 1 or 2 substituents selected independently of one another from the group methyl and methoxy, and wherein 5- and 6-membered heteroaryl can be substituted with 1 or 2 substituents selected independently of one another from the group fluorine, trifluoromethyl and methyl, or a salt thereof.

2. The compound of claim 1, in which

L stands for a group $\#^1$—$CR^{7A}R^{7B}$-$\#^2$, wherein $\#^1$ stands for the point of attachment to the carbonyl group, $\#^2$ stands for the point of attachment to the pyrimidine ring, $R^{7A}$ stands for hydrogen, fluorine, methyl, ethyl, hydroxy or amino, $R^{7B}$ stands for hydrogen, fluorine, difluoromethyl, trifluoromethyl, $(C_1-C_4)$-alkyl, methoxycarbonylamino, cyano, cyclopropyl, cyclobutyl, cyclopentyl, phenyl or a group of formula -M-$R^{13}$, in which $(C_1-C_4)$-alkyl can be substituted with 1 to 3 substituents selected independently of one another from the group fluorine, cyano, trifluoromethyl, cyclopropyl, cyclobutyl, cyclopentyl, hydroxy, difluoromethoxy, trifluoromethoxy, methoxy, ethoxy, hydroxycarbonyl, methoxycarbonyl, ethoxycarbonyl and amino, and in which M stands for a bond or methylene, $R^{13}$ stands for —(C=O)$_r$—$NR^{14}R^{15}$, —C(=S)—$NR^{14}R^{15}$, oxadiazolonyl, oxadiazolethionyl, phenyl, oxazolyl, thiazolyl, pyrazolyl, triazolyl, oxadiazolyl, thiadiazolyl, pyridyl, pyrimidinyl or pyrazinyl, in which r denotes the number 0 or 1, $R^{14}$ and $R^{15}$ each stand, independently of one another, for hydrogen, methyl, ethyl, isopropyl, cyclopropyl, cyclobutyl, cyclopentyl, oxetanyl, azetidinyl, tetrahydrofuranyl, pyrrolidinyl, tetrahydropyranyl, piperidinyl, piperazinyl, morpholinyl, phenyl, pyrazolyl or pyridyl, in which methyl, ethyl and iso-propyl can be further substituted with 1 or 2 substituents selected independently of one another from the group fluorine, difluoromethyl, trifluoromethyl, cyclopropyl, cyclobutyl, cyclopentyl, hydroxy, difluoromethoxy, trifluoromethoxy, methoxy, ethoxy, hydroxycarbonyl, methoxycarbonyl, ethoxycarbonyl and amino, and in which oxadiazolonyl, oxadiazolethionyl, phenyl, oxazolyl, thiazolyl, pyrazolyl, triazolyl, oxadiazolyl, thiadiazolyl, pyridyl, pyrimidinyl and pyrazinyl for their part can be substituted with 1 or 2 substituents selected independently of one another from the group fluorine, chlorine, cyano, difluoromethyl, trifluoromethyl, methyl, ethyl, isopropyl, 2,2,2-trifluoroethyl, 1,1,2,2,2-pentafluoroethyl, cyclopropyl, cyclobutyl, cyclopropylmethyl, cyclobutylmethyl, hydroxy, methoxy and ethoxy, or $R^{7A}$ and $R^{7B}$ together with the carbon atom to which they are bound, form a cyclopropyl, cyclobutyl, cyclopentyl, azetidinyl, tetrahydrofuranyl, pyrrolidinyl or tetrahydropyranyl ring, in which the cyclopropyl, cyclobutyl, cyclopentyl, azetidinyl, tetrahydrofuranyl, pyrrolidinyl and tetrahydropyranyl ring can be substituted with 1 or 2 substituents selected independently of one another from the group fluorine and methyl, the ring Q stands for a group of formula

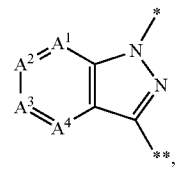
(a-1)

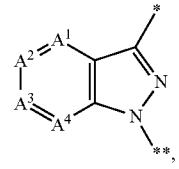
(b-1)

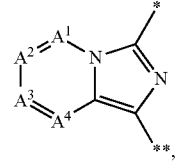
(c-1)

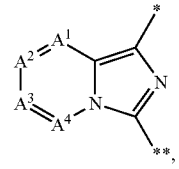
(d-1)

-continued (e-1) 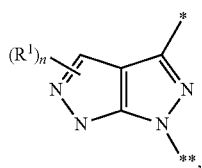

(f-1) 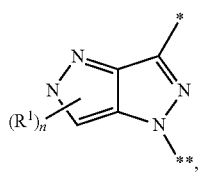

(g-1) 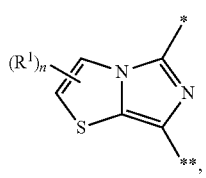

(h-1) 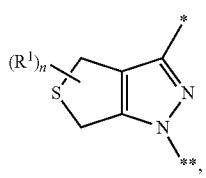

(i-1) 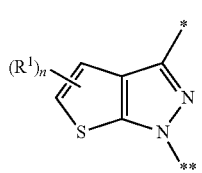

(j-1) 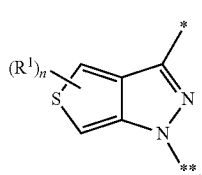

(k-1) 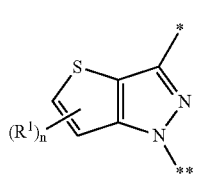

(l-1) 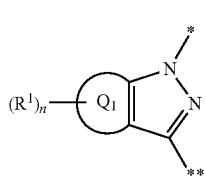

(m-1) 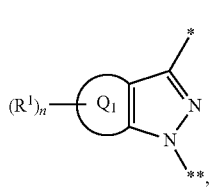

-continued (n-1) 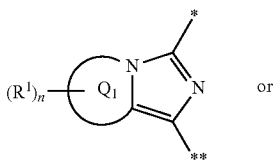 or (o-1) 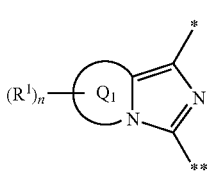

wherein
* stands for the point of attachment to —CH$_2$—R$^2$,
** stands for the point of attachment to the pyrimidine,
the ring Q$_1$ together with the atoms to which it is bound, forms a 5- to 7-membered saturated or partially unsaturated carbocycle or a 5- to 7-membered saturated or partially unsaturated heterocycle,
R$^1$ stands for fluorine, chlorine or methyl,
n stands for a number 0, 1 or 2,
A$^1$, A$^2$, A$^3$ and A$^4$ independently of one another stand in each case for N, CH or CR$^1$,
with the proviso that at most two of the groups A$^1$, A$^2$, A$^3$ and A$^4$ stand for N,
R$^3$ stands for —OR$^4$ or —NR$^5$R$^6$,
wherein
R$^4$ stands for (C$_1$-C$_6$)-alkyl, cyclopropyl, cyclobutyl, cyclopentyl, oxetanyl, azetidinyl, tetrahydrofuranyl, pyrrolidinyl, tetrahydropyranyl, piperidinyl, piperazinyl, morpholinyl, phenyl, pyrazolyl, oxazolyl, thiazolyl, triazolyl, oxadiazolyl, thiadiazolyl, pyridyl or pyrimidinyl,
in which (C$_1$-C$_6$)-alkyl can be substituted with 1 to 3 substituents selected independently of one another from the group fluorine, difluoromethyl, trifluoromethyl, cyclopropyl, cyclobutyl, cyclopentyl, difluoromethoxy, trifluoromethoxy, —(C=O)$_p$—OR$^9$, —(C=O)$_p$—NR$^9$R$^{10}$, and —NR$^8$—(C=O)—R$^{10}$,
and
in which cyclopropyl, cyclobutyl, cyclopentyl, oxetanyl, azetidinyl, tetrahydrofuranyl, pyrrolidinyl, tetrahydropyranyl, piperidinyl, piperazinyl, morpholinyl, phenyl, pyrazolyl, oxazolyl, thiazolyl, triazolyl, oxadiazolyl, thiadiazolyl, pyridyl or pyrimidinyl can be substituted with 1 to 3 substituents selected independently of one another from the group fluorine, difluoromethyl, trifluoromethyl, 2,2,2-trifluoroethyl, 1,1,2,2,2-pentafluoroethyl, methyl, ethyl, isopropyl, cyclopropyl, cyclobutyl, cyclopentyl, difluoromethoxy, trifluoromethoxy, oxo, —(C=O)$_p$—OR$^9$ and —(C=O)$_p$—NR$^9$R$^{10}$,
in which
p denotes the number 0 or 1,
R$^9$ and R$^{10}$ each stand, independently of one another, for hydrogen, methyl, ethyl, isopropyl, trifluoromethyl, 2,2,2-trifluoroethyl, 1,1,2,2,2-pentafluoroethyl, cyclopropyl, cyclobutyl or cyclopentyl,
or
R$^9$ and R$^{10}$ form, together with the respective atom(s) to which they are bound, an azetidinyl, pyrrolidinyl, piperidinyl, piperazinyl or morpholinyl ring, in which the azetidinyl, pyrrolidinyl, piperidinyl, piperazinyl and morpholinyl ring for its part can be substituted with 1 or 2 substituents selected independently of one another from the group fluorine, trifluoromethyl, methyl, ethyl, hydroxy, oxo, methoxy, ethoxy, amino, methylamino, ethylamino, dimethylamino and diethylamino, $R^5$ stands for hydrogen, methyl or ethyl, $R^6$ stands for $(C_1-C_6)$-alkyl, cyclopropyl, $(C_3-C_6)$-cycloalkyl, oxetanyl, azetidinyl, tetrahydrofuranyl, pyrrolidinyl, tetrahydropyranyl, piperidinyl, piperazinyl, morpholinyl, phenyl, pyrazolyl, oxazolyl, thiazolyl, triazolyl, oxadiazolyl, thiadiazolyl, pyridyl or pyrimidinyl, in which $(C_1-C_6)$-alkyl and $(C_3-C_6)$-cycloalkyl are substituted with 1 to 3 substituents selected independently of one another from the group fluorine, difluoromethyl, trifluoromethyl methyl, ethyl, cyclopropyl, cyclobutyl, cyclopentyl, difluoromethoxy, trifluoromethoxy, —(C=O)$_p$—OR$^9$, —(C=O)$_p$—NR$^9$R$^{10}$, —NR$^9$—(C=O)—R$^{10}$, oxetanyl, azetidinyl, tetrahydrofuranyl, pyrrolidinyl, tetrahydropyranyl, piperidinyl, piperazinyl, morpholinyl, phenyl, furanyl, pyrazolyl, imidazolyl, oxazolyl, thiazolyl, triazolyl, oxadiazolyl, thiadiazolyl, pyridyl and pyrimidinyl, in which cyclopropyl, cyclobutyl, cyclopentyl, oxetanyl, azetidinyl, tetrahydrofuranyl, pyrrolidinyl, tetrahydropyranyl, piperidinyl, piperazinyl, morpholinyl, phenyl, furanyl, pyrazolyl, imidazolyl, oxazolyl, thiazolyl, triazolyl, oxadiazolyl, thiadiazolyl, pyridyl and pyrimidinyl for their part can be substituted with 1 or 2 substituents selected independently of one another from the group fluorine, chlorine, cyano, difluoromethyl, trifluoromethyl, methyl, ethyl, cyclopropyl, cyclobutyl, cyclopentyl, hydroxy, oxo, difluoromethoxy, trifluoromethoxy, methoxy and ethoxy, in which oxetanyl, azetidinyl, tetrahydrofuranyl, pyrrolidinyl, tetrahydropyranyl, piperidinyl, piperazinyl, morpholinyl, phenyl, pyrazolyl, oxazolyl, thiazolyl, triazolyl, oxadiazolyl, thiadiazolyl, pyridyl and pyrimidinyl can be substituted with 1 to 3 substituents selected independently of one another from the group fluorine, difluoromethyl, trifluoromethyl, methyl, ethyl, cyclopropyl, cyclobutyl, cyclopentyl, difluoromethoxy, trifluoromethoxy, oxo, —(C=O)$_p$—OR$^9$ and —(C=O)$_p$—NR$^9$R$^{10}$, in which p denotes the number 0 or 1, $R^9$ and $R^{10}$ each stand, independently of one another, for hydrogen, methyl, ethyl, isopropyl, trifluoromethyl, 2,2,2-trifluoroethyl, 1,1,2,2,2-pentafluoroethyl, cyclopropyl, cyclobutyl or cyclopentyl, or $R^9$ and $R^{10}$ form, together with the respective atom(s) to which they are bound, an azetidinyl, pyrrolidinyl, piperidinyl, piperazinyl or morpholinyl ring, in which the azetidinyl, pyrrolidinyl, piperidinyl, piperazinyl and morpholinyl ring for its part can be substituted with 1 or 2 substituents selected independently of one another from the group fluorine, trifluoromethyl, methyl, ethyl, hydroxy, oxo, methoxy, ethoxy, amino, methylamino, ethylamino, dimethylamino and diethylamino, or $R^5$ and $R^6$ form, together with the nitrogen atom to which they are bound, an azetidinyl, pyrrolidinyl, imidazolidinyl, piperidinyl, dihydropiperidinyl, piperazinyl, morpholinyl, pyrazolyl, imidazolyl or triazolyl ring, in which the azetidinyl, pyrrolidinyl, imidazolidinyl, piperidinyl, dihydropiperidinyl, piperazinyl, morpholinyl, pyrazolyl, imidazolyl and triazolyl ring can be substituted with 1 or 2 substituents selected independently of one another from the group fluorine, cyano, difluoromethyl, trifluoromethyl, 2,2,2-trifluoroethyl, 1,1,2,2,2-pentafluoroethyl, methyl, ethyl, 1-hydroxyethyl, cyclopropyl, cyclobutyl, cyclopentyl, hydroxy, oxo, methoxy, ethoxy, difluoromethoxy, trifluoromethoxy, oxetanyl, azetidinyl, tetrahydrofuranyl, pyrrolidinyl, tetrahydropyranyl, piperidinyl, piperazinyl and morpholinyl, $R^2$ stands for trifluoromethyl, 2,2,2-trifluoroethyl, 3,3,3-trifluoroprop-1-yl, 2,2,3,3,3-pentafluoroprop-1-yl, cyclopropyl, cyclobutyl, cyclopentyl, cyclohexyl, phenyl, pyridyl, pyrimidinyl, pyrazinyl or pyridazinyl, wherein phenyl is substituted with 1 to 3 fluorine substituents, and wherein cyclopropyl, cyclobutyl, cyclopentyl, cyclohexyl, pyridyl, pyrimidinyl, pyrazinyl and pyridazinyl can be substituted with 1 or 2 fluorine substituents, or a salt thereof.

3. The compound of claim 1, in which

L stands for a group #$^1$—CR$^{7A}$R$^{7B}$-#$^2$, wherein

$^1$ stands for the point of attachment to the carbonyl group,

$^2$ stands for the point of attachment to the pyrimidine ring, $R^{7A}$ stands for hydrogen, fluorine, methyl or hydroxy, $R^{7B}$ stands for hydrogen, fluorine, trifluoromethyl, methyl or 2,2,2-trifluoroethyl, or $R^{7A}$ and $R^{7B}$ together with the carbon atom to which they are bound, form a tetrahydrofuranyl ring, the ring Q stands for a group of formula

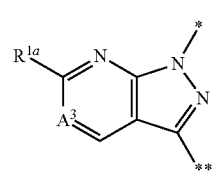

(a-1)

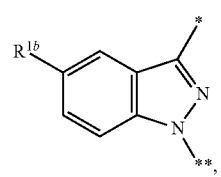

(b-1)

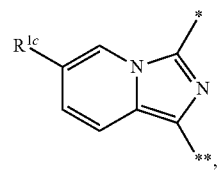

(c-1a)

-continued

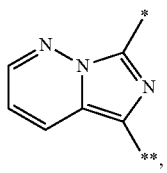 (c-1a)

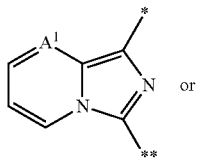 (d-1)

or

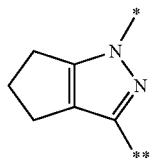 (l-1)

wherein
* stands for the point of attachment to —CH$_2$—R$^2$,
** stands for the point of attachment to the pyrimidine,
R$^{1a}$ stands for hydrogen or methyl,
R$^{1b}$ stands for hydrogen or fluorine,
R$^{1c}$ stands for hydrogen or chlorine,
A$^1$ stands for N or CH,
A$^3$ stands for N, CH or C—F,
R$^3$ stands for —NR$^5$R$^6$,
  wherein
  R$^5$ stands for hydrogen,
  R$^6$ stands for (C$_1$-C$_6$)-alkyl,
    in which (C$_1$-C$_6$)-alkyl is substituted with 1 or 2 substituents selected independently of one another from the group fluorine, difluoromethyl, trifluoromethyl or —(C═O)$_p$—OR$^9$,
    in which
    p denotes the number 0,
    R$^9$ stands for hydrogen,
R$^2$ stands for 2-fluorophenyl, 2,3-difluorophenyl or 3-fluoropyrid-2-yl,
or a salt thereof.

4. Compounds of formula (I) according to claims 1 to 3, in which
L stands for a group #$^1$—CR$^{7A}$R$^{7B}$-#$^2$,
  wherein
  #$^1$ stands for the point of attachment to the carbonyl group,
  #$^2$ stands for the point of attachment to the pyrimidine ring,
  R$^{7A}$ stands for methyl,
  R$^{7B}$ stands for methyl,
the ring Q stands for a group of formula

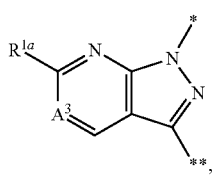 (a-1)

-continued

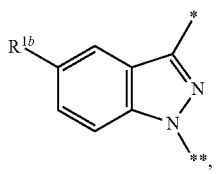 (b-1)

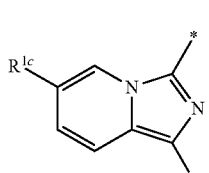 (c-1a)

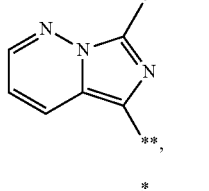 (c-1a)

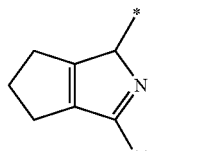 (d-1)

or

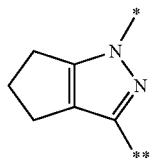 (l-1)

wherein
* stands for the point of attachment to —CH$_2$—R$^2$,
** stands for the point of attachment to the pyrimidine,
R$^{1a}$ stands for hydrogen or methyl,
R$^{1b}$ stands for hydrogen or fluorine,
R$^{1c}$ stands for hydrogen or chlorine,
A$^1$ stands for N or CH,
A$^3$ stands for N, CH or C—F,
R$^3$ stands for —NR$^5$R$^6$,
  wherein
  R$^5$ stands for hydrogen, methyl or ethyl,
  R$^6$ stands for (C$_1$-C$_6$)-alkyl, oxetanyl, azetidinyl, tetrahydrofuranyl, pyrrolidinyl, tetrahydropyranyl, piperidinyl, piperazinyl, morpholinyl, phenyl, pyrazolyl, oxazolyl, thiazolyl, triazolyl, oxadiazolyl, thiadiazolyl, pyridyl or pyrimidinyl,
    in which (C$_1$-C$_6$)-alkyl is substituted with 1 or 2 substituents selected independently of one another from the group fluorine, difluoromethyl, trifluoromethyl cyclopropyl, cyclobutyl, cyclopentyl, trifluoromethoxy, —(C═O)$_p$—OR$^9$, —(C═O)$_p$—NR$^9$R$^{10}$, tetrahydrofuranyl, pyrrolidinyl, tetrahydropyranyl, phenyl, furanyl, pyrazolyl, imidazolyl, triazolyl and pyridyl,
    in which
    p denotes the number 0 or 1,
    R$^9$ and R$^{10}$ each stand, independently of one another, for hydrogen, methyl, ethyl, trifluoromethyl, 2,2,2-trifluoroethyl, 1,1,2,2,2-pentafluoroethyl, cyclopropyl or cyclobutyl, and
in which tetrahydrofuranyl, pyrrolidinyl, tetrahydropyranyl, phenyl, furanyl, pyrazolyl, imidazolyl, triazolyl and pyridyl for their part can be substituted with 1 or 2 substituents selected independently of one another from the group fluorine, chlorine, cyano, difluoromethyl, trifluoromethyl, methyl, ethyl and oxo, in which oxetanyl, azetidinyl, tetrahydrofuranyl, pyrrolidinyl, tetrahydropyranyl, piperidinyl, piperazinyl, morpholinyl, phenyl, pyrazolyl, oxazolyl, thiazolyl, triazolyl, oxadiazolyl, thiadiazolyl, pyridyl and pyrimidinyl can be substituted with 1 or 2 substituents selected independently of one another from the group fluorine, difluoromethyl, trifluoromethyl, methyl, ethyl and oxo, or $R^5$ and $R^6$ form, together with the nitrogen atom to which they are bound, an azetidinyl, pyrrolidinyl, imidazolidinyl, piperidinyl, dihydropiperidinyl, piperazinyl, morpholinyl, pyrazolyl or imidazolyl ring, in which the azetidinyl, pyrrolidinyl, imidazolidinyl, piperidinyl, dihydropiperidinyl, piperazinyl, morpholinyl, pyrazolyl and imidazolyl ring can be substituted with 1 or 2 substituents selected independently of one another from the group fluorine, cyano, difluoromethyl, trifluoromethyl, 2,2,2-trifluoroethyl, 1,1,2,2,2-pentafluoroethyl, methyl, ethyl, 1-hydroxyethyl, cyclopropyl, cyclobutyl, cyclopentyl, hydroxy, oxo, methoxy, ethoxy, difluoromethoxy and trifluoromethoxy, $R^2$ stands for 3,3,3-trifluoroeth-1-yl, 2,2,3,3,3-pentafluoroprop-1-yl, phenyl or pyridyl,
wherein phenyl is substituted with 1 to 3 fluorine substituents,
and
wherein pyridyl can be substituted with 1 fluorine substituent,
or a salt thereof.

5. The compound of claim 1, in which
L stands for a group $\#^1$—$CR^{7A}R^{7B}$-$\#^2$,
wherein
$\#^1$ stands for the point of attachment to the carbonyl group,
$\#^2$ stands for the point of attachment to the pyrimidine ring,
$R^{7A}$ stands for hydrogen, fluorine, methyl, hydroxy,
$R^{7B}$ stands for hydrogen, fluorine, methyl or trifluoromethyl,
or
$R^{7A}$ and $R^{7B}$ together with the carbon atom to which they are bound, form a tetrahydrofuranyl ring,
the ring Q stands for a group of formula

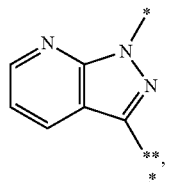 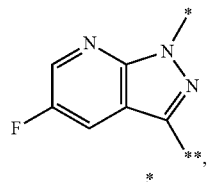

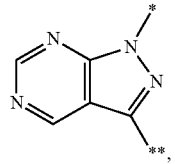 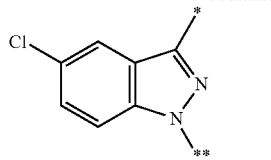

-continued wherein
\* stands for the point of attachment to —$CH_2$—$R^2$,
\*\* stands for the point of attachment to the pyrimidine,
$R^3$ stands for —$OR^4$ or —$NR^5R^6$,
wherein
$R^4$ stands for ($C_1$-$C_6$)-alkyl or pyrazolyl,
in which ($C_1$-$C_6$)-alkyl can be substituted with 1 to 3 substituents selected independently of one another from the group fluorine, trifluoromethyl, —(C=O)$_p$—$OR^9$ and —(C=O)$_p$—$NR^9R^{10}$,
in which
p denotes the number 0 or 1,
$R^9$ and $R^{10}$ independently of one another stand in each case for hydrogen or methyl,
and
in which pyrazolyl can be substituted with 1 or 2 substituents selected independently of one another from the group fluorine, difluoromethyl, trifluoromethyl, 2,2,2-trifluoroethyl, 1,1,2,2,2-pentafluoroethyl, methyl, cyclopropyl, cyclobutyl, cyclopentyl, $R^5$ stands for hydrogen, methyl or ethyl,
$R^6$ stands for ($C_1$-$C_6$)-alkyl, oxetanyl, azetidinyl, tetrahydrofuranyl, pyrrolidinyl, tetrahydropyranyl, piperidinyl, piperazinyl, morpholinyl, phenyl, pyrazolyl, oxazolyl, thiazolyl, triazolyl, oxadiazolyl, thiadiazolyl, pyridyl or pyrimidinyl,
in which ($C_1$-$C_6$)-alkyl is substituted with 1 or 2 substituents selected independently of one another from the group fluorine, difluoromethyl, trifluoromethyl cyclopropyl, cyclobutyl, cyclopentyl, trifluoromethoxy, —(C=O)$_p$—$OR^9$, —(C=O)$_p$—$NR^9R^{10}$, tetrahydrofuranyl, pyrrolidinyl, tetrahydropyranyl, phenyl, furanyl, pyrazolyl, imidazolyl, triazolyl and pyridyl,
in which
p denotes the number 0 or 1,
$R^9$ and $R^{10}$ each stand, independently of one another, for hydrogen, methyl, ethyl, trifluoromethyl, 2,2,2-trifluoroethyl, 1,1,2,2,2-pentafluoroethyl, cyclopropyl or cyclobutyl,
and
in which cyclopropyl, cyclobutyl, cyclopentyl, tetrahydrofuranyl, pyrrolidinyl, tetrahydropyranyl, phenyl, furanyl, pyrazolyl, imidazolyl, triazolyl and pyridyl for their part can be substituted with 1 or 2 substituents selected independently of one another from the group fluorine, chlorine, cyano, difluoromethyl, trifluoromethyl, methyl, ethyl, oxo and hydroxy,
in which oxetanyl, azetidinyl, tetrahydrofuranyl, pyrrolidinyl, tetrahydropyranyl, piperidinyl, piperazinyl, morpholinyl, phenyl, pyrazolyl, oxazolyl, thiazolyl, triazolyl, oxadiazolyl, thiadiazolyl, pyridyl and pyrimidinyl can be substituted with 1 or 2 substituents selected independently of one another from the group fluorine, difluoromethyl, trifluoromethyl, methyl, ethyl, oxo, azetidinyl and pyrrolidinyl, or R⁵ and R⁶ form, together with the nitrogen atom to which they are bound, an azetidinyl, pyrrolidinyl, imidazolidinyl, piperidinyl, dihydropiperidinyl, piperazinyl, morpholinyl, pyrazolyl or imidazolyl ring,
in which the azetidinyl, pyrrolidinyl, imidazolidinyl, piperidinyl, dihydropiperidinyl, piperazinyl, morpholinyl, pyrazolyl and imidazolyl ring can be substituted with 1 or 2 substituents selected independently of one another from the group fluorine, cyano, difluoromethyl, trifluoromethyl, 2,2,2-trifluoroethyl, 1,1,2,2,2-pentafluoroethyl, methyl, ethyl, 1-hydroxyethyl, cyclopropyl, cyclobutyl, cyclopentyl, hydroxy, oxo, methoxy, ethoxy, difluoromethoxy and trifluoromethoxy, R² stands for 2-fluorophenyl, 2,3-difluorophenyl or 3-fluoropyrid-2-yl, or a salt thereof.

6. The compound of claim 1, in which

L stands for a group #¹—CR^{7A}R^{7B}-#²,
wherein
¹ stands for the point of attachment to the carbonyl group,
² stands for the point of attachment to the pyrimidine ring,
R^{7A} stands for methyl,
R^{7B} stands for methyl,
or
R^{7A} and R^{7B} together with the carbon atom to which they are bound, form a tetrahydrofuranyl ring, the ring Q stands for a group of formula

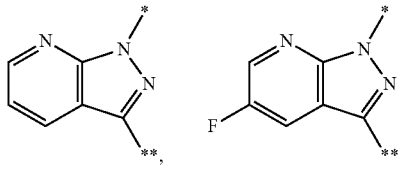

wherein
* stands for the point of attachment to —CH₂—R²,
** stands for the point of attachment to the pyrimidine,
R³ stands for —OR⁴ or —NR⁵R⁶,
wherein
R⁴ stands for (C₁-C₆)-alkyl or pyrazolyl,
in which (C₁-C₆)-alkyl can be substituted with 1 to 3 substituents selected independently of one another from the group fluorine, trifluoromethyl, —(C═O)_p—OR⁹ and —(C═O)_p—NR⁹R¹⁰,
in which
p denotes the number 0 or 1,
R⁹ and R¹⁰ independently of one another stand in each case for hydrogen or methyl,
and
in which pyrazolyl can be substituted with 1 or 2 substituents selected independently of one another from the group fluorine, difluoromethyl, trifluoromethyl, 2,2,2-trifluoroethyl, 1,1,2,2,2-pentafluoroethyl, methyl, cyclopropyl, cyclobutyl, cyclopentyl,
R⁵ stands for hydrogen, methyl or ethyl,
R⁶ stands for (C₁-C₆)-alkyl, oxetanyl, azetidinyl, tetrahydrofuranyl, pyrrolidinyl, tetrahydropyranyl, piperidinyl, piperazinyl, morpholinyl, phenyl, pyrazolyl, oxazolyl, thiazolyl, triazolyl, oxadiazolyl, thiadiazolyl, pyridyl or pyrimidinyl,
in which (C₁-C₆)-alkyl is substituted with 1 or 2 substituents selected independently of one another from the group fluorine, difluoromethyl, trifluoromethyl cyclopropyl, cyclobutyl, cyclopentyl, trifluoromethoxy, —(C═O)_p—OR⁹, —(C═O)_p—NR⁹R¹⁰, tetrahydrofuranyl, pyrrolidinyl, tetrahydropyranyl, phenyl, furanyl, pyrazolyl, imidazolyl, triazolyl and pyridyl,
in which
p denotes the number 0 or 1,
R⁹ and R¹⁰ each stand, independently of one another, for hydrogen, methyl, ethyl, trifluoromethyl, 2,2,2-trifluoroethyl, 1,1,2,2,2-pentafluoroethyl, cyclopropyl or cyclobutyl,
and
in which cyclopropyl, cyclobutyl, cyclopentyl, tetrahydrofuranyl, pyrrolidinyl, tetrahydropyranyl, phenyl, furanyl, pyrazolyl, imidazolyl, triazolyl and pyridyl for their part can be substituted with 1 or 2 substituents selected independently of one another from the group fluorine, chlorine, cyano, difluoromethyl, trifluoromethyl, methyl, ethyl, oxo and hydroxy,
in which oxetanyl, azetidinyl, tetrahydrofuranyl, pyrrolidinyl, tetrahydropyranyl, piperidinyl, piperazinyl, morpholinyl, phenyl, pyrazolyl, oxazolyl, thiazolyl, triazolyl, oxadiazolyl, thiadiazolyl, pyridyl and pyrimidinyl can be substituted with 1 or 2 substituents selected independently of one another from the group fluorine, difluoromethyl, trifluoromethyl, methyl, ethyl, oxo, azetidinyl and pyrrolidinyl, or R⁵ and R⁶ form, together with the nitrogen atom to which they are bound, an azetidinyl, pyrrolidinyl, imidazolidinyl, piperidinyl, dihydropiperidinyl, piperazinyl, morpholinyl, pyrazolyl or imidazolyl ring,
in which the azetidinyl, pyrrolidinyl, imidazolidinyl, piperidinyl, dihydropiperidinyl, piperazinyl, morpholinyl, pyrazolyl and imidazolyl ring can be substituted with 1 or 2 substituents selected independently of one another from the group fluorine, cyano, difluoromethyl, trifluoromethyl, 2,2,2-trifluoroethyl, 1,1,2,2,2-pentafluoroethyl, methyl, ethyl, 1-hydroxyethyl, cyclopropyl, cyclobutyl, cyclopentyl, hydroxy, oxo, methoxy, ethoxy, difluoromethoxy and trifluoromethoxy, R² stands for 2-fluorophenyl, 2,3-difluorophenyl or 3-fluoropyrid-2-yl, or a salt thereof.

7. A pharmaceutical composition comprising the compound of claim 1 and an inert, non-toxic, pharmaceutically suitable excipient.

8. A method of production of compounds of formula (I), as defined in claim 1, comprising:
converting compound of formula (II)

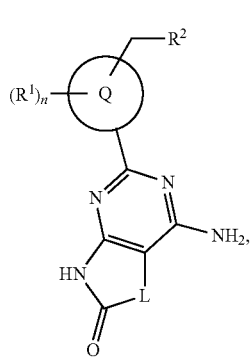

(II)

in which n, L, Q, $R^1$ and $R^2$ in each case have the meanings stated in claim 1,
in an inert solvent with isopentyl nitrite and a halogen equivalent into a compound of formula (III)

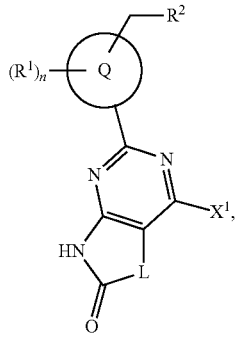

(III)

in which n, L, Q, $R^1$ and $R^2$ in each case have the meanings given in claim 1 and
$X^1$ stands for bromine or iodine
reacting the compound of formula (III) in an inert solvent, optionally in the presence of a suitable base, with a compound of formula (IV)

$R^3$—H    (IV), in which $R^3$ has the meaning given in claim 1,
thereby producing a compound of formula (I)

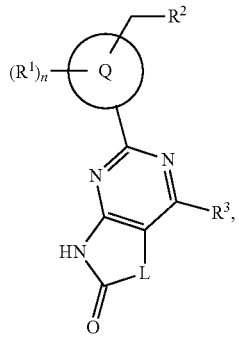

(I)

in which n, L, Q, $R^1$, $R^2$ and $R^3$ in each case have the meanings given in claim 1,
and optionally the resultant compounds of formula (I) optionally with the corresponding (i) solvents and/or (ii) acids or bases are transformed to their solvates, salts and/or solvates of the salts.

\* \* \* \* \*